US010995335B2

(12) United States Patent
Li et al.

(10) Patent No.: US 10,995,335 B2
(45) Date of Patent: May 4, 2021

(54) RNAI AGENTS AND COMPOSITIONS FOR INHIBITING EXPRESSION OF ANGIOPOIETIN-LIKE 3 (ANGPTL3), AND METHODS OF USE

(71) Applicant: Arrowhead Pharmaceuticals, Inc., Pasadena, CA (US)

(72) Inventors: Zhen Li, Monona, WI (US); Rui Zhu, Middleton, WI (US); So Wong, Oregon, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 16/130,377

(22) Filed: Sep. 13, 2018

(65) Prior Publication Data

US 2019/0078089 A1     Mar. 14, 2019

Related U.S. Application Data

(60) Provisional application No. 62/694,976, filed on Jul. 7, 2018, provisional application No. 62/651,284, filed on Apr. 2, 2018, provisional application No. 62/583,919, filed on Nov. 9, 2017, provisional application No. 62/558,819, filed on Sep. 14, 2017.

(51) Int. Cl.
    *C12N 15/11*        (2006.01)
    *C12N 15/113*     (2010.01)
    *A61P 3/06*         (2006.01)

(52) U.S. Cl.
CPC .............. *C12N 15/113* (2013.01); *A61P 3/06* (2018.01); *C12N 2310/14* (2013.01); *C12N 2310/315* (2013.01); *C12N 2310/317* (2013.01); *C12N 2310/332* (2013.01); *C12N 2310/343* (2013.01); *C12N 2310/346* (2013.01); *C12N 2310/351* (2013.01)

(58) Field of Classification Search
CPC ... C12N 15/113; C12N 2310/14; C12N 15/67
See application file for complete search history.

(56) References Cited

U.S. PATENT DOCUMENTS

| | | | |
|---|---|---|---|
| 4,522,811 A | 6/1985 | Eppstein et al. | |
| 5,885,968 A | 3/1999 | Biessen et al. | |
| 5,998,203 A | 12/1999 | Matulic-Adamic et al. | |
| 9,322,018 B2 | 4/2016 | Bettencourt et al. | |
| 9,382,540 B2 | 7/2016 | Prakash et al. | |
| 2004/0224405 A1 | 11/2004 | Leake et al. | |
| 2004/0266707 A1 | 12/2004 | Leake et al. | |
| 2005/0245475 A1 | 11/2005 | Khvorova et al. | |
| 2005/0255487 A1 | 11/2005 | Khvorova et al. | |
| 2007/0134250 A1 | 6/2007 | Ferrara et al. | |
| 2012/0283309 A1* | 11/2012 | Avkin-Nachum ... | C12N 15/113 514/44 A |
| 2013/0023579 A1* | 1/2013 | Crooke ..................... | A61P 9/00 514/44 A |
| 2014/0179768 A1 | 6/2014 | Bettencourt et al. | |
| 2015/0299696 A1* | 10/2015 | Carr ....................... | C12N 15/111 514/44 A |
| 2015/0315594 A1 | 11/2015 | Prakash et al. | |
| 2016/0194349 A1 | 7/2016 | Prakash et al. | |
| 2017/0037409 A1 | 2/2017 | Freier et al. | |
| 2017/0096665 A1* | 4/2017 | Melquist ............... | C12N 15/113 |
| 2017/0306334 A1* | 10/2017 | Darimont ............... | C12N 15/87 |

FOREIGN PATENT DOCUMENTS

| | | |
|---|---|---|
| WO | 2000053722 A2 | 9/2000 |
| WO | 2001042499 A1 | 6/2001 |
| WO | 2006006948 A2 | 1/2006 |
| WO | 2008022309 A2 | 2/2008 |
| WO | 2009073809 A2 | 6/2009 |
| WO | 2011085271 A2 | 7/2011 |
| WO | 2011104169 A1 | 9/2011 |
| WO | 2012058210 A1 | 5/2012 |

(Continued)

OTHER PUBLICATIONS

Kamola et al., The siRNA non-seed region and its target sequences are auxiliary determinants of off-target effects, PLOS Computational Biology, vol. 11 (12):e1004656, pp. 1-17. (Year: 2015).*

Ando et al.; "A decreased expression of angiopoietin-like 3 is protective against atherosclerosis in apoE-deficient mice"; Journal of Lipid Research; vol. 44; 1216-1223; 2003.

Amarzguioui et al.; "Tolerance for mutations and chemical modifications in a siRNA"; Nucleic Acids Research; vol. 31, No. 2; 589-595; 2003.

Baenziger et al.; "Galactose and N-Acetylgalactosamine-Specific Endocytosis of Glycopeptides by Isolated Rat Hepatocytes"; Cell; vol. 22; 611-620; 1980.

(Continued)

*Primary Examiner* — Dana H Shin
(74) *Attorney, Agent, or Firm* — Robert M. Teigen; Paul VanderVelde

(57) ABSTRACT

The present disclosure relates to RNAi agents, e.g., double stranded RNAi agents, able to inhibit Angiopoietin-like 3 (also called ANGPTL3, ANGPL3, angiopoietin-like protein 3) gene expression, and compositions that include ANGPTL3 RNAi agents. Also disclosed are methods of use of ANGPTL3 RNAi agents and compositions. The ANGPTL3 RNAi agents disclosed herein may be conjugated to targeting ligands to facilitate the delivery to cells, including to hepatocytes. Pharmaceutical compositions that include one or more ANGPTL3 RNAi agents, optionally with one or more additional therapeutics, are described. Delivery of the ANGPTL3 RNAi agents in vivo provides for inhibition of ANGPTL3 gene expression, and can result in lower triglycerides and/or cholesterol levels in the subject. The RNAi agents can be used in methods of treatment of ANGPTL3-related diseases and disorders, including cardiometabolic diseases such as hypertriglyceridemia and hyperlipidemia.

19 Claims, 20 Drawing Sheets

Specification includes a Sequence Listing.

(56) References Cited

FOREIGN PATENT DOCUMENTS

| WO | 2012083185 A2 | 6/2012 |
| WO | 2012/177784 A2 | 12/2012 |
| WO | 2013032829 A1 | 3/2013 |
| WO | 2013074974 A2 | 5/2013 |
| WO | 2013158141 A1 | 10/2013 |
| WO | 2015/100394 A1 | 7/2015 |
| WO | 2015168589 A2 | 11/2015 |
| WO | 2016028649 A1 | 2/2016 |
| WO | 2016154127 A1 | 9/2016 |
| WO | 2016168286 A1 | 10/2016 |
| WO | 2017156012 A1 | 9/2017 |
| WO | 2018044350 A1 | 3/2018 |

OTHER PUBLICATIONS

Biessen et al.; "Synthesis of Cluster Galactosides with High Affinity for the Hepatic Asialoglycoprotein Receptor"; J. Med. Chem.; 38; 1538-1546; 1995.

Connolly et al.; "Binding and Endocytosis of Cluster Blycosides by Rabbit Hepatocytes"; The Journal of Biological Chemistry; vol. 257, No. 2; 939-945; 1982.

Czauderna et al.; "Structural variations and stabilizing modifications of synthetic siRNAs in mammalian cells"; Nucleic Acids Research; vol. 31, No. 11; 2705-2716; 2003.

Dahlgren et al.; "Analysis of siRNA specificity on targets with double-nucleotide mismatches"; Nucleic Acids Research; vol. 36, No. 9, e53; pp. 1-7; 2008.

Du et al.; "A systematic analysis of the silencing effects of an active siRNA at all single-nucleotide mismatched target sites"; Nucleic Acids Research; vol. 33, No. 5; 1671-1677; 2005.

Elbashir et al.; "Functional anatomy of siRNAs for mediating efficient RNAi in *Drosophila melanogaster* embryo lysate"; The EMBO Journal; vol. 20, No. 23; 6877-6888; 2001.

Iobst et al.; "Selective Sugar Binding to the Carbohydrate Recognition Domains of the Rat Hepatic and Macrophage Asialoglycoprotein Receptors"; The Journal of Biological Chemistry; vol. 271, No. 12; 6686-6693; 1996.

Reynolds et al; "Rational siRNA design for RNA interference"; Nature Biotechnology; vol. 22, No. 3; 326-330; 2004.

GenBank NM_014495.3; "*Homo sapiens* angiopoietin like 3 (ANGPTL3), mRNA" (2013).

Graham et al.; "Cardiovascular and Metabolic Effects of ANGPTL3 Antisense Oligonucleotides"; N Engl J Med.; vol. 377, No. 3, pp. 222-232; May 24, 2017.

International Search Report and Written Opinion for corresponding International Application No. PCT/US2018/050848 dated Jan. 29, 2019.

\* cited by examiner

RNAI AGENTS AND COMPOSITIONS FOR INHIBITING EXPRESSION OF ANGIOPOIETIN-LIKE 3 (ANGPTL3), AND METHODS OF USE

CROSS REFERENCE TO RELATED APPLICATIONS

This application claims priority from U.S. Provisional Patent Application Ser. No. 62/694,976, filed on Jul. 7, 2018, U.S. Provisional Patent Application Ser. No. 62/651,284, filed on Apr. 2, 2018, U.S. Provisional Patent Application Ser. No. 62/583,919, filed on Nov. 9, 2017, and U.S. Provisional Patent Application Ser. No. 62/558,819, filed on Sep. 14, 2017, the contents of each of which are incorporated herein by reference in their entirety.

SEQUENCE LISTING

This application contains a Sequence Listing which has been submitted in ASCII format and is hereby incorporated by reference in its entirety. The ASCII copy is named 30658_SequenceListingUS1 and is 111 kb in size.

FIELD OF THE INVENTION

The present disclosure relates to RNA interference (RNAi) agents, e.g., double stranded RNAi agents, for inhibition of angiopoietin-like 3 gene expression, compositions that include angiopoietin-like 3 RNAi agents, and methods of use thereof.

BACKGROUND

Angiopoietin-like 3 (also called ANGPTL3, ANGPL3, ANG3, or angiopoietin-like protein 3) is an angiopoietin protein encoded by the human angiopoietin-like 3 gene that is reported to be involved in regulating lipid metabolism. ANGPTL3 is a 460-amino acid polypeptide that consists of a signal peptide, N-terminal coiled-coil domain, and a C-terminal fibrinogen (FBN)-like domain. ANGPTL3 is known to be primarily produced in hepatocytes in humans, and after synthesis is secreted into circulation. ANGPTL3 acts as an inhibitor of lipoprotein lipase, which catalyzes hydrolysis of triglycerides, and endothelial lipase, which hydrolyzes lipoprotein phospholipids. Inhibition of these enzymes can cause increases in plasma levels of triglycerides, high-density lipoproteins (HDL), and phospholipids. Further, loss-of-function mutations in ANGPTL3 lead to familial hypobetalipoproteinemia, which is characterized by low levels of triglycerides and low-density lipoprotein (LDL-C) in plasma. In humans, loss-of-function in ANGPTL3 is also correlated with a decreased risk of atherosclerotic cardiovascular disease.

An effective therapeutic that targets ANGPTL3 could provide a beneficial impact in the treatment (including prophylactic treatment) of cardiometabolic diseases such as hypertriglyceridemia, obesity, hyperlipidemia, abnormal lipid and/or cholesterol metabolism, atherosclerosis, type II diabetes mellitus, cardiovascular disease, coronary artery disease, non-alcoholic steatohepatitis, non-alcoholic fatty liver disease, homozygous and heterozygous familial hypercholesterolemia, statin resistant hypercholesterolemia and other metabolic-related disorders and diseases. While certain double-stranded RNA-based compounds have been identified as being capable of inhibiting the expression of an ANGPTL3 gene (see, e.g., International Patent Application Publication Nos. WO 2012/177784, WO 2016/168286, and WO 2016/154127), the ANGPTL3 RNAi agents disclosed herein were not previously disclosed or known, and provide for highly potent and highly efficient ANGPTL3-specific inhibition of expression of an ANGTPL3 gene.

SUMMARY

There exists a need for novel ANGPTL3-specific RNA interference (RNAi) agents (also herein termed RNAi agent, RNAi trigger, or trigger), e.g., double stranded RNAi agents, that are able to selectively and efficiently inhibit the expression of an ANGPTL3 gene. Further, there exists a need for compositions that include novel ANGPTL3-specific RNAi agents for the treatment of diseases associated with, among other things, elevated triglyceride (TG) levels.

In general, the present disclosure features ANGPTL3 gene-specific RNAi agents, compositions that include ANGPTL3 RNAi agents, and methods for inhibiting expression of an ANGPTL3 gene in vitro and/or in vivo using the ANGPTL3 RNAi agents and compositions that include ANGPTL3 RNAi agents described herein. The ANGPTL3 RNAi agents described herein can selectively and efficiently decrease or inhibit expression of an ANGPTL3 gene, and thereby reduce TG levels and/or cholesterol levels in a subject, e.g., a human or animal subject.

The described ANGPTL3 RNAi agents can be used in methods for therapeutic treatment (including the prophylactic and preventative treatment) of symptoms and diseases associated with elevated TG levels and/or elevated cholesterol levels, including, but not limited to hypertriglyceridemia, obesity, hyperlipidemia, abnormal lipid and/or cholesterol metabolism, atherosclerosis, type II diabetes mellitus, cardiovascular disease, coronary artery disease, non-alcoholic steatohepatitis, non-alcoholic fatty liver disease, homozygous and heterozygous familial hypercholesterolemia, statin resistant hypercholesterolemia and other metabolic-related disorders and diseases. The ANGPTL3 RNAi agents disclosed herein can selectively reduce ANGPTL3 gene expression, which can lead to a reduction in, among other things, TG levels and/or cholesterol levels, in a subject. The methods disclosed herein include the administration of one or more ANGPTL3 RNAi agents to a subject, e.g., a human or animal subject, using any suitable methods known in the art, such as subcutaneous injection or intravenous administration.

In one aspect, the disclosure features RNAi agents for inhibiting expression of the human ANGPTL3 gene, wherein the RNAi agent includes a sense strand and an antisense strand. Also described herein are compositions that include or consist of an RNAi agent capable of inhibiting the expression of an ANGPTL3 gene, wherein the RNAi agent includes or consists of a sense strand and an antisense strand, and the composition further comprises at least one pharmaceutically acceptable excipient. The compositions described herein that include one or more of the disclosed ANGPTL3 RNAi agents are able to selectively and efficiently decrease expression of an ANGPTL3 gene. The compositions that include one or more ANGPTL3 RNAi agents can be administered to a subject, such as a human or animal subject, for the treatment (including prophylactic treatment or inhibition) of symptoms and diseases associated with elevated TG, elevated cholesterol, and/or enhanced ANGPTL3 expression.

An ANGPTL3 RNAi agent described herein includes a sense strand (also referred to as a passenger strand), and an antisense strand (also referred to as a guide strand). The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the sense and/or antisense strands are independently 16, 17, 18, 19, 20, 21, 22, 23, 24, 25, 26, 27, 28, 29, or 30 nucleotides in length. The RNAi agents described herein, upon delivery to a cell expressing ANGPTL3, inhibit the expression of one or more ANGPTL3 genes in vivo or in vitro.

A sense strand of the ANGPTL3 RNAi agents described herein includes at least 16 consecutive nucleotides that have at least 85% identity to a core stretch sequence (also referred to herein as a "core stretch" or "core sequence") of the same number of nucleotides in an ANGPTL3 mRNA. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of an ANGPTL3 RNAi agent described herein includes at least 16 consecutive nucleotides that have at least 85% complementarity to a core stretch of the same number of nucleotides in an ANGPTL3 mRNA and to a core stretch of the same number of nucleotides in the corresponding sense strand. In some embodiments, this antisense strand core stretch is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length In some embodiments, the ANGPTL3 RNAi agents disclosed herein target the portion of an ANGPTL3 gene having the sequence of any of the sequences disclosed in Table 1.

Examples of ANGPTL3 RNAi agent sense strands and antisense strands that can be included in the ANGPTL3 RNAi agents disclosed herein are provided in Table 3 and Table 4. Examples of ANGPTL3 RNAi agent duplexes are provided in Table 5. Examples of 19-nucleotide core stretch sequences that consist of or are included in the sense strands and antisense strands of ANGPTL3 RNAi agents disclosed herein, are provided in Table 2.

In another aspect, the disclosure features methods for delivering ANGPTL3 RNAi agents to liver cells in a subject, such as a mammal, in vivo. Also described herein are compositions for use in such methods. The one or more ANGPTL3 RNAi agents can be delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors, or Dynamic Polyconjugates™ (DPCs) (see, for example WO 2000/053722, WO 2008/0022309, WO 2011/104169, and WO 2012/083185, each of which is incorporated herein by reference).

In some embodiments, an ANGPTL3 RNAi agent is delivered to target cells or tissues by covalently linking or conjugating the RNAi agent to a targeting group, such as an asialoglycoprotein receptor ligand (i.e., a ligand that includes a compound having affinity for the asialoglycoprotein receptor). In some embodiments, an asialoglycoprotein receptor ligand includes, consists of, or consists essentially of, a galactose or galactose derivative cluster. In some embodiments, an ANGPTL3 RNAi agent is linked to a targeting ligand comprising the galactose derivative N-acetyl-galactosamine. In some embodiments, a galactose derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer. In some embodiments, the ANGPTL3 RNAi agents that are conjugated to targeting ligands that include N-acetyl-galactosamine are selectively internalized by liver cells, and hepatocytes in particular, either through receptor-mediated endocytosis or by other means. Examples of targeting groups useful for delivering RNAi agents are disclosed, for example, in International Patent Application Publication Nos. WO 2018/044350 and WO 2017/156012, which are incorporated by reference herein in their entirety.

A targeting group can be linked to the 3' or 5' end of a sense strand or an antisense strand of an ANGPTL3 RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

A targeting group, with or without a linker, can be linked to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In some embodiments, described herein are compositions that include one or more ANGPTL3 RNAi agents that have the duplex structures disclosed in Table 5.

In a further aspect, described herein are pharmaceutical compositions that include one or more described ANGPTL3 RNAi agent(s), optionally combined with one or more additional (i.e., second, third, etc.) therapeutics. In some embodiments, the pharmaceutical compositions that include one or more described ANGPTL3 RNAi agent(s), optionally combined with one or more additional (i.e., second, third, etc.) therapeutics, can be formulated in a pharmaceutically acceptable carrier or diluent. In some embodiments, these compositions can be administered to a subject, such as a mammal. In some embodiments, the mammal is a human.

In some embodiments, described herein are compositions that include a combination or cocktail of at least two ANGPTL3 RNAi agents having different nucleotide sequences. In some embodiments, the two or more different ANGPTL3 RNAi agents are each separately and independently linked to targeting groups. In some embodiments, the two or more different ANGPTL3 RNAi agents are each linked to targeting groups that include or consist of targeting ligands that include one or more moieties that target the asialoglycoprotein receptor. In some embodiments, the two or more different ANGPTL3 RNAi agents are each linked to targeting groups that include or consist of targeting ligands that include one or more galactose-derivatives. In some embodiments, the two or more different ANGPTL3 RNAi agents are each linked to targeting groups that include or consist of targeting ligands that include one or more N-acetyl-galactosamines.

In another aspect, the disclosure features methods for inhibiting expression of an ANGPTL3 gene, wherein the methods include administering to a subject or to a cell of a subject an amount of an ANGPTL3 RNAi agent capable of inhibiting the expression of an ANGPTL3 gene, wherein the ANGPTL3 RNAi agent comprises a sense strand and an antisense strand, and wherein the antisense strand includes the sequence of any one of the antisense strand nucleotide sequences in Table 2 or Table 3. In some embodiments, disclosed herein are methods of inhibiting expression of an ANGPTL3 gene, wherein the methods include administering to a subject or to a cell an amount of an ANGPTL3 RNAi agent capable of inhibiting the expression of an ANGPTL3 gene, wherein the ANGPTL3 RNAi agent comprises a sense strand and an antisense strand, and wherein the sense strand includes the sequence of any one of the sense strand nucleotide sequences in Tables 2 or 4. Also described herein are compositions for use in such methods.

In a further aspect, the disclosure features methods of treatment (including preventative or prophylactic treatment) of diseases or symptoms caused by elevated TG levels and/or elevated cholesterol levels, wherein the methods include administering to a subject in need thereof an ANGPTL3 RNAi agent having an antisense strand that includes the sequence of any of the sequences in Tables 2 or 3. In some embodiments, described herein are methods of treatment (including preventative treatment) of diseases or symptoms caused by elevated TG levels and/or elevated cholesterol levels, wherein the methods include administering to a subject in need thereof an ANGPTL3 RNAi agent having a sense strand comprising the sequence of any of the sequences in Tables 2 or 4. Also described herein are compositions for use in such methods.

Also described are methods of treating a human subject having a pathological state (such as a condition or disease), or being at risk of developing a pathological state, that is mediated at least in part by ANGPTL3 gene expression, the methods comprising the step of administering to the subject a therapeutically effective amount of a ANGPTL3 RNAi agent and/or ANGPTL3 RNAi agent-containing composition. The method of treating a subject with an ANGPTL3 RNAi agent and/or ANGPTL3 RNAi agent-containing composition can optionally be combined with one or more steps of administering one or more additional (i.e., second, third, etc.) therapeutics or treatments. An additional therapeutic can be another ANGPTL3 RNAi agent (e.g., an ANGPTL3 RNAi agent that targets a different sequence within the ANGPTL3 gene). An additional therapeutic can also be a small molecule drug, antibody, antibody fragment, and/or aptamer. In some embodiments, the one or more additional therapeutics is a statin, such as atorvastatin, fluvastatin, pravastatin, pitavastatin, rosuvastatin, or simvastatin.

In some embodiments, the described ANGPTL3 RNAi agent(s) are optionally combined with one or more additional therapeutics. The ANGPTL3 RNAi agent and additional therapeutic(s) can be administered in a single composition or they can be administered separately. In some embodiments, the one or more additional therapeutics is administered separately in separate dosage forms from the RNAi agent (e.g., the ANGPTL3 RNAi agent is administered by subcutaneous injection, while the additional therapeutic involved in the method of treatment dosing regimen is administered orally). In some embodiments, the described ANGPTL3 RNAi agent(s) are administered to a subject in need thereof via subcutaneous injection, and the one or more optional additional therapeutics are administered orally, which together provide for a treatment regimen for diseases and conditions associated with elevated TG and/or cholesterol levels. In some embodiments, the described ANGPTL3 RNAi agent(s) are administered to a subject in need thereof via subcutaneous injection, and the one or more optional additional therapeutics are administered via a separate subcutaneous injection. In some embodiments, the ANGPTL3 RNAi agent and one or more additional therapeutics are combined into a single dosage form (e.g., a "cocktail" formulated into a single composition for subcutaneous injection). The ANGPTL3 RNAi agents, with or without the one or more additional therapeutics, can be combined with one or more excipients to form pharmaceutical compositions.

In some embodiments, disclosed herein are methods for inhibiting expression of an ANGPTL3 gene in a cell or a subject, wherein the methods include administering to the cell or subject an ANGPTL3 RNAi agent having a sense strand comprising the sequence of any of the sequences in Table 4, and an antisense strand comprising the sequence of any of the sequences in Table 3.

In some embodiments, compositions for delivering an ANGPTL3 RNAi agent to a liver cell, particularly hepatocytes, in vivo, are described, the compositions comprising: an ANGPTL3 RNAi agent conjugated to a targeting group. In some embodiments, the targeting group is an asialoglycoprotein receptor ligand.

In some embodiments, disclosed herein are methods for inhibiting expression of an ANGPTL3 gene in a cell, the methods comprising administering one or more ANGPTL3 RNAi agents having the duplex structure of a duplex set forth in Table 5.

In some embodiments, disclosed herein are methods of treatment (including prophylactic or preventative treatment) of diseases, disorders, or symptoms caused by elevated TG levels and/or elevated cholesterol levels, wherein the methods include administering to a subject in need thereof a therapeutically effective amount of an ANGPTL3 RNAi agent that includes an antisense strand that is at least partially complementary to the portion of the ANGPTL3 mRNA having the sequence in Table 1. In some embodiments, disclosed herein are methods of treatment (including prophylactic or preventative treatment) of diseases or symptoms caused by elevated TG levels and/or elevated cholesterol levels, wherein the methods include administering to a subject in need thereof a therapeutically effective amount of an ANGPTL3 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of treatment (including prophylactic or preventative treatment) of diseases or symptoms caused by elevated TG levels and/or elevated cholesterol levels, wherein the methods include administering to a subject in need thereof a therapeutically effective amount of an ANGPTL3 RNAi agent that includes a sense strand that comprises any of the sequences in Tables 2 or 4, and an antisense strand comprising the sequence of any of the sequences in Tables 2 or 3 that is at least partially complementary to the sense strand.

In some embodiments, disclosed herein are methods for inhibiting expression of an ANGPTL3 gene in a cell, wherein the methods include administering to the cell an ANGPTL3 RNAi agent that includes an antisense strand that is at least partially complementary to the portion of the ANGPTL3 mRNA having the sequence in Table 1. In some embodiments, disclosed herein are methods of inhibiting expression of an ANGPTL3 gene in a cell, wherein the methods include administering to a cell an ANGPTL3 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of inhibiting expression of an ANGPTL3 gene in a cell, wherein the methods include administering an ANGPTL3 RNAi agent that includes a sense strand that comprises any of the sequences in Tables 2 or 4, and an antisense strand that includes the sequence of any of the sequences in Tables 2 or 3 that is at least partially complementary to the sense strand.

In some embodiments, disclosed herein are compositions for inhibiting expression of an ANGPTL3 gene in a cell, wherein the methods include administering a composition that comprises an ANGPTL3 RNAi agent having the duplex structure of a duplex set forth in Table 5.

In some embodiments, disclosed herein are compositions for delivering an ANGPTL3 RNAi agent to a liver cell in vivo, the composition including an ANGPTL3 RNAi agent conjugated or linked to a targeting group. In some embodiments, the targeting group is an asialoglycoprotein receptor ligand. In some embodiments, compositions for delivering an ANGPTL3 RNAi agent to a liver cell in vivo are described, the composition including an ANGPTL3 RNAi agent linked to an N-acetyl-galactosamine targeting ligand.

The ANGPTL3 RNAi agents disclosed herein are designed to target specific positions on an ANGPTL3 gene (SEQ ID NO:1). As defined herein, an antisense strand sequence is designed to target an ANGPTL3 gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target an ANGPTL3 gene at position 304 requires that when base pairing to the gene, the 5' terminal nucleobase of the antisense strand is aligned with position 322 of the ANGPTL3 gene.

As provided herein, an ANGPTL3 RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for an ANGPTL3 RNAi agent disclosed herein that is designed to target position 304 of an ANGPTL3 gene, the 5' terminal nucleobase of the antisense strand of the of the ANGPTL3 RNAi agent must be aligned with position 322 of the gene; however, the 5' terminal nucleobase of the antisense strand may be, but is not required to be, complementary to position 322 of an ANGPTL3 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the ANGPTL3 RNAi agent (e.g., whether the ANGPTL3 RNAi agent is designed to target an ANGPTL3 gene at position 304, at position 921, at position 922, or at some other position) is important to the level of inhibition achieved by the ANGPTL3 RNAi agent.

The use of ANGPTL3 RNAi agents provides methods for therapeutic (including prophylactic) treatment of diseases/disorders associated with elevated TG and/or cholesterol levels and/or enhanced or elevated ANGPTL3 expression. The described ANGPTL3 RNAi agents mediate RNA interference to inhibit the expression of one or more genes necessary for production of ANGPTL3. ANGPTL3 RNAi agents can also be used to treat or prevent various diseases or disorders, including hypertriglyceridemia, obesity, hyperlipidemia, abnormal lipid and/or cholesterol metabolism, atherosclerosis, diabetes, cardiovascular disease, coronary artery disease, and other metabolic-related disorders and diseases. Furthermore, compositions for delivery of ANGPTL3 RNAi agents to liver cells in vivo are described.

The pharmaceutical compositions including one or more ANGPTL3 RNAi agents can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

In some embodiments, disclosed herein are compositions for delivering an ANGPTL3 RNAi agent to a liver cell in vivo, wherein the composition includes an ANGPTL3 RNAi agent conjugated or linked to a targeting group. In some embodiments, the targeting group is an asialoglycoprotein receptor ligand. In some embodiments, compositions for delivering an ANGPTL3 RNAi agent to a liver cell in vivo are described, wherein the composition includes an ANGPTL3 RNAi agent linked to a targeting ligand that includes N-acetyl-galactosamine.

In some embodiments, the ANGPTL3 RNAi agents described herein can include one or more targeting groups having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

In some embodiments, the ANGPTL3 RNAi agents described herein include one targeting group at the 5' end of the sense strand having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

The described ANGPTL3 RNAi agents and/or compositions that include ANGPTL3 RNAi agents can be used in methods for therapeutic treatment of diseases or conditions caused by elevated TG and/or cholesterol levels. Such methods include administration of an ANGPTL3 RNAi agent as described herein to a subject, e.g., a human or animal subject.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGC (SEQ ID NO:3). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGC (SEQ ID NO:3), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGC (SEQ ID NO:3), wherein SEQ ID NO:3 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usAfscsUfgAfuCfaAfa-UfaUfgUfuGfaGfsc (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 5A through 5K showing all internucleoside linkages). In some embodiments, an ANGPTL3 RNAi agent disclosed herein includes an antisense strand that consists of, consists essentially of, or comprises the nucleotide sequence (5'→3') usAfscsUfgAfuCfaAfaUfaUfgUfuGfaGfsc (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usAfscUfgAfuCfaAfa-UfaUfgUfuGfasGfsc (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 5A through 5K showing all internucleoside linkages). In some embodiments, an ANGPTL3 RNAi agent disclosed herein includes an antisense strand that consists of, consists essentially of, or comprises the nucleotide sequence (5'→3') usAfscUfgAfuCfaAfaUfaUfgUfuGfasGfsc (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGU (SEQ ID NO:6). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGU (SEQ ID NO:6), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGU (SEQ ID NO:6), wherein SEQ ID NO:5 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usAfscsUfgAfuCfaAfa-UfaUfgUfuGfaGfsu (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 5A through 5K showing all internucleoside linkages). In some embodiments, an ANGPTL3 RNAi agent disclosed herein includes an antisense strand that consists of, consists essentially of, or comprises the nucleotide sequence (5'→3') usAfscsUfgAfuCfaAfaUfaUfgUfuGfaGfsu (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGC (SEQ ID NO:8). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UUUGAAUUAAUGUCCAUGGGC (SEQ ID NO:8), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGC (SEQ ID NO:8), wherein SEQ ID NO:8 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usUfsusGfaAfuUfaAf-uGfuCfcAfuGfggsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ANGPTL3 RNAi agent disclosed herein includes an antisense strand that consists of, consists essentially of, or comprises the nucleotide sequence (5'→3') usUfsusGfaAfuUfaAf-uGfuCfcAfuGfggsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGU (SEQ ID NO:10). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UUUGAAUUAAUGUCCAUGGGU (SEQ ID NO:10), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGU (SEQ ID NO:10), wherein SEQ ID NO:10 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usUfsusGfaAfuUfaAf-uGfuCfcAfuGfgGfsu (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ANGPTL3 RNAi agent disclosed herein includes an antisense strand that consists of, consists essentially of, or comprises the nucleotide sequence (5'→3') usUfsusGfaAfuUfaAf-uGfuCfcAfuGfgGfsu (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UGUUGAAUUAAUGUCCAUGGA (SEQ ID NO:12). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UGUUGAAUUAAUGUCCAUGGA (SEQ ID NO:12), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UGUUGAAUUAAUGUCCAUGGA (SEQ ID NO:12), wherein SEQ ID NO:12 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usGfsusug-aauuaaUfgUfcCfaUfgGfsa (SEQ ID NO:11), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ANGPTL3 RNAi agent disclosed herein includes an antisense strand that consists of, consists essentially of, or comprises the nucleotide sequence (5'→3') usGfsusug-aauuaaUfgUfcCfaUfgGfsa (SEQ ID NO:11), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') usGfsusUfgAfaUfuA-faUfgUfcCfaUfgGfsa (SEQ ID NO:13), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ANGPTL3 RNAi agent disclosed herein includes an antisense strand that consists of, consists essentially of, or comprises the nucleotide sequence (5'→3') usGfsusUfgAfaUfuA-faUfgUfcCfaUfgGfsa (SEQ ID NO:13), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') ACAUCGUCUAACAUAGCAACC (SEQ ID NO:15). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') ACAUCGUCUAACAUAGCAACC (SEQ ID NO:15), wherein all or substantially all of the nucleotides are modified nucleotides. In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') ACAUCGU-CUAACAUAGCAACC (SEQ ID NO:15), wherein SEQ ID NO:14 is located at positions 1-21 (5'→3') of the antisense strand.

In some embodiments, an ANGPTL3 RNAi agent disclosed herein includes an antisense strand that consists of, consists essentially of, or comprises a modified nucleotide sequence differing by no more than 1 nucleotide from the nucleotide sequence (5'→3') asCfsasUfcGfucuaaCfaUf-aGfcAfaCfsc (SEQ ID NO:14), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. In some embodiments, an ANGPTL3 RNAi agent disclosed herein includes an antisense strand that consists of, consists essentially of, or comprises the nucleotide sequence (5'→3') asCfsasUfcGfucuaaCfaUf-aGfcAfaCfsc (SEQ ID NO:14), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGC (SEQ ID NO:3) and a sense strand that consists of, consists essentially of, or comprises a nucleobase sequence differing by 0 or 1 nucleobases from the nucleotide sequence (5'→3') GCU-CAACAUAUUGAUCAGUA (SEQ ID NO:17). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGC (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') GCUCAACAUAUUUGAUCAGUA (SEQ ID NO:17), wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGC (SEQ ID NO:3) and a sense strand that consists of, consists essentially of, or comprises a nucleobase sequence differing by 0 or 1 nucleobases from the nucleotide sequence (5'→3') GCU-CAACAU($A^{2N}$)UUUGAUCAGUA (SEQ ID NO:19), wherein ($A^{2N}$) represents a 2-aminoadenine nucleotide. In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGC (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') GCUCAACAU($A^{2N}$)UUUGAUCAGUA (SEQ ID NO:19), wherein ($A^{2N}$) represents a 2-aminoadenine nucleotide, and wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGC (SEQ ID NO:3) and a sense strand that consists of, consists essentially of, or comprises a nucleobase sequence differing by 0 or 1 nucleobases from the nucleotide sequence (5'→3') GCU-CAAC($A^{2N}$)U($A^{2N}$)UUUGAUCAGUA (SEQ ID NO:21), wherein ($A^{2N}$) represents a 2-aminoadenine nucleotide. In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGC (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') GCUCAAC($A^{2N}$)U($A^{2N}$)UUUGAUC-AGUA (SEQ ID NO:21), wherein ($A^{2N}$) represents a 2-aminoadenine nucleotide, and wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UACUGAUCAAAUAUGUUGAGU (SEQ ID NO:6) and a sense strand that consists of, consists essentially of, or comprises a nucleobase sequence differing by 0 or 1 nucleobases from the nucleotide sequence (5'→3') ACU-CAACAUAUUUGAUCAGUA (SEQ ID NO:24). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UACUGAUCAAAUAUGUUGAGU (SEQ ID NO:6), wherein all or substantially all of the nucleotides are modified nucleotides, and a sense strand that consists of, consists essentially of, or comprises a nucleotide sequence differing by no more than 1 nucleotide from the nucleotide sequence (5'→3') ACUCAACAUAUUUGAUCAGUA (SEQ ID NO:24), wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGC (SEQ ID NO:8) and a sense strand that consists of, consists essentially of, or comprises a nucleobase sequence differing by 0 or 1 nucleobases from the nucleotide sequence (5'→3') GCC-CAUGGACAUUAAUUCAAA (SEQ ID NO:26). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UUUGAAUUAAUGUCCAUGGGC (SEQ ID NO:8), wherein all or substantially all of the nucleotides are modified nucleotides, and a sense strand that consists of, consists essentially of, or comprises a nucleotide sequence differing by no more than 1 nucleotide from the nucleotide sequence (5'→3') GCCCAUGGACAUUAAUUCAAA (SEQ ID NO:26), wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UUUGAAUUAAUGUCCAUGGGU (SEQ ID NO:10) and a sense strand that consists of, consists essentially of, or comprises a nucleobase sequence differing by 0 or 1 nucleobases from the nucleotide sequence (5'→3') ACCCAUGGACAUUAAUUCAAA (SEQ ID NO:28). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UUUGAAUUAAUGUCCAUGGGU (SEQ ID NO:10), wherein all or substantially all of the nucleotides are modified nucleotides, and a sense strand that consists of, consists essentially of, or comprises a nucleotide sequence differing by no more than 1 nucleotide from the nucleotide sequence (5'→3') ACCCAUGGACAUUAAUUCAAA (SEQ ID NO:28), wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') UGUUGAAUUAAUGUCCAUGGA (SEQ ID NO:12) and a sense strand that consists of, consists essentially of, or comprises a nucleobase sequence differing by 0 or 1 nucleobases from the nucleotide sequence (5'→3') UCCAUGGACAUUAAUUCAACA (SEQ ID NO:30). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') UGUUGAAUUAAUGUCCAUGGA (SEQ ID NO:12), wherein all or substantially all of the nucleotides are modified nucleotides, and a sense strand that consists of, consists essentially of, or comprises a nucleotide sequence differing by no more than 1 nucleotide from the nucleotide sequence (5'→3') UCCAUGGACAUUAAUUCAACA (SEQ ID NO:30), wherein all or substantially all of the nucleotides are modified nucleotides.

In some embodiments, an ANGPTL3 RNAi agent disclosed herein includes an antisense strand that consists of, consists essentially of, or comprises a nucleobase sequence differing by 0 or 1 nucleobases from the nucleotide sequence (5'→3') ACAUCGUCUAACAUAGCAACC (SEQ ID NO:15) and a sense strand that consists of, consists essentially of, or comprises a nucleobase sequence differing by 0 or 1 nucleobases from the nucleotide sequence (5'→3') GGUUGCUAUGUUAGACGAUGU (SEQ ID NO:32). In some embodiments, an ANGPTL3 RNAi agent disclosed herein includes an antisense strand that consists of, consists essentially of, or comprises a nucleotide sequence differing by no more than 1 nucleotide from the nucleotide sequence (5'→3') ACAUCGUCUAACAUAGCAACC (SEQ ID NO:15), wherein all or substantially all of the nucleotides are modified nucleotides, and a sense strand that consists of, consists essentially of, or comprises a nucleotide sequence differing by no more than 1 nucleotide from the nucleotide sequence (5'→3') GGUUGCUAUGUUAGACGAUGU (SEQ ID NO:32), wherein all or substantially all of the nucleotides are modified nucleotides.

In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaacaUfAfUfuugaucagua (SEQ ID NO:16), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaacaUfAfUfuugaucagua (SEQ ID NO:16), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaacaUfa_2NUfuugaucagua (SEQ ID NO:18), wherein a, c, g, and u represent 2'-O-methyl adenosine, cytidine, guanosine, or uridine, respectively; a 2N represents 2'-O-methyl-2-aminoadenosine (see Table 6); Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaacaUfa_2NUfuugaucagua (SEQ ID NO:18), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usAfscUfgAfuCfaAfaUfaUfgUfuGfasGfsc (SEQ ID NO:4), and a sense strand that consists of, consists essentially of, or comprises the modified nucleotide sequence (5'→3') gcucaacaUfAfUfuugaucagua (SEQ ID NO:16), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscUfgAfuCfaAfaUfaUfgUfuGfasGfsc (SEQ ID NO:4), and a sense strand that consists of, consists essentially of, or comprises the modified nucleotide sequence (5'→3') gcucaacaUfAfUfuugaucagua (SEQ ID NO:16), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaaca_2NUfa_2NUfuugaucagua (SEQ ID NO:20), wherein a, c, g, and u represent 2'40-methyl adenosine, cytidine, guanosine, or uridine, respectively; a 2N represents 2'-O-methyl-2-aminoadenosine (see Table 6); Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcucaaca_2NUfa_2NUfuugaucagua (SEQ ID NO:20), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcUfcAfaCfaUfAfUfuugaucagua (SEQ ID NO:22), wherein a, c, g, and u represent 2'-O-methyl adenosine, cytidine, guanosine, or uridine, respectively; a 2N represents 2'-O-methyl-2-aminoadenosine (see Table 6); Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsc (SEQ ID NO:2), and a sense strand that consists of, consists essentially of, or comprises the modified nucleotide sequence (5'→3') gcUfcAfaCfaUfAfUfuugaucagua (SEQ ID NO:22), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsu (SEQ ID NO:5), and a sense strand that consists of, consists essentially of, or comprises the modified nucleotide sequence (5'→3') acucaacaUfAfUfuugaucagua (SEQ ID NO:23), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usAfscsUfgAfuCfaAfaUfaUfgUfuGfaGfsu (SEQ ID NO:5), and a sense strand that consists of, consists essentially of, or comprises the modified nucleotide sequence (5'→3') acucaacaUfAfUfuugaucagua (SEQ ID NO:23), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usUfsusGfaAfuUfaAfuGfuCfcAfuGfggsc (SEQ ID NO:7), and a sense strand that consists of, consists essentially of, or comprises the modified nucleotide sequence (5'→3') gcccauggAfCfAfuuaauucaaa (SEQ ID NO:25), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usUfsusGfaAfuUfaAfuGfuCfcAfuGfggsc (SEQ ID NO:7), and a sense strand that consists of, consists essentially of, or comprises the modified nucleotide sequence (5'→3') gcccauggAfCfAfuuaauucaaa (SEQ ID NO:25), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→ 3') usUfsusGfaAfuUfaAfuGfuCfcAfuGfgGfsu (SEQ ID NO:9), and a sense strand that consists of, consists essentially of, or comprises the modified nucleotide sequence (5'→3') acccauggAfCfAfuuaauucaaa (SEQ ID NO:27), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usUfsusGfaAfuUfaAfuGfuCfcAfuGfgGfsu (SEQ ID NO:9), and a sense strand that consists of, consists essentially of, or comprises the modified nucleotide sequence (5'→3') acccauggAfCfAfuuaauucaaa (SEQ ID NO:27), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usGfsusugaauuaaUfgUfcCfaUfgGfsa (SEQ ID NO:11), and a sense strand that consists of, consists essentially of, or comprises the modified nucleotide sequence (5'→3') uccauggaCfAfUfuaauucaaca (SEQ ID NO:29), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usGfsusugaauuaaUfgUfcCfaUfgGfsa (SEQ ID NO:11), and a sense strand that consists of, consists essentially of, or comprises the modified nucleotide sequence (5'→3') uccauggaCfAfUfuaauucaaca (SEQ ID NO:29), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') usGfsusUfgAfaUfuAfaUfgUfcCfaUfgGfsa (SEQ ID NO:13), and a sense strand that consists of, consists essentially of, or comprises the modified nucleotide sequence (5'→3') uccauggaCfAfUfuaauucaaca (SEQ ID NO:29), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') usGfsusUfgAfaUfuAfaUfgUfcCfaUfgGfsa (SEQ ID NO:13), and a sense strand that consists of, consists essentially of, or comprises the modified nucleotide sequence (5'→3') uccauggaCfAfUfuaauucaaca (SEQ ID NO:29), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises the modified nucleotide sequence (5'→3') asCfsasUfcGfucuaaCfaUfaGfcAfaCfsc (SEQ ID NO:14), and a sense strand that consists of, consists essentially of, or comprises the modified nucleotide sequence (5'→3') gguugcuaUfGfUfuagacgaugu (SEQ ID NO:31), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an ANGPTL3 RNAi agent disclosed herein includes an antisense strand that consists of, consists essentially of, or comprises the modified nucleotide sequence (5'→3') asCfsasUfcGfucuaaCfaUfaGfcAfaCfsc (SEQ ID NO:14), and a sense strand that consists of, consists essentially of, or comprises the modified nucleotide sequence (5'→3') cccuaaaaGfGfGfacaguauucu (SEQ ID NO:31), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 3)
        UACUGAUCAAAUAUGUUGAGC;

(SEQ ID NO: 6)
        UACUGAUCAAAUAUGUUGAGU;

(SEQ ID NO: 8)
        UUUGAAUUAAUGUCCAUGGGC;

(SEQ ID NO: 10)
        UUUGAAUUAAUGUCCAUGGGU;

(SEQ ID NO: 12)
        UGUUGAAUUAAUGUCCAUGGA;
        or
                                    (SEQ ID NO: 15)
        ACAUCGUCUAACAUAGCAACC;
``` wherein the ANGPTL3 RNAi agent further includes a sense strand that is at least partially complementary to the antisense strand; and wherein all or substantially all of the nucleotides on both the antisense strand and the sense strand are modified nucleotides.

In some embodiments, an ANGPTL3 RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 3)
        UACUGAUCAAAUAUGUUGAGC;

(SEQ ID NO: 6)
        UACUGAUCAAAUAUGUUGAGU;

(SEQ ID NO: 8)
        UUUGAAUUAAUGUCCAUGGGC;

(SEQ ID NO: 10)
        UUUGAAUUAAUGUCCAUGGGU;

(SEQ ID NO: 12)
        UGUUGAAUUAAUGUCCAUGGA;
        or
                                    (SEQ ID NO: 15)
        ACAUCGUCUAACAUAGCAACC;
``` wherein the ANGPTL3 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises a nucleotide sequence that differs by 0 or 1 nucleotides from one of the following nucleotide sequences (5'→3'):

UACUGAUCAAAUAUGUUGAGC;   (SEQ ID NO: 3)

UACUGAUCAAAUAUGUUGAGU;   (SEQ ID NO: 6)

UUUGAAUUAAUGUCCAUGGGC;   (SEQ ID NO: 8)

UUUGAAUUAAUGUCCAUGGGU;   (SEQ ID NO: 10)

UGUUGAAUUAAUGUCCAUGGA;   (SEQ ID NO: 12)
or

ACAUCGUCUAACAUAGCAACC;   (SEQ ID NO: 15)

wherein the ANGPTL3 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine; and wherein the respective antisense strand sequence is located at positions 1-21 of the antisense strand.

In some embodiments, an ANGPTL3 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:
  UACUGAUCAAAUAUGUUGAGC (SEQ ID NO:3) and GCUCAACAUAUUUGAUCAGUA (SEQ ID NO:17);
  UACUGAUCAAAUAUGUUGAGC (SEQ ID NO:3) and GCUCAACAU($A^{2N}$)UUUGAUCAGUA (SEQ ID NO:19), wherein ($A^{2N}$) represents a 2-aminoadenine nucleotide;
  UACUGAUCAAAUAUGUUGAGC (SEQ ID NO:3) and GCUCAAC($A^{2N}$)U($A^{2N}$)UUUGAUCAGUA (SEQ ID NO:21), wherein ($A^{2N}$) represents a 2-aminoadenine nucleotide;
  UACUGAUCAAAUAUGUUGAGU (SEQ ID NO:6) and ACUCAACAUAUUUGAUCAGUA (SEQ ID NO:24);
  UUUGAAUUAAUGUCCAUGGGC (SEQ ID NO:8) and GCCCAUGGACAUUAAUUCAAA (SEQ ID NO:26);
  UUUGAAUUAAUGUCCAUGGGU (SEQ ID NO:10) and ACCCAUGGACAUUAAUUCAAA (SEQ ID NO:28);
  UGUUGAAUUAAUGUCCAUGGA (SEQ ID NO:12) and UCCAUGGACAUUAAUUCAACA (SEQ ID NO:30); or
  ACAUCGUCUAACAUAGCAACC (SEQ ID NO:15) and GGUUGCUAUGUUAGACGAUGU (SEQ ID NO:32);
  wherein all or substantially all of the nucleotides on both the antisense strand and the sense strand are modified nucleotides.

In some embodiments, an ANGPTL3 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:
  UACUGAUCAAAUAUGUUGAGC (SEQ ID NO:3) and GCUCAACAUAUUUGAUCAGUA (SEQ ID NO:17);
  UACUGAUCAAAUAUGUUGAGC (SEQ ID NO:3) and GCUCAACAU($A^{2N}$)UUUGAUCAGUA (SEQ ID NO:19), wherein ($A^{2N}$) represents a 2-aminoadenine nucleotide;
  UACUGAUCAAAUAUGUUGAGC (SEQ ID NO:3) and GCUCAAC($A^{2N}$)U($A^{2N}$)UUUGAUCAGUA (SEQ ID NO:21), wherein ($A^{2N}$) represents a 2-aminoadenine nucleotide;
  UACUGAUCAAAUAUGUUGAGU (SEQ ID NO:6) and ACUCAACAUAUUUGAUCAGUA (SEQ ID NO:24);
  UUUGAAUUAAUGUCCAUGGGC (SEQ ID NO:8) and GCCCAUGGACAUUAAUUCAAA (SEQ ID NO:26);
  UUUGAAUUAAUGUCCAUGGGU (SEQ ID NO:10) and ACCCAUGGACAUUAAUUCAAA (SEQ ID NO:28);
  UGUUGAAUUAAUGUCCAUGGA (SEQ ID NO:12) and UCCAUGGACAUUAAUUCAACA (SEQ ID NO:30); or
  ACAUCGUCUAACAUAGCAACC (SEQ ID NO:15) and GGUUGCUAUGUUAGACGAUGU (SEQ ID NO:32);
  wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that consists of, consists essentially of, or comprises a modified nucleotide sequence that differs by 0 or 1 nucleotides from one of the following nucleotide sequences (5'→3'):

usAfscsUfgAfuCfaAfaUfaUfgUfuGfaGfsc;   (SEQ ID NO: 2)

usAfscUfgAfuCfaAfaUfaUfgUfuGfasGfsc;   (SEQ ID NO: 4)

usAfscsUfgAfuCfaAfaUfaUfgUfuGfaGfsu;   (SEQ ID NO: 5)

usUfsusGfaAfuUfaAfuGfuCfcAfuGfggsc;   (SEQ ID NO: 7)

usUfsusGfaAfuUfaAfuGfuCfcAfuGfgGfsu;   (SEQ ID NO: 9)

usGfsusugaauuaaUfgUfcCfaUfgGfsa;   (SEQ ID NO: 11)

usGfsusUfgAfaUfuAfaUfgUfcCfaUfgGfsa;   (SEQ ID NO: 13)

asCfsasUfcGfucuaaCfaUfaGfcAfaCfsc;   (SEQ ID NO: 14)

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage; and wherein the ANGPTL3 RNAi agent further includes the sense strand that is at least partially complementary to the antisense strand; and wherein all or substantially all of the nucleotides on the sense strand are modified nucleotides.

In some embodiments, an ANGPTL3 RNAi agent disclosed herein includes an antisense strand that consists of, consists essentially of, or comprises a modified nucleotide sequence that differs by 0 or 1 nucleotides from one of the following nucleotide sequences (5'→3'):

```
                                       (SEQ ID NO: 2)
usAfscsUfgAfuCfaAfaUfaUfgUfuGfaGfsc;

(SEQ ID NO: 4)
usAfscUfgAfuCfaAfaUfaUfgUfuGfasGfsc;

(SEQ ID NO: 5)
usAfscsUfgAfuCfaAfaUfaUfgUfuGfaGfsu;

(SEQ ID NO: 7)
usUfsusGfaAfuUfaAfuGfuCfcAfuGfggsc;

(SEQ ID NO: 9)
usUfsusGfaAfuUfaAfuGfuCfcAfuGfgGfsu;

(SEQ ID NO: 11)
usGfsusugaauuaaUfgUfcCfaUfgGfsa;

(SEQ ID NO: 13)
usGfsusUfgAfaUfuAfaUfgUfcCfaUfgGfsa;

(SEQ ID NO: 14)
asCfsasUfcGfucuaaCfaUfaGfcAfaCfsc;
``` wherein the ANGPTL3 RNAi agent further includes the sense strand that is at least partially complementary to the antisense strand; wherein all or substantially all of the nucleotides on the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

```
                                       (SEQ ID NO: 2)
usAfscsUfgAfuCfaAfaUfaUfgUfuGfaGfsc
and
                                       (SEQ ID NO: 16)
gcucaacaUfAfUfuugaucagua;

(SEQ ID NO: 2)
usAfscsUfgAfuCfaAfaUfaUfgUfuGfaGfsc
and
                                       (SEQ ID NO: 18)
gcucaacaUfa_2NUfuugaucagua;

(SEQ ID NO: 4)
usAfscUfgAfuCfaAfaUfaUfgUfuGfasGfsc
and
                                       (SEQ ID NO: 16)
gcucaacaUfAfUfuugaucagua;

(SEQ ID NO: 2)
usAfscsUfgAfuCfaAfaUfaUfgUfuGfaGfsc
and
                                       (SEQ ID NO: 20)
gcucaaca_2NUfa_2NUfuugaucagua;

(SEQ ID NO: 2)
usAfscsUfgAfuCfaAfaUfaUfgUfuGfaGfsc
and
                                       (SEQ ID NO: 22)
gcUfcAfaCfaUfAfUfuugaucagua;

(SEQ ID NO: 5)
usAfscsUfgAfuCfaAfaUfaUfgUfuGfaGfsu
and
                                       (SEQ ID NO: 23)
acucaacaUfAfUfuugaucagua;

(SEQ ID NO: 7)
usUfsusGfaAfuUfaAfuGfuCfcAfuGfggsc
and
                                       (SEQ ID NO: 25)
gcccauggAfCfAfuuaauucaaa;

(SEQ ID NO: 9)
usUfsusGfaAfuUfaAfuGfuCfcAfuGfgGfsu
and
                                       (SEQ ID NO: 27)
acccauggAfCfAfuuaauucaaa;

(SEQ ID NO: 11)
usGfsusugaauuaaUfgUfcCfaUfgGfsa
and
                                       (SEQ ID NO: 29)
uccauggaCfAfUfuaauucaaca;

(SEQ ID NO: 13)
usGfsusUfgAfaUfuAfaUfgUfcCfaUfgGfsa
and
                                       (SEQ ID NO: 29)
uccauggaCfAfUfuaauucaaca;
or
                                       (SEQ ID NO: 14)
asCfsasUfcGfucuaaCfaUfaGfcAfaCfsc
and
                                       (SEQ ID NO: 31)
gguugcuaUfGfUfuagacgaugu;
``` wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; a_2N represents 2'-O-methyl-2-aminoadenosine (see Table 6); and s represents a phosphorothioate linkage.

In some embodiments, an ANGPTL3 RNAi agent disclosed herein includes an antisense strand and a sense strand that consists of, consists essentially of, or comprises one of the following nucleotide sequence pairs (5'→3'):

```
                                       (SEQ ID NO: 2)
usAfscsUfgAfuCfaAfaUfaUfgUfuGfaGfsc
and
```

-continued gcucaacaUfAfUfuugaucagua; (SEQ ID NO: 16)

usAfscsUfgAfuCfaAfaUfaUfgUfuGfaGfsc (SEQ ID NO: 2)
and gcucaacaUfa_2NUfuugaucagua; (SEQ ID NO: 18)

usAfscUfgAfuCfaAfaUfaUfgUfuGfasGfsc (SEQ ID NO: 4)
and gcucaacaUfAfUfuugaucagua; (SEQ ID NO: 16)

usAfscsUfgAfuCfaAfaUfaUfgUfuGfaGfsc (SEQ ID NO: 2)
and gcucaaca_2NUfa_2NUfuugaucagua; (SEQ ID NO: 20)

usAfscsUfgAfuCfaAfaUfaUfgUfuGfaGfsc (SEQ ID NO: 2)
and gcUfcAfaCfaUfAfUfuugaucagua; (SEQ ID NO: 22)

usAfscsUfgAfuCfaAfaUfaUfgUfuGfaGfsu (SEQ ID NO: 5)
and acucaacaUfAfUfuugaucagua; (SEQ ID NO: 23)

usUfsusGfaAfuUfaAfuGfuCfcAfuGfggsc (SEQ ID NO: 7)
and gcccauggAfCfAfuuaauucaaa; (SEQ ID NO: 25)

usUfsusGfaAfuUfaAfuGfuCfcAfuGfgGfsu (SEQ ID NO: 9)
and acccauggAfCfAfuuaauucaaa; (SEQ ID NO: 27)

usGfsusugaauuaaUfgUfcCfaUfgGfsa (SEQ ID NO: 11)
and uccauggaCfAfUfuaauucaaca; (SEQ ID NO: 29)

usGfsusUfgAfaUfuAfaUfgUfcCfaUfgGfsa (SEQ ID NO: 13)
and uccauggaCfAfUfuaauucaaca; (SEQ ID NO: 29)
or asCfsasUfcGfucuaaCfaUfaGfcAfaCfsc (SEQ ID NO: 14)
and gguugcuaUfGfUfuagacgaugu; (SEQ ID NO: 31)

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; a_2N represents 2'-O-methyl-2-aminoadenosine (see Table 6); s represents a phosphorothioate linkage; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an ANGPTL3 RNAi agent disclosed herein includes an antisense strand that includes a nucleobase sequence that differs by 0 or 1 nucleobases from the nucleotide sequences selected from the group consisting of (5'→3'):

UACUGAUCAAAUAUGUUGA; (SEQ ID NO: 50)

UGUUGAAUUAAUGUCCAUG; (SEQ ID NO: 55)

UUUGAAUUAAUGUCCAUGG; (SEQ ID NO: 60)
or

ACAUCGUCUAACAUAGCAA. (SEQ ID NO: 64)

In some embodiments, an ANGPTL3 RNAi agent disclosed herein includes an antisense strand that includes a nucleobase sequence that differs by 0 or 1 nucleobases from the nucleotide sequences selected from the group consisting of (5'→3'):

UACUGAUCAAAUAUGUUGA; (SEQ ID NO: 50)

UGUUGAAUUAAUGUCCAUG; (SEQ ID NO: 55)

UUUGAAUUAAUGUCCAUGG; (SEQ ID NO: 60)
or

ACAUCGUCUAACAUAGCAA; (SEQ ID NO: 64)

and
wherein all or substantially all of the nucleotides are modified nucleotides.

In some embodiments, an ANGPTL3 RNAi agent disclosed herein includes an antisense strand that includes a nucleobase sequence that differs by 0 or 1 nucleobases from the nucleotide sequences selected from the group consisting of (5'→3'):

UACUGAUCAAAUAUGUUGA; (SEQ ID NO: 50)

UGUUGAAUUAAUGUCCAUG; (SEQ ID NO: 55)

UUUGAAUUAAUGUCCAUGG; (SEQ ID NO: 60)
or

ACAUCGUCUAACAUAGCAA; (SEQ ID NO: 64)

and
wherein all or substantially all of the nucleotides are modified nucleotides, and wherein SEQ ID NO:50, SEQ ID NO:55, SEQ ID NO:60, or SEQ ID NO:64, respectively, is located at nucleotide positions 1-19 (5'→3') of the antisense strand.

In some embodiments, an ANGPTL3 RNAi agent disclosed herein includes an antisense strand and a sense strand that each include a nucleobase sequences that differs by 0 or 1 nucleobases from the nucleotide sequence pairs selected from the group consisting of (5'→3'):

UACUGAUCAAAUAUGUUGA (SEQ ID NO:50) and UCAACAUAUUUGAUCAGUA (SEQ ID NO:130);
UACUGAUCAAAUAUGUUGA (SEQ ID NO:50) and UCAACAU(A$^{2N}$)UUUGAUCAGUA (SEQ ID NO:131), wherein (A') represents a 2-aminoadenine nucleotide;
UACUGAUCAAAUAUGUUGA (SEQ ID NO:50) and UCAAC(A$^{2N}$)U(A$^{2N}$)UUUGAUCAGUA (SEQ ID NO:132), wherein (A') represents a 2-aminoadenine nucleotide;
UGUUGAAUUAAUGUCCAUG (SEQ ID NO:55) and CAUGGACAUUAAUUCAACA (SEQ ID NO:145);
UUUGAAUUAAUGUCCAUGG (SEQ ID NO:60) and CCAUGGACAUUAAUUCAAA (SEQ ID NO:150);
ACAUCGUCAACAUAGCAA (SEQ ID NO:64) and UUGCUAUGUUAGACGAUGU (SEQ ID NO:154).

In some embodiments, an ANGPTL3 RNAi agent disclosed herein includes an antisense strand and a sense strand that each include a nucleobase sequences that differs by 0 or 1 nucleobases from the nucleotide sequence pairs selected from the group consisting of (5'→3'):

UACUGAUCAAAUAUGUUGA (SEQ ID NO:50) and UCAACAUAUUUGAUCAGUA (SEQ ID NO:130);
UACUGAUCAAAUAUGUUGA (SEQ ID NO:50) and UCAACAU(A$^{2N}$)UUUGAUCAGUA (SEQ ID NO:131), wherein (A') represents a 2-aminoadenine nucleotide;
UACUGAUCAAAUAUGUUGA (SEQ ID NO:50) and UCAAC(A$^{2N}$)U(A$^{2N}$)UUUGAUCAGUA (SEQ ID NO:132), wherein (A') represents a 2-aminoadenine nucleotide;
UGUUGAAUUAAUGUCCAUG (SEQ ID NO:55) and CAUGGACAUUAAUUCAACA (SEQ ID NO:145);
UUUGAAUUAAUGUCCAUGG (SEQ ID NO:60) and CCAUGGACAUUAAUUCAAA (SEQ ID NO:150);
ACAUCGUCAACAUAGCAA (SEQ ID NO:64) and UUGCUAUGUUAGACGAUGU (SEQ ID NO:154); and wherein all or substantially all of the nucleotides are modified nucleotides.

In some embodiments, the compositions described herein comprising one or more ANGPTL3 RNAi agents are packaged in a kit, container, pack, dispenser, pre-filled syringes, or vials. In some embodiments, the compositions described herein are administered parenterally.

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. ANGPTL3 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an ANGPTL3 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the preventative treatment, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol ⌇ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

BRIEF DESCRIPTION OF THE DRAWINGS

FIG. 5A discloses SEQ ID NOs: 2 and 300.

The following abbreviations are used in FIGS. 5A to 5K: a, c, g, and u are 2'-O-methyl modified nucleotides; Af, Cf, Gf, and Uf are 2'-fluoro modified nucleotides; p is a phosphodiester linkage; s is a phosphorothioate linkage; invAb is an inverted abasic residue; a_2N is a 2'-O-methyl-2-aminoadenosine modified nucleotide (see Table 6); and (NAG37)s is a tridentate N-acetyl-galactosamine targeting ligand having the structure depicted in Table 6.

Figure 1A:
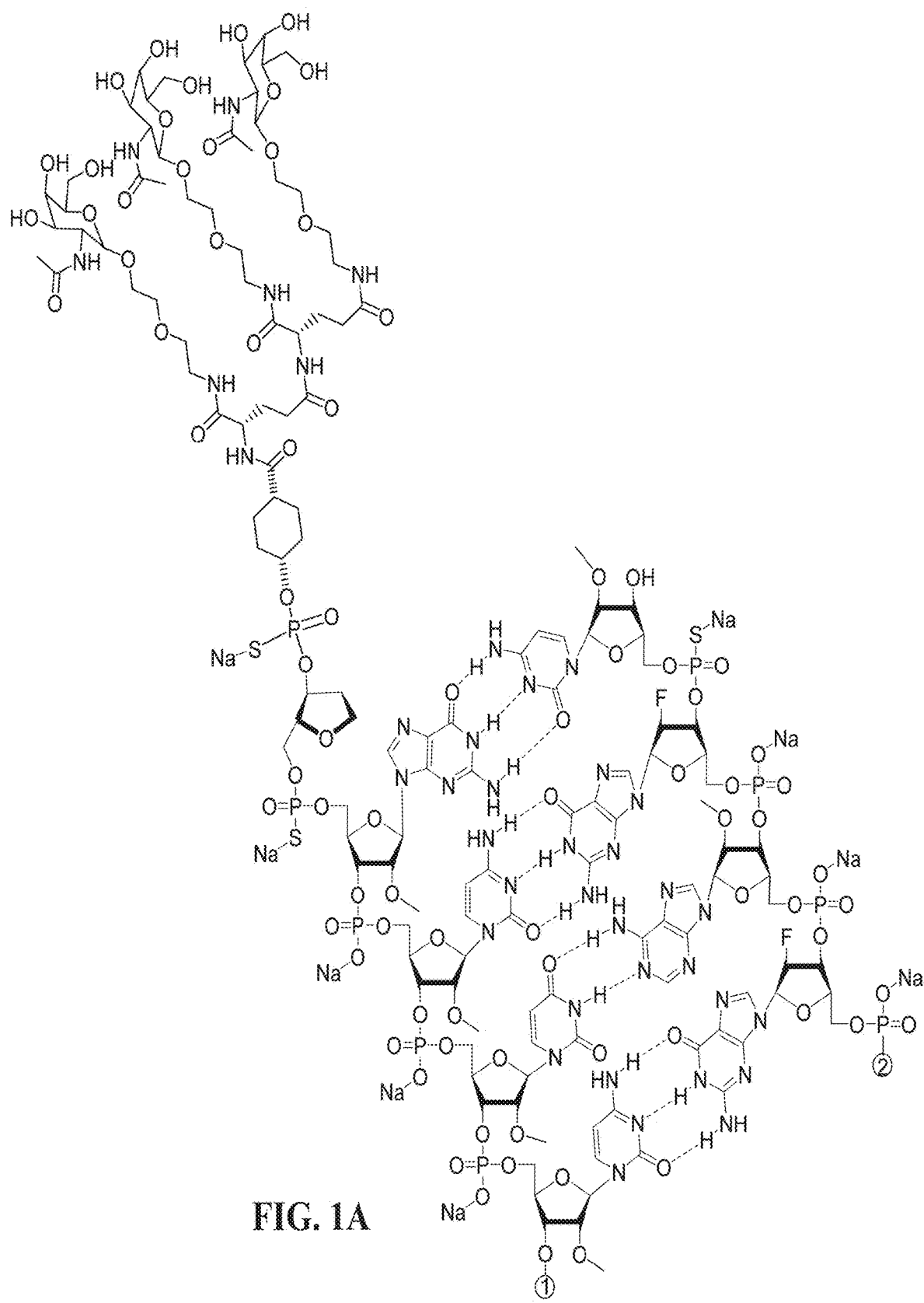
FIG. 1A to 1D. Chemical structure representation of ANGPTL3 RNAi agent AD05488, conjugated to an N-acetyl-galactosamine tridentate ligand having the structure of (NAG37)s (see Table 6) at the 5' terminal end of the sense strand, shown in a sodium salt form.
Figure 1B:
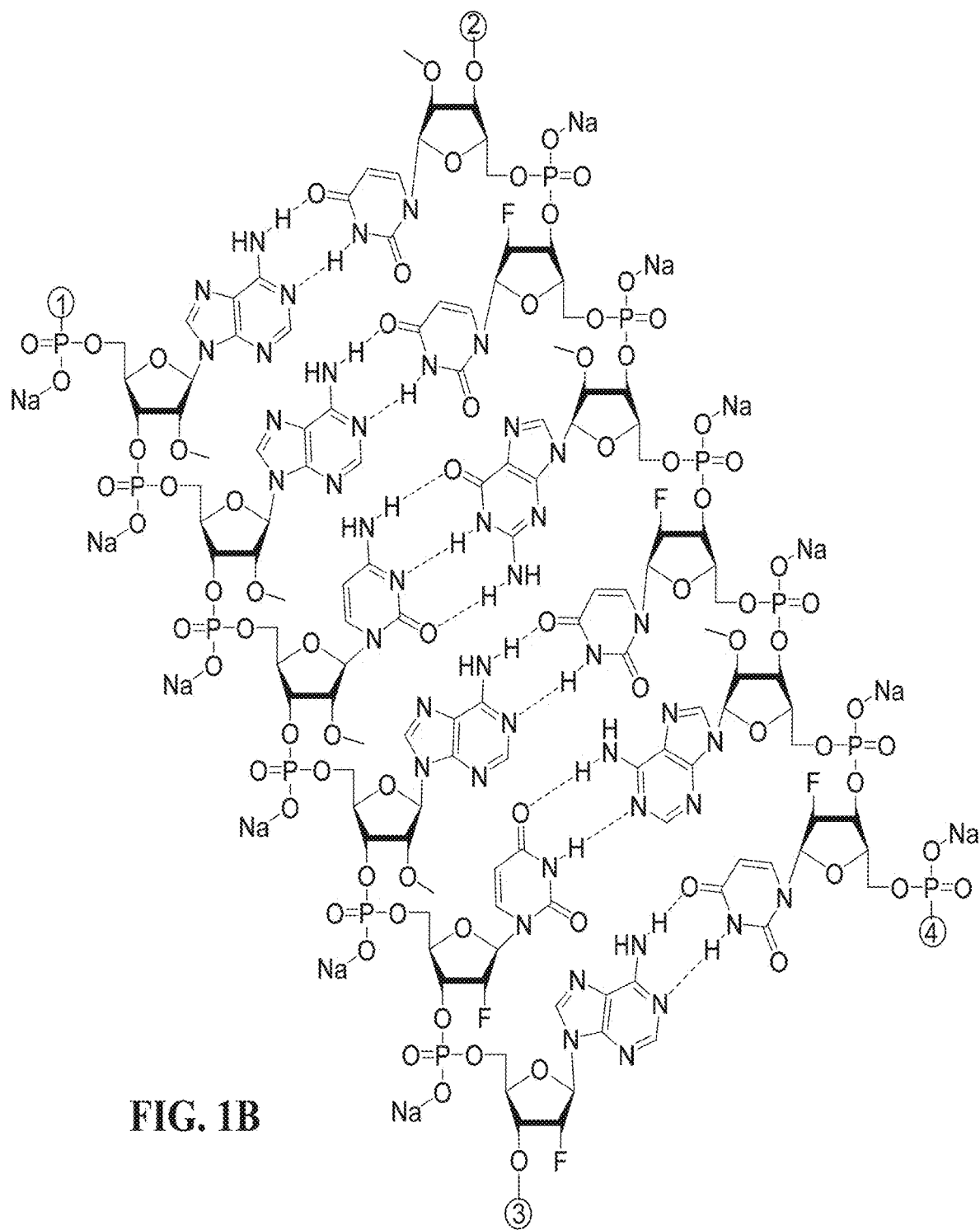
Figure 1C:
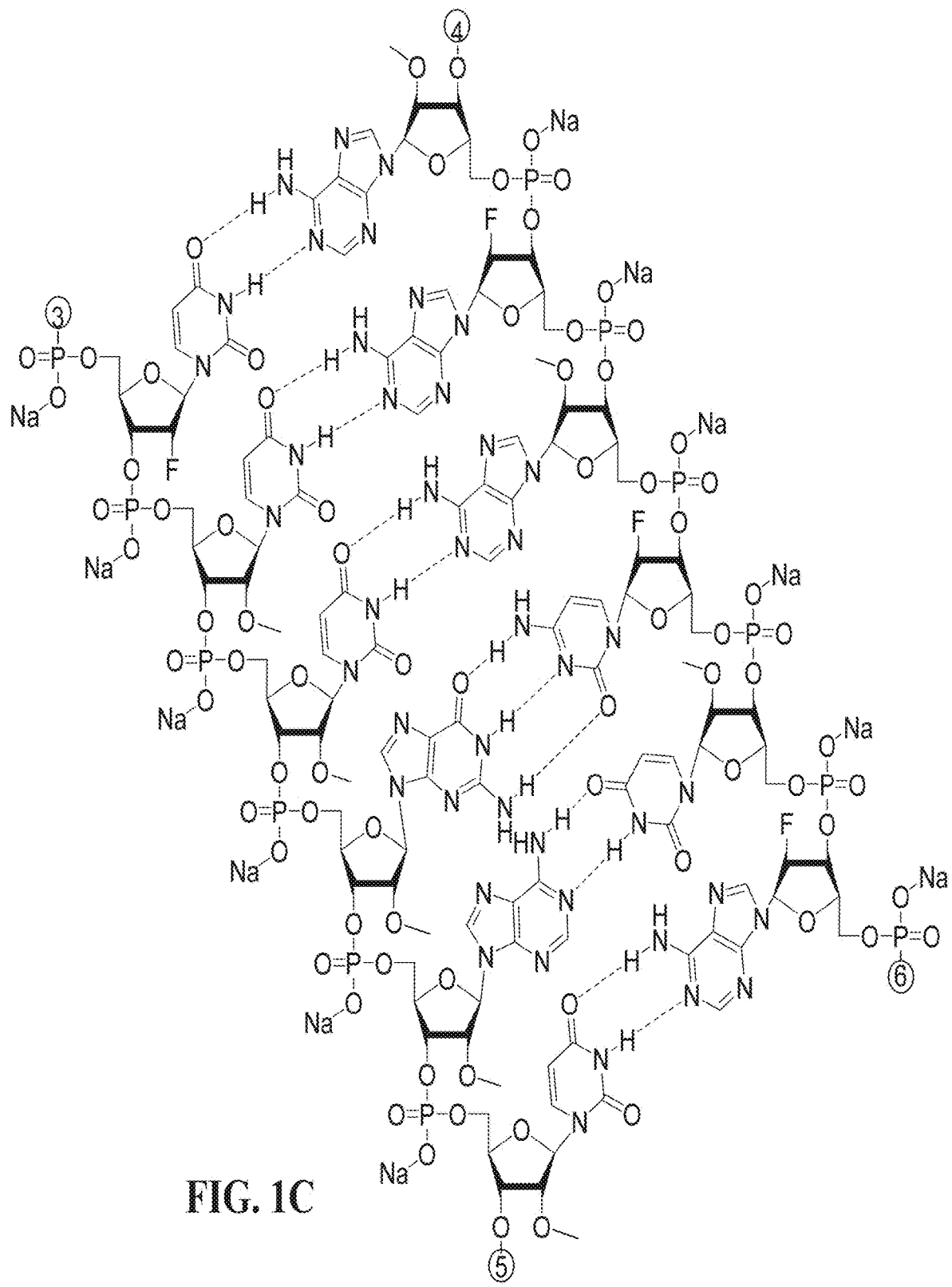
Figure 1D:
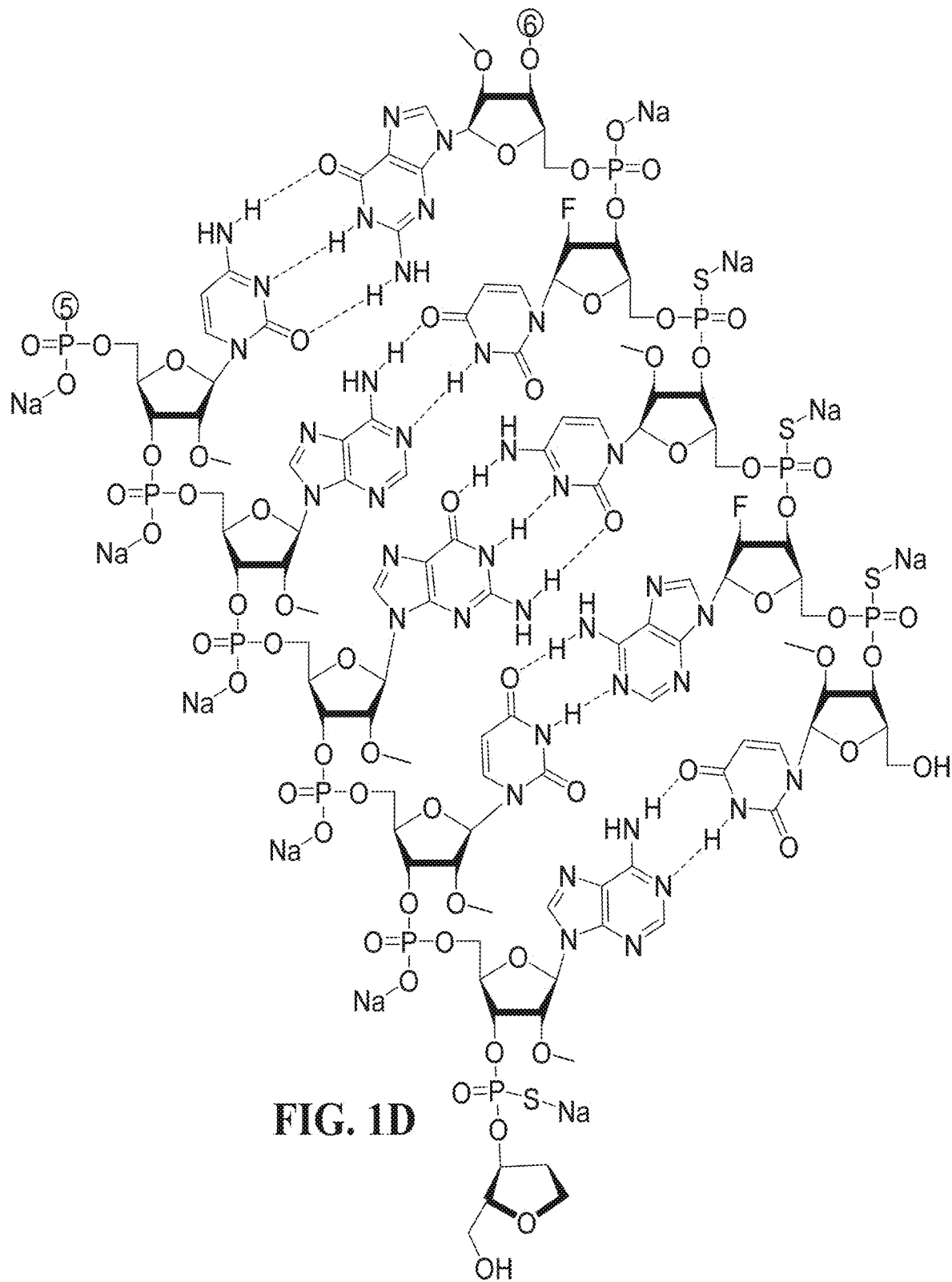
Figure 2A:
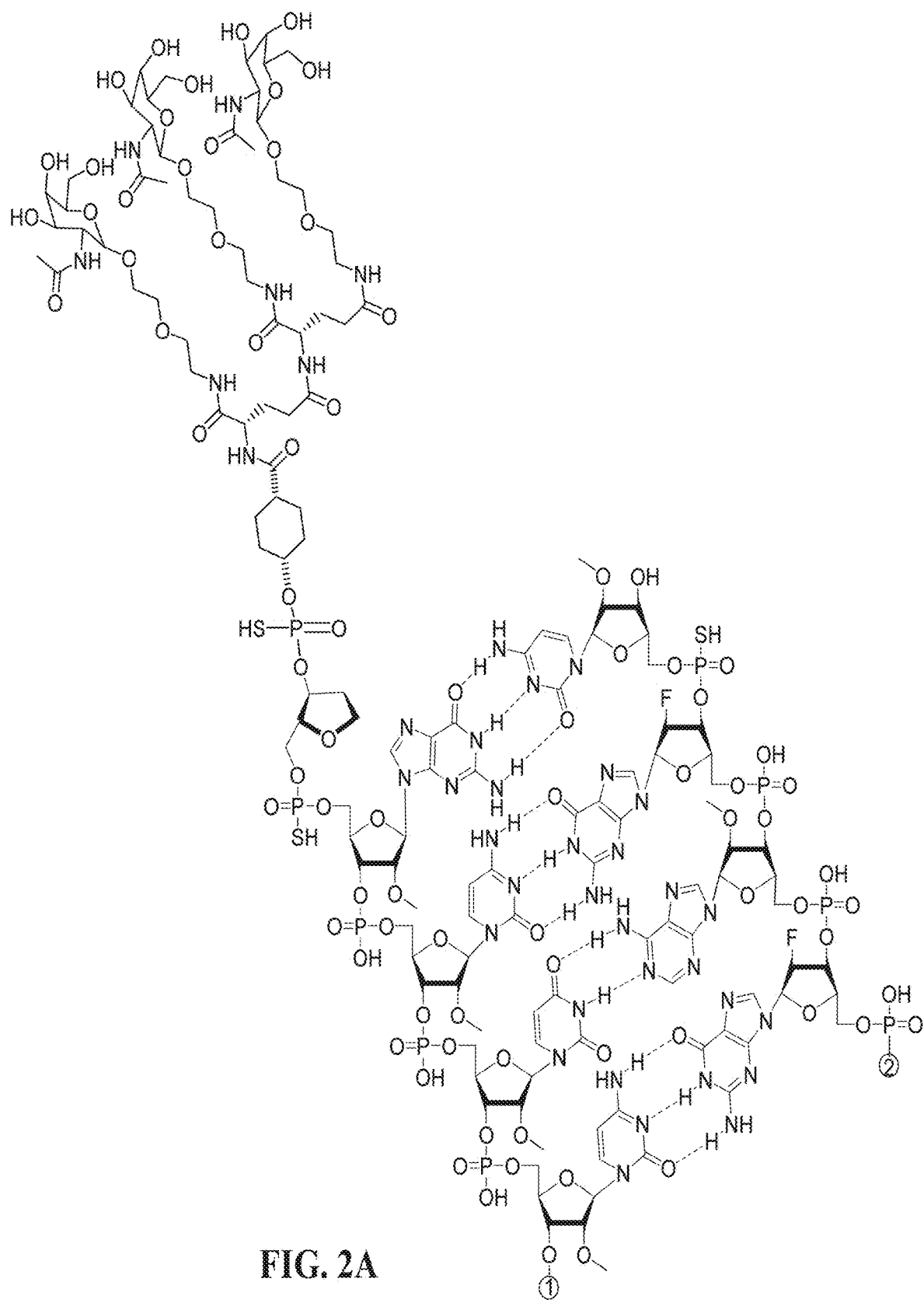
FIG. 2A to 2D. Chemical structure representation of ANGPTL3 RNAi agent AD05488, conjugated to an N-acetyl-galactosamine tridentate ligand having the structure of (NAG37)s (see Table 6) at the 5' terminal end of the sense strand, shown in a free acid form.
Figure 2B:
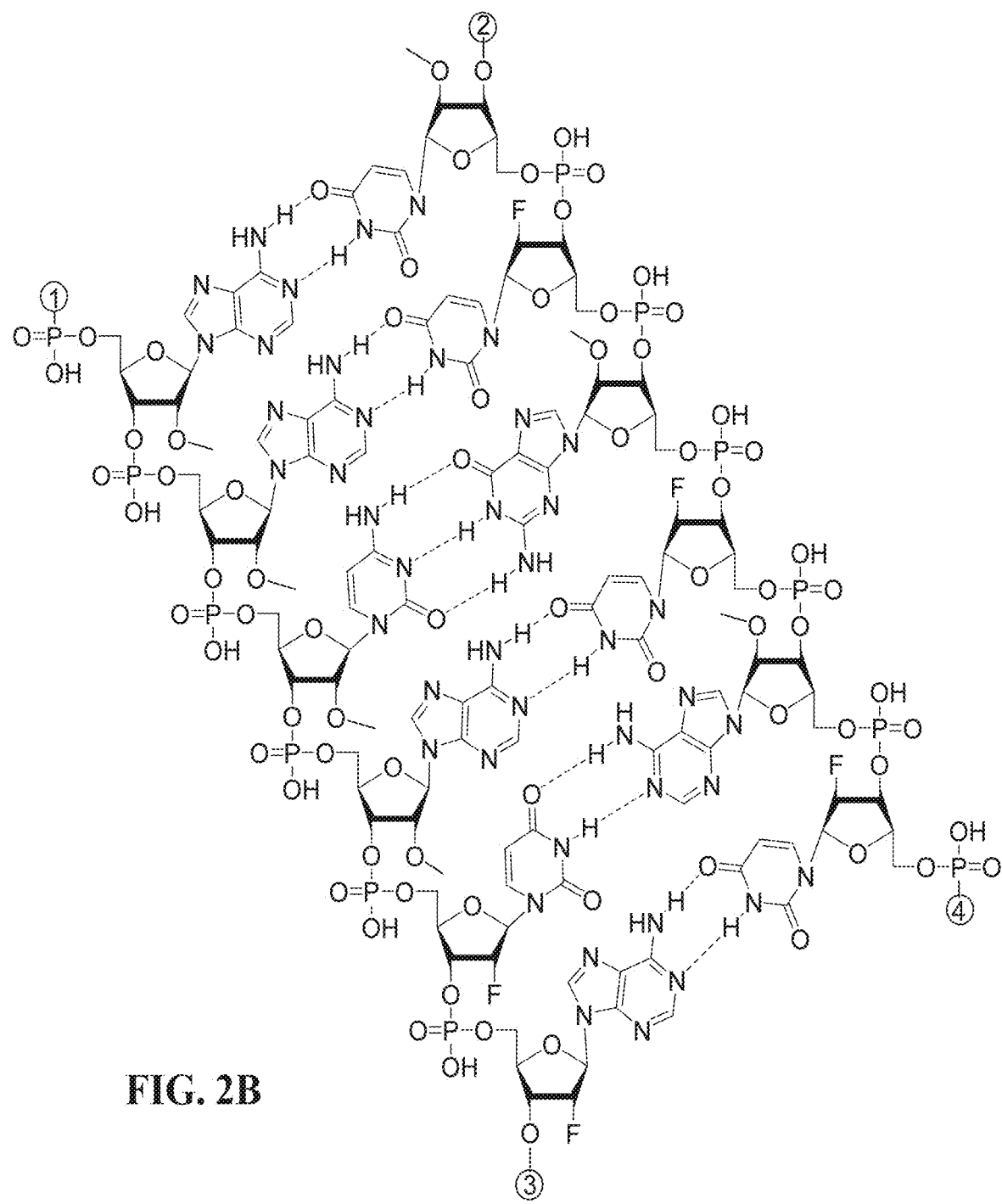
Figure 2C:
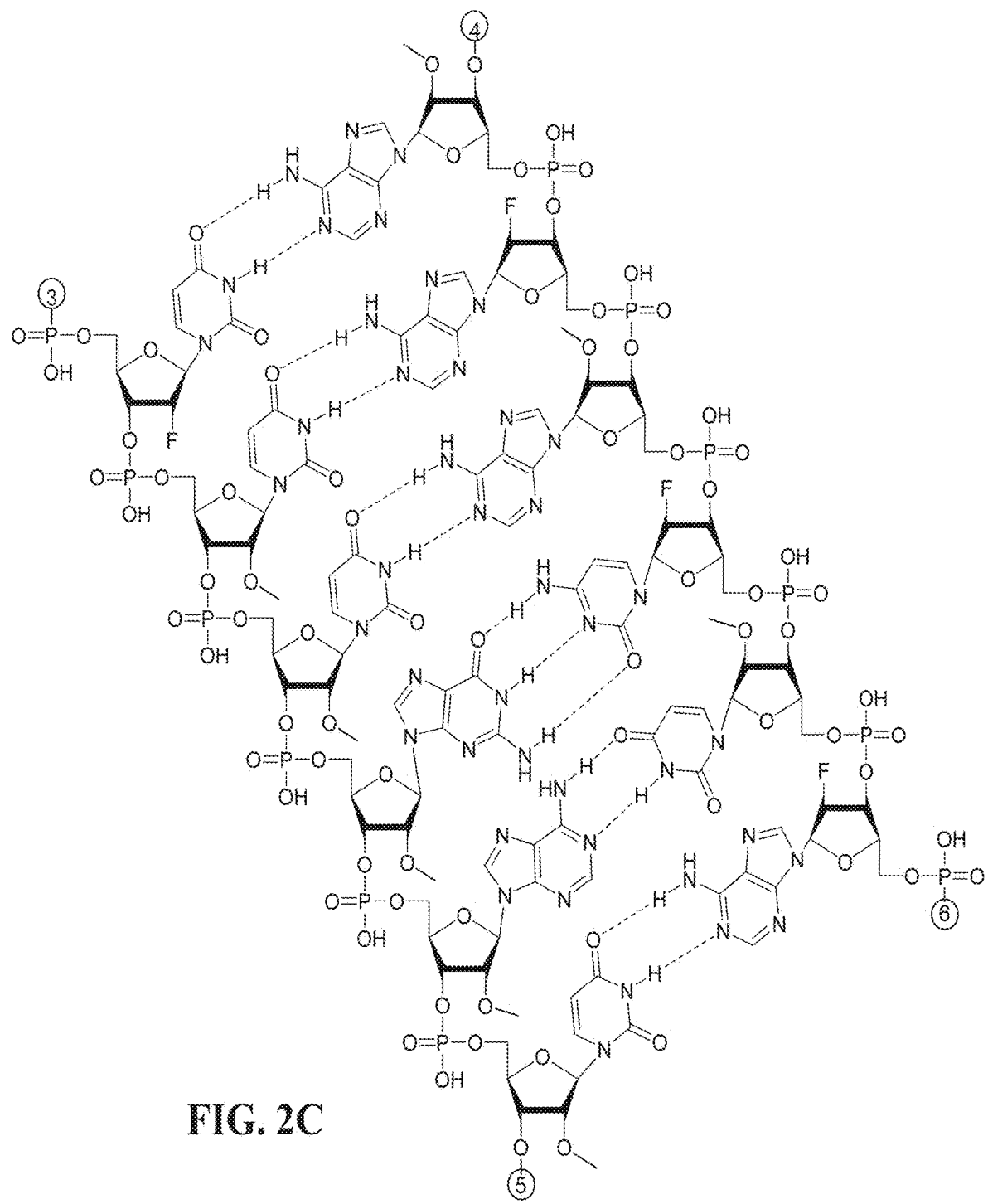
Figure 2D:
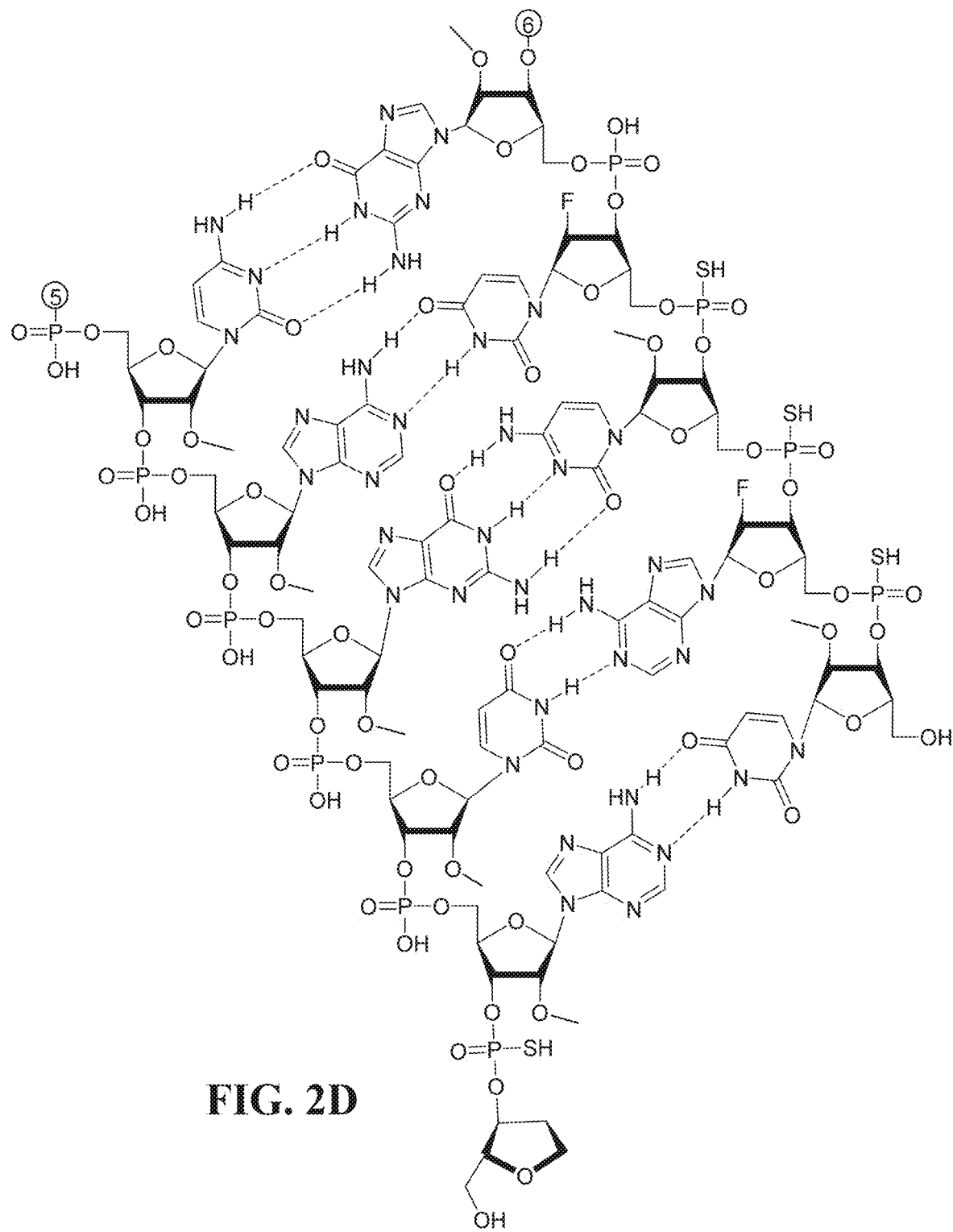
Figure 3A:
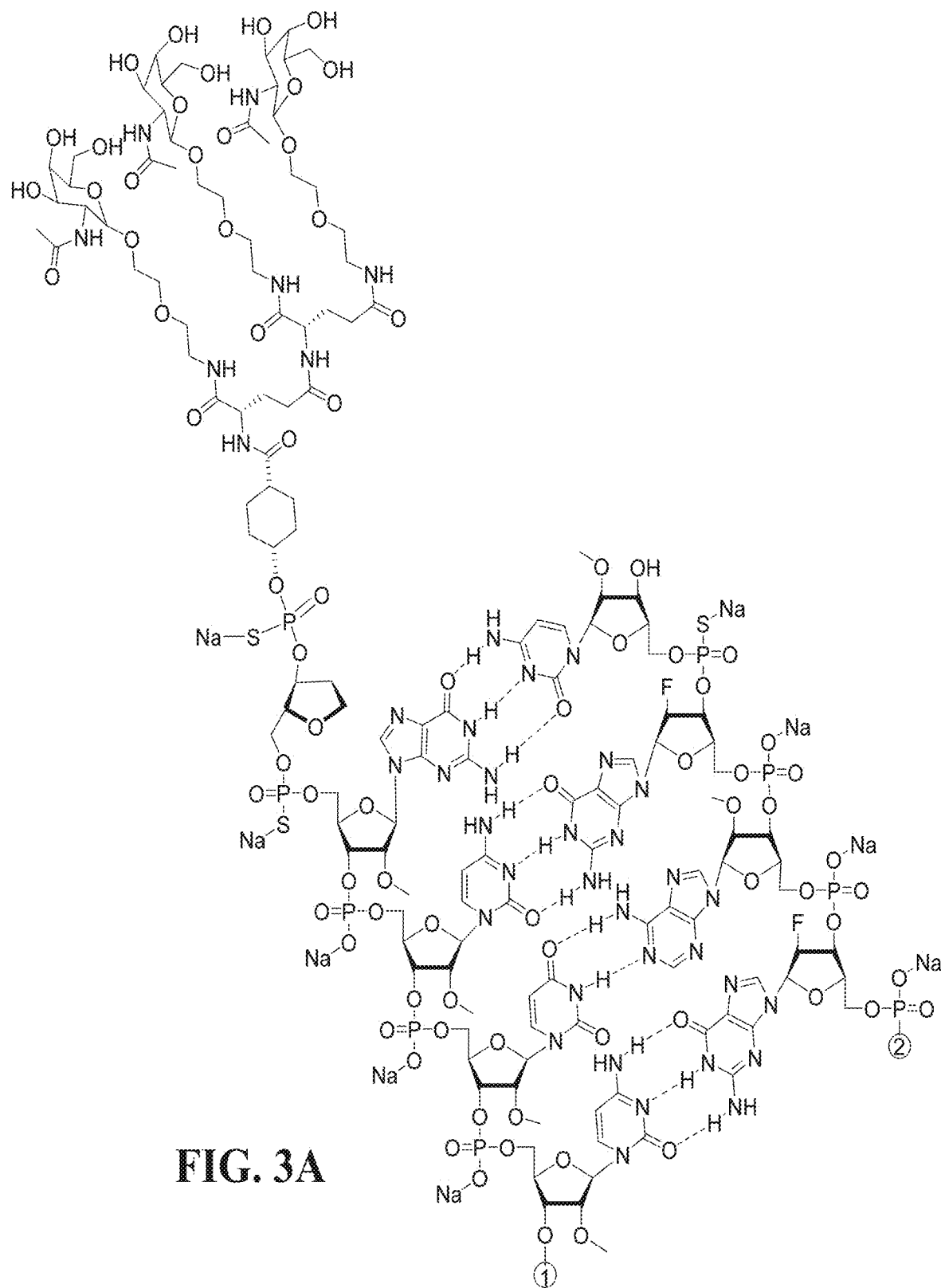
FIG. 3A to 3D. Chemical structure representation of ANGPTL3 RNAi agent AD05775, conjugated to an N-acetyl-galactosamine tridentate ligand having the structure of (NAG37)s (see Table 6) at the 5' terminal end of the sense strand, shown in a sodium salt form.
Figure 3B:
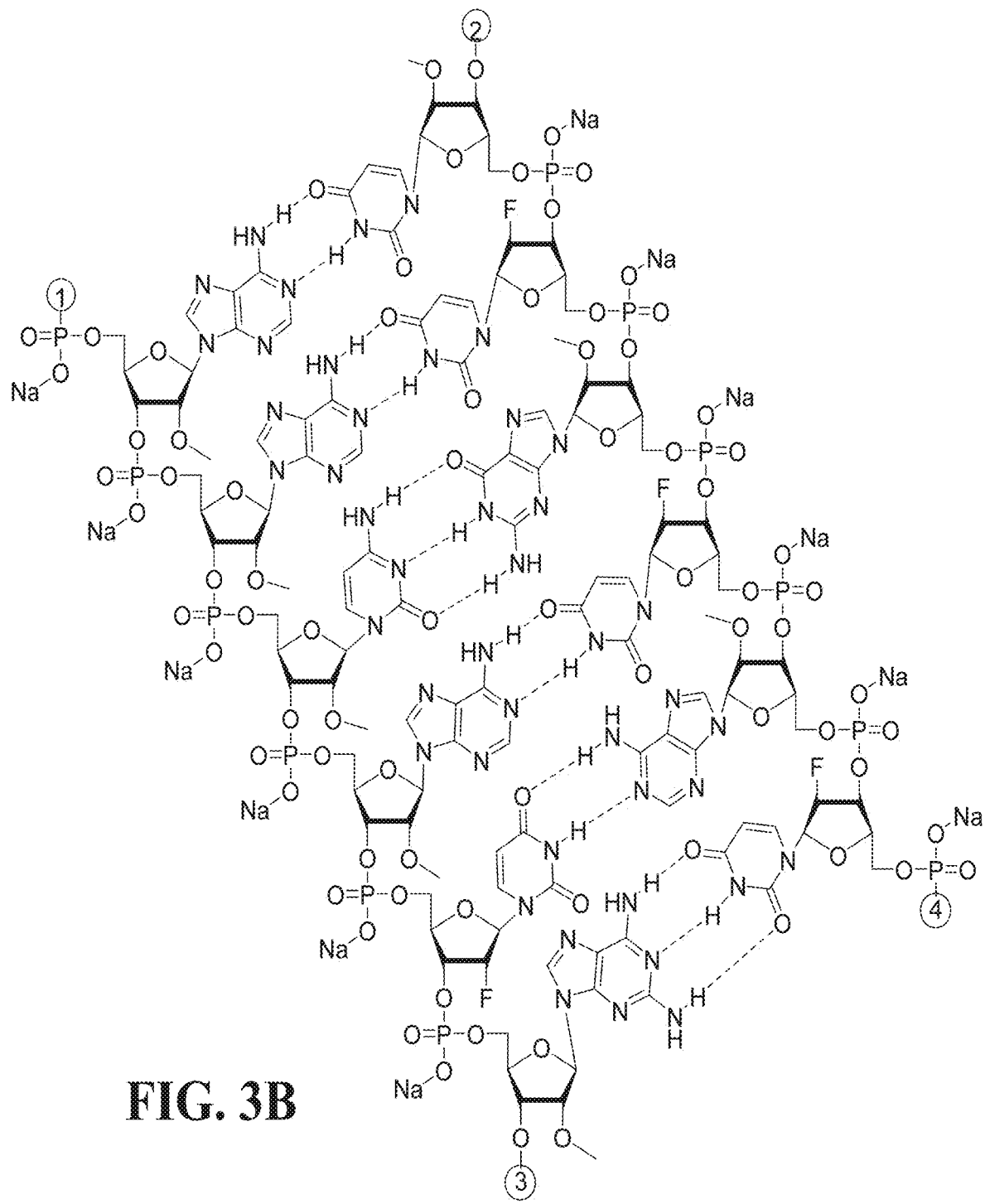
Figure 3C:
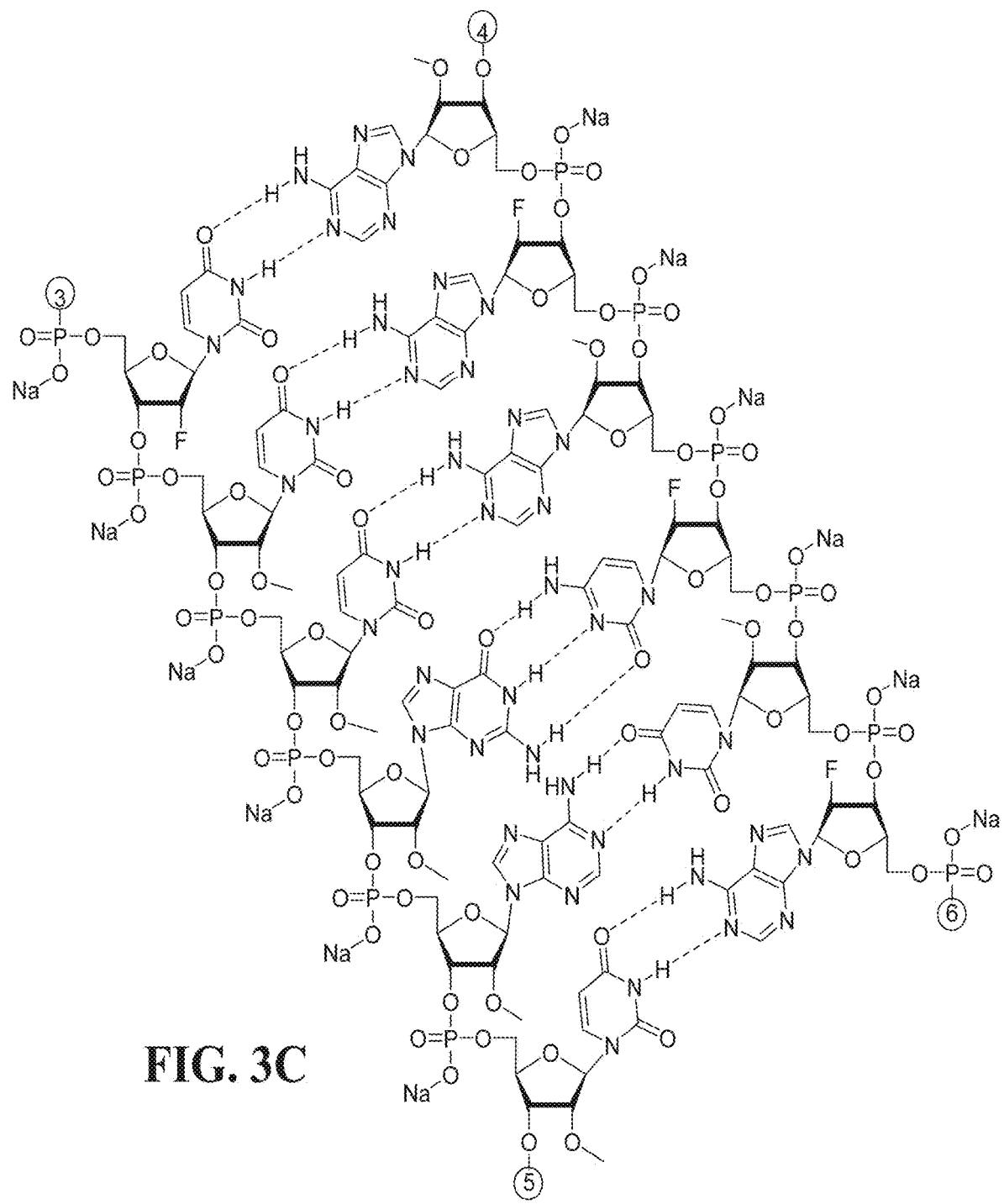
Figure 3D:
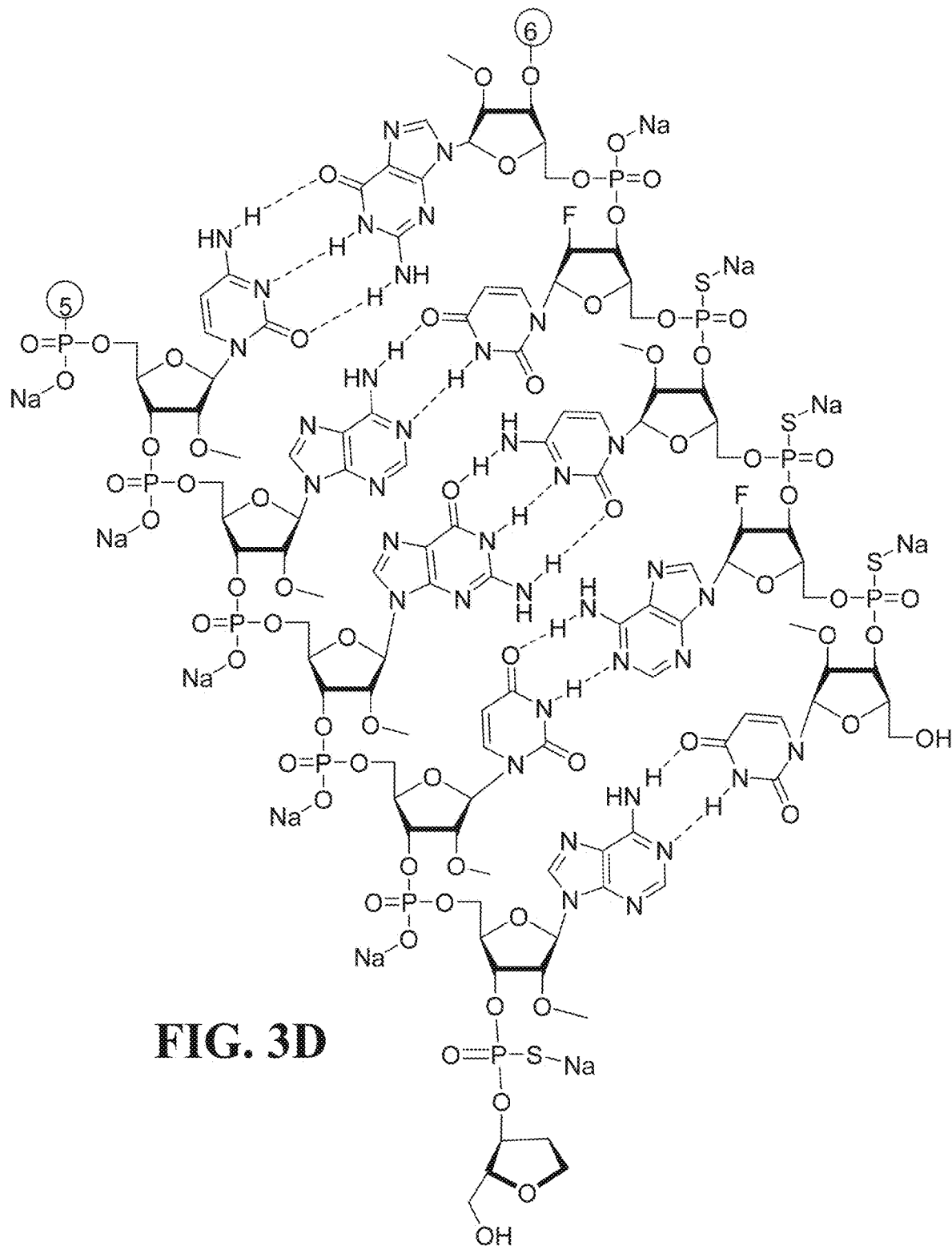
Figure 4A:
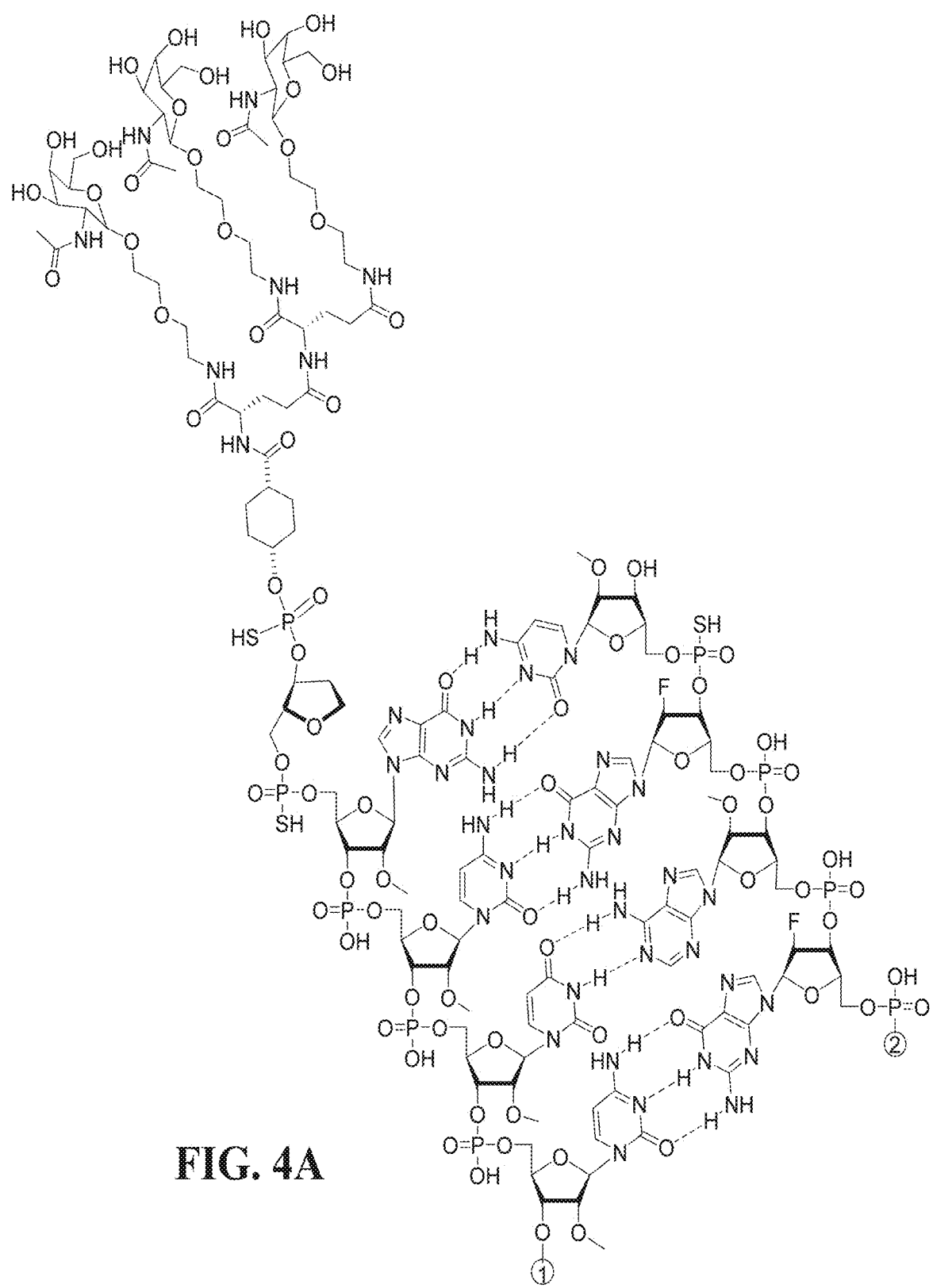
FIG. 4A to 4D. Chemical structure representation of ANGPTL3 RNAi agent AD05775, conjugated to an N-acetyl-galactosamine tridentate ligand having the structure of (NAG37)s (see Table 6) at the 5' terminal end of the sense strand, shown in a free acid form.
Figure 4B:
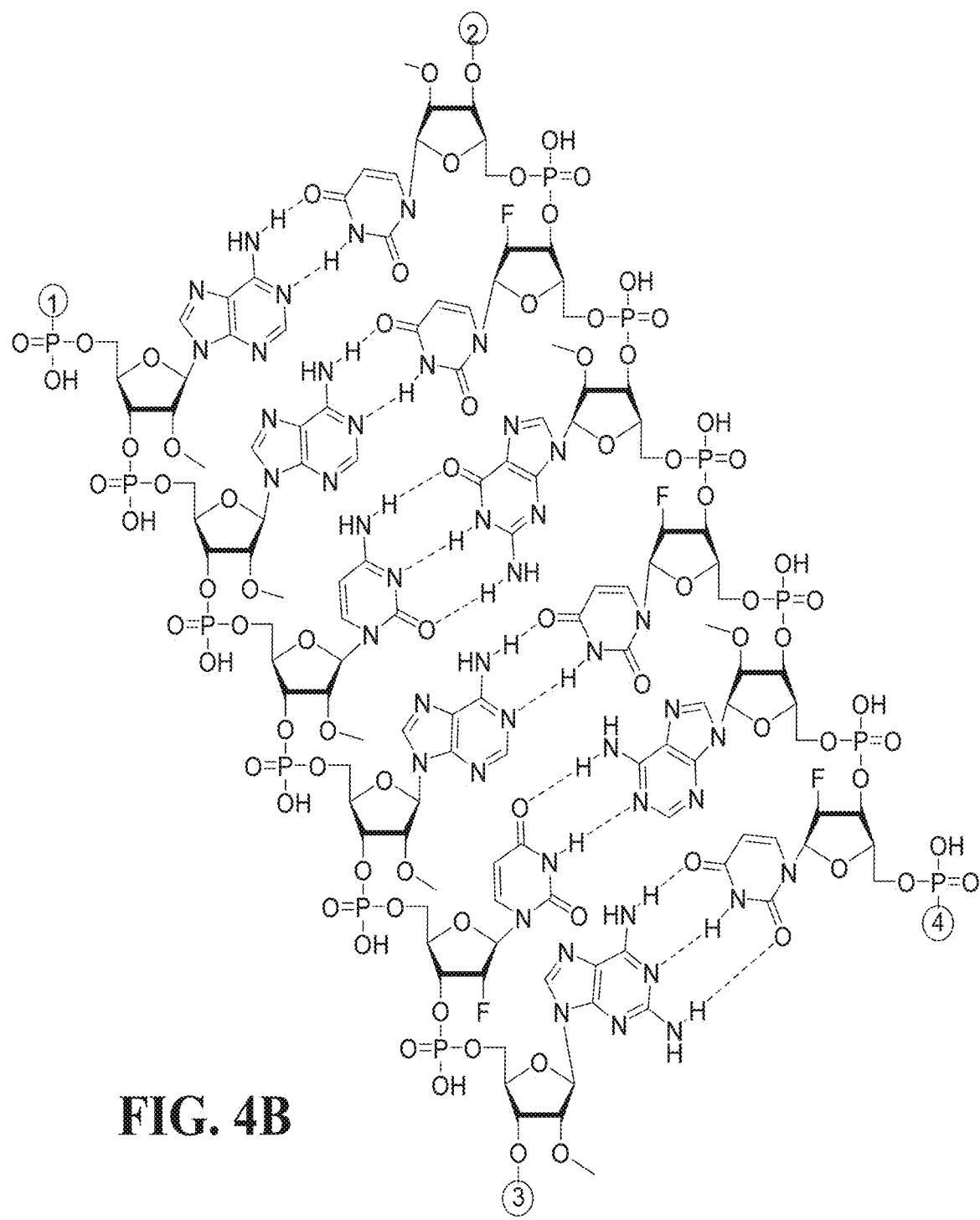
Figure 4C:
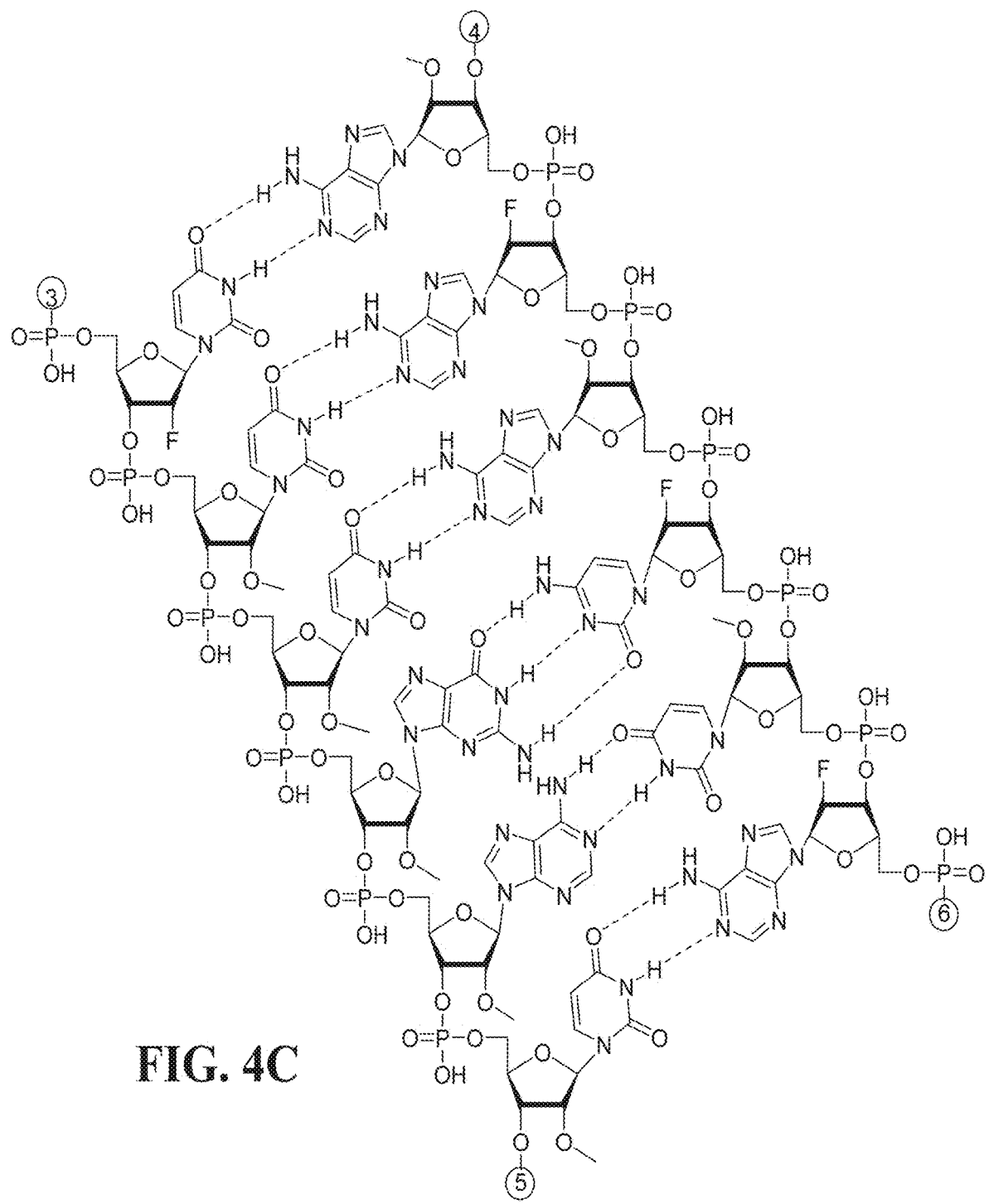
Figure 4D:
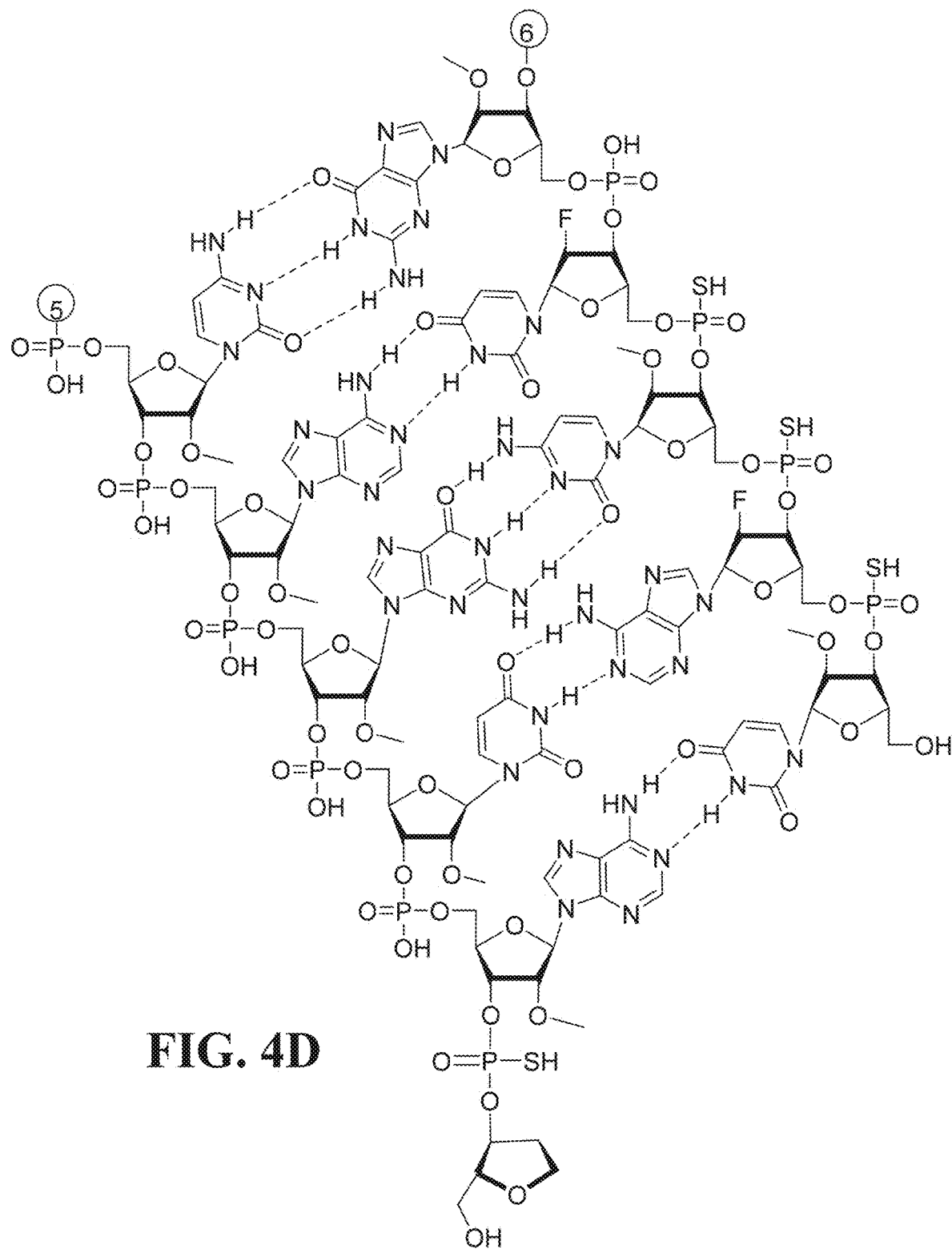
Figure 5A:
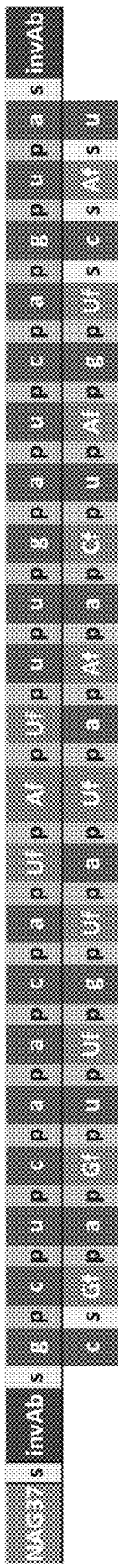
FIG. 5A. Schematic diagram of the modified sense and antisense strands of ANGPTL3 RNAi agent AD05488 (see Tables 3-5), conjugated to an N-acetyl-galactosamine tridentate ligand having the structure of (NAG37)s (see Table 6).
Figure 5B:
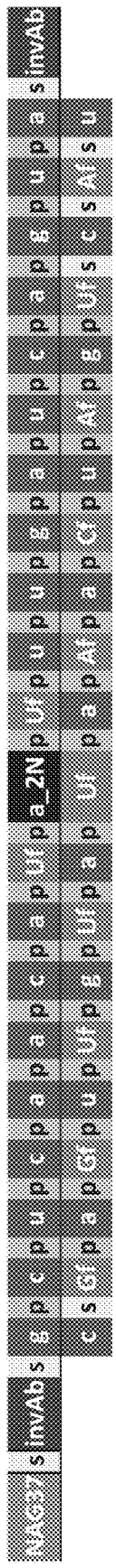

FIG. 5B. Schematic diagram of the modified sense and antisense strands of ANGPTL3 RNAi agent AD05775 (see Tables 3-5), conjugated to an N-acetyl-galactosamine tridentate ligand having the structure of (NAG37)s (see Table 6). FIG. 5B discloses SEQ ID NOs: 2 and 334.

Figure 5C:
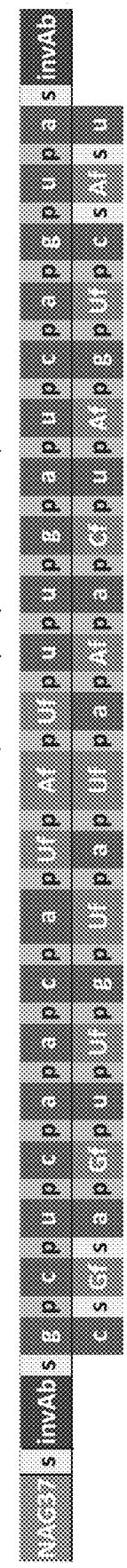

FIG. 5C. Schematic diagram of the modified sense and antisense strands of ANGPTL3 RNAi agent AD05791 (see Tables 3-5), conjugated to an N-acetyl-galactosamine tridentate ligand having the structure of (NAG37)s (see Table 6). FIG. 5C discloses SEQ ID NOs: 4 and 300.

Figure 5D:
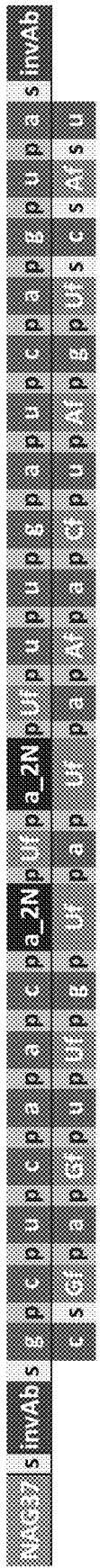

FIG. 5D. Schematic diagram of the modified sense and antisense strands of ANGPTL3 RNAi agent AD05777 (see Tables 3-5), conjugated to an N-acetyl-galactosamine tridentate ligand having the structure of (NAG37)s (see Table 6). FIG. 5D discloses SEQ ID NOs: 2 and 336.

Figure 5E:

FIG. 5E. Schematic diagram of the modified sense and antisense strands of ANGPTL3 RNAi agent AD05743 (see Tables 3-5), conjugated to an N-acetyl-galactosamine tridentate ligand having the structure of (NAG37)s (see Table 6). FIG. 5E discloses SEQ ID NOs: 2 and 326.

Figure 5F:
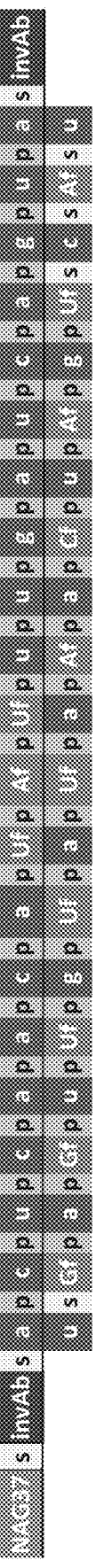

FIG. 5F. Schematic diagram of the modified sense and antisense strands of ANGPTL3 RNAi agent AD05487 (see Tables 3-5), conjugated to an N-acetyl-galactosamine tridentate ligand having the structure of (NAG37)s (see Table 6). FIG. 5F discloses SEQ ID NOs: 5 and 299.

Figure 5G:

FIG. 5G. Schematic diagram of the modified sense and antisense strands of ANGPTL3 RNAi agent AD05307 (see Tables 3-5), conjugated to an N-acetyl-galactosamine tridentate ligand having the structure of (NAG37)s (see Table 6). FIG. 5G discloses SEQ ID NOs: 7 and 278.

Figure 5H:
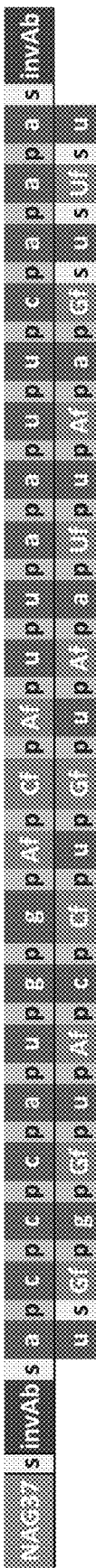

FIG. 5H. Schematic diagram of the modified sense and antisense strands of ANGPTL3 RNAi agent AD05418 (see Tables 3-5), conjugated to an N-acetyl-galactosamine tridentate ligand having the structure of (NAG37)s (see Table 6). FIG. 5H discloses SEQ ID NOs: 9 and 292.

Figure 5I:
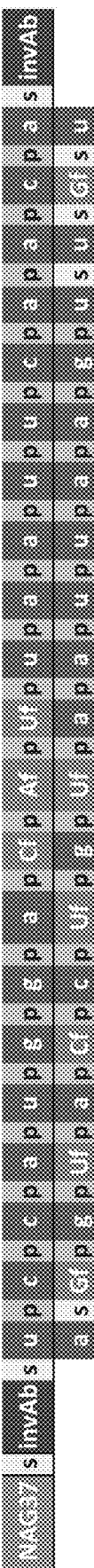

FIG. 5I. Schematic diagram of the modified sense and antisense strands of ANGPTL3 RNAi agent AD05577 (see Tables 3-5), conjugated to an N-acetyl-galactosamine tridentate ligand having the structure of (NAG37)s (see Table 6). FIG. 5I discloses SEQ ID NOs: 11 and 279.

Figure 5J:
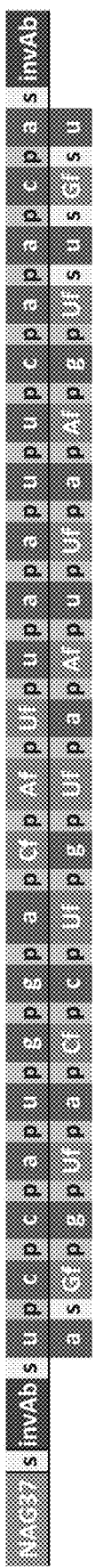

FIG. 5J. Schematic diagram of the modified sense and antisense strands of ANGPTL3 RNAi agent AD05308 (see Tables 3-5), conjugated to an N-acetyl-galactosamine tridentate ligand having the structure of (NAG37)s (see Table 6). FIG. 5J discloses SEQ ID NOs: 13 and 279.

Figure 5K:
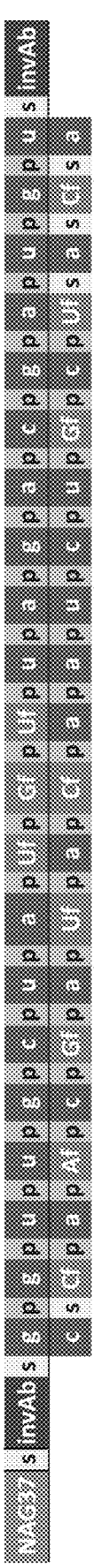

FIG. 5K. Schematic diagram of the modified sense and antisense strands of ANGPTL3 RNAi agent AD05840 (see Tables 3-5), conjugated to an N-acetyl-galactosamine tridentate ligand having the structure of (NAG37)s (see Table 6). FIG. 5K discloses SEQ ID NOs: 15 and 357.

DETAILED DESCRIPTION

RNAi Agents

Described herein are RNAi agents for inhibiting expression of an ANGPTL3 gene (referred to herein as ANGPTL3 RNAi agents or ANGPTL3 RNAi triggers). Each ANGPTL3 RNAi agent comprises a sense strand and an antisense strand. The sense strand and the antisense strand each can be 16 to 30 nucleotides in length. The sense and antisense strands can be either the same length or they can be different lengths. In some embodiments, the sense and antisense strands are each independently 17 to 27 nucleotides in length. In some embodiments, the sense and antisense strands are each independently 17-21 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, 26, or 27 nucleotides in length. In some embodiments, a double-stranded RNAi agent has a duplex length of about 16, 17, 18, 19, 20, 21, 22, 23 or 24 nucleotides.

In some embodiments, the region of perfect, substantial, or partial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

The sense strand and antisense strand each contain a core stretch (also referred to herein as a "core sequence" or a "core stretch sequence") that is 16 to 23 nucleotides in length. An antisense strand core stretch is 1009/o (perfectly) complementary or at least about 85% (substantially) complementary to a nucleotide sequence (sometimes referred to, e.g., as a target sequence) present in the ANGPTL3 mRNA target. A sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence (target sequence) present in the ANGPTL3 mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of nucleotide sequences used in forming ANGPTL3 RNAi agents are provided in Tables 2, 3, and 4. Examples of RNAi agent duplexes, that include the sense strand and antisense strand sequences in Tables 2, 3, and 4, are shown in Table 5.

The ANGPTL3 RNAi agent sense and antisense strands anneal to form a duplex. A sense strand and an antisense strand of an ANGPTL3 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an ANGPTL3 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an ANGPTL3 RNAi agent disclosed herein differs by 0, 1, 2, or 3 nucleotides from any of the antisense strand sequences in Table 2 or Table 3. In some embodiments, the sense strand of an ANGPTL3 RNAi agent disclosed herein differs by 0, 1, 2, or 3 nucleotides from any of the sense strand sequences in Table 2 or Table 4.

The sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the ANGPTL3 mRNA.

The sense strand additional nucleotides, if present, may or may not be identical to the corresponding sequence in the ANGPTL3 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an ANGPTL3 RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, an ANGPTL3 RNAi agent comprises an antisense strand having a 3' extension of 1, 2, 3, 4, 5, or 6 nucleotides in length. In other embodiments, an ANGPTL3 RNAi agent comprises an antisense strand having a 3' extension of 1, 2, or 3 nucleotides in length. In some embodiments, one or more of the antisense strand extension nucleotides comprise uracil or thymidine nucleotides or nucleotides that are complementary to the corresponding ANGPTL3 mRNA sequence.

In some embodiments, the 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See, e.g., U.S. Pat. No. 5,998,203). In some embodiments, Ab or AbAb can be added to the 3' end of the antisense strand.

In some embodiments, the sense strand or the antisense strand may include a "terminal cap," which as used herein is a non-nucleotide compound or other moiety that can be incorporated at one or more termini of a strand of an RNAi agent disclosed herein, and can provide the RNAi agent, in some instances, with certain beneficial properties, such as, for example, protection against exonuclease degradation. In some embodiments, inverted abasic residues (invAb) are added as terminal caps (see Table 6). (See, e.g., F. Czauderna, Nucleic Acids Res., 2003, 31(11), 2705-16). Terminal caps are generally known in the art, and include, for example, inverted abasic residues as well as carbon chains such as a terminal C3, C6, or C12 groups. In some embodiments, a terminal cap is present at either the 5' terminal end, the 3' terminal end, or both the 5' and 3' terminal ends of the sense strand.

In some embodiments, an ANGPTL3 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to nucleotides in the ANGPTL3 mRNA sequence. In some embodiments, the 3' sense strand extension includes or consists of one of the following sequences, but is not limited to: T, UT, TT, UU, UUT, TTT, or TTTT (each listed 5' to 3').

In some embodiments, the 3' end of the sense strand may include additional abasic residues or inverted abasic terminal caps. In some embodiments, UUAb, UAb, or Ab are added to the 3' end of the sense strand.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleobase sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, an ANGPTL3 RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides that correspond to nucleotides in the ANGPTL3 mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand can have a 3' extension and/or a 5' extension.

In some embodiments, the 5' end of the sense strand can include one or more additional abasic residues (e.g., (Ab) or (AbAb)). In some embodiments, one or more inverted abasic residues (invAb) are added to the 5' end of the sense strand. In some embodiments, one or more inverted abasic residues can be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent. In some embodiments, an abasic (deoxyribose) residue can be replaced with a ribitol (abasic ribose) residue.

In some embodiments, the 3' end of the antisense strand core stretch sequence, or the 3' end of the antisense strand sequence, may include an inverted abasic residue (invAb) (see Table 6).

Examples of sequences used in forming ANGPTL3 RNAi agents are provided in Tables 2, 3, and 4. In some embodiments, an ANGPTL3 RNAi agent antisense strand includes a sequence of any of the sequences in Tables 2 or 3. In certain embodiments, an ANGPTL3 RNAi agent antisense strand comprises or consists of any one of the modified sequences in Table 3. In some embodiments, an ANGPTL3 RNAi agent antisense strand includes the sequence of nucleotides (from 5' end→3' end) 1-17, 2-15, 2-17, 1-18, 2-18, 1-19, 2-19, 1-20, 2-20, 1-21, 2-21, 1-22, 2-22, 1-23, 2-23, 1-24, or 2-24 of any of the sequences in Tables 2 or 3. In some embodiments, an ANGPTL3 RNAi agent sense strand includes the sequence of any of the sequences in Tables 2 or 4. In some embodiments, an ANGPTL3 RNAi agent sense strand includes the sequence of nucleotides (from 5' end→3' end) 1-18, 1-19, 1-20, 1-21, 1-22, 1-23, 1-24, 1-25, 1-26, 2-19, 2-20, 2-21, 2-22, 2-23, 2-24, 3-20, 3-21, 3-22, 3-23, 3-24, 4-21, 4-22, 4-23, 4-24, 5-22, 5-23, or 5-24 of any of the sequences in Tables 2 or 4. In certain embodiments, an ANGPTL3 RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

Modified nucleotides, when used in various polynucleotide or oligonucleotide constructs, can preserve activity of the compound in cells while at the same time increasing the serum stability of these compounds, and can also minimize the possibility of activating interferon activity in humans upon administering of the polynucleotide or oligonucleotide construct.

In some embodiments, an ANGPTL3 RNAi agent is prepared or provided as a salt, mixed salt, or a free-acid. In some embodiments, an ANGPTL3 RNAi agent is prepared as a sodium salt. Such forms that are well known in the art are within the scope of the inventions disclosed herein.

Modified Nucleotides

In some embodiments, an ANGPTL3 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn), modified nucleobase-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e., a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (also referred to herein as 2'-fluoro nucleotide, and represented herein as NO, 2'-deoxy nucleotides (represented herein as dN), 2'-methoxyethyl (2'-O-2-methoxylethyl) nucleotides (also referred to herein as 2'-MOE, and represented herein as NM), 2'-amino nucleotides, and 2'-alkyl nucleotides. It is not necessary for all positions in a given compound to be uniformly modified. Conversely, more than one modification can be incorporated in a single ANGPTL3 RNAi agent or even in a single nucleotide thereof. The ANGPTL3 RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxy methyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

Modified Internucleoside Linkages

In some embodiments, one or more nucleotides of an ANGPTL3 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, amino alkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an ANGPTL3 RNAi agent can contain 1, 2, 3, 4, 5, or 6 phosphorothioate linkages, an antisense strand of an ANGPTL3 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an ANGPTL3 RNAi agent can contain 1, 2, 3, or 4 phosphorothioate linkages, an antisense strand of an ANGPTL3 RNAi agent can contain 1, 2, 3, or 4 phosphorothioate linkages, or both the sense strand and the antisense strand independently can contain 1, 2, 3, or 4 phosphorothioate linkages.

In some embodiments, an ANGPTL3 RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, one phosphorothioate internucleoside linkage is at the 5' end of the sense strand, and another phosphorothioate linkage is at the 3' end of the sense strand. In some embodiments, two phosphorothioate internucleoside linkage are located at the 5' end of the sense strand, and another phosphorothioate linkage is at the 3' end of the sense strand. In some embodiments, the sense strand dose not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, an ANGPTL3 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, an ANGPTL3 RNAi agent contains at least three or four phosphorothioate internucleoside linkages in the antisense strand.

In some embodiments, an ANGPTL3 RNAi agent contains one or more modified nucleotides and one or more modified internucleoside linkages. In some embodiments, a 2'-modified nucleoside is combined with modified internucleoside linkage.

ANGPTL3 RNAi Agents

In some embodiments, the ANGPTL3 RNAi agents disclosed herein target an ANGPTL3 gene at or near the positions of the ANGPTL3 gene sequence shown in Table 1. In some embodiments, the antisense strand of an ANGPTL3 RNAi agent disclosed herein includes a core stretch sequence that is fully, substantially, or at least partially complementary to a target ANGPTL3 19-mer sequence disclosed in Table 1.

TABLE 1

ANGPTL3 19-mer mRNA Target Sequences (taken from *homo sapiens* angiopoietin like 3 (ANGPTL3) transcript, GenBank NM_014495.3 (SEQ ID NO: 1))

| SEQ ID No. | ANGPTL3 19-mer Target Sequences (5' → 3') | Corresponding Positions on SEQ ID NO: 1 |
|---|---|---|
| 33 | UCAACAUAUUUGAUCAGUC | 304-322 |
| 34 | CAUGGACAUUAAUUCAACA | 922-940 |
| 35 | CCAUGGACAUUAAUUCAAC | 921-939 |
| 36 | UUGCUAUGUUAGACGAUGU | 190-208 |
| 37 | AAGAUAUACUCCAUAGUGA | 1035-1053 |
| 38 | CAGAGCCAAAAUCAAGAUU | 172-190 |
| 39 | GACAUGGUCUUAAAGACUU | 241-259 |
| 40 | AGCACCAAGAACUACUCCC | 743-761 |
| 41 | GCACCAAGAACUACUCCCU | 744-762 |
| 42 | GAUGGAGAAUUUUGGUUGG | 1008-1026 |
| 43 | AUGGAGAAUUUUGGUUGGG | 1009-1027 |
| 44 | ACUCCAUAGUGAAGCAAUC | 1042-1060 |
| 45 | CACGAAACCAACUAUACGC | 1140-1158 |
| 46 | CUACUUGGGAUCACAAAGC | 1225-1243 |
| 47 | CUUGGGAUCACAAAGCAAA | 1228-1246 |
| 48 | UGUGGAGAAAACAACCUAA | 1302-1320 |
| 49 | UGGAGAAAACAACCUAAAU | 1304-1322 |

In some embodiments, an ANGPTL3 RNAi agent includes an antisense strand wherein position 19 of the antisense strand (5'→3') is capable of forming a base pair with position 1 of a 19-mer target sequence disclosed in Table 1. In some embodiments, an ANGPTL3 RNAi agent includes an antisense strand wherein position 1 of the antisense strand (5'→3') is capable of forming a base pair with position 19 of the 19-mer target sequence disclosed in Table 1.

In some embodiments, an ANGPTL3 RNAi agent includes an antisense strand wherein position 2 of the antisense strand (5'→3') is capable of forming a base pair with position 18 of the 19-mer target sequence disclosed in Table 1. In some embodiments, an ANGPTL3 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the ANGPTL3 gene, or can be non-complementary to the ANGPTL3 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an ANGPTL3 RNAi agent antisense strand comprises the sequence of nucleotides (from 5' end→3' end) 2-18 or 2-19 of any of the antisense strand sequences in Table 2 or Table 3. In some embodiments, an ANGPTL3 RNAi sense strand comprises the sequence of nucleotides (from 5' end→3' end) 1-17, 1-18, or 2-18 of any of the sense strand sequences in Table 2 or Table 4.

In some embodiments, an ANGPTL3 RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

In some embodiments, the ANGPTL3 RNAi agents include core 19-mer nucleotide sequences shown in the following Table 2.

TABLE 2

ANGPTL3 RNAi Agent Antisense Strand and Sense Strand Core Stretch Base Sequences (N = any nucleobase)

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions on SEQ ID NO: 1 |
|---|---|---|---|---|
| 50 | UACUGAUCAAAUAUGUUGA | 130 | UCAACAUAUUUGAUCAGUA | 304-322 |
| 50 | UACUGAUCAAAUAUGUUGA | 131 | UCAACAU(A$^{2N}$)UUUGAUCAGUA | 304-322 |
| 50 | UACUGAUCAAAUAUGUUGA | 132 | UCAAC(A$^{2N}$)U(A$^{2N}$)UUUGAUCAGUA | 304-322 |
| 51 | AACUGAUCAAAUAUGUUGA | 133 | UCAACAUAUUUGAUCAGUU | 304-322 |
| 51 | AACUGAUCAAAUAUGUUGA | 134 | UCAACAU(A$^{2N}$)UUUGAUCAGUU | 304-322 |
| 51 | AACUGAUCAAAUAUGUUGA | 135 | UCAAC(A$^{2N}$)U(A$^{2N}$)UUUGAUCAGUU | 304-322 |
| 52 | GACUGAUCAAAUAUGUUGA | 136 | UCAACAUAUUUGAUCAGUC | 304-322 |

TABLE 2-continued

ANGPTL3 RNAi Agent Antisense Strand and Sense Strand
Core Stretch Base Sequences (N = any nucleobase)

| SEQ ID No. | Antisense Strand Base Sequence (5' → 3') (Shown as an Unmodified Nucleotide Sequence) | SEQ ID No. | Sense Strand Base Sequence (Shown as an Unmodified Nucleotide Sequence) | Corresponding Positions on SEQ ID NO: 1 |
|---|---|---|---|---|
| 52 | GACUGAUCAAAUAUGUUGA | 137 | UCAACAU(A$^{2N}$)UUUGAUCAGUC | 304-322 |
| 52 | GACUGAUCAAAUAUGUUGA | 138 | UCAAC(A$^{2N}$)U(A$^{2N}$)UUUGAUCAGUC | 304-322 |
| 53 | NACUGAUCAAAUAUGUUGA | 139 | UCAACAUAUUUGAUCAGUN | 304-322 |
| 53 | NACUGAUCAAAUAUGUUGA | 140 | UCAACAU(A$^{2N}$)UUUGAUCAGUN | 304-322 |
| 53 | NACUGAUCAAAUAUGUUGA | 141 | UCAAC(A$^{2N}$)U(A$^{2N}$)UUUGAUCAGUN | 304-322 |
| 54 | NACUGAUCAAAUAUGUUGN | 142 | NCAACAUAUUUGAUCAGUN | 304-322 |
| 54 | NACUGAUCAAAUAUGUUGN | 143 | NCAACAU(A$^{2N}$)UUUGAUCAGUN | 304-322 |
| 54 | NACUGAUCAAAUAUGUUGN | 144 | NCAAC(A$^{2N}$)U(A$^{2N}$)UUUGAUCAGUN | 304-322 |
| 55 | UGUUGAAUUAAUGUCCAUG | 145 | CAUGGACAUUAAUUCAACA | 922-940 |
| 56 | AGUUGAAUUAAUGUCCAUG | 146 | CAUGGACAUUAAUUCAACU | 922-940 |
| 57 | NGUUGAAUUAAUGUCCAUG | 147 | CAUGGACAUUAAUUCAACN | 922-940 |
| 58 | NGUUGAAUUAAUGUCCAUN | 148 | NAUGGACAUUAAUUCAACN | 922-940 |
| 59 | GUUGAAUUAAUGUCCAUGG | 149 | CCAUGGACAUUAAUUCAAC | 921-939 |
| 60 | UUUGAAUUAAUGUCCAUGG | 150 | CCAUGGACAUUAAUUCAAA | 921-939 |
| 61 | AUUGAAUUAAUGUCCAUGG | 151 | CCAUGGACAUUAAUUCAAU | 921-939 |
| 62 | NUUGAAUUAAUGUCCAUGG | 152 | CCAUGGACAUUAAUUCAAN | 921-939 |
| 63 | NUUGAAUUAAUGUCCAUGN | 153 | NCAUGGACAUUAAUUCAAN | 921-939 |
| 64 | ACAUCGUCUAACAUAGCAA | 154 | UUGCUAUGUUAGACGAUGU | 190-208 |
| 65 | UCAUCGUCUAACAUAGCAA | 155 | UUGCUAUGUUAGACGAUGA | 190-208 |
| 66 | NCAUCGUCUAACAUAGCAA | 156 | UUGCUAUGUUAGACGAUGN | 190-208 |
| 67 | NCAUCGUCUAACAUAGCAN | 157 | NUGCUAUGUUAGACGAUGN | 190-208 |
| 68 | UCACUAUGGAGUAUAUCUU | 158 | AAGAUAUACUCCAUAGUGA | 1035-1053 |
| 69 | ACACUAUGGAGUAUAUCUU | 159 | AAGAUAUACUCCAUAGUGU | 1035-1053 |
| 70 | NCACUAUGGAGUAUAUCUU | 160 | AAGAUAUACUCCAUAGUGN | 1035-1053 |
| 71 | NCACUAUGGAGUAUAUCUN | 161 | NAGAUAUACUCCAUAGUGN | 1035-1053 |
| 72 | AAUCUUGAUUUUGGCUCUG | 162 | CAGAGCCAAAAUCAAGAUU | 172-190 |
| 73 | UAUCUUGAUUUUGGCUCUG | 163 | CAGAGCCAAAAUCAAGAUA | 172-190 |
| 74 | NAUCUUGAUUUUGGCUCUG | 164 | CAGAGCCAAAAUCAAGAUN | 172-190 |
| 75 | NAUCUUGAUUUUGGCUCUN | 165 | NAGAGCCAAAAUCAAGAUN | 172-190 |
| 76 | AAGUCUUUAAGACCAUGUC | 166 | GACAUGGUCUUAAAGACUU | 241-259 |
| 77 | UAGUCUUUAAGACCAUGUC | 167 | GACAUGGUCUUAAAGACUA | 241-259 |
| 78 | NAGUCUUUAAGACCAUGUC | 168 | GACAUGGUCUUAAAGACUN | 241-259 |
| 79 | NAGUCUUUAAGACCAUGUN | 169 | NACAUGGUCUUAAAGACUN | 241-259 |
| 80 | GGGAGUAGUUCUUGGUGCU | 170 | AGCACCAAGAACUACUCCC | 743-761 |
| 81 | UGGAGUAGUUCUUGGUGCU | 171 | AGCACCAAGAACUACUCCA | 743-761 |
| 82 | AGGAGUAGUUCUUGGUGCU | 172 | AGCACCAAGAACUACUCCU | 743-761 |

TABLE 2-continued

ANGPTL3 RNAi Agent Antisense Strand and Sense Strand
Core Stretch Base Sequences (N = any nucleobase)

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions on SEQ ID NO: 1 |
|---|---|---|---|---|
| 83 | NGGAGUAGUUCUUGGUGCU | 173 | AGCACCAAGAACUACUCCN | 743-761 |
| 84 | NGGAGUAGUUCUUGGUGCN | 174 | NGCACCAAGAACUACUCCN | 743-761 |
| 85 | AGGGAGUAGUUCUUGGUGC | 175 | GCACCAAGAACUACUCCCU | 744-762 |
| 86 | UGGGAGUAGUUCUUGGUGC | 176 | GCACCAAGAACUACUCCCA | 744-762 |
| 87 | NGGGAGUAGUUCUUGGUGC | 177 | GCACCAAGAACUACUCCCN | 744-762 |
| 88 | NGGGAGUAGUUCUUGGUGN | 178 | NCACCAAGAACUACUCCCN | 744-762 |
| 89 | AGAGAGUAGUUCUUGGUGC | 179 | GCACCAAGAACUACUCUCU | 744-762 |
| 90 | UGAGAGUAGUUCUUGGUGC | 180 | GCACCAAGAACUACUCUCA | 744-762 |
| 91 | NGAGAGUAGUUCUUGGUGC | 181 | GCACCAAGAACUACUCUCN | 744-762 |
| 92 | NGAGAGUAGUUCUUGGUGN | 182 | NCACCAAGAACUACUCUCN | 744-762 |
| 93 | CCAACCAAAAUUCUCCAUC | 183 | GAUGGAGAAUUUUGGUUGG | 1008-1026 |
| 94 | UCAACCAAAAUUCUCCAUC | 184 | GAUGGAGAAUUUUGGUUGA | 1008-1026 |
| 95 | ACAACCAAAAUUCUCCAUC | 185 | GAUGGAGAAUUUUGGUUGU | 1008-1026 |
| 96 | NCAACCAAAAUUCUCCAUC | 186 | GAUGGAGAAUUUUGGUUGN | 1008-1026 |
| 97 | NCAACCAAAAUUCUCCAUN | 187 | NAUGGAGAAUUUUGGUUGN | 1008-1026 |
| 98 | CCCAACCAAAAUUCUCCAU | 188 | AUGGAGAAUUUUGGUUGGG | 1009-1027 |
| 99 | UCCAACCAAAAUUCUCCAU | 189 | AUGGAGAAUUUUGGUUGGA | 1009-1027 |
| 100 | ACCAACCAAAAUUCUCCAU | 190 | AUGGAGAAUUUUGGUUGGU | 1009-1027 |
| 101 | NCCAACCAAAAUUCUCCAU | 191 | AUGGAGAAUUUUGGUUGGN | 1009-1027 |
| 102 | NCCAACCAAAAUUCUCCAN | 192 | NUGGAGAAUUUUGGUUGGN | 1009-1027 |
| 103 | UAUUGCUUCACUAUGGAGU | 193 | ACUCCAUAGUGAAGCAAUA | 1042-1060 |
| 104 | AAUUGCUUCACUAUGGAGU | 194 | ACUCCAUAGUGAAGCAAUU | 1042-1060 |
| 105 | GAUUGCUUCACUAUGGAGU | 195 | ACUCCAUAGUGAAGCAAUC | 1042-1060 |
| 106 | NAUUGCUUCACUAUGGAGU | 196 | ACUCCAUAGUGAAGCAAUN | 1042-1060 |
| 107 | NAUUGCUUCACUAUGGAGN | 197 | ACUCCAUAGUGAAGCAAUN | 1042-1060 |
| 108 | UCGUAUAGUUGGUUUCGUG | 198 | CACGAAACCAACUAUACGA | 1140-1158 |
| 109 | ACGUAUAGUUGGUUUCGUG | 199 | CACGAAACCAACUAUACGU | 1140-1158 |
| 110 | GCGUAUAGUUGGUUUCGUG | 200 | CACGAAACCAACUAUACGC | 1140-1158 |
| 111 | NCGUAUAGUUGGUUUCGUG | 201 | CACGAAACCAACUAUACGN | 1140-1158 |
| 112 | NCGUAUAGUUGGUUUCGUN | 202 | NACGAAACCAACUAUACGN | 1140-1158 |
| 113 | UCUUUGUGAUCCCAAGUAG | 203 | CUACUUGGGAUCACAAAGA | 1225-1243 |
| 114 | ACUUUGUGAUCCCAAGUAG | 204 | CUACUUGGGAUCACAAAGU | 1225-1243 |
| 115 | GCUUUGUGAUCCCAAGUAG | 205 | CUACUUGGGAUCACAAAGC | 1225-1243 |
| 116 | NCUUUGUGAUCCCAAGUAG | 206 | CUACUUGGGAUCACAAAGN | 1225-1243 |
| 117 | NCUUUGUGAUCCCAAGUAN | 207 | NUACUUGGGAUCACAAAGN | 1225-1243 |
| 118 | UUUGCUUUGUGAUCCCAAG | 208 | CUUGGGAUCACAAAGCAAA | 1228-1246 |

TABLE 2-continued

ANGPTL3 RNAi Agent Antisense Strand and Sense Strand
Core Stretch Base Sequences (N = any nucleobase)

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions on SEQ ID NO: 1 |
|---|---|---|---|---|
| 119 | AUUGCUUUGUGAUCCCAAG | 209 | CUUGGGAUCACAAAGCAAU | 1228-1246 |
| 120 | NUUGCUUUGUGAUCCCAAG | 210 | CUUGGGAUCACAAAGCAAN | 1228-1246 |
| 121 | NUUGCUUUGUGAUCCCAAN | 211 | NUUGGGAUCACAAAGCAAN | 1228-1246 |
| 122 | UUAGGUUGUUUUCUCCACA | 212 | UGUGGAGAAAACAACCUAA | 1302-1320 |
| 123 | AUAGGUUGUUUUCUCCACA | 213 | UGUGGAGAAAACAACCUAU | 1302-1320 |
| 124 | NUAGGUUGUUUUCUCCACA | 214 | UGUGGAGAAAACAACCUAN | 1302-1320 |
| 125 | NUAGGUUGUUUUCUCCACN | 215 | NGUGGAGAAAACAACCUAN | 1302-1320 |
| 126 | AUUUAGGUUGUUUUCUCCA | 216 | UGGAGAAAACAACCUAAAU | 1304-1322 |
| 127 | UUUUAGGUUGUUUUCUCCA | 217 | UGGAGAAAACAACCUAAAA | 1304-1322 |
| 128 | NUUUAGGUUGUUUUCUCCA | 218 | UGGAGAAAACAACCUAAAN | 1304-1322 |
| 129 | NUUUAGGUUGUUUUCUCCN | 219 | NGGAGAAAACAACCUAAAN | 1304-1322 |

($A^{2N}$) = 2-aminoadenine nucleotide

The ANGPTL3 RNAi agent sense strands and antisense strands that comprise or consist of the sequences in Table 2 can be modified nucleotides or unmodified nucleotides. In some embodiments, the ANGPTL3 RNAi agents having the sense and antisense strand sequences that comprise or consist of the sequences in Table 2 are all or substantially all modified nucleotides.

In some embodiments, the antisense strand of an ANGPTL3 RNAi agent disclosed herein differs by 0, 1, 2, or 3 nucleotides from any of the antisense strand sequences in Table 2. In some embodiments, the sense strand of an ANGPTL3 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified ANGPTL3 RNAi agent antisense strands, as well as their underlying unmodified nucleobase sequences, are provided in Table 3. Certain modified ANGPTL3 RNAi agent sense strands, as well as their underlying unmodified nucleobase sequences, are provided in Table 4. In forming ANGPTL3 RNAi agents, each of the nucleotides in each of the underlying base sequences listed in Tables 3 and 4, as well as in Table 2, above, can be a modified nucleotide.

The ANGPTL3 RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, an ANGPTL3 RNAi agent antisense strand comprises a nucleotide sequence of any of the sequences in Table 2 or Table 3.

In some embodiments, an ANGPTL3 RNAi agent comprises or consists of a duplex having the nucleobase sequences of the sense strand and the antisense strand of any of the sequences in Table 2, Table 3 or Table 4.

Examples of antisense strands containing modified nucleotides are provided in Table 3. Examples of sense strands containing modified nucleotides are provided in Table 4.

As used in Tables 3 and 4, the following notations are used to indicate modified nucleotides, targeting groups, and linking groups:
A=adenosine-3'-phosphate;
C=cytidine-3'-phosphate;
G=guanosine-3'-phosphate;
U=uridine-3'-phosphate
I=inosine-3'-phosphate
n=any 2'-OMe modified nucleotide
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate u=2'-O-methyluridine-3'-phosphate
us=2'-O-methyluridine-3'-phosphorothioate
i=2'-O-methylinosine-3'-phosphate
is =2'-O-methylinosine-3'-phosphorothioate
Nf=any 2'-fluoro modified nucleotide
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dA=2'-deoxyadenosine-3'-phosphate
dAs=2'-deoxyadenosine-3'-phosphorothioate
dC=2'-deoxycytidine-3'-phosphate
dCs=2'-deoxycytidine-3'-phosphorothioate
dG=2'-deoxyguanosine-3'-phosphate
dGs=2'-deoxyguanosine-3'-phosphorothioate
dT=2'-deoxythymidine-3'-phosphate
dTs=2'-deoxythymidine-3'-phosphorothioate
dU=2'-deoxyuridine-3'-phosphate
dUs=2'-deoxyuridine-3'-phosphorothioate
$N_{UNA}$=2',3'-seco nucleotide mimics (unlocked nucleobase analogs)-3'-Phosphate
$N_{UNA}$s=2',3'-seco nucleotide mimics (unlocked nucleobase analogs)-3'-phosphorothioate
$A_{UNA}$=2',3'-seco-adenosine-3'-phosphate
$A_{UNA}$S=2',3'-seco-adenosine-3'-phosphorothioate
$C_{UNA}$=2',3'-seco-cytidine-3'-phosphate
$C_{UNA}$s=2',3'-seco-cytidine-3'-phosphorothioate
$G_{UNA}$=2',3'-seco-guanosine-3'-phosphate
$G_{UNA}$s=2',3'-seco-guanosine-3'-phosphorothioate
$U_{UNA}$=2',3'-seco-uridine-3'-phosphate
$U_{UNA}$s=2',3'-seco-uridine-3'-phosphorothioate
a_2N=see Table 6
a_2Ns=see Table 6
pu_2N=see Table 6
pu_2Ns=see Table 6
$N_{LNA}$=locked nucleotide
$N_{fANA}$=2'-F-Arabino nucleotide
NM=2'-O-methoxyethyl nucleotide
AM=2'-O-methoxyethyladenosine-3'-phosphate
AMs=2'-O-methoxyethyladenosine-3'-phosphorothioate
GM=2'-O-methoxyethylguanosine-3'-phosphate
GMs=2'-O-methoxyethylguanosine-3'-phosphorothioate
TM=2'-O-methoxyethylthymidine-3'-phosphate
TMs=2'-O-methoxyethylthymidine-3'-phosphorothioate
mCM=see Table 6
mCMs=see Table 6
R=ribitol
(invdN)=any inverted deoxyribonucleotide (3'-3' linked nucleotide)
(invAb)=inverted (3'-3' linked) abasic deoxyribonucleotide, see Table 6
(invAb)s=inverted (3'-3' linked) abasic deoxyribonucleotide-5'-phosphorothioate, see Table 6
(invn)=any inverted 2'-OMe nucleotide (3'-3' linked nucleotide)
s=phosphorothioate linkage
sp=see Table 6
D2u=see Table 6
pD2u=see Table 6
vpdN=vinyl phosphonate deoxyribonucleotide
(5Me-Nf)=5'-Me, 2'-fluoro nucleotide
cPrp=cyclopropyl phosphonate, see Table 6
epTcPr=see Table 6
epTM=see Table 6

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 5A through 5K showing all internucleoside linkages). Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Moreover, as the person of ordinary skill would readily understand and appreciate, while the phosphorothioate chemical structures depicted herein typically show the anion on the sulfur atom, the inventions disclosed herein encompass all phosphorothioate tautomers and/or diastereomers (e.g., where the sulfur atom has a double-bond and the anion is on an oxygen atom). Unless expressly indicated otherwise herein, such understandings of the person of ordinary skill in the art are used when describing the ANGPTL3 RNAi agents and compositions of ANGPTL3 RNAi agents disclosed herein.

Certain examples of targeting groups and linking groups used with the ANGPTL3 RNAi agents disclosed herein are provided below in Table 6. More specifically, targeting groups and linking groups include the following, for which their chemical structures are provided below in Table 6: (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed herein, as well as other targeting or linking groups, conjugated to the 5' and/or 3' end of the sequence.

TABLE 3

ANGPTL3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM06999-AS | usUfsusGfaAfuUfaAfuGfuCfcAfuGfgAfsc | 220 | UUUGAAUUAAUGUCCAUGGAC | 363 |
| AM07001-AS | usUfsusGfaAfuUfaAfuGfuCfcAfuGfggsc | 7 | UUUGAAUUAAUGUCCAUGGGC | 8 |

TABLE 3-continued

ANGPTL3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM07003-AS | usGfsusUfgAfaUfaAfaUfgUfcCfaUfgGfsa | 13 | UGUUGAAUUAAUGUCCAUGGA | 12 |
| AM07005-AS | usGfsusUfgAfaUfaAfaUfgUfcCfaUfgGfsc | 221 | UGUUGAAUUAAUGUCCAUGGC | 364 |
| AM07007-AS | usUfsasGfgUfuGfuUfuUfcUfcCfaCfaCfsu | 222 | UUAGGUUGUUUUCUCCACACU | 365 |
| AM07009-AS | usUfsasGfgUfuGfuUfuUfcUfcCfaCfaCfsc | 223 | UUAGGUUGUUUUCUCCACACC | 366 |
| AM07011-AS | usUfsusUfaGfgUfuGfuUfuUfcUfcCfaCfsc | 224 | UUUUAGGUUGUUUUCUCCACC | 367 |
| AM07061-AS | usGfsgsAfgUfaguucUfuGfgUfgCfuCfsu | 225 | UGGAGUAGUUCUUGGUGCUCU | 368 |
| AM07062-AS | usGfsgsAfgUfaguucUfuGfgUfgCfuCfsc | 226 | UGGAGUAGUUCUUGGUGCUCC | 369 |
| AM07063-AS | asGfsgsGfaGfuaguuCfuUfgGfuGfcUfsc | 227 | AGGGAGUAGUUCUUGGUGCUC | 370 |
| AM07148-AS | usUfsusGfaAfuUfaAfuGfuCfcAfuGfgAfsg | 228 | UUUGAAUUAAUGUCCAUGGAG | 371 |
| AM07149-AS | usUfsusGfaAfU$_{UNA}$UfaAfuGfuCfcAfuGfgAfsg | 229 | UUUGAAUUAAUGUCCAUGGAG | 371 |
| AM07155-AS | usUfsusGfaAfuUfaAfuGfuCfcAfuGfgCfsg | 230 | UUUGAAUUAAUGUCCAUGGCG | 372 |
| AM07157-AS | usUfsusGfaAfuUfaAfuGfuCfcAfuGfgGfsg | 231 | UUUGAAUUAAUGUCCAUGGGG | 373 |
| AM07159-AS | usUfsusGfaAfuUfaAfuGfuCfcAfuGfgGfsu | 9 | UUUGAAUUAAUGUCCAUGGGU | 10 |
| AM07161-AS | usGfsusUfgAfaUfaAfuGfuCfcAfuGfgGfsg | 232 | UGUUGAAUUAAUGUCCAUGGG | 374 |
| AM07163-AS | usGfsusUfgAfaUfaAfuGfuCfcAfuGfgGfsu | 233 | UGUUGAAUUAAUGUCCAUGGU | 375 |
| AM07164-AS | usGfsusUfgAfA$_{UNA}$UfuAfaUfgUfcCfaUfgGfsu | 234 | UGUUGAAUUAAUGUCCAUGGU | 375 |
| AM07233-AS | usAfscsUfgAfuCfaAfaUfaUfgUfuGfaGfsu | 5 | UACUGAUCAAAUAUGUUGAGU | 6 |
| AM07235-AS | usAfscsUfgAfuCfaAfaUfaUfgUfuGfaGfsc | 2 | UACUGAUCAAAUAUGUUGAGC | 3 |
| AM07237-AS | asAfsusCfuUfgAfuUfuUfgGfcUfcUfgGfsa | 235 | AAUCUUGAUUUUGGCUCUGGA | 376 |
| AM07239-AS | asAfsusCfuUfgAfuUfuUfgGfcUfcUfgGfsu | 236 | AAUCUUGAUUUUGGCUCUGGU | 377 |
| AM07241-AS | usCfsasAfcCfaAfaAfuUfcUfcCfaUfcAfsc | 237 | UCAACCAAAAUUCUCCAUCAC | 378 |
| AM07243-AS | usCfsasAfcCfaAfaAfuUfcUfcCfaUfcGfsc | 238 | UCAACCAAAAUUCUCCAUCGC | 379 |
| AM07245-AS | usCfscsAfaCfcAfaAfaUfuCfuCfcAfuCfsa | 239 | UCCAACCAAAAUUCUCCAUCA | 380 |
| AM07347-AS | usGfsusUfgAfauuaaUfgUfcCfaUfgGfsa | 240 | UGUUGAAUUAAUGUCCAUGGA | 12 |
| AM07348-AS | usGfsusugAfauuaaUfgUfcCfaUfgGfsa | 241 | UGUUGAAUUAAUGUCCAUGGA | 12 |
| AM07349-AS | usGfsusUfgaauuaaUfgUfcCfaUfgGfsa | 242 | UGUUGAAUUAAUGUCCAUGGA | 12 |
| AM07350-AS | usGfsusugaauuaaUfgUfcCfaUfgGfsa | 11 | UGUUGAAUUAAUGUCCAUGGA | 12 |
| AM07351-AS | usGfsusugAfauuAfaUfgUfcCfauggsa | 243 | UGUUGAAUUAAUGUCCAUGGA | 12 |
| AM07352-AS | usGfsusUfgAfaUfaAfaUfgUfccauggsa | 244 | UGUUGAAUUAAUGUCCAUGGA | 12 |
| AM07356-AS | usGfsusugAfauuaaaugUfcCfauggsa | 245 | UGUUGAAUUAAUGUCCAUGGA | 12 |
| AM07357-AS | usGfsusugaauuaaUfgUfcCfaUfgGfsg | 246 | UGUUGAAUUAAUGUCCAUGGG | 12 |
| AM07454-AS | asAfscsUfgAfuCfaAfaUfaUfgUfuGfaGfsc | 247 | AACUGAUCAAAUAUGUUGAGC | 382 |
| AM07456-AS | D2usAfscsUfgAfuCfaAfaUfaUfgUfuGfaGfsc | 248 | UACUGAUCAAAUAUGUUGAGC | 3 |
| AM07457-AS | pD2usAfscsUfgAfuCfaAfaUfaUfgUfuGfaGfsc | 249 | UACUGAUCAAAUAUGUUGAGC | 3 |
| AM07458-AS | pusAfscsUfgAfuCfaAfaUfaUfgUfuGfaGfsc | 250 | UACUGAUCAAAUAUGUUGAGC | 3 |
| AM07461-AS | usAfscsUfgAfuCfaAfaUfaUfgUfuGfaGfsg | 251 | UACUGAUCAAAUAUGUUGAGG | 385 |

TABLE 3-continued

ANGPTL3 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| AM07463-AS | usAfscsUfgAfuCfaAfaUfaUfgUfuGfgGfsc | 252 | UACUGAUCAAAUAUGUUGGGC | 386 |
| AM07465-AS | usAfscsUfgAfuCfaAfaUfaUfgUfuGfcGfsc | 253 | UACUGAUCAAAUAUGUUGCGC | 387 |
| AM07467-AS | usAfscsUfgAfuCfaAfaUfaUfgUfuGfgGfsu | 254 | UACUGAUCAAAUAUGUUGGGU | 388 |
| AM07469-AS | usAfscsUfgAfuCfaAfaUfaUfgUfuGfcGfsu | 255 | UACUGAUCAAAUAUGUUGCGU | 389 |
| AM07505-AS | usUfsTMsGfaAfuUfaAfuGfuCfcAfuGfgGfsu | 256 | UUTGAAUUAAUGUCCAUGGGU | 390 |
| AM07506-AS | usUfsusGfAMAfuUfaAfuGfuCfcAfuGfgGfsu | 257 | UUUGAAUUAAUGUCCAUGGGU | 10 |
| AM07507-AS | usUfsusGfaAfTMUfaAfuGfuCfcAfuGfgGfsu | 258 | UUUGAATUAAUGUCCAUGGGU | 392 |
| AM07508-AS | usUfsTMsGfAMAfuUfaAfuGfuCfcAfuGfgGfsu | 259 | UUTGAAUUAAUGUCCAUGGGU | 390 |
| AM07581-AS | usAfscsugaucaaaUfaUfgUfuGfaGfsc | 260 | UACUGAUCAAAUAUGUUGAGC | 3 |
| AM07583-AS | usascsugaucaaaUfaUfgUfuGfaGfsc | 261 | UACUGAUCAAAUAUGUUGAGC | 3 |
| AM07588-AS | usAfscsugaucaaauaUfgUfuGfaGfsc | 262 | UACUGAUCAAAUAUGUUGAGC | 3 |
| AM07589-AS | usAfscsUfgAfuCfaAfiUfaUfgUfuGfaGfsc | 263 | UACUGAUCAAIUAUGUUGAGC | 393 |
| AM07623-AS | usAfscsUfgAfuCfaAfaUfaUfgUfuGfasGfsc | 264 | UACUGAUCAAAUAUGUUGAGC | 3 |
| AM07624-AS | usAfscUfgAfuCfaAfaUfaUfgUfuGfasGfsc | 265 | UACUGAUCAAAUAUGUUGAGC | 3 |
| AM07634-AS | usUfsusgaauuaauGfuCfcAfuGfgGfsu | 266 | UUUGAAUUAAUGUCCAUGGGU | 10 |
| AM07660-AS | asAfsgsUfcUfuuaagAfcCfaUfgUfcCfsc | 267 | AAGUCUUUAAGACCAUGUCCC | 394 |
| AM07662-AS | usAfsusUfgCfuucacUfaUfgGfaGfuAfsg | 268 | UAUUGCUUCACUAUGGAGUAG | 395 |
| AM07664-AS | usUfsusGfcUfuugugAfuCfcCfaAfgUfsc | 269 | UUUGCUUUGUGAUCCCAAGUC | 396 |
| AM07681-AS | asCfsasUfcGfucuaaCfaUfaGfcAfaCfsc | 14 | ACAUCGUCUAACAUAGCAACC | 15 |
| AM07683-AS | usCfsasCfuAfuggagUfaUfaUfcUfuCfsc | 270 | UCACUAUGGAGUAUAUCUUCC | 397 |
| AM07685-AS | usCfsgsUfaUfaguugGfuUfuCfgUfgAfsc | 271 | UCGUAUAGUUGGUUUCGUGAC | 398 |
| AM07687-AS | usCfsusUfuGfugaucCfcAfaGfuAfgAfsc | 272 | UCUUUGUGAUCCCAAGUAGAC | 399 |
| AM07911-AS | usCfsasCfuAfuG$_{UNA}$gagUfaUfaUfcUfuCfsc | 273 | UCACUAUGGAGUAUAUCUUCC | 397 |

TABLE 4

ANGPTL3 RNAi Agent Sense Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| AM06992-SS | (NAG37)s(invAb)sagagcaccAfAfGfaacuacuccas(invAb) | 274 | AGAGCACCAAGAACUACUCCA | 400 |
| AM06994-SS | (NAG37)s(invAb)sggagcaccAfAfGfaacuacuucas(invAb) | 275 | GGAGCACCAAGAACUACUUCA | 401 |
| AM06996-SS | (NAG37)s(invAb)sgagcaccaAfGfAfacuacucucus(invAb) | 276 | GAGCACCAAGAACUACUCUCU | 402 |
| AM06998-SS | (NAG37)s(invAb)sguccauggaAfCfAfuuaauucaaas(invAb) | 277 | GUCCAUGGACAUUAAUUCAAA | 403 |
| AM07000-SS | (NAG37)s(invAb)sgcccauggaAfCfAfuuaauucaaas(invAb) | 278 | GCCCAUGGACAUUAAUUCAAA | 26 |
| AM07002-SS | (NAG37)s(invAb)succauggaCfAfUfuaauucaacas(invAb) | 279 | UCCAUGGACAUUAAUUCAACA | 30 |
| AM07004-SS | (NAG37)s(invAb)sgccauggaCfAfUfuaauucaacas(invAb) | 280 | GCCAUGGACAUUAAUUCAACA | 406 |

TABLE 4-continued

ANGPTL3 RNAi Agent Sense Strand Sequences

| Sense Strand ID: | Modified Sense Strand (5' → 3') | Underlying Base Sequence SEQ(5' → 3') ID (Shown as an Unmodified NO. Nucleotide Sequence) | SEQ ID NO. |
|---|---|---|---|
| AM07006-SS | (NAG37)s(invAb)sagugugGfAfAfaacaaccuaas(invAb) | 281 AGUGUGGAGAAAACAACCUAA | 407 |
| AM07008-SS | (NAG37)s(invAb)sgguguggaGfAfAfaacaaccuaas(invAb) | 282 GGUGUGGAGAAAACAACCUAA | 408 |
| AM07010-SS | (NAG37)s(invAb)sggguggagaAfAfAfcaaccuaaaas(invAb) | 283 GGUGGAGAAAACAACCUAAAA | 409 |
| AM07147-SS | (NAG37)s(invAb)sccauggaAfCfAfuuaauucaaas(invAb) | 284 CUCCAUGGACAUUAAUUCAAA | 410 |
| AM07147-SS | (NAG37)s(invAb)sccauggaAfCfAfuuaauucaaas(invAb) | 285 CUCCAUGGACAUUAAUUCAAA | 410 |
| AM07150-SS | (NAG37)s(invAb)sccauggaAfCfAfuUaauucaaas(invAb) | 286 CUCCAUGGACAUUAAUUCAAA | 410 |
| AM07151-SS | (NAG37)s(invAb)sccauggaAfCfAfuuaauucaa_2Nas(invAb) | 287 CUCCAUGGACAUUAAUUCA($A^{2N}$)A | 411 |
| AM07152-SS | (NAG37)s(invAb)sccauggaAfCfAfuuaauuca_2Naas(invAb) | 288 CUCCAUGGACAUUAAUUC($A^{2N}$)AA | 412 |
| AM07153-SS | (NAG37)s(invAb)sccauggaAfCfAfuua_2Nauucaaas(invAb) | 289 CUCCAUGGACAUU($A^{2N}$)AUUCAAA | 413 |
| AM07154-SS | (NAG37)s(invAb)sgccauggaAfCfAfuuaauucaaas(invAb) | 290 CGCCAUGGACAUUAAUUCAAA | 414 |
| AM07156-SS | (NAG37)s(invAb)sccccauggaAfCfAfuuaauucaaas(invAb) | 291 CCCCAUGGACAUUAAUUCAAA | 415 |
| AM07158-SS | (NAG37)s(invAb)sacccauggaAfCfAfuuaauucaaas(invAb) | 292 ACCCAUGGACAUUAAUUCAAA | 28 |
| AM07160-SS | (NAG37)s(invAb)scccauggaCfAfUfuaauucaacas(invAb) | 293 CCCAUGGACAUUAAUUCAACA | 417 |
| AM07162-SS | (NAG37)s(invAb)saccauggaCfAfUfuaauucaacas(invAb) | 294 ACCAUGGACAUUAAUUCAACA | 418 |
| AM07165-SS | (NAG37)s(invAb)saccauggaCfAfUfuAauucaacas(invAb) | 295 ACCAUGGACAUUAAUUCAACA | 418 |
| AM07166-SS | (NAG37)s(invAb)saccauggaCfAfUfuaa_2Nuucaacas(invAb) | 296 ACCAUGGACAUUA($A^{2N}$)UUCAACA | 419 |
| AM07167-SS | (NAG37)s(invAb)sacca_2NuggaCfAfUfuaauucaacas(invAb) | 297 ACC($A^{2N}$)UGGACAUUAAUUCAACA | 420 |
| AM07168-SS | (NAG37)s(invAb)sa_2NccauggaCfAfUfuaauucaacas(invAb) | 298 ($A^{2N}$)CCAUGGACAUUAAUUCAACA | 421 |
| AM07232-SS | (NAG37)s(invAb)sacucaacaUfAfUfuugaucaguas(invAb) | 299 ACUCAACAUAUUUGAUCAGUA | 24 |
| AM07234-SS | (NAG37)s(invAb)sgcucaacaUfAfUfuugaucaguas(invAb) | 300 GCUCAACAUAUUUGAUCAGUA | 17 |
| AM07236-SS | (NAG37)s(invAb)succagagcCfAfAfaaucaagauus(invAb) | 301 UCCAGAGCCAAAAUCAAGAUU | 424 |
| AM07238-SS | (NAG37)s(invAb)saccagagcCfAfAfaaucaagauus(invAb) | 302 ACCAGAGCCAAAAUCAAGAUU | 425 |
| AM07240-SS | (NAG37)s(invAb)sgugauggaGfAfAfuuuugguugas(invAb) | 303 GUGAUGGAGAAUUUUGGUUGA | 426 |
| AM07242-SS | (NAG37)s(invAb)sgcgauggaGfAfAfuuuugguugas(invAb) | 304 GCGAUGGAGAAUUUUGGUUGA | 427 |
| AM07244-SS | (NAG37)s(invAb)sugauggagAfAfUfuuuggguugas(invAb) | 305 UGAUGGAGAAUUUUGGUUGGA | 428 |
| AM07246-SS | (NAG37)uccauggaCfAfUfuaauucaacas(invAb) | 306 UCCAUGGACAUUAAUUCAACA | 30 |
| AM07247-SS | (NAG37)asccauggaCfAfUfuaauucaacas(invAb) | 307 ACCAUGGACAUUAAUUCAACA | 418 |
| AM07345-SS | (NAG37)s(invAb)succauggaCfAfUfuaauucaa_2Ncas(invAb) | 308 UCCAUGGACAUUAAUUCA($A^{2N}$)CA | 429 |
| AM07346-SS | (NAG37)s(invAb)succauggaCfAfUfuaauuca_2Nacas(invAb) | 309 UCCAUGGACAUUAAUUC($A^{2N}$)ACA | 430 |
| AM07353-SS | (NAG37)s(invAb)succauggaCfaUfuAfauucaacas(invAb) | 310 UCCAUGGACAUUAAUUCAACA | 30 |
| AM07354-SS | (NAG37)s(invAb)succauggaCfaUfUfaauucaacas(invAb) | 311 UCCAUGGACAUUAAUUCAACA | 30 |
| AM07355-SS | (NAG37)s(invAb)succaugGfaCfAfUfaauucaacas(invAb) | 312 UCCAUGGACAUUAAUUCAACA | 30 |
| AM07358-SS | (NAG37)s(invAb)sccccauggaCfaUfuAfauucaacas(invAb) | 313 CCCAUGGACAUUAAUUCAACA | 417 |
| AM07359-SS | (NAG37)ascccauggaAfCfAfuuaauucaaas(invAb) | 314 ACCCAUGGACAUUAAUUCAAA | 28 |
| AM07453-SS | (NAG37)s(invAb)sgcucaacaUfAfUfuugaucaguus(invAb) | 315 GCUCAACAUAUUUGAUCAGUU | 431 |
| AM07455-SS | (NAG37)s(invAb)sgcucaacaUfAfUfuugaucaiuas(invAb) | 316 GCUCAACAUAUUUGAUCAIUA | 432 |
| AM07459-SS | (NAG37)gscucaacaUfAfUfuugaucaguas(invAb) | 317 GCUCAACAUAUUUGAUCAGUA | 17 |

TABLE 4-continued

ANGPTL3 RNAi Agent Sense Strand Sequences

| Sense Strand ID: | Modified Sense Strand (5' → 3') | Underlying Base Sequence SEQ ID NO. (Shown as an Unmodified Nucleotide Sequence) | SEQ ID NO. |
|---|---|---|---|
| AM07460-SS | (NAG37)s(invAb)sccucaacaUfAfUfuugaucaguas(invAb) | 318 CCUCAACAUAUUUGAUCAGUA | 433 |
| AM07462-SS | (NAG37)s(invAb)sgcccaacaUfAfUfuugaucaguas(invAb) | 319 GCCCAACAUAUUUGAUCAGUA | 434 |
| AM07464-SS | (NAG37)s(invAb)sgcgcaacaUfAfUfuugaucaguas(invAb) | 320 GCGCAACAUAUUUGAUCAGUA | 435 |
| AM07466-SS | (NAG37)s(invAb)sacccaacaUfAfUfuugaucaguas(invAb) | 321 ACCCAACAUAUUUGAUCAGUA | 436 |
| AM07468-SS | (NAG37)s(invAb)sacgcaacaUfAfUfuugaucaguas(invAb) | 322 ACGCAACAUAUUUGAUCAGUA | 437 |
| AM07502-SS | (NAG37)s(invAb)sacCfcAfuGfgAfCfAfuuaauucaaas(invAb) | 323 ACCCAUGGACAUUAAUUCAAA | 28 |
| AM07503-SS | (NAG37)s(invAb)sacccauggAfCfAfuuaauucaAMas(invAb) | 324 ACCCAUGGACAUUAAUUCAAA | 28 |
| AM07504-SS | (NAG37)s(invAb)sacccauggAfCfAfuuaaTMumCMaAMas(invAb) | 325 ACCCAUGGACAUUAAUCAAA | 438 |
| AM07579-SS | (NAG37)s(invAb)sgcUfcAfaCfaUfAfUfuugaucaguas(invAb) | 326 GCUCAACAUAUUUGAUCAGUA | 17 |
| AM07580-SS | (NAG37)s(invAb)sgcUfcAfaCfaUfaUfuugaucaguas(invAb) | 327 GCUCAACAUAUUUGAUCAGUA | 17 |
| AM07582-SS | (NAG37)s(invAb)sgcucaacaUfaUfuUfgaucaguas(invAb) | 328 GCUCAACAUAUUUGAUCAGUA | 17 |
| AM07584-SS | (NAG37)s(invAb)sgcucaacaUfaUfuugaucaguas(invAb) | 329 GCUCAACAUAUUUGAUCAGUA | 17 |
| AM07585-SS | (NAG37)s(invAb)sgcucaacaUfauuugaucaguas(invAb) | 330 GCUCAACAUAUUUGAUCAGUA | 17 |
| AM07586-SS | (NAG37)s(invAb)sgcucaacauaUfuugaucaguas(invAb) | 331 GCUCAACAUAUUUGAUCAGUA | 17 |
| AM07587-SS | (NAG37)s(invAb)sgcUfcAfaCfaUfauuugaucaguas(invAb) | 332 GCUCAACAUAUUUGAUCAGUA | 17 |
| AM07607-SS | (NAG37)s(invAb)sgcucaacaUfAfUfuuga_2Nucaguas(invAb) | 333 GCUCAACAUAUUUG($A^{2N}$)UCAGUA | 439 |
| AM07608-SS | (NAG37)s(invAb)sgcucaacaUfa_2NUfuugaucaguas(invAb) | 334 GCUCAACAU($A^{2N}$)UUUGAUCAGUA | 19 |
| AM07609-SS | (NAG37)s(invAb)sgcucaaca_2NUfAfUfuugaucaguas(invAb) | 335 GCUCAAC($A^{2N}$)UAUUUGAUCAGUA | 441 |
| AM07610-SS | (NAG37)s(invAb)sgcucaaca_2NUfa_2NUfuugaucaguas(invAb) | 336 GCUCAAC($A^{2N}$)U($A^{2N}$)UUUGAUCAGUA | 21 |
| AM07625-SS | (NAG25)s(invAb)sgcucaacaUfAfUfuugaucaguas(invAb) | 337 GCUCAACAUAUUUGAUCAGUA | 17 |
| AM07626-SS | (NAG37)s(invAb)sgcucaacaUfAfUfuUfgaucaguas(invAb) | 338 GCUCAACAUAUUUGAUCAGUA | 17 |
| AM07627-SS | (NAG37)s(invAb)sgcucaacaUfAfUfUfugaucaguas(invAb) | 339 GCUCAACAUAUUUGAUCAGUA | 17 |
| AM07628-SS | (NAG37)s(invAb)sgcucaacAfUfAfUfuugaucaguas(invAb) | 340 GCUCAACAUAUUUGAUCAGUA | 17 |
| AM07629-SS | (NAG37)s(invAb)sgcUfcAfaCfaUfAfUfuUfgaucaguas(invAb) | 341 GCUCAACAUAUUUGAUCAGUA | 17 |
| AM07630-SS | (NAG37)s(invAb)sgcUfcAfaCfaUfAfUfUfugaucaguas(invAb) | 342 GCUCAACAUAUUUGAUCAGUA | 17 |
| AM07631-SS | (NAG37)s(invAb)sgcucaacAMUfAfUfuugaucaguas(invAb) | 343 GCUCAACAUAUUUGAUCAGUA | 17 |
| AM07632-SS | (NAG37)s(invAb)sgcucaacaUfAfUfuugaucaGMuas(invAb) | 344 GCUCAACAUAUUUGAUCAGUA | 17 |
| AM07633-SS | (NAG37)s(invAb)sgmCMumCMaAMcaUfAfUfuugaucaguas(invAb) | 345 GCUCAACAUAUUUGAUCAGUA | 17 |
| AM07635-SS | (NAG37)s(invAb)sacccauggAfCfAfuUfaAfuucaaas(invAb) | 346 ACCCAUGGACAUUAAUUCAAA | 28 |
| AM07636-SS | (NAG37)s(invAb)sacccauggAfCfAfuUfAfAfuucaaas(invAb) | 347 ACCCAUGGACAUUAAUUCAAA | 28 |
| AM07637-SS | (NAG37)s(invAb)sacccauggAfCfAfuUfaAfuUfcaaas(invAb) | 348 ACCCAUGGACAUUAAUUCAAA | 28 |
| AM07638-SS | (NAG37)s(invAb)sacccauggAfCfAfuuAMauucaaas(invAb) | 349 ACCCAUGGACAUUAAUUCAAA | 28 |
| AM07639-SS | (NAG37)s(invAb)sacccauggAfCfAfuuAMaTMucaaas(invAb) | 350 ACCCAUGGACAUUAAUCAAA | 438 |
| AM07640-SS | (NAG37)s(invAb)sacccauggAfCfAfuUfAMAfuucaaas(invAb) | 351 ACCCAUGGACAUUAAUUCAAA | 28 |
| AM07641-SS | (NAG37)s(invAb)sacccauggAfCfAfuuAMaTMucaAMas(invAb) | 352 ACCCAUGGACAUUAAUCAAA | 438 |
| AM07642-SS | (NAG25)s(invAb)sacccauggAfCfAfuuaauucaaas(invAb) | 353 ACCCAUGGACAUUAAUUCAAA | 28 |

TABLE 4-continued

ANGPTL3 RNAi Agent Sense Strand Sequences

| Sense Strand ID: | Modified Sense Strand (5' → 3') | Underlying Base Sequence SEQ(5' → 3') ID (Shown as an Unmodified NO. Nucleotide Sequence) | SEQ ID NO. |
|---|---|---|---|
| AM07659-SS | (NAG37)s(invAb)sgggacaugGfUfCfuuaaagacuus(invAb) | 354 GGGACAUGGUCUUAAAGACUU | 443 |
| AM07661-SS | (NAG37)s(invAb)scuacuccaUfAfGfugaagcaauas(invAb) | 355 CUACUCCAUAGUGAAGCAAUA | 444 |
| AM07663-SS | (NAG37)s(invAb)sgacuugggAfUfCfacaaagcaaas(invAb) | 356 GACUUGGGAUCACAAAGCAAA | 445 |
| AM07680-SS | (NAG37)s(invAb)sgguugcuaUfGfUfuagacgaugus(invAb) | 357 GGUUGCUAUGUUAGACGAUGU | 32 |
| AM07682-SS | (NAG37)s(invAb)sggaagauaUfAfCfuccauagugas(invAb) | 358 GGAAGAUAUACUCCAUAGUGA | 447 |
| AM07684-SS | (NAG37)s(invAb)sgucacgaaAfCfCfaacuauacgas(invAb) | 359 GUCACGAAACCAACUAUACGA | 448 |
| AM07686-SS | (NAG37)s(invAb)sgucuacuuGfGfGfaucacaaagas(invAb) | 360 GUCUACUUGGGAUCACAAAGA | 449 |
| AM07910-SS | (NAG37)s(invAb)sggaagauaUfAfCfucC$_{UNA}$auagugas(invAb) | 361 GGAAGAUAUACUCCAUAGUGA | 447 |
| AM07912-SS | (NAG37)s(invAb)sggaagauaUfAfCfuccauaiugas(invAb) | 362 GGAAGAUAUACUCCAUAIUGA | 450 |

($A^{2N}$) = 2-aminoadenine nucleotide

The ANGPTL3 RNAi agents described herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of an ANGPTL3 RNAi agent disclosed herein differs by 0, 1, 2, or 3 nucleotides from any of the antisense strand sequences in Table 3. In some embodiments, the sense strand of an ANGPTL3 RNAi agent disclosed herein differs by 0, 1, 2, or 3 nucleotides from any of the sense strand sequences in Table 4.

In some embodiments, an ANGPTL3 RNAi agent antisense strand comprises a nucleotide sequence of any of the sequences in Table 2 or Table 3. In some embodiments, an ANGPTL3 RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2 or Table 3. In certain embodiments, an ANGPTL3 RNAi agent antisense strand comprises or consists of a modified sequence of any one of the modified sequences in Table 3.

In some embodiments, an ANGPTL3 RNAi agent sense strand comprises the nucleotide sequence of any of the sequences in Table 2 or Table 4. In some embodiments, an ANGPTL3 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24 of any of the sequences in Table 2 or Table 4. In certain embodiments, an ANGPTL3 RNAi agent sense strand comprises or consists of a modified sequence of any one of the modified sequences in Table 4.

For the ANGPTL3 RNAi agents disclosed herein, the nucleotide at position 1 of the antisense strand (from 5' end→3' end) can be perfectly complementary to an ANGPTL3 gene, or can be non-complementary to an ANGPTL3 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

In some embodiments, an ANGPTL3 RNAi agent antisense strand comprises the sequence of nucleotides (from 5' end→3' end) 2-18 or 2-19 of any of the antisense strand sequences in Table 2 or Table 3. In some embodiments, an ANGPTL3 RNAi sense strand comprises the sequence of nucleotides (from 5' end→3' end) 1-17 or 1-18 of any of the sense strand sequences in Table 2 or Table 4.

In some embodiments, an ANGPTL3 RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the ANGPTL3 RNAi agent has a sense strand consisting of the modified sequence of any of the modified sequences in Table 4, and an antisense strand consisting of the modified sequence of any of the modified sequences in Table 3. Certain representative sequence pairings are exemplified by the Duplex ID Nos. shown in Table 5.

In some embodiments, an ANGPTL3 RNAi agent comprises, consists of, or consists essentially of a duplex represented by any one of the Duplex ID Nos. presented herein. In some embodiments, an ANGPTL3 RNAi agent comprises the sense strand and antisense strand nucleotide sequences of any of the duplexes represented by any of the Duplex ID Nos. presented herein. In some embodiments, an ANGPTL3 RNAi agent comprises the sense strand and antisense strand nucleotide sequences of any of the duplexes represented by any of the Duplex ID Nos. presented herein and a targeting group and/or linking group wherein the targeting group and/or linking group is covalently linked (i.e., conjugated) to the sense strand or the antisense strand. In some embodiments, an ANGPTL3 RNAi agent includes the sense strand and antisense strand modified nucleotide sequences of any of the Duplex ID Nos. presented herein. In some embodiments, an ANGPTL3 RNAi agent comprises the sense strand and antisense strand modified nucleotide sequences of any of the Duplex ID Nos. presented herein and a targeting group and/or linking group, wherein the targeting group and/or linking group is covalently linked to the sense strand or the antisense strand.

In some embodiments, an ANGPTL3 RNAi agent comprises an antisense strand and a sense strand having the nucleotide sequences of any of the antisense strand/sense strand duplexes of Table 2 or Table 5, and further comprises a targeting group. In some embodiments, an ANGPTL3 RNAi agent comprises an antisense strand and a sense strand having the nucleotide sequences of any of the antisense strand/sense strand duplexes of Table 2 or Table 5, and further comprises an asialoglycoprotein receptor ligand targeting group.

In some embodiments, an ANGPTL3 RNAi agent comprises an antisense strand and a sense strand having the nucleotide sequences of any of the antisense strand/sense strand duplexes of Table 2 or Table 5, and further comprises a targeting group selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, each as defined in Table 6. In some embodiments, the targeting group is (NAG25) or (NAG25)s as defined in Table 6. In other embodiments, the targeting group is (NAG37) or (NAG37)s as defined in Table 6.

In some embodiments, an ANGPTL3 RNAi agent comprises an antisense strand and a sense strand having the modified nucleotide sequence of any of the antisense strand and/or sense strand nucleotide sequences in Table 3 or Table 4.

In some embodiments, an ANGPTL3 RNAi agent comprises an antisense strand and a sense strand having a modified nucleotide sequence of any of the antisense strand and/or sense strand nucleotide sequences of any of the duplexes Table 5, and further comprises an asialoglycoprotein receptor ligand targeting group.

In some embodiments, an ANGPTL3 RNAi agent comprises, consists of, or consists essentially of any of the duplexes of Table 5.

TABLE 5

ANGPTL3 RNAi Agents Duplexes with Corresponding Sense and Antisense Strand ID Numbers

| Duplex ID | Antisense Strand ID | Sense Strand ID |
|---|---|---|
| AD05306 | AM06999-AS | AM06998-SS |
| AD05307 | AM07001-AS | AM07000-SS |
| AD05308 | AM07003-AS | AM07002-SS |
| AD05309 | AM07005-AS | AM07004-SS |
| AD05310 | AM07007-AS | AM07006-SS |
| AD05311 | AM07009-AS | AM07008-SS |
| AD05312 | AM07011-AS | AM07010-SS |
| AD05342 | AM07061-AS | AM06992-SS |
| AD05343 | AM07062-AS | AM06994-SS |
| AD05344 | AM07063-AS | AM06996-SS |
| AD05410 | AM07148-AS | AM07147-SS |
| AD05411 | AM07149-AS | AM07147-SS |

TABLE 5-continued

ANGPTL3 RNAi Agents Duplexes with Corresponding Sense and Antisense Strand ID Numbers

| Duplex ID | Antisense Strand ID | Sense Strand ID |
|---|---|---|
| AD05412 | AM07148-AS | AM07150-SS |
| AD05413 | AM07148-AS | AM07151-SS |
| AD05414 | AM07148-AS | AM07152-SS |
| AD05415 | AM07148-AS | AM07153-SS |
| AD05416 | AM07155-AS | AM07154-SS |
| AD05417 | AM07157-AS | AM07156-SS |
| AD05418 | AM07159-AS | AM07158-SS |
| AD05419 | AM07161-AS | AM07160-SS |
| AD05420 | AM07163-AS | AM07162-SS |
| AD05421 | AM07164-AS | AM07162-SS |
| AD05422 | AM07163-AS | AM07165-SS |
| AD05423 | AM07163-AS | AM07166-SS |
| AD05424 | AM07163-AS | AM07167-SS |
| AD05425 | AM07163-AS | AM07168-SS |
| AD05487 | AM07233-AS | AM07232-SS |
| AD05488 | AM07235-AS | AM07234-SS |
| AD05489 | AM07237-AS | AM07236-SS |
| AD05490 | AM07239-AS | AM07238-SS |
| AD05491 | AM07241-AS | AM07240-SS |
| AD05492 | AM07243-AS | AM07242-SS |
| AD05493 | AM07245-AS | AM07244-SS |
| AD05494 | AM07003-AS | AM07246-SS |
| AD05495 | AM07163-AS | AM07247-SS |
| AD05572 | AM07003-AS | AM07345-SS |
| AD05573 | AM07003-AS | AM07346-SS |
| AD05574 | AM07347-AS | AM07002-SS |
| AD05575 | AM07348-AS | AM07002-SS |
| AD05576 | AM07349-AS | AM07002-SS |
| AD05577 | AM07350-AS | AM07002-SS |
| AD05578 | AM07351-AS | AM07002-SS |
| AD05579 | AM07352-AS | AM07002-SS |
| AD05580 | AM07347-AS | AM07353-SS |
| AD05581 | AM07348-AS | AM07353-SS |
| AD05582 | AM07350-AS | AM07353-SS |
| AD05583 | AM07351-AS | AM07353-SS |
| AD05584 | AM07347-AS | AM07354-SS |
| AD05585 | AM07356-AS | AM07355-SS |
| AD05586 | AM07357-AS | AM07160-SS |
| AD05587 | AM07357-AS | AM07358-SS |
| AD05588 | AM07159-AS | AM07359-SS |
| AD05652 | AM07454-AS | AM07453-SS |
| AD05653 | AM07235-AS | AM07455-SS |
| AD05654 | AM07456-AS | AM07234-SS |
| AD05655 | AM07457-AS | AM07234-SS |
| AD05656 | AM07458-AS | AM07234-SS |
| AD05657 | AM07235-AS | AM07459-SS |
| AD05658 | AM07461-AS | AM07460-SS |
| AD05659 | AM07463-AS | AM07462-SS |
| AD05660 | AM07465-AS | AM07464-SS |
| AD05661 | AM07467-AS | AM07466-SS |
| AD05662 | AM07469-AS | AM07468-SS |
| AD05693 | AM07159-AS | AM07502-SS |
| AD05694 | AM07159-AS | AM07503-SS |
| AD05695 | AM07159-AS | AM07504-SS |
| AD05696 | AM07505-AS | AM07158-SS |
| AD05697 | AM07506-AS | AM07158-SS |
| AD05698 | AM07507-AS | AM07158-SS |
| AD05699 | AM07508-AS | AM07158-SS |
| AD05743 | AM07235-AS | AM07579-SS |
| AD05744 | AM07235-AS | AM07580-SS |
| AD05745 | AM07581-AS | AM07234-SS |
| AD05746 | AM07581-AS | AM07582-SS |
| AD05747 | AM07583-AS | AM07582-SS |
| AD05748 | AM07581-AS | AM07584-SS |
| AD05749 | AM07581-AS | AM07585-SS |
| AD05750 | AM07581-AS | AM07586-SS |
| AD05751 | AM07581-AS | AM07580-SS |
| AD05752 | AM07588-AS | AM07587-SS |
| AD05753 | AM07589-AS | AM07234-SS |
| AD05756 | AM07593-AS | AM07234-SS |
| AD05774 | AM07235-AS | AM07607-SS |
| AD05775 | AM07235-AS | AM07608-SS |
| AD05776 | AM07235-AS | AM07609-SS |
| AD05777 | AM07235-AS | AM07610-SS |
| AD05790 | AM07623-AS | AM07234-SS |

TABLE 5-continued

ANGPTL3 RNAi Agents Duplexes with Corresponding Sense and Antisense Strand ID Numbers

| Duplex ID | Antisense Strand ID | Sense Strand ID |
| --- | --- | --- |
| AD05791 | AM07624-AS | AM07234-SS |
| AD05792 | AM07235-AS | AM07625-SS |
| AD05793 | AM07235-AS | AM07626-SS |
| AD05794 | AM07235-AS | AM07627-SS |
| AD05795 | AM07235-AS | AM07628-SS |
| AD05796 | AM07235-AS | AM07629-SS |
| AD05797 | AM07235-AS | AM07630-SS |
| AD05798 | AM07235-AS | AM07631-SS |
| AD05799 | AM07235-AS | AM07632-SS |
| AD05800 | AM07235-AS | AM07633-SS |
| AD05801 | AM07634-AS | AM07158-SS |
| AD05802 | AM07634-AS | AM07635-SS |
| AD05803 | AM07634-AS | AM07636-SS |
| AD05804 | AM07634-AS | AM07637-SS |
| AD05805 | AM07634-AS | AM07638-SS |
| AD05806 | AM07634-AS | AM07639-SS |
| AD05807 | AM07634-AS | AM07640-SS |
| AD05808 | AM07634-AS | AM07641-SS |
| AD05809 | AM07159-AS | AM07642-SS |
| AD05826 | AM07660-AS | AM07659-SS |
| AD05827 | AM07662-AS | AM07661-SS |
| AD05828 | AM07664-AS | AM07663-SS |
| AD05840 | AM07681-AS | AM07680-SS |
| AD05841 | AM07683-AS | AM07682-SS |
| AD05842 | AM07685-AS | AM07684-SS |
| AD05843 | AM07687-AS | AM07686-SS |
| AD05991 | AM07683-AS | AM07910-SS |
| AD05992 | AM07911-AS | AM07682-SS |
| AD05993 | AM07683-AS | AM07912-SS |

In some embodiments, an ANGPTL3 RNAi agent is prepared or provided as a salt, mixed salt, or a free-acid. The RNAi agents described herein, upon delivery to a cell expressing an ANGPTL3 gene, inhibit or knockdown expression of one or more ANGPTL3 genes in vivo and/or in vitro.

Targeting Groups, Linking Groups, and Delivery Vehicles

In some embodiments, an ANGPTL3 RNAi agent is conjugated to one or more non-nucleotide groups including, but not limited to, a targeting group, a linking group, a delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, an ANGPTL3 RNAi agent contains a non-nucleotide group linked to the 3' and/or 5' end of the sense strand. In some embodiments, a non-nucleotide group is linked to the 5' end of an ANGPTL3 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which can in some instances serve as linkers. In some embodiments, a targeting group comprises a galactose-derivative cluster.

The ANGPTL3 RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

In some embodiments, a targeting group comprises an asialoglycoprotein receptor ligand. As used herein, an asialoglycoprotein receptor ligand is a ligand that contains a compound having affinity for the asialoglycoprotein receptor. As noted herein, the asialoglycoprotein receptor is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative) or multimeric (e.g., having multiple galactose derivatives). The galactose derivative or galactose derivative cluster can be attached to the 3' or 5' end of the sense or antisense strand of the RNAi agent using methods known in the art. The preparation of targeting groups, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem. 1995 Vol. 39 p. 1538-1546). In some embodiments, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering an ANGPTL3 RNAi agent to a liver cell in vivo. Such pharmaceutical compositions can include, for example, an ANGPTL3 RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

Targeting groups include, but are not limited to, (PAZ), (NAG13), (NAG13)s, (NAG18), (NAG18)s, (NAG24), (NAG24)s, (NAG25), (NAG25)s, (NAG26), (NAG26)s, (NAG27) (NAG27)s, (NAG28) (NAG28)s, (NAG29) (NAG29)s, (NAG30) (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s as defined in Table 6. Other targeting groups, including galactose cluster targeting ligands, are known in the art.

In some embodiments, a linking group is conjugated to the RNAi agent. The linking group facilitates covalent linkage of the agent to a targeting group, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage can optionally include a spacer that increases the distance between the two joined atoms. A spacer can further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, when two or more RNAi agents are included in a single composition, each of the RNAi agents may be linked to the same targeting group or two a different targeting groups (i.e., targeting groups having different chemical structure). In some embodiments, targeting groups are linked to the ANGPTL3 RNAi agents disclosed herein without the use of an additional linker. In some embodiments, the targeting group itself is designed having a linker or other site to facilitate conjugation readily present. In some embodiments, when two or more ANGPTL3 RNAi agents are included in a single, each of the RNAi agents may utilize the same linker or different linkers (i.e., linkers having different chemical structures).

Any of the ANGPTL3 RNAi agent nucleotide sequences listed in Tables 2, 3, or 4, whether modified or unmodified, can contain 3' and/or 5' targeting group(s) or linking group (s). Any of the ANGPTL3 RNAi agent sequences listed in Table 3 or 4, or are otherwise described herein, which contain a 3' or 5' targeting group or linking group, can alternatively contain no 3' or 5' targeting group or linking group, or can contain a different 3' or 5' targeting group or linking group including, but not limited to, those depicted in Table 6. Any of the ANGPTL3 RNAi agent duplexes listed in Table 5, whether modified or unmodified, can further comprise a targeting group or linking group, including, but not limited to, those depicted in Table 6, and the targeting group or linking group can be attached to the 3' or 5' terminus of either the sense strand or the antisense strand of the ANGPTL3 RNAi agent duplex.

Examples of targeting groups and linking groups are provided in Table 6. Table 4 provides several embodiments of ANGPTL3 RNAi agent sense strands having a targeting group or linking group linked to the 5' or 3' end.

TABLE 6
Structures Representing Various Modified Nucleotides, Targeting Groups, and Linking Groups
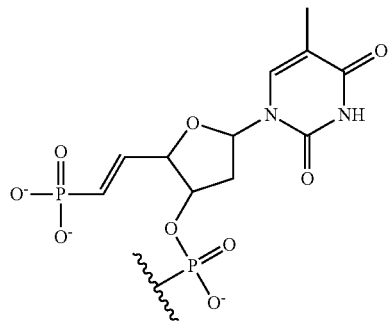 [SMILES: *P(=O)([O-])OC1CC(n2cc(C)c(=O)[nH]c2=O)OC1/C=C/P(=O)([O-])[O-]]
vpdT
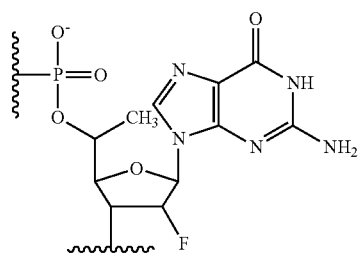 [SMILES: *C1C(F)C(n2cnc3c(=O)[nH]c(N)nc32)OC1C(C)OP(*)(=O)[O-]]
5Me-Gf
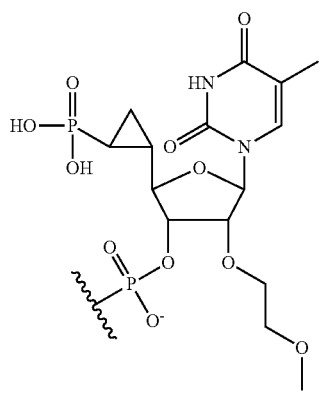 [SMILES: *P(=O)([O-])OC1C(C2CC2P(=O)(O)O)OC(n2cc(C)c(=O)[nH]c2=O)C1OCCOC]
cPrpTM
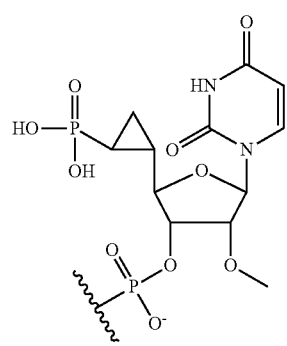
cPrpu TABLE 6-continued
Structures Representing Various Modified Nucleotides, Targeting Groups, and Linking Groups
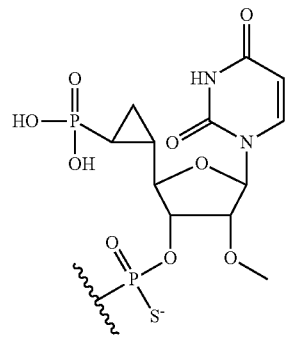 [SMILES: *P(=O)([S-])OC1C(C2CC2P(=O)(O)O)OC(n2ccc(=O)[nH]c2=O)C1OC]
cPrpus
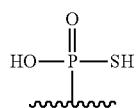
sp
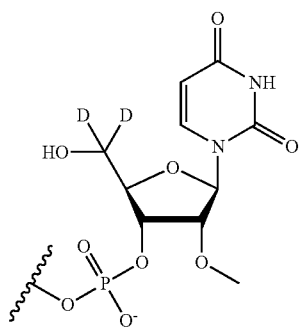
D2u
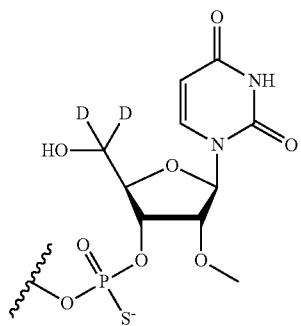
D2us
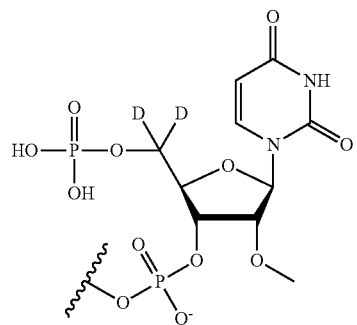

TABLE 6-continued
Structures Representing Various Modified Nucleotides, Targeting Groups, and Linking Groups
pD2u
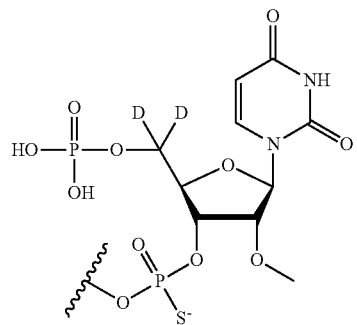
pD2us
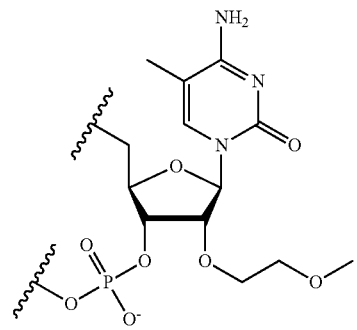
mCM
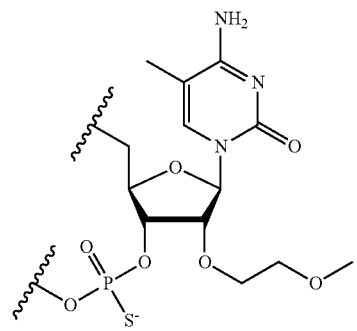
mCMs
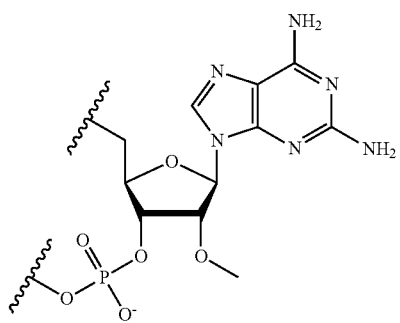
a_2N TABLE 6-continued
Structures Representing Various Modified Nucleotides, Targeting Groups, and Linking Groups
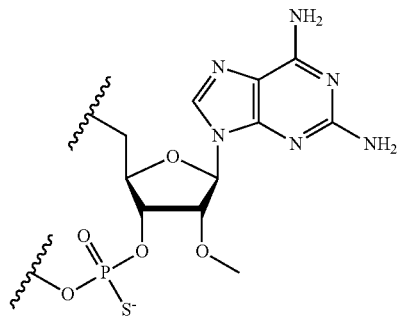
a_2Ns
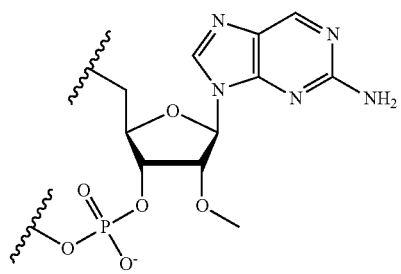
pu_2N
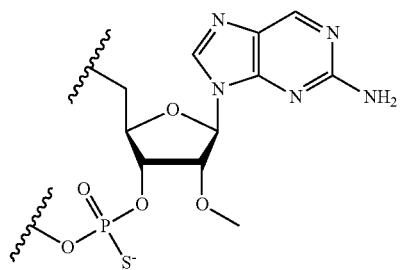
pu_2Ns
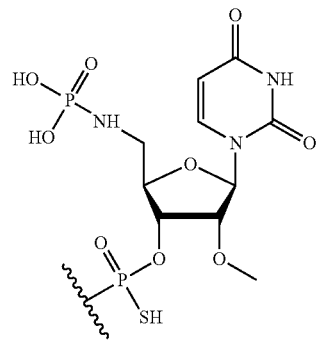
Npus TABLE 6-continued
Structures Representing Various Modified Nucleotides, Targeting Groups, and Linking Groups
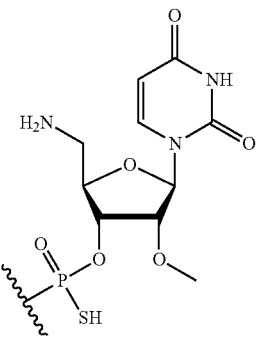
Nus
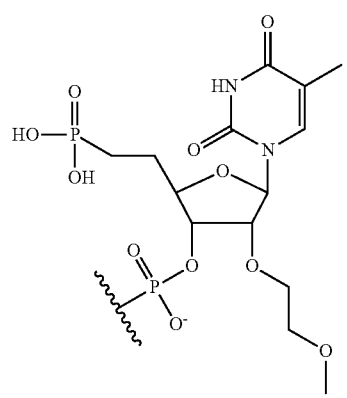 [SMILES: *P(=O)([O-])OC1C(CCP(=O)(O)O)OC(n2cc(C)c(=O)[nH]c2=O)C1OCCOC]
epTM
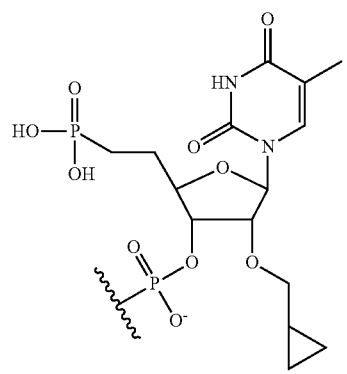 [SMILES: *P(=O)([O-])OC1C(CCP(=O)(O)O)OC(n2cc(C)c(=O)[nH]c2=O)C1OCC1CC1]
epTcPr
When positioned internally in oligonucleotide:
linkage towards 5' end of
oligonucleotide
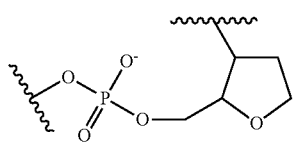
linkage towards 3' end of
oligonucleotide
(invAb)
When positioned internally in oligonucleotide:
linkage towards 5' end of
oligonucleotide TABLE 6-continued
Structures Representing Various Modified Nucleotides, Targeting Groups, and Linking Groups
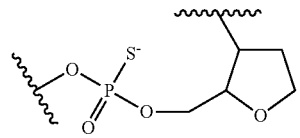 [SMILES: *OP(=O)([O-])OCC1OCCC1*]
linkage towards 3' end of
oligonucleotide
(invAb)s
When positioned at the 3' terminal end of oligonucleotide:
linkage towards 5' end of
oligonucleotide
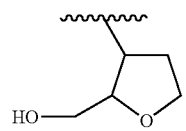
(invAb)
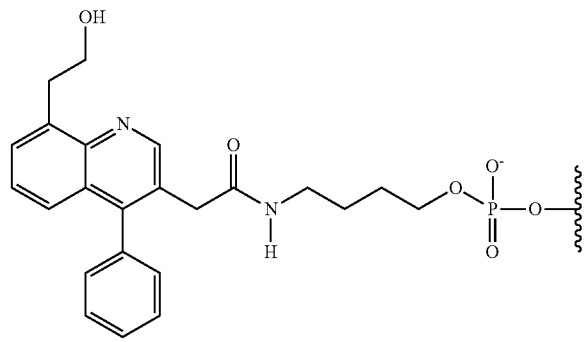 [SMILES: *OP(=O)([O-])OCCCCNC(=O)Cc1cnc2c(CCO)cccc2c1-c1ccccc1]
(PAZ)
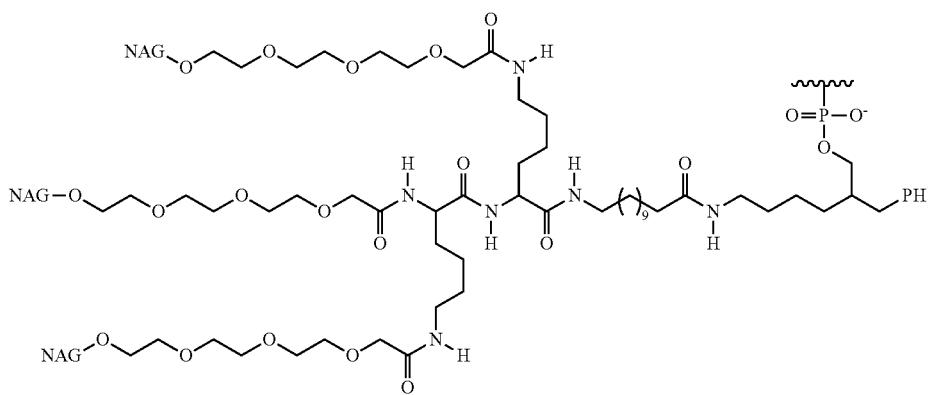
(NAG13)

TABLE 6-continued
Structures Representing Various Modified Nucleotides, Targeting Groups, and Linking Groups
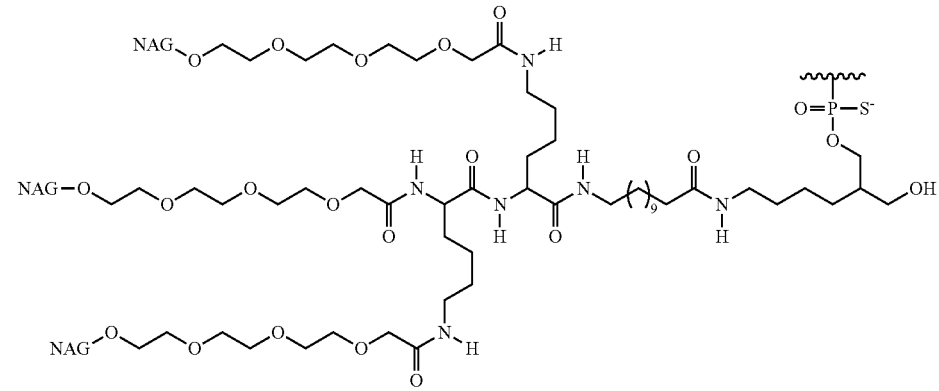
(NAG13)s
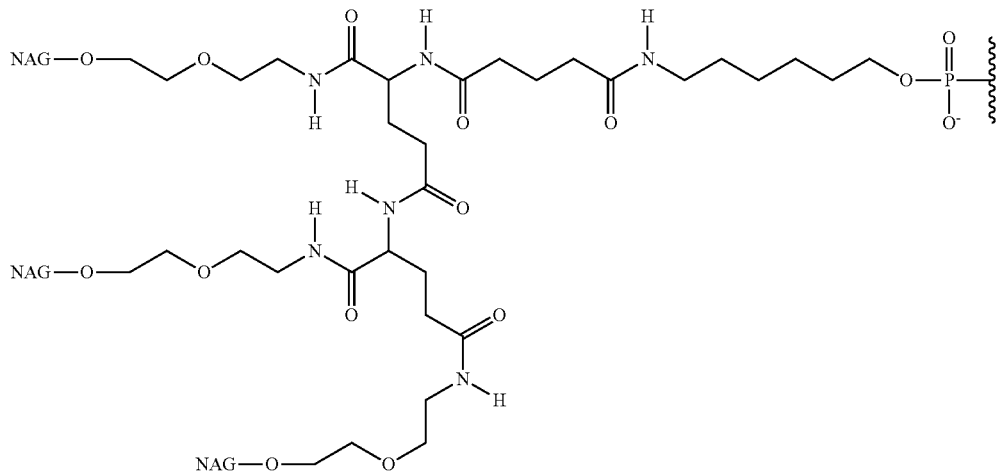
(NAG18)
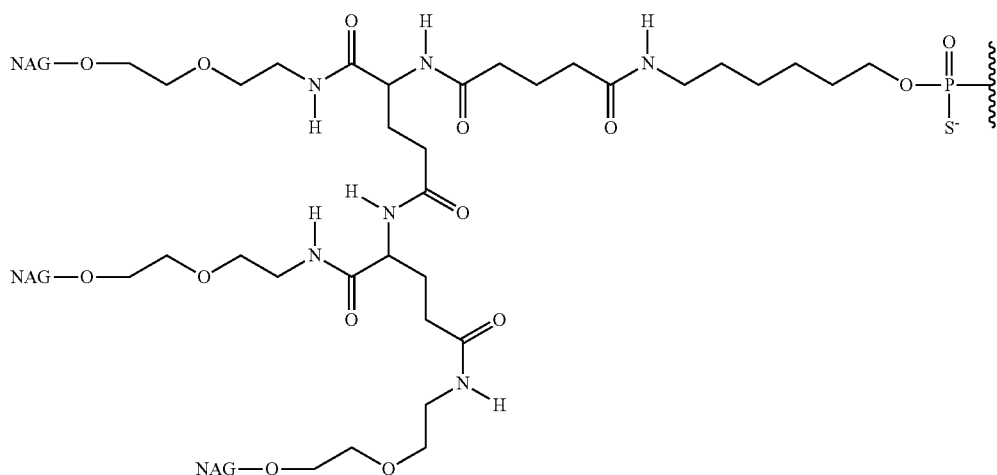
(NAG18)s TABLE 6-continued
Structures Representing Various Modified Nucleotides, Targeting Groups, and Linking Groups
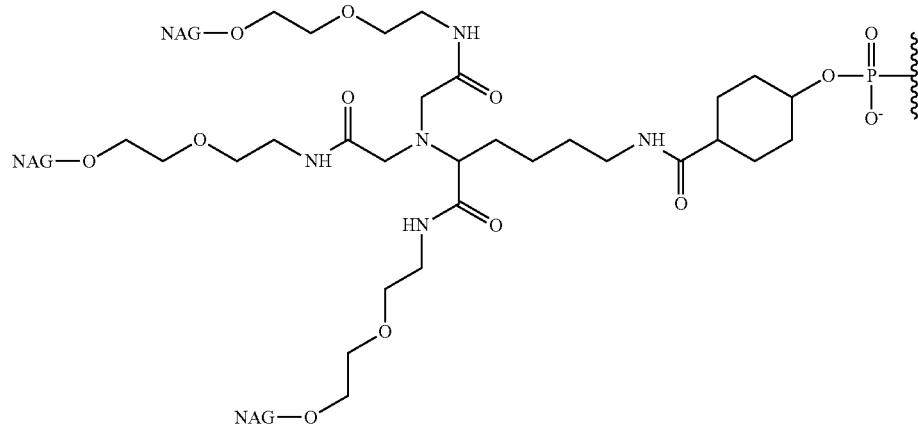
(NAG24)
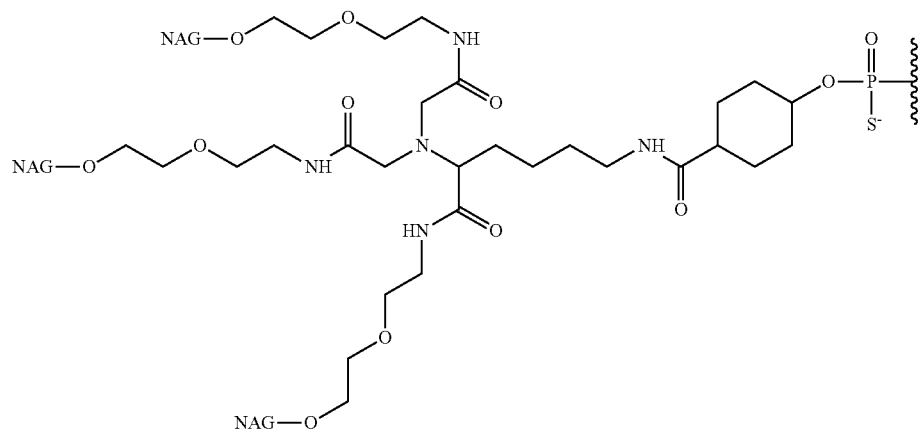
(NAG24)s
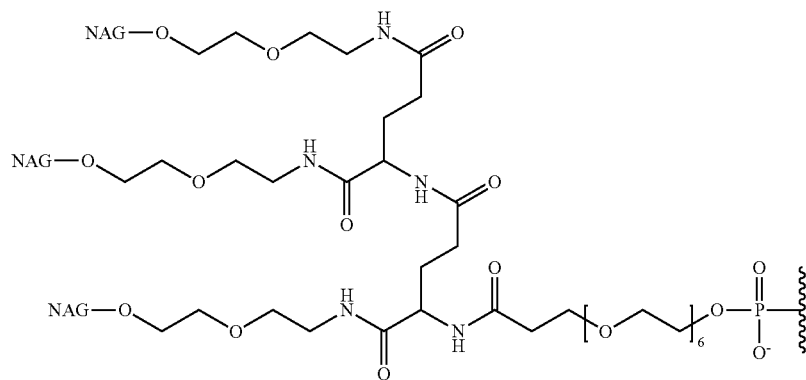
(NAG25)

TABLE 6-continued
Structures Representing Various Modified Nucleotides, Targeting Groups, and Linking Groups
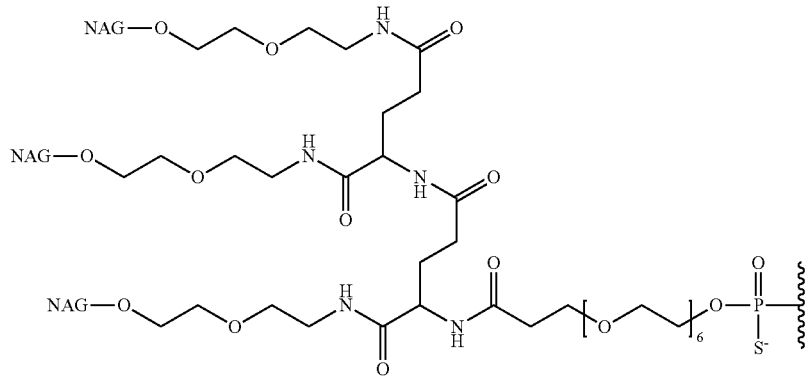
(NAG25)s
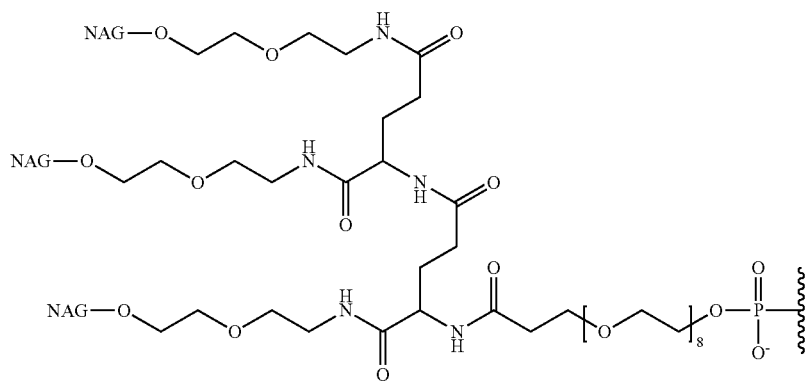
(NAG26)
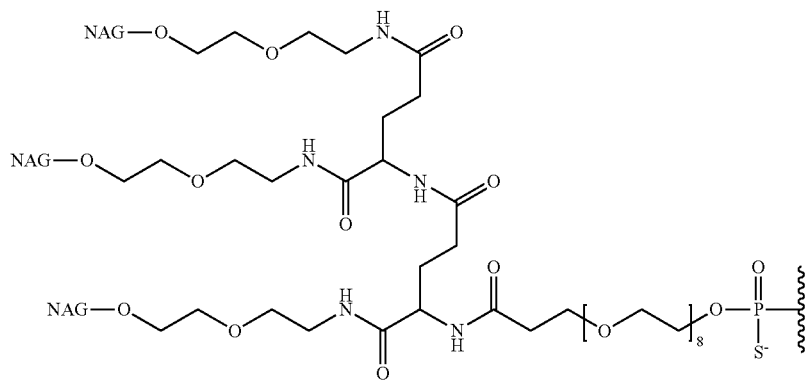
(NAG26)s TABLE 6-continued
Structures Representing Various Modified Nucleotides, Targeting Groups, and Linking Groups
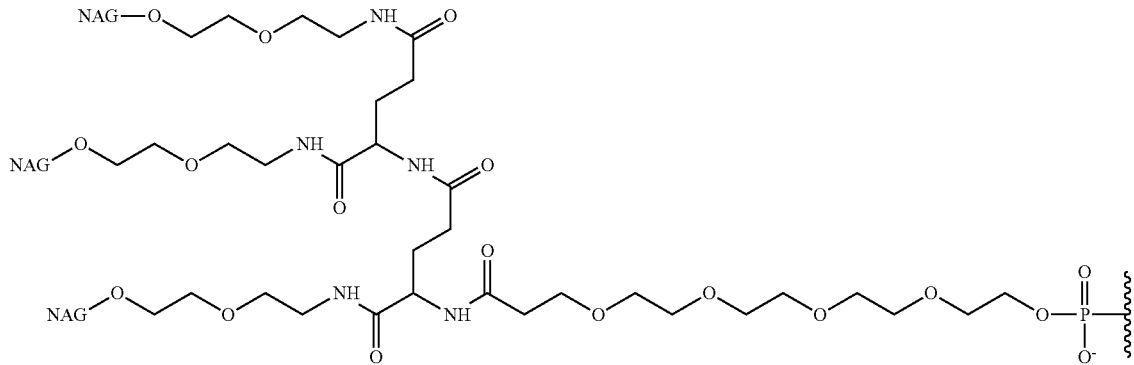
(NAG27)
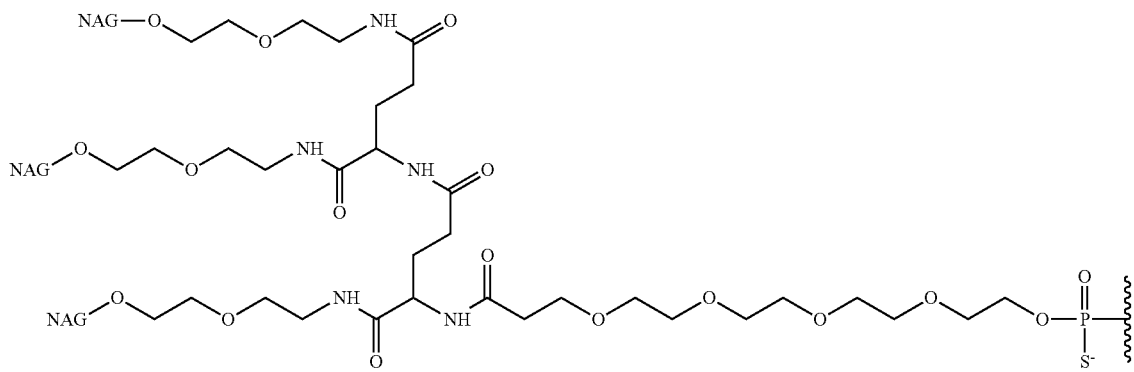
(NAG27)s
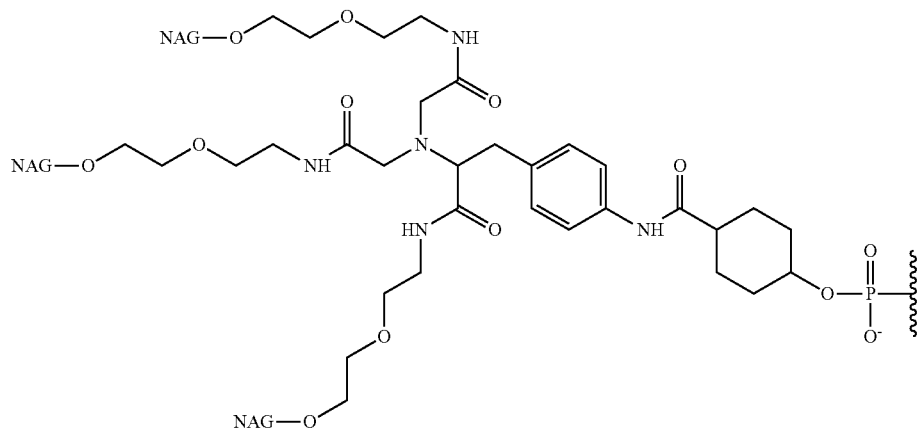
(NAG28)

TABLE 6-continued
Structures Representing Various Modified Nucleotides, Targeting Groups, and Linking Groups
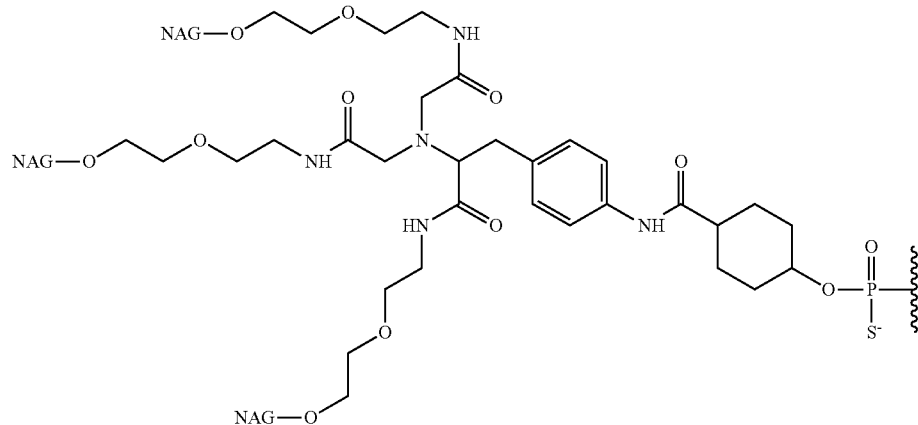
(NAG28)s
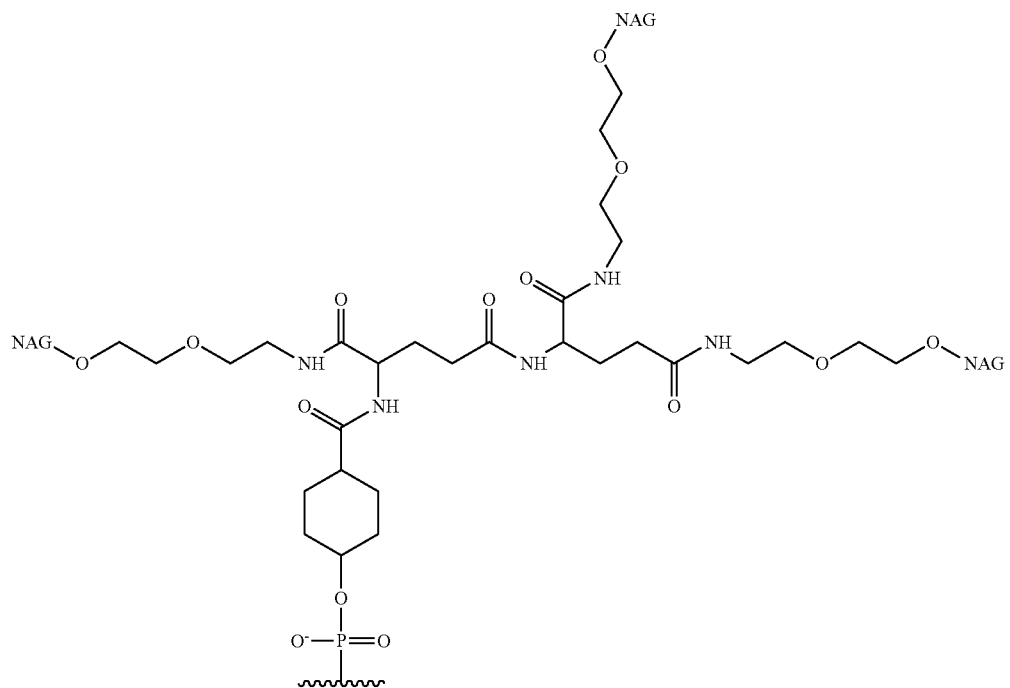
(NAG29)

TABLE 6-continued
Structures Representing Various Modified Nucleotides, Targeting Groups, and Linking Groups
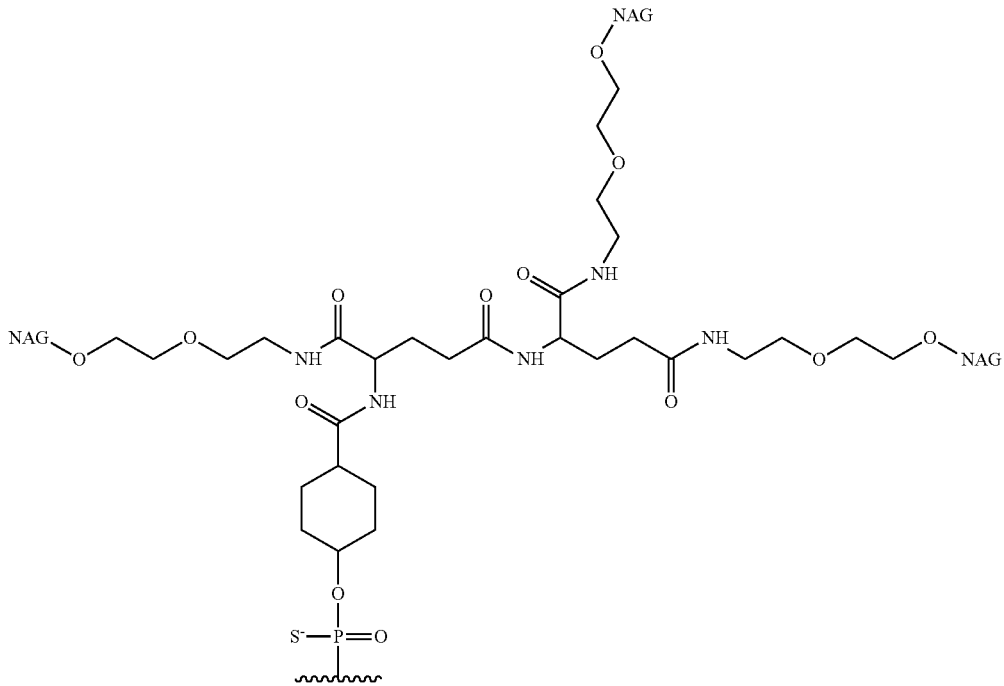
(NAG29)s
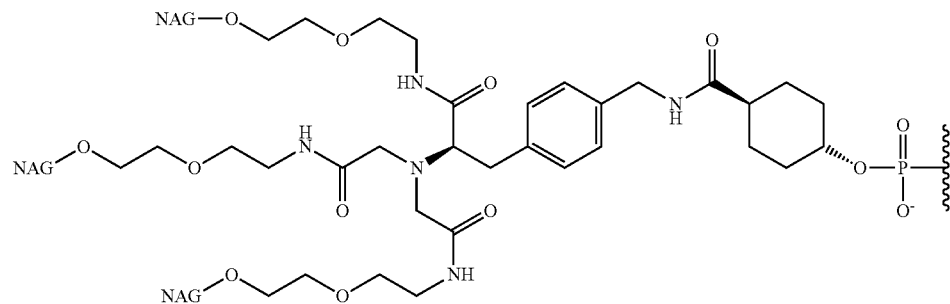
(NAG30)
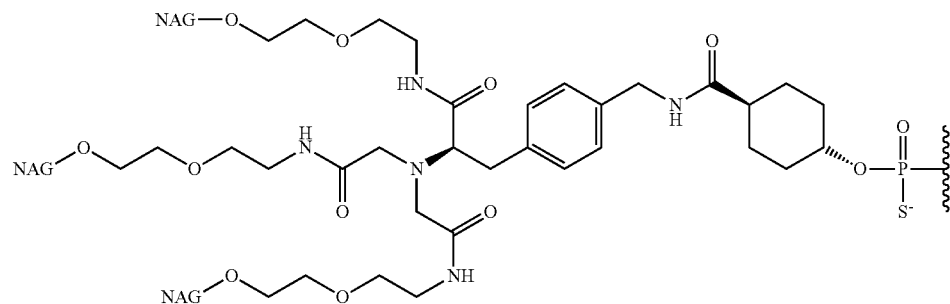
(NAG30)s TABLE 6-continued
Structures Representing Various Modified Nucleotides, Targeting Groups, and Linking Groups
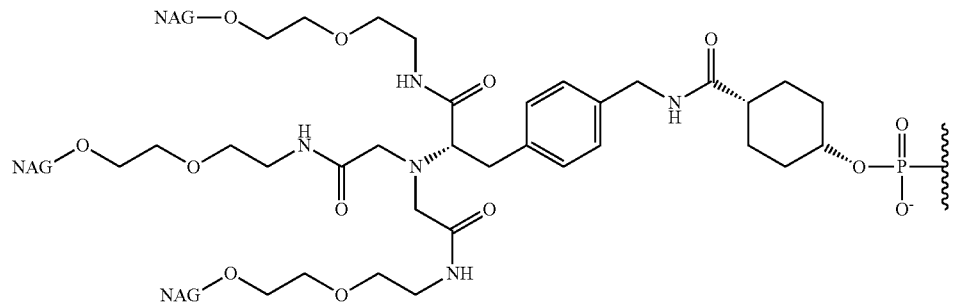
(NAG31)
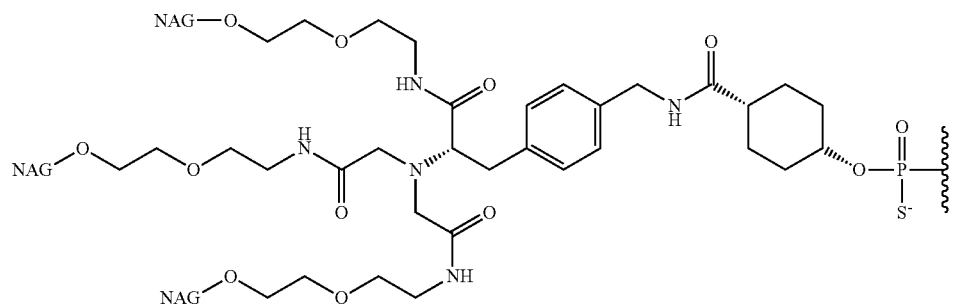
(NAG31)s
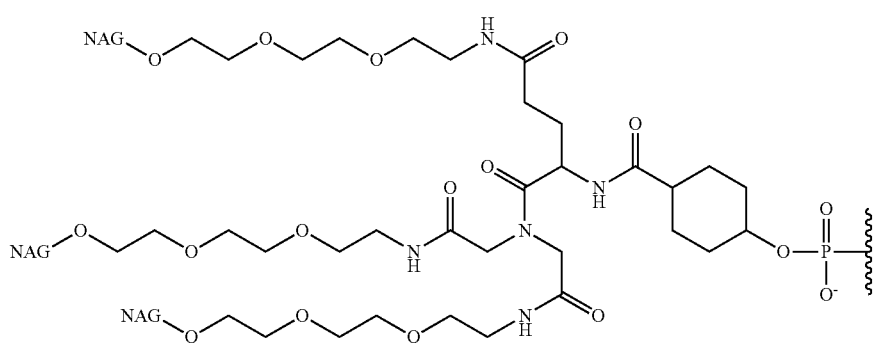
(NAG32)
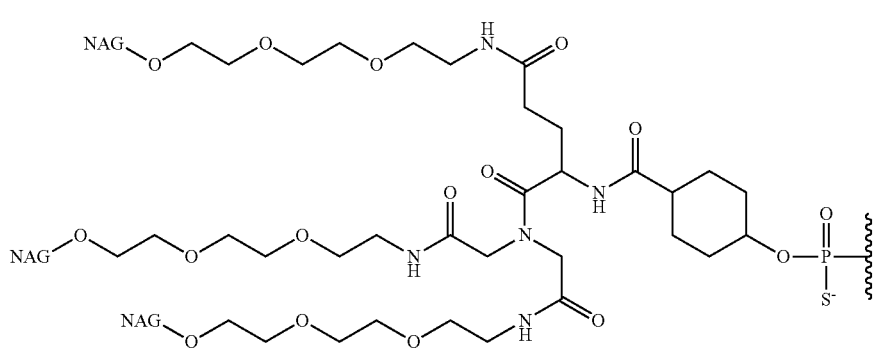
(NAG32)s TABLE 6-continued
Structures Representing Various Modified Nucleotides, Targeting Groups, and Linking Groups
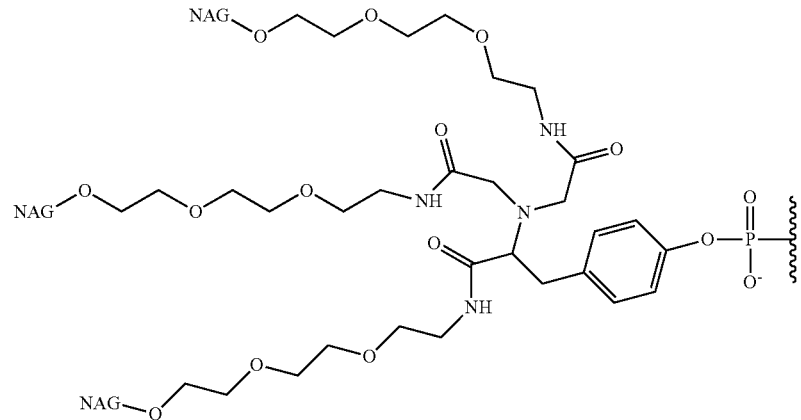
(NAG33)
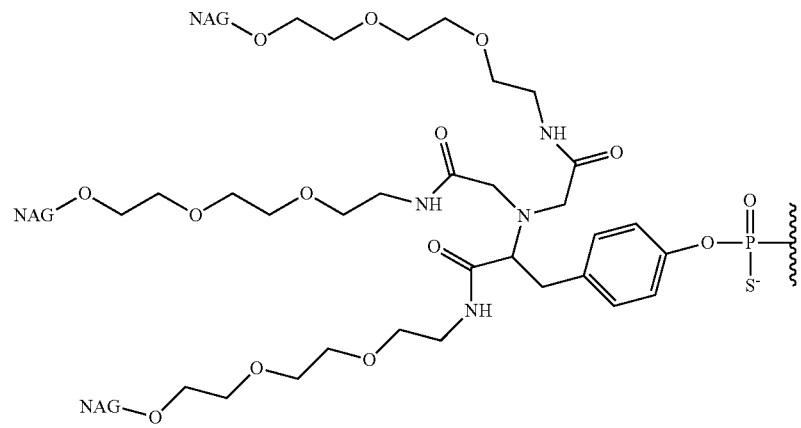
(NAG33)s
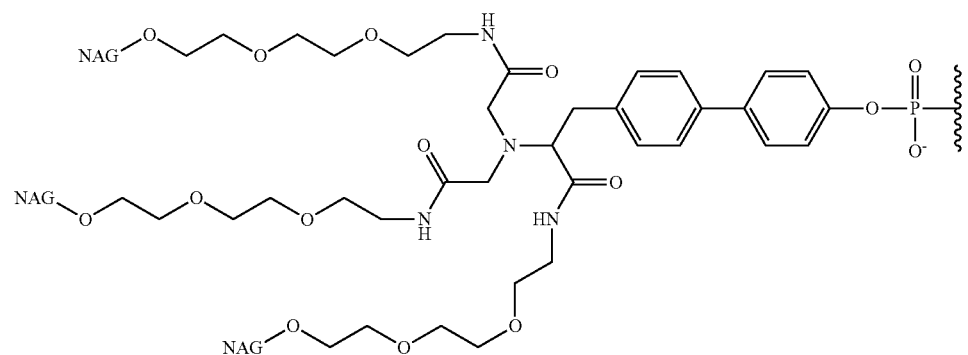
(NAG34)

TABLE 6-continued
Structures Representing Various Modified Nucleotides, Targeting Groups, and Linking Groups
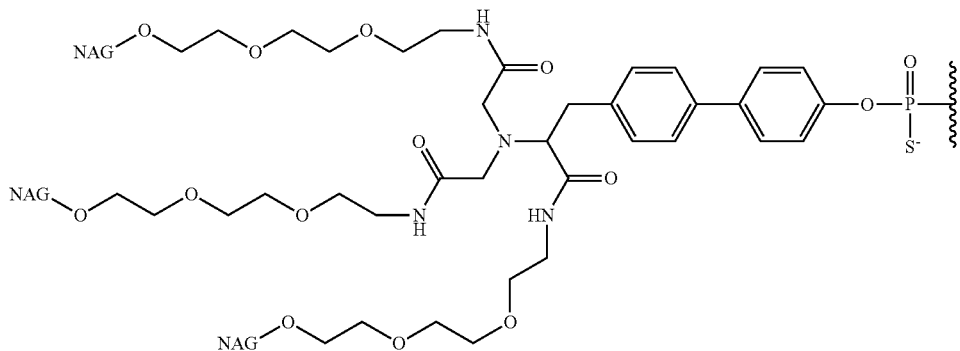
(NAG34)s
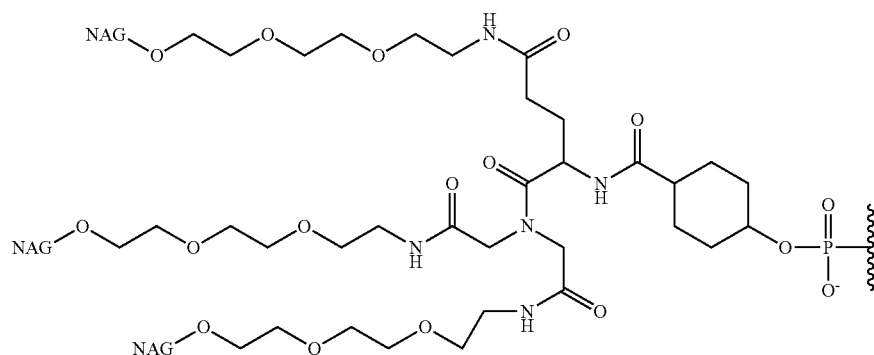
(NAG35)
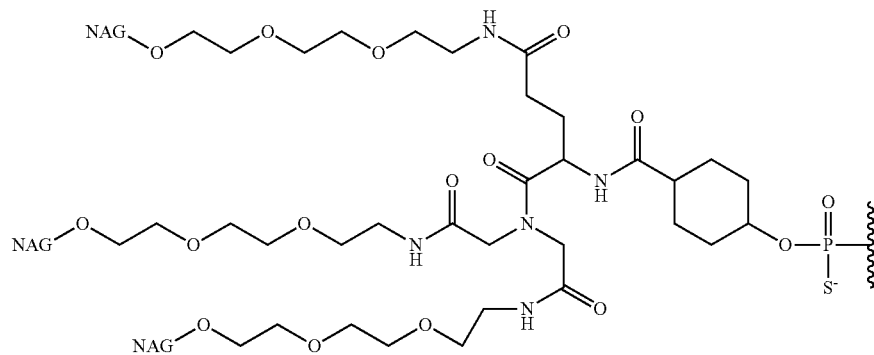
(NAG35)s TABLE 6-continued
Structures Representing Various Modified Nucleotides, Targeting Groups, and Linking Groups
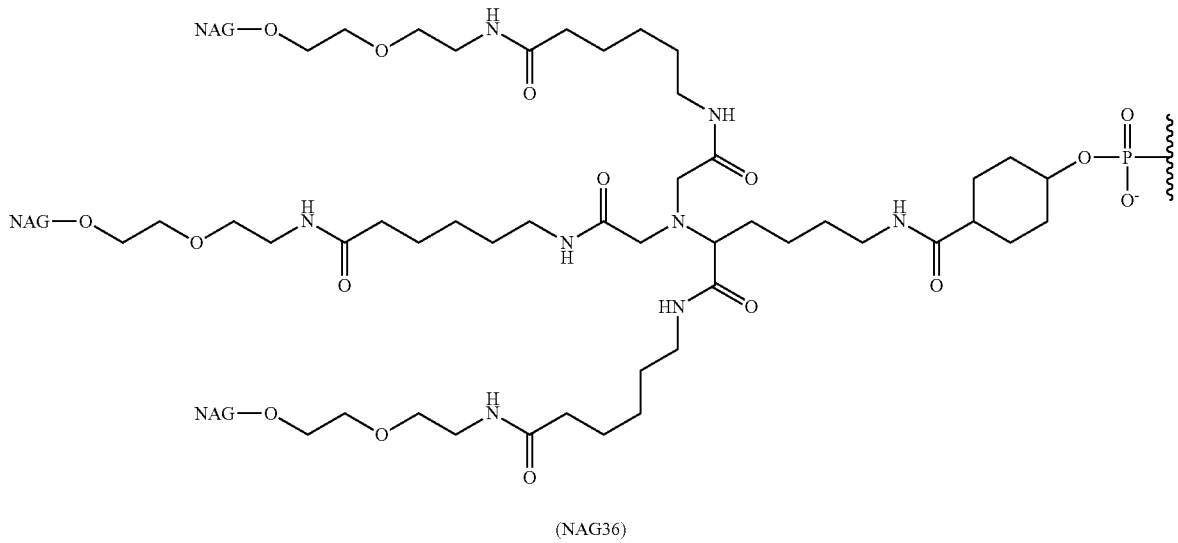
(NAG36)
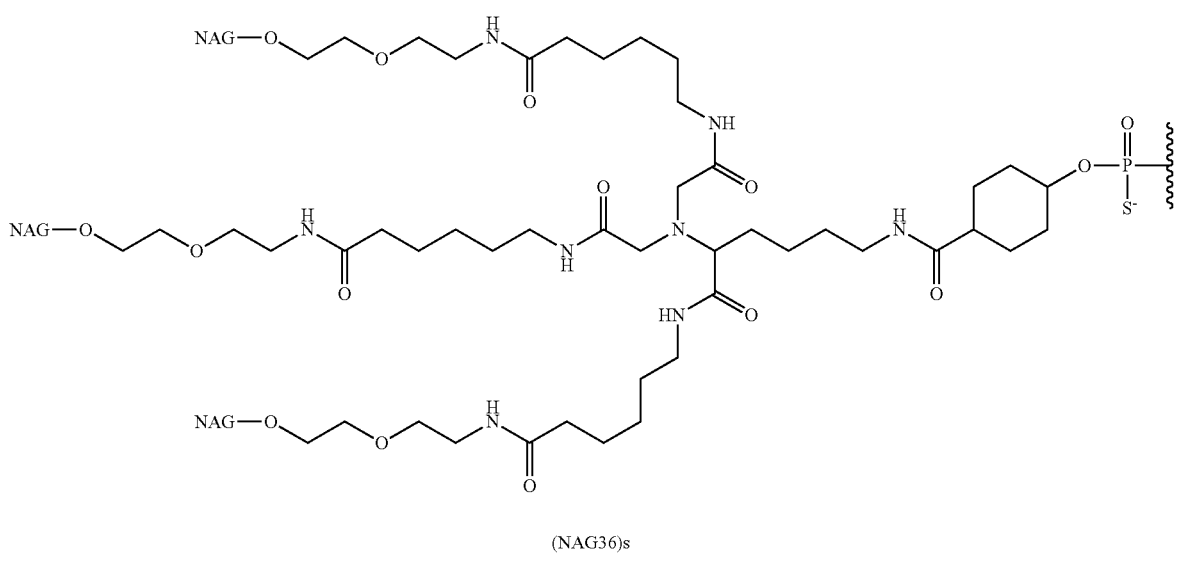
(NAG36)s
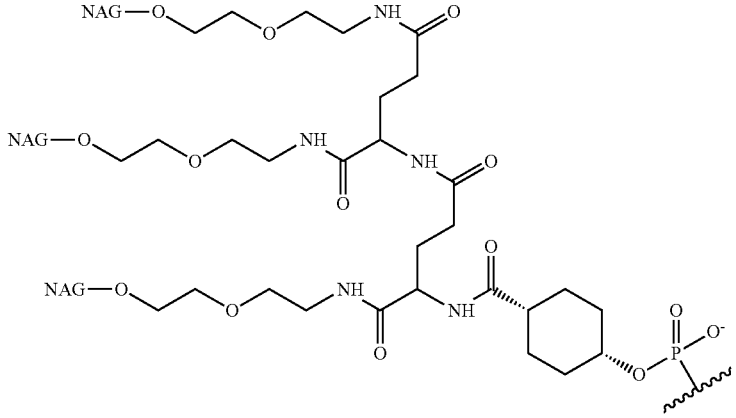
(NAG37)

TABLE 6-continued
Structures Representing Various Modified Nucleotides, Targeting Groups, and Linking Groups
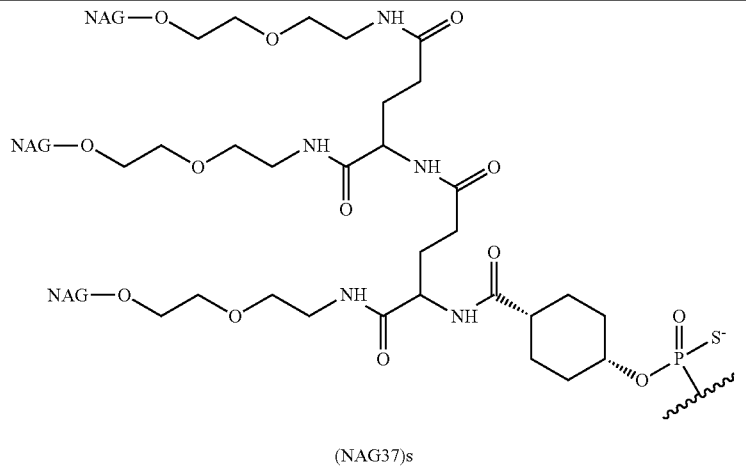
(NAG37)s
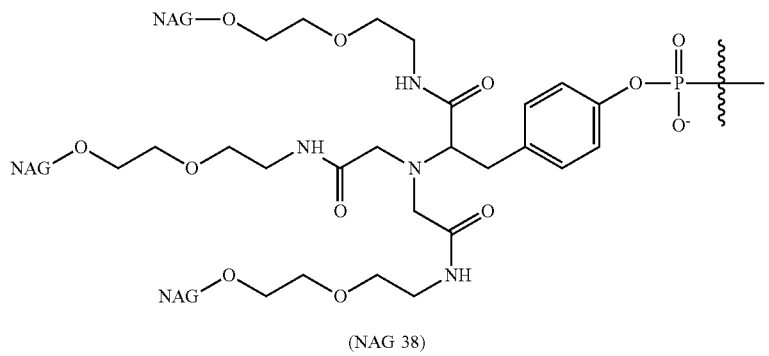
(NAG 38)
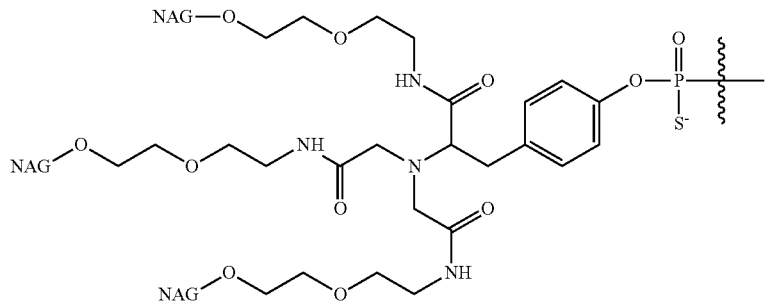
(NAG 38)s
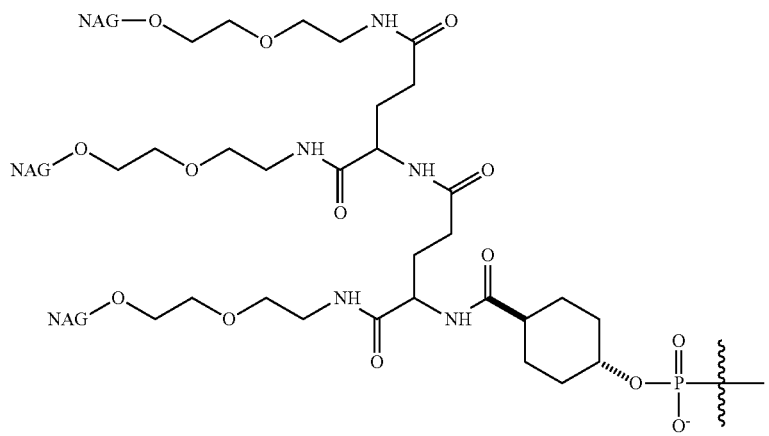

TABLE 6-continued

Structures Representing Various Modified Nucleotides, Targeting Groups, and Linking Groups

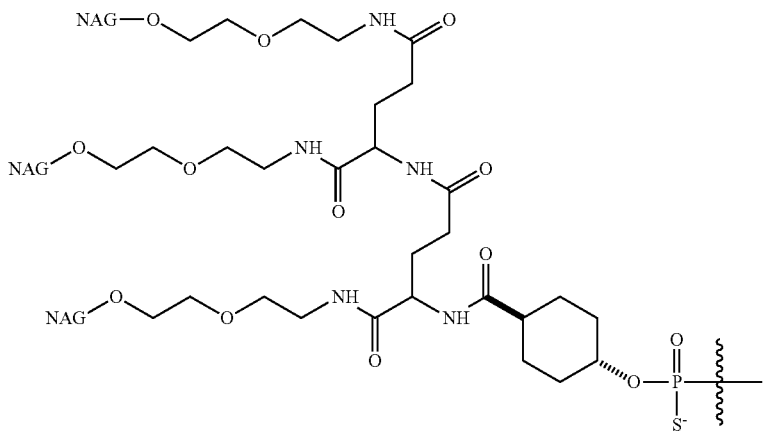

(NAG39)s

In each of the above structures in Table 6, NAG comprises an N-acetyl-galactosamine or another galactose derivative, as would be understood by a person of ordinary skill in the art to be attached in view of the structures above and description provided herein. For example, in some embodiments, NAG in the structures provided in Table 6 is represented by the following structure:

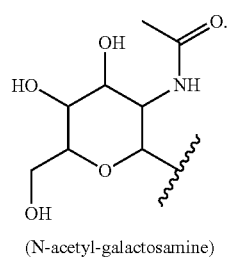

(N-acetyl-galactosamine)

Each (NAGx) may be attached to an ANGPTL3 RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

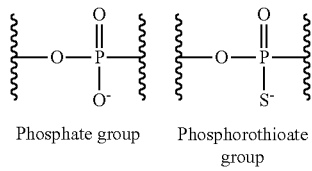

Phosphate group    Phosphorothioate group

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

Pharmaceutical Compositions and Formulations

The ANGPTL3 RNAi agents disclosed herein can be prepared as pharmaceutical compositions or formulations (also referred to herein as "medicaments"). In some embodiments, pharmaceutical compositions include at least one ANGPTL3 RNAi agent. These pharmaceutical compositions are particularly useful in the inhibition of the expression of the target mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. The pharmaceutical compositions can be used to treat a subject at risk of developing a disease, disorder, or condition that would benefit from reduction of the level of the target mRNA or an inhibition in expression the target gene. In one embodiment, the method includes administering an ANGPTL3 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include an ANGPTL3 RNAi agent, thereby forming a pharmaceutical formulation or medicament suitable for in vivo delivery to a subject, including a human.

The pharmaceutical compositions that include an ANGPTL3 RNAi agent and methods disclosed herein decrease the level of the target mRNA in a cell, group of cells, group of cells, tissue, organ, or subject, including by administering to the subject a therapeutically effective amount of a herein described ANGPTL3 RNAi agent, thereby inhibiting the expression of ANGPTL3 mRNA in the subject. In some embodiments, the subject has been previously identified or diagnosed as having a pathogenic upregulation of the target gene in the targeted cell or tissue. In some embodiments, the subject has been previously identified or diagnosed as having elevated triglyceride (TG) and/or elevated cholesterol levels or some other dyslipidemia. In some embodiments, the subject has been previously diagnosed with having one or more cardiometabolic diseases such as hypertriglyceridemia, obesity, hyperlipidemia, abnormal lipid and/or cholesterol metabolism, atherosclerosis, atherosclerosis, type II diabetes mellitus, cardiovascular disease, coronary artery disease, non-alcoholic steatohepatitis, non-alcoholic fatty liver disease, homozygous and heterozygous familial hypercholesterolemia, statin resistant hypercholesterolemia and other metabolic-related disorders and diseases. In some embodiments, the subject has been suffering from symptoms associated with one or more cardiometabolic diseases that is associated with or caused by elevated or increased TG levels, elevated or increased cholesterol levels, or hepatic steatosis.

In some embodiments, the described pharmaceutical compositions including an ANGPTL3 RNAi agent are used for treating or managing clinical presentations associated with elevated TG levels, elevated cholesterol levels, hepatic steatosis, and/or over-expression of ANGPTL3 mRNA in a subject. In some embodiments, a therapeutically (including prophylactically) effective amount of one or more of pharmaceutical compositions is administered to a subject in need of such treatment. In some embodiments, administration of any of the disclosed ANGPTL3 RNAi agents can be used to decrease the number, severity, and/or frequency of symptoms of a disease in a subject.

The described pharmaceutical compositions that include an ANGPTL3 RNAi agent can be used to treat at least one symptom in a subject having a disease or disorder that would benefit from reduction or inhibition in expression of ANGPTL3 mRNA. In some embodiments, the subject is administered a therapeutically effective amount of one or more pharmaceutical compositions that include an ANGPTL3 RNAi agent thereby treating the symptom. In other embodiments, the subject is administered a prophylactically effective amount of one or more ANGPTL3 RNAi agents, thereby preventing or inhibiting the at least one symptom.

The route of administration is the path by which an ANGPTL3 RNAi agent is brought into contact with the body. In general, methods of administering drugs and oligonucleotides and nucleic acids for treatment of a mammal are well known in the art and can be applied to administration of the compositions described herein. The ANGPTL3 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including an ANGPTL3 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., ANGPTL3 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, N.J.) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The ANGPTL3 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another ANGPTL3 RNAi agent (e.g., an ANGPTL3 RNAi agent that targets a different sequence within the ANGPTL3 target). In other embodiments, the second therapeutic can be a small molecule drug, an antibody, an antibody fragment, or an aptamer.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including an ANGPTL3 RNAi agent can be combined with an excipient or with a second therapeutic agent or treatment including, but not limited to: a second or other RNAi agent, a small molecule drug, an antibody, an antibody fragment, peptide and/or an aptamer.

The described ANGPTL3 RNAi. agents, when added to pharmaceutically acceptable excipients or adjuvants, can be packaged into kits, containers, packs, or dispensers. The pharmaceutical compositions described herein may be packaged in pre-filled syringes or vials.

Methods of Treatment and Inhibition of Expression

The ANGPTL3 RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from reduction and/or inhibition in expression of ANGPTL3 mRNA and/or ANGPTL3 protein levels, for example, a subject that has been diagnosed with hypertriglyceridemia, obesity, hyperlipidemia, abnormal lipid and/or cholesterol metabolism, atherosclerosis, type II diabetes mellitus, cardiovascular disease, coronary artery disease, non-alcoholic steatohepatitis, non-alcoholic fatty liver disease, homozygous and heterozygous familial hypercholesterolemia, statin resistant hypercholesterolemia and other metabolic-related disorders and diseases.

In some embodiments, the subject is administered a therapeutically effective amount of any one or more ANGPTL3 RNAi agents. Treatment of a subject can include therapeutic and/or prophylactic treatment. The subject is administered a therapeutically effective amount of any one or more ANGPTL3 RNAi agents described herein. The subject can be a human, patient, or human patient. The subject may be an adult, adolescent, child, or infant. Administration of a pharmaceutical composition described herein can be to a human being or animal.

The ANGPTL3 RNAi agents described herein can be used to treat at least one symptom in a subject having an ANGPTL3-related disease or disorder, or having a disease or disorder that is mediated at least in part by ANGPTL3 gene expression. In some embodiments, the ANGPTL3 RNAi agents are used to treat or manage a clinical presentation of a subject with an ANGPTL3-related disease or disorder. The subject is administered a therapeutically effective amount of one or more of the ANGPTL3 RNAi agents or ANGPTL3 RNAi agent-containing compositions described herein. In some embodiments, the methods disclosed herein comprise administering a composition comprising an ANGPTL3 RNAi agent described herein to a subject to be treated. In some embodiments, the subject is administered a prophylactically effective amount of any one or more of the described ANGPTL3 RNAi agents, thereby treating the subject by preventing or inhibiting the at least one symptom.

In certain embodiments, the present disclosure provides methods for treatment of diseases, disorders, conditions, or pathological states mediated at least in part by ANGPTL3 gene expression, in a patient in need thereof, wherein the methods include administering to the patient any of the ANGPTL3 RNAi agents described herein.

In some embodiments, the gene expression level and/or mRNA level of an ANGPTL3 gene in a subject to whom a described ANGPTL3 RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the ANGPTL3 RNAi agent or to a subject not receiving the ANGPTL3 RNAi agent. The gene expression level and/or mRNA level in the subject may be reduced in a cell, group of cells, and/or tissue of the subject.

In some embodiments, the ANGPTL3 protein level in a subject to whom a described ANGPTL3 RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the ANGPTL3 RNAi agent or to a subject not receiving the ANGPTL3 RNAi agent. The protein level in the subject may be reduced in a cell, group of cells, tissue, blood, and/or other fluid of the subject.

In some embodiments, the triglyceride (TG) levels in a subject to whom a described ANGPTL3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the ANGPTL3 RNAi agent or to a subject not receiving the ANGPTL3 RNAi agent. The TG level in the subject may be reduced in a cell, group of cells, tissue, blood, and/or other fluid of the subject.

In some embodiments, the total cholesterol levels in a subject to whom a described ANGPTL3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the ANGPTL3 RNAi agent or to a subject not receiving the ANGPTL3 RNAi agent. In some embodiments, the low-density lipoprotein (LDL) cholesterol levels in a subject to whom a described ANGPTL3 RNAi agent has been administered is reduced by at least about 10%, 20%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the ANGPTL3 RNAi agent or to a subject not receiving the ANGPTL3 RNAi agent. The total cholesterol levels and/or LDL cholesterol levels in the subject may be reduced in a cell, group of cells, tissue, blood, and/or other fluid of the subject.

A reduction in ANGPTL3 mRNA levels, ANGPTL3 protein levels, TG levels, cholesterol levels, and LDL cholesterol levels can be assessed by any methods known in the art. As used herein, a reduction or decrease in ANGPTL3 mRNA level and/or protein level are collectively referred to herein as a reduction or decrease in ANGPTL3 or inhibiting or reducing the expression of ANGPTL3. The Examples set forth herein illustrate known methods for assessing inhibition of ANGPTL3 gene expression.

Cells, Tissues, Organs, and Non-Human Organisms

Cells, tissues, organs, and non-human organisms that include at least one of the ANGPTL3 RNAi agents described herein are contemplated. The cell, tissue, organ, or non-human organism is made by delivering the RNAi agent to the cell, tissue, organ or non-human organism.

The above provided embodiments and items are now illustrated with the following, non-limiting examples.

EXAMPLES

Example 1. Synthesis of ANGPTL3 RNAi Agents

ANGPTL3 RNAi agent duplexes shown in Table 5, above, were synthesized in accordance with the following general procedures:

A. Synthesis.

The sense and antisense strands of the RNAi agents were synthesized according to phosphoramidite technology on solid phase used in oligonucleotide synthesis. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA) All RNA and 2'-modified RNA phosphoramidites were purchased from Thermo Fisher Scientific (Milwaukee, Wis., USA) or Hongene Biotech (Shanghai, PRC). The 2'-O-methyl phosphoramidites included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxytrityl-$N^4$-(acetyl)-2'-O-methylcytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-(4,4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. 5'-dimethoxytrityl-2'-O-methyl-inosine-3-O-(2-cyanoethyl-N,N-diisopropylamino) phosphoramidites were purchased from Glen Research (Virginia) or Hongene Biotech. The abasic (3'-O-dimethoxytrityl-2'-deoxyribose-5'-O-(2-cyanoethyl-N,N-diisopropylamino) phosphoramidites were purchased from ChemGenes (Wilmington, Mass., USA) or SAFC (St Louis, Mo., USA) The 5'-O-dimethoxytrityl-$N^2$, $N^6$-(phenoxyacetate)-2'-O-methyl-diaminopurine-3'-O-(2-cyanoethyl-N,N-diisopropylamino) phosphoramidite was obtained from ChemGenes or Hongene Biotech.

Targeting ligand containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed. Unless specifically identified as a "naked" RNAi agent having no targeting ligand present, each of the ANGPTL3 RNAi agent duplexes synthesized and tested in the following Examples utilized N-acetyl-galactosamine as "NAG" in the targeting ligand chemical structures represented in Table 6.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered. DI water or 100 mM ammonium bicarbonate, pH 6.7 and 20% Acetonitrile.

D. Annealing.

Complementary strands were mixed by combining equimolar RNA solutions (sense and antisense) in 1× Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1× Phosphate-Buffered Saline. The solution absorbance at 260 nm was then multiplied by a conversion factor and the dilution factor to determine the duplex concentration. The conversion factor used was either 0.037 mg/(mL·cm) or was calculated from an experimentally determined extinction coefficient.

Example 2. In Vivo Testing of ANGPTL3 RNAi Agents in Mice

To assess the in vivo activity of ANGPTL3 RNAi agents that are designed to target different positions on the ANGPTL3 gene, six- to eight-week-old female C57bl/6 mice were used. Pre-dose serum samples were taken at day −1 after a four hour fast. At day 1, each mouse was given a single subcutaneous administration of 200 μl containing either 3 mg/kg (mpk) of an ANGPTL3 RNAi agent in D5W (dextrose in 5% water), or control (D5W) with no RNAi agent, according to the dosing groups recited in Table 7.

TABLE 7

Dosing Groups of Example 2

| Group | RNAi Agent and Dose | Dosing Regimen |
|---|---|---|
| 1 | D5W (no RNAi agent) | Single injection on day 1 |
| 2 | 3.0 mg/kg AD05342 | Single injection on day 1 |
| 3 | 3.0 mg/kg AD05343 | Single injection on day 1 |
| 4 | 3.0 mg/kg AD05344 | Single injection on day 1 |
| 5 | 3.0 mg/kg AD05306 | Single injection on day 1 |
| 6 | 3.0 mg/kg AD05307 | Single injection on day 1 |
| 7 | 3.0 mg/kg AD05308 | Single injection on day 1 |
| 8 | 3.0 mg/kg AD05309 | Single injection on day 1 |
| 9 | 3.0 mg/kg AD05310 | Single injection on day 1 |
| 10 | 3.0 mg/kg AD05311 | Single injection on day 1 |
| 11 | 3.0 mg/kg AD05312 | Single injection on day 1 |

Each of the RNAi agents included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Three (3) mice in each group were tested (n=3). Serum was collected on days 8, 13, 22, 29, and day 36 (for Groups 1 and 5-11 only). Mice were fasted for four hours prior to each collection. ANGPTL3 protein levels in serum were measured by ELISA assay (R&D Systems), according to the manufacturer's recommendations. Triglycerides, high-density lipoprotein (HDL), and total cholesterol in serum were measured on a Cobas® Integra 400 (Roche Diagnostics), according to the manufacturer's recommendations.

The ANGPTL3 protein levels, triglyceride levels, HDL levels, and total cholesterol levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 8 through 11:

TABLE 8

Average ANGPTL3 Protein Normalized to Pre-Treatment and Control from Example 2

| | Day 8 | | Day 13 | | Day 22 | | Day 29 | | Day 36 | |
|---|---|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (D5W) | 1.000 | 0.338 | 1.000 | 0.234 | 1.000 | 0.341 | 1.000 | 0.217 | 1.000 | 0.226 |
| Group 2 (3.0 mg/kg AD05342) | 0.640 | 0.072 | 0.720 | 0.122 | 0.811 | 0.041 | 0.907 | 0.020 | | |
| Group 3 (3.0 mg/kg AD05343) | 0.939 | 0.238 | 1.024 | 0.371 | 1.146 | 0.116 | 0.914 | 0.120 | | |

TABLE 8-continued

Average ANGPTL3 Protein Normalized to Pre-Treatment and Control from Example 2

| Group ID | Day 8 | | Day 13 | | Day 22 | | Day 29 | | Day 36 | |
|---|---|---|---|---|---|---|---|---|---|---|
| | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 4 (3.0 mg/kg AD05344) | 0.521 | 0.040 | 0.584 | 0.164 | 0.731 | 0.150 | 0.829 | 0.139 | | |
| Group 5 (3.0 mg/kg AD05306) | 0.113 | 0.019 | 0.135 | 0.045 | 0.154 | 0.022 | 0.240 | 0.054 | 0.292 | 0.079 |
| Group 6 (3.0 mg/kg AD05307) | 0.117 | 0.072 | 0.120 | 0.069 | 0.134 | 0.054 | 0.206 | 0.119 | 0.216 | 0.086 |
| Group 7 (3.0 mg/kg AD05308) | 0.106 | 0.030 | 0.076 | 0.043 | 0.084 | 0.048 | 0.088 | 0.030 | 0.167 | 0.075 |
| Group 8 (3.0 mg/kg AD05309) | 0.197 | 0.055 | 0.240 | 0.028 | 0.206 | 0.066 | 0.274 | 0.112 | 0.321 | 0.092 |
| Group 9 (3.0 mg/kg AD05310) | 0.196 | 0.058 | 0.331 | 0.118 | 0.343 | 0.171 | 0.589 | 0.289 | 0.637 | 0.273 |
| Group 10 (3.0 mg/kg AD05311) | 0.143 | 0.025 | 0.206 | 0.055 | 0.183 | 0.019 | 0.288 | 0.050 | 0.389 | 0.020 |
| Group 11 (3.0 mg/kg AD05312) | 0.162 | 0.073 | 0.216 | 0.069 | 0.229 | 0.077 | 0.326 | 0.079 | 0.386 | 0.072 |

TABLE 9

Average Triglycerides Normalized to Pre-Treatment and Control from Example 2

| Group ID | Day 8 | | Day 13 | | Day 22 | | Day 29 | | Day 36 | |
|---|---|---|---|---|---|---|---|---|---|---|
| | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 1 (D5W) | 1.000 | 0.047 | 1.000 | 0.016 | 1.000 | 0.068 | 1.000 | 0.144 | 1.000 | 0.206 |
| Group 2 (3.0 mg/kg AD05342) | 0.726 | 0.028 | 0.870 | 0.101 | 0.832 | 0.119 | 0.771 | 0.159 | N/A | N/A |
| Group 3 (3.0 mg/kg AD05343) | 0.636 | 0.186 | 0.878 | 0.301 | 0.591 | 0.228 | 0.810 | 0.146 | N/A | N/A |
| Group 4 (3.0 mg/kg AD05344) | 0.709 | 0.131 | 0.821 | 0.094 | 0.617 | 0.160 | 0.783 | 0.105 | N/A | N/A |
| Group 5 (3.0 mg/kg AD05306) | 0.571 | 0.083 | 0.752 | 0.088 | 0.712 | 0.167 | 0.742 | 0.019 | 0.768 | 0.143 |
| Group 6 (3.0 mg/kg AD05307) | 0.504 | 0.084 | 0.655 | 0.047 | 0.459 | 0.050 | 0.629 | 0.122 | 0.602 | 0.076 |
| Group 7 (3.0 mg/kg AD05308) | 0.375 | 0.026 | 0.554 | 0.040 | 0.399 | 0.028 | 0.473 | 0.099 | 0.430 | 0.045 |
| Group 8 (3.0 mg/kg AD05309) | 0.390 | 0.060 | 0.604 | 0.092 | 0.406 | 0.047 | 0.587 | 0.129 | 0.581 | 0.161 |
| Group 9 (3.0 mg/kg AD05310) | 0.494 | 0.142 | 0.538 | 0.051 | 0.443 | 0.076 | 0.482 | 0.029 | 0.535 | 0.090 |
| Group 10 (3.0 mg/kg AD05311) | 0.402 | 0.077 | 0.640 | 0.095 | 0.518 | 0.052 | 0.614 | 0.136 | 0.567 | 0.092 |
| Group 11 (3.0 mg/kg AD05312) | 0.379 | 0.117 | 0.539 | 0.119 | 0.417 | 0.044 | 0.558 | 0.087 | 0.483 | 0.081 |

TABLE 10

Average Total Cholesterol Normalized to Pre-Treatment and Control from Example 2

| Group ID | Day 8 | | Day 13 | | Day 22 | | Day 29 | | Day 36 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.067 | 1.000 | 0.067 | 1.000 | 0.132 | 1.000 | 0.047 | 1.000 | 0.019 |
| Group 2 (3.0 mg/kg AD05342) | 1.051 | 0.105 | 1.111 | 0.052 | 0.988 | 0.117 | 0.974 | 0.169 | N/A | N/A |
| Group 3 (3.0 mg/kg AD05343) | 1.234 | 0.104 | 1.290 | 0.107 | 1.222 | 0.043 | 1.105 | 0.106 | N/A | N/A |
| Group 4 (3.0 mg/kg AD05344) | 1.062 | 0.162 | 1.033 | 0.115 | 1.101 | 0.035 | 1.017 | 0.050 | N/A | N/A |

TABLE 10-continued

Average Total Cholesterol Normalized to Pre-Treatment and Control from Example 2

| Group ID | Day 8 | | Day 13 | | Day 22 | | Day 29 | | Day 36 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 5 (3.0 mg/kg AD05306) | 0.686 | 0.124 | 0.733 | 0..089 | 0.800 | 0.081 | 0.810 | 0.076 | 0.938 | 0.078 |
| Group 6 (3.0 mg/kg AD05307) | 0.649 | 0.160 | 0.570 | 0.057 | 0.628 | 0.015 | 0.753 | 0.099 | 0.755 | 0.134 |
| Group 7 (3.0 mg/kg AD05308) | 0.671 | 0.037 | 0.645 | 0.129 | 0.621 | 0.160 | 0.669 | 0.088 | 0.905 | 0.171 |
| Group 8 (3.0 mg/kg AD05309) | 0.677 | 0.093 | 0.817 | 0.054 | 0.703 | 0.011 | 0.842 | 0.052 | 0.951 | 0.153 |
| Group 9 (3.0 mg/kg AD05310) | 0.844 | 0.149 | 0.913 | 0.135 | 0.911 | 0.162 | 0.932 | 0.102 | 1.114 | 0.183 |
| Group 10 (3.0 mg/kg AD05311) | 0.659 | 0.068 | 0.757 | 0.124 | 0.666 | 0.063 | 0.778 | 0.093 | 0.998 | 0.160 |
| Group 11 (3.0 mg/kg AD05312) | 0.730 | 0.150 | 0.826 | 0.153 | 0.704 | 0.062 | 0.876 | 0.080 | 0.978 | 0.068 |

TABLE 11

Average HDL Normalized to Pre-Treatment and Control from Example 2

| Group ID | Day 8 | | Day 13 | | Day 22 | | Day 29 | | Day 36 | |
|---|---|---|---|---|---|---|---|---|---|---|
| | Avg HDL | Std Dev (+/−) | Avg HDL | Std Dev (+/−) | Avg HDL | Std Dev (+/−) | Avg HDL | Std Dev (+/−) | Avg HDL | Std Dev (+/−) |
| Group 1 (D5W) | 1.000 | 0.069 | 1.000 | 0.068 | 1.000 | 0.143 | 1.000 | 0.056 | 1.000 | 0.007 |
| Group 2 (3.0 mg/kg AD05342) | 1.063 | 0.088 | 1.085 | 0.045 | 0.974 | 0.111 | 1.004 | 0.199 | N/A | N/A |
| Group 3 (3.0 mg/kg AD05343) | 1.253 | 0.116 | 1.250 | 0.108 | 1.202 | 0.039 | 1.069 | 0.103 | N/A | N/A |
| Group 4 (3.0 mg/kg AD05344) | 1.089 | 0.141 | 1.023 | 0.127 | 1.101 | 0.064 | 1.023 | 0.032 | N/A | N/A |
| Group 5 (3.0 mg/kg AD05306) | 0.654 | 0.119 | 0.643 | 0.063 | 0.721 | 0.059 | 0.756 | 0.052 | 0.856 | 0.091 |
| Group 6 (3.0 mg/kg AD05307) | 0.633 | 0.151 | 0.524 | 0.048 | 0.588 | 0.023 | 0.724 | 0.082 | 0.702 | 0.128 |
| Group 7 (3.0 mg/kg AD05308) | 0.634 | 0.035 | 0.583 | 0.138 | 0.572 | 0.161 | 0.606 | 0.086 | 0.854 | 0.177 |
| Group 8 (3.0 mg/kg AD05309) | 0.665 | 0.094 | 0.791 | 0.059 | 0.688 | 0.021 | 0.826 | 0.007 | 0.901 | 0.115 |
| Group 9 (3.0 mg/kg AD05310) | 0.792 | 0.131 | 0.867 | 0.122 | 0.867 | 0.161 | 0.914 | 0.098 | 1.045 | 0.158 |
| Group 10 (3.0 mg/kg AD05311) | 0.648 | 0.063 | 0.708 | 0.120 | 0.621 | 0.065 | 0.755 | 0.086 | 0.953 | 0.178 |
| Group 11 (3.0 mg/kg AD05312) | 0.671 | 0.158 | 0.761 | 0.159 | 0.652 | 0.059 | 0.849 | 0.089 | 0.958 | 0.048 |

The ANGPTL3 RNAi agents AD05342 and AD05343 (Groups 2 and 3) included nucleotide sequences that were designed to inhibit expression of an ANGPTL3 gene at position 743 of the gene; ANGPTL3 RNAi agent AD05344 (Group 4) included nucleotide sequences designed to inhibit expression of an ANGPTL3 gene at position 744 of the gene; ANGPTL3 RNAi agents AD05306 and AD05307 (Groups 5 and 6) included nucleotide sequences designed to inhibit expression of an ANGPTL3 gene at position 921 of the gene; ANGPTL3 RNAi agents AD05308 and AD05309 (Groups 7 and 8) included nucleotide sequences designed to inhibit expression of an ANGPTL3 gene at position 922 of the gene; ANGPTL3 RNAi agents AD05310 and AD05311 (Groups 9 and 10) included nucleotide sequences designed to inhibit expression of an ANGPTL3 gene at position 1302 of the gene; and ANGPTL3 RNAi agents AD05312 (Group 11) included nucleotide sequences designed to inhibit expression of an ANGPTL3 gene at position 1304 of the gene. (See SEQ ID NO:1 for the ANGPTL3 gene sequence referenced).

As shown in Table 8, above, each of the RNAi agents in at least Groups 5, 6, 7, 8, 9, 10, and 11 showed ANGPTL3 inhibition. For example, on day 29, Group 7 (ANGPTL3 RNAi agent AD05308), which included nucleotide sequences designed to target position 922 of the ANGPTL3 gene, showed an approximately 91% percent reduction (0.088) in ANGPTL3 protein compared to control. Similarly, both Group 5 (ANGPTL3 RNAi agent AD05306) and Group 6 (ANGPTL3 RNAi agent AD05307), which were designed to target position 921 of the ANGPTL3 gene, showed greater than 75% reduction in ANGPTL3 protein at day 29 (i.e., 0.240 and 0.206).

Example 3. In Vivo Testing of ANGPTL3 RNAi Agents in Mice

To assess the in vivo activity of ANGPTL3 RNAi agents that are designed to target positions 921 and 922 on the ANGPTL3 gene, six- to eight-week-old female C57bl/6 mice were used. Pre-dose serum samples were taken at day −1 after a four hour fast. At day 1, each mouse was given a single subcutaneous administration of 200 μl containing either 1 mg/kg (mpk) of an ANGPTL3 RNAi agent in D5W (dextrose in 5% water), or control (D5W) with no RNAi agent, according to the dosing groups recited in Table 12.

TABLE 12

Dosing Groups of Example 3

| Group | RNAi Agent and Dose | Dosing Regimen |
|---|---|---|
| 1 | D5W (no RNAi agent) | Single injection on day 1 |
| 2 | 1.0 mg/kg AD05307 | Single injection on day 1 |
| 3 | 1.0 mg/kg AD05410 | Single injection on day 1 |
| 4 | 1.0 mg/kg AD05411 | Single injection on day 1 |
| 5 | 1.0 mg/kg AD05412 | Single injection on day 1 |
| 6 | 1.0 mg/kg AD05413 | Single injection on day 1 |
| 7 | 1.0 mg/kg AD05414 | Single injection on day 1 |
| 8 | 1.0 mg/kg AD05415 | Single injection on day 1 |
| 9 | 1.0 mg/kg AD05416 | Single injection on day 1 |
| 10 | 1.0 mg/kg AD05417 | Single injection on day 1 |
| 11 | 1.0 mg/kg AD05418 | Single injection on day 1 |
| 12 | 1.0 mg/kg AD05308 | Single injection on day 1 |
| 13 | 1.0 mg/kg AD05419 | Single injection on day 1 |
| 14 | 1.0 mg/kg AD05420 | Single injection on day 1 |
| 15 | 1.0 mg/kg AD05421 | Single injection on day 1 |
| 16 | 1.0 mg/kg AD05422 | Single injection on day 1 |
| 17 | 1.0 mg/kg AD05423 | Single injection on day 1 |
| 18 | 1.0 mg/kg AD05424 | Single injection on day 1 |
| 19 | 1.0 mg/kg AD05425 | Single injection on day 1 |

Each of the RNAi agents included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Three (3) mice in each group were tested (n=3). Serum was collected on days 9, 15, 22, and 29. Mice were fasted for four hours prior to each collection. ANGPTL3 protein levels in serum were measured by ELISA assay (R&D Systems), according to the manufacturer's recommendations. Triglycerides, high-density lipoprotein (HDL), and total cholesterol in serum were measured on a Cobas® Integra 400 (Roche Diagnostics), according to the manufacturer's recommendations.

The ANGPTL3 protein levels, triglyceride levels, HDL levels, and total cholesterol levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 13 through 16:

TABLE 13

Average ANGPTL3 Protein Normalized to Pre-Treatment and Control from Example 3

| | Day 8 | | Day 15 | | Day 22 | | Day 29 | |
|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (D5W) | 1.000 | 0.294 | 1.000 | 0.154 | 1.000 | 0.167 | 1.000 | 0.191 |
| Group 2 (1.0 mg/kg AD05307) | 0.323 | 0.117 | 0.311 | 0.098 | 0.346 | 0.142 | 0.486 | 0.096 |
| Group 3 (1.0 mg/kg AD05410) | 0.376 | 0.042 | 0.406 | 0.140 | 0.515 | 0.089 | 0.571 | 0.085 |
| Group 4 (1.0 mg/kg AD05411) | 0.750 | 0.066 | 0.822 | 0.176 | 0.670 | 0.091 | 0.821 | 0.206 |
| Group 5 (1.0 mg/kg AD05412) | 0.289 | 0.066 | 0.348 | 0.073 | 0.387 | 0.075 | 0.564 | 0.111 |
| Group 6 (1.0 mg/kg AD05413) | 0.274 | 0.054 | 0.348 | 0.025 | 0.373 | 0.051 | 0.500 | 0.102 |
| Group 7 (1.0 mg/kg AD05414) | 0.559 | 0.292 | 0.608 | 0.209 | 0.753 | 0.275 | 0.706 | 0.171 |
| Group 8 (1.0 mg/kg AD05415) | 0.291 | 0.079 | 0.340 | 0.065 | 0.415 | 0.015 | 0.498 | 0.100 |
| Group 9 (1.0 mg/kg AD05416) | 0.325 | 0.141 | 0.382 | 0.146 | 0.417 | 0.189 | 0.607 | 0.128 |
| Group 10 (1.0 mg/kg AD05417) | 0.352 | 0.103 | 0.287 | 0.057 | 0.371 | 0.053 | 0.416 | 0.111 |
| Group 11 (1.0 mg/kg AD05418) | 0.236 | 0.049 | 0.290 | 0.084 | 0.394 | 0.058 | 0.517 | 0.113 |
| Group 12 (1.0 mg/kg AD05308) | 0.196 | 0.008 | 0.202 | 0.040 | 0.209 | 0.027 | 0.309 | 0.026 |
| Group 13 (1.0 mg/kg AD05419) | 0.268 | 0.020 | 0.305 | 0.101 | 0.404 | 0.037 | 0.361 | 0.024 |
| Group 14 (1.0 mg/kg AD05420) | 0.391 | 0.106 | 0.548 | 0.233 | 0.564 | 0.240 | 0.572 | 0.167 |

TABLE 13-continued

Average ANGPTL3 Protein Normalized to Pre-Treatment and Control from Example 3

| Group ID | Day 8 Avg ANGPTL3 | Day 8 Std Dev (+/−) | Day 15 Avg ANGPTL3 | Day 15 Std Dev (+/−) | Day 22 Avg ANGPTL3 | Day 22 Std Dev (+/−) | Day 29 Avg ANGPTL3 | Day 29 Std Dev (+/−) |
|---|---|---|---|---|---|---|---|---|
| Group 15 (1.0 mg/kg AD05421) | 0.308 | 0.089 | 0.407 | 0.115 | 0.383 | 0.058 | 0.570 | 0.117 |
| Group 16 (1.0 mg/kg AD05422) | 0.463 | 0.130 | 0.758 | 0.205 | 0.717 | 0.144 | 0.921 | 0.184 |
| Group 17 (1.0 mg/kg AD05423) | 0.302 | 0.055 | 0.353 | 0.079 | 0.331 | 0.067 | 0.454 | 0.137 |
| Group 18 (1.0 mg/kg AD05424) | 0.260 | 0.031 | 0.308 | 0.077 | 0.310 | 0.053 | 0.375 | 0.006 |
| Group 19 (1.0 mg/kg AD05425) | 0.319 | 0.056 | 0.383 | 0.071 | 0.423 | 0.108 | 0.518 | 0.190 |

TABLE 14

Average Triglycerides Normalized to Pre-Treatment and Control from Example 3

| Group ID | Day 8 Avg TG | Day 8 Std Dev (+/−) | Day 15 Avg TG | Day 15 Std Dev (+/−) | Day 22 Avg TG | Day 22 Std Dev (+/−) | Day 29 Avg TG | Day 29 Std Dev (+/−) |
|---|---|---|---|---|---|---|---|---|
| Group 1 (D5W) | 1.000 | 0.117 | 1.000 | 0.122 | 1.000 | 0.184 | 1.000 | 0.186 |
| Group 2 (1.0 mg/kg AD05307) | 0.786 | 0.027 | 0.692 | 0.041 | 0.903 | 0.153 | 0.852 | 0.054 |
| Group 3 (1.0 mg/kg AD05410) | 0.873 | 0.152 | 1.005 | 0.133 | 1.259 | 0.288 | 1.046 | 0.167 |
| Group 4 (1.0 mg/kg AD05411) | 1.302 | 0.214 | 1.311 | 0.181 | 1.687 | 0.390 | 1.498 | 0.174 |
| Group 5 (1.0 mg/kg AD05412) | 0.642 | 0.019 | 0.617 | 0.052 | 1.139 | 0.601 | 0.780 | 0.216 |
| Group 6 (1.0 mg/kg AD05413) | 0.720 | 0.028 | 0.728 | 0.097 | 0.889 | 0.058 | 0.925 | 0.087 |
| Group 7 (1.0 mg/kg AD05414) | 0.765 | 0.160 | 0.660 | 0.169 | 0.905 | 0.281 | 0.626 | 0.096 |
| Group 8 (1.0 mg/kg AD05415) | 0.675 | 0.173 | 0.780 | 0.204 | 0.877 | 0.196 | 0.647 | 0.048 |
| Group 9 (1.0 mg/kg AD05416) | 0.785 | 0.136 | 0.821 | 0.100 | 0.944 | 0.104 | 0.787 | 0.116 |
| Group 10 (1.0 mg/kg AD05417) | 0.898 | 0.054 | 0.906 | 0.194 | 1.121 | 0.227 | 0.898 | 0.259 |
| Group 11 (1.0 mg/kg AD05418) | 0.718 | 0.035 | 0.791 | 0.124 | 0.855 | 0.090 | 0.881 | 0.123 |
| Group 12 (1.0 mg/kg AD05308) | 0.952 | 0.319 | 0.749 | 0.262 | 0.854 | 0.239 | 1.009 | 0.136 |
| Group 13 (1.0 mg/kg AD05419) | 0.652 | 0.024 | 0.786 | 0.074 | 0.794 | 0.092 | 0.901 | 0.045 |
| Group 14 (1.0 mg/kg AD05420) | 0.644 | 0.234 | 0.861 | 0.244 | 0.978 | 0.313 | 0.836 | 0.260 |
| Group 15 (1.0 mg/kg AD05421) | 0.597 | 0.253 | 0.586 | 0.085 | 0.796 | 0.048 | 0.700 | 0.088 |
| Group 16 (1.0 mg/kg AD05422) | 0.698 | 0.137 | 0.594 | 0.066 | 0.972 | 0.129 | 0.837 | 0.073 |
| Group 17 (1.0 mg/kg AD05423) | 0.811 | 0.140 | 0.593 | 0.076 | 1.157 | 0.429 | 0.848 | 0.031 |
| Group 18 (1.0 mg/kg AD05424) | 0.847 | 0.219 | 0.667 | 0.173 | 1.171 | 0.297 | 0.898 | 0.264 |
| Group 19 (1.0 mg/kg AD05425) | 0.710 | 0.063 | 0.517 | 0.018 | 0.721 | 0.149 | 0.682 | 0.077 |

TABLE 15

Average Total Cholesterol Normalized to Pre-Treatment and Control from Example 3

| Group ID | Day 8 | | Day 15 | | Day 22 | | Day 29 | |
| --- | --- | --- | --- | --- | --- | --- | --- | --- |
| | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.060 | 1.000 | 0.047 | 1.000 | 0.079 | 1.000 | 0.115 |
| Group 2 (1.0 mg/kg AD05307) | 0.940 | 0.181 | 0.840 | 0.031 | 0.948 | 0.086 | 1.088 | 0.051 |
| Group 3 (1.0 mg/kg AD05410) | 0.929 | 0.071 | 0.881 | 0.087 | 1.022 | 0.124 | 0.945 | 0.134 |
| Group 4 (1.0 mg/kg AD05411) | 1.043 | 0.013 | 0.905 | 0.060 | 1.017 | 0.056 | 1.071 | 0.060 |
| Group 5 (1.0 mg/kg AD05412) | 0.886 | 0.117 | 0.857 | 0.022 | 0.972 | 0.104 | 1.063 | 0.155 |
| Group 6 (1.0 mg/kg AD05413) | 0.940 | 0.095 | 0.893 | 0.027 | 0.982 | 0.106 | 0.854 | 0.065 |
| Group 7 (1.0 mg/kg AD05414) | 1.076 | 0.197 | 0.919 | 0.103 | 1.064 | 0.093 | 0.969 | 0.088 |
| Group 8 (1.0 mg/kg AD05415) | 0.897 | 0.063 | 0.817 | 0.059 | 0.927 | 0.026 | 0.986 | 0.109 |
| Group 9 (1.0 mg/kg AD05416) | 0.893 | 0.104 | 0.841 | 0.080 | 0.950 | 0.118 | 0.925 | 0.116 |
| Group 10 (1.0 mg/kg AD05417) | 1.045 | 0.074 | 0.838 | 0.093 | 1.054 | 0.082 | 1.045 | 0.076 |
| Group 11 (1.0 mg/kg AD05418) | 0.783 | 0.032 | 0.842 | 0.096 | 0.916 | 0.049 | 0.953 | 0.090 |
| Group 12 (1.0 mg/kg AD05308) | 0.872 | 0.071 | 0.768 | 0.034 | 1.048 | 0.424 | 0.978 | 0.088 |
| Group 13 (1.0 mg/kg AD05419) | 0.876 | 0.016 | 0.848 | 0.060 | 1.106 | 0.102 | 0.985 | 0.051 |
| Group 14 (1.0 mg/kg AD05420) | 1.036 | 0.183 | 0.950 | 0.188 | 1.014 | 0.122 | 1.033 | 0.125 |
| Group 15 (1.0 mg/kg AD05421) | 0.893 | 0.059 | 0.914 | 0.045 | 1.011 | 0.019 | 1.049 | 0.020 |
| Group 16 (1.0 mg/kg AD05422) | 1.034 | 0.143 | 1.042 | 0.096 | 0.982 | 0.063 | 1.130 | 0.153 |
| Group 17 (1.0 mg/kg AD05423) | 1.004 | 0.055 | 0.997 | 0.129 | 0.973 | 0.076 | 0.947 | 0.087 |
| Group 18 (1.0 mg/kg AD05424) | 0.762 | 0.048 | 0.776 | 0.118 | 0.824 | 0.080 | 0.847 | 0.111 |
| Group 19 (1.0 mg/kg AD05425) | 1.032 | 0.127 | 0.835 | 0.061 | 0.954 | 0.138 | 1.045 | 0.161 |

TABLE 16

Average HDL Normalized to Pre-Treatment and Control from Example 3

| Group ID | Day 8 | | Day 15 | | Day 22 | | Day 29 | |
| --- | --- | --- | --- | --- | --- | --- | --- | --- |
| | Avg HDL | Std Dev (+/−) | Avg HDL | Std Dev (+/−) | Avg HDL | Std Dev (+/−) | Avg HDL | Std Dev (+/−) |
| Group 1 (D5W) | 1.000 | 0.060 | 1.000 | 0.043 | 1.000 | 0.067 | 1.000 | 0.120 |
| Group 2 (1.0 mg/kg AD05307) | 0.916 | 0.181 | 0.856 | 0.009 | 0.913 | 0.083 | 1.053 | 0.026 |
| Group 3 (1.0 mg/kg AD05410) | 0.904 | 0.062 | 0.878 | 0.065 | 1.003 | 0.121 | 0.916 | 0.103 |
| Group 4 (1.0 mg/kg AD05411) | 1.025 | 0.011 | 0.910 | 0.059 | 0.997 | 0.065 | 1.007 | 0.025 |
| Group 5 (1.0 mg/kg AD05412) | 0.869 | 0.190 | 0.875 | 0.065 | 0.954 | 0.128 | 1.044 | 0.159 |
| Group 6 (1.0 mg/kg AD05413) | 0.935 | 0.072 | 0.916 | 0.023 | 0.964 | 0.091 | 0.867 | 0.066 |
| Group 7 (1.0 mg/kg AD05414) | 1.059 | 0.163 | 0.960 | 0.095 | 1.079 | 0.086 | 0.993 | 0.083 |
| Group 8 (1.0 mg/kg AD05415) | 0.889 | 0.048 | 0.832 | 0.047 | 0.942 | 0.053 | 1.013 | 0.071 |
| Group 9 (1.0 mg/kg AD05416) | 0.848 | 0.112 | 0.838 | 0.077 | 0.921 | 0.112 | 0.928 | 0.098 |
| Group 10 (1.0 mg/kg AD05417) | 0.986 | 0.074 | 0.820 | 0.076 | 0.996 | 0.095 | 1.026 | 0.089 |
| Group 11 (1.0 mg/kg AD05418) | 0.766 | 0.049 | 0.823 | 0.094 | 0.910 | 0.064 | 0.916 | 0.098 |

TABLE 16-continued

Average HDL Normalized to Pre-Treatment and Control from Example 3

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 12 (1.0 mg/kg AD05308) | 0.838 | 0.053 | 0.754 | 0.019 | 0.739 | 0.052 | 0.953 | 0.090 |
| Group 13 (1.0 mg/kg AD05419) | 0.865 | 0.022 | 0.851 | 0.072 | 1.093 | 0.097 | 0.991 | 0.061 |
| Group 14 (1.0 mg/kg AD05420) | 1.021 | 0.155 | 0.967 | 0.164 | 1.020 | 0.111 | 1.039 | 0.123 |
| Group 15 (1.0 mg/kg AD05421) | 0.865 | 0.052 | 0.920 | 0.068 | 0.972 | 0.037 | 1.043 | 0.054 |
| Group 16 (1.0 mg/kg AD05422) | 0.987 | 0.115 | 1.032 | 0.080 | 0.953 | 0.052 | 1.101 | 0.124 |
| Group 17 (1.0 mg/kg AD05423) | 0.968 | 0.069 | 0.999 | 0.126 | 0.972 | 0.056 | 0.945 | 0.072 |
| Group 18 (1.0 mg/kg AD05424) | 0.760 | 0.077 | 0.790 | 0.099 | 0.831 | 0.105 | 0.854 | 0.101 |
| Group 19 (1.0 mg/kg AD05425) | 0.985 | 0.115 | 0.840 | 0.080 | 0.929 | 0.145 | 1.022 | 0.150 |

While having different sequences and modification patterns, the ANGPTL3 RNAi agents in Groups 2 through 11 included nucleotide sequences that were each designed to inhibit expression of an ANGPTL3 gene at position 921 of the gene; and the ANGPTL3 RNAi agents in Groups 12 through 19 included nucleotide sequences that were each designed to inhibit expression of an ANGPTL3 gene at position 922 of the gene. (See SEQ ID NO:1 for the ANGPTL3 gene sequence referenced). As shown in Table 12 above, each of the RNAi agents achieved inhibition of ANGPTL3 as compared to control. For example, Group 12 (ANGPTL3 RNAi agent AD05308) achieved nearly an 80% reduction in ANGPTL3 protein levels compared in control (0.209) on day 22.

Example 4. In Vivo Testing of ANGPTL3 RNAi Agents in Mice

To assess the in vivo activity of ANGPTL3 RNAi agents that are designed to target additional positions on the ANGPTL3 gene, six- to eight-week-old female C57bl/6 mice were used. Pre-dose serum samples were taken at day −1 after a four hour fast. At day 1, each mouse was given a single subcutaneous administration of 200 µl containing either 1 mg/kg (mpk) or 0.5 mg/kg (mpk) of an ANGPTL3 RNAi agent in D5W (dextrose in 5% water), or control (D5W) with no RNAi agent, according to the dosing groups recited in Table 17.

TABLE 17

Dosing Groups of Example 4

| Group | RNAi Agent and Dose | Dosing Regimen |
|---|---|---|
| 1 | D5W (no RNAi agent) | Single injection on day 1 |
| 2 | 1.0 mg/kg AD05487 | Single injection on day 1 |
| 3 | 1.0 mg/kg AD05488 | Single injection on day 1 |
| 4 | 1.0 mg/kg AD05489 | Single injection on day 1 |
| 5 | 1.0 mg/kg AD05490 | Single injection on day 1 |
| 6 | 1.0 mg/kg AD05491 | Single injection on day 1 |
| 7 | 1.0 mg/kg AD05492 | Single injection on day 1 |
| 8 | 1.0 mg/kg AD05493 | Single injection on day 1 |
| 9 | 1.0 mg/kg AD05494 | Single injection on day 1 |
| 10 | 1.0 mg/kg AD05495 | Single injection on day 1 |
| 11 | 1.0 mg/kg AD05308 | Single injection on day 1 |

TABLE 17-continued

Dosing Groups of Example 4

| Group | RNAi Agent and Dose | Dosing Regimen |
|---|---|---|
| 12 | 0.5 mg/kg AD05308 | Single injection on day 1 |
| 13 | 1.0 mg/kg AD05418 | Single injection on day 1 |

Each of the RNAi agents included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Three (3) mice in each group were tested (n=3). Serum was collected on days 8, 15, 22, 29, and day 43 (Groups 1-3, 9, and 11-13 only). Mice were fasted for four hours prior to each collection. ANGPTL3 protein levels in serum were measured by ELISA assay (R&D Systems), according to the manufacturer's recommendations. Triglycerides, high-density lipoprotein (HDL), and total cholesterol in serum were measured on a Cobas® Integra 400 (Roche Diagnostics), according to the manufacturer's recommendations.

The ANGPTL3 protein levels, triglyceride levels, HDL levels, and total cholesterol levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 18 through 22:

TABLE 18

Average ANGPTL3 Protein Normalized to Pre-Treatment and Control from Example 4

| Group ID | Day 8 | | Day 15 | | Day 22 | | Day 29 | | Day 43 | |
| --- | --- | --- | --- | --- | --- | --- | --- | --- | --- | --- |
| | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (D5W) | 1.000 | 0.355 | 1.000 | 0.428 | 1.000 | 0.431 | 1.000 | 0.443 | 1.000 | 0.256 |
| Group 2 (1.0 mg/kg AD05487) | 0.173 | 0.022 | 0.170 | 0.056 | 0.138 | 0.030 | 0.226 | 0.034 | 0.477 | 0.052 |
| Group 3 (1.0 mg/kg AD05488) | 0.090 | 0.011 | 0.070 | 0.023 | 0.092 | 0.011 | 0.124 | 0.024 | 0.254 | 0.074 |
| Group 4 (1.0 mg/kg AD05489) | 0.875 | 0.229 | 0.933 | 0.181 | 0.911 | 0.288 | 1.009 | 0.331 | | |
| Group 5 (1.0 mg/kg AD05490) | 0.821 | 0.064 | 0.826 | 0.091 | 0.773 | 0.216 | 0.837 | 0.173 | | |
| Group 6 (1.0 mg/kg AD05491) | 0.822 | 0.030 | 0.739 | 0.180 | 0.851 | 0.128 | 1.034 | 0.212 | | |
| Group 7 (1.0 mg/kg AD05492) | 0.498 | 0.016 | 0.575 | 0.018 | 0.561 | 0.025 | 0.716 | 0.031 | | |
| Group 8 (1.0 mg/kg AD05493) | 0.667 | 0.078 | 0.774 | 0.084 | 0.765 | 0.129 | 0.802 | 0.250 | | |
| Group 9 (1.0 mg/kg AD05494) | 0.174 | 0.023 | 0.192 | 0.027 | 0.238 | 0.044 | 0.230 | 0.053 | 0.467 | 0.056 |
| Group 10 (1.0 mg/kg AD05495) | 0.448 | 0.263 | 0.680 | 0.526 | 0.721 | 0.609 | 0.745 | 0.319 | | |
| Group 11 (1.0 mg/kg AD05308) | 0.299 | 0.103 | 0.298 | 0.116 | 0.252 | 0.100 | 0.322 | 0.097 | 0.643 | 0.277 |
| Group 12 (0.5 mg/kg AD05308) | 0.340 | 0.038 | 0.310 | 0.030 | 0.319 | 0.021 | 0.345 | 0.040 | 0.582 | 0.020 |
| Group 13 (1.0 mg/kg AD05418) | 0.258 | 0.033 | 0.270 | 0.027 | 0.387 | 0.064 | 0.407 | 0.010 | 0.847 | 0.054 |

TABLE 19

Average Triglycerides Normalized to Pre-Treatment and Control from Example 4

| Group ID | Day 8 | | Day 15 | | Day 22 | | Day 29 | | Day 43 | |
| --- | --- | --- | --- | --- | --- | --- | --- | --- | --- | --- |
| | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 1 (D5W) | 1.000 | 0.085 | 1.000 | 0.013 | 1.000 | 0.291 | 1.000 | 0.131 | 1.000 | 0.193 |
| Group 2 (1.0 mg/kg AD05487) | 0.776 | 0.051 | 0.912 | 0.117 | 0.761 | 0.070 | 0.556 | 0.228 | 0.757 | 0.119 |
| Group 3 (1.0 mg/kg AD05488) | 0.624 | 0.040 | 0.795 | 0.106 | 0.837 | 0.047 | 0.721 | 0.077 | 0.901 | 0.316 |
| Group 4 (1.0 mg/kg AD05489) | 0.877 | 0.065 | 1.424 | 0.231 | 1.189 | 0.155 | 1.216 | 0.030 | | |
| Group 5 (1.0 mg/kg AD05490) | 0.930 | 0.196 | 1.341 | 0.359 | 1.385 | 0.215 | 0.820 | 0.424 | | |
| Group 6 (1.0 mg/kg AD05491) | 1.240 | 0.334 | 1.896 | 0.376 | 1.590 | 0.311 | 1.238 | 0.071 | | |
| Group 7 (1.0 mg/kg AD05492) | 0.775 | 0.086 | 0.991 | 0.154 | 1.085 | 0.128 | 1.188 | 0.129 | | |
| Group 8 (1.0 mg/kg AD05493) | 1.255 | 0.320 | 1.459 | 0.436 | 1.326 | 0.494 | 1.190 | 0.281 | | |
| Group 9 (1.0 mg/kg AD05494) | 0.667 | 0.054 | 1.118 | 0.249 | 1.341 | 0.198 | 0.909 | 0.183 | 0.995 | 0.256 |
| Group 10 (1.0 mg/kg AD05495) | 0.864 | 0.061 | 1.343 | 0.211 | 1.294 | 0.097 | 1.116 | 0.444 | | |
| Group 11 (1.0 mg/kg AD05308) | 0.749 | 0.074 | 1.164 | 0.037 | 1.152 | 0.121 | 1.021 | 0.057 | 0.994 | 0.072 |
| Group 12 (0.5 mg/kg AD05308) | 1.330 | 0.203 | 1.598 | 0.419 | 1.732 | 0.342 | 1.446 | 0.515 | 1.547 | 0.174 |
| Group 13 (1.0 mg/kg AD05418) | 0.858 | 0.068 | 1.065 | 0.029 | 1.079 | 0.072 | 0.980 | 0.037 | 0.892 | 0.136 |

TABLE 20

Average Total Cholesterol Normalized to Pre-Treatment and Control from Example 4

| Group ID | Day 8 | | Day 15 | | Day 22 | | Day 29 | | Day 43 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.110 | 1.000 | 0.159 | 1.000 | 0.074 | 1.000 | 0.153 | 1.000 | 0.122 |
| Group 2 (1.0 mg/kg AD05487) | 0.728 | 0.055 | 0.944 | 0.110 | 0.697 | 0.050 | 0.560 | 0.305 | 0.923 | 0.086 |
| Group 3 (1.0 mg/kg AD05488) | 0.827 | 0.096 | 0.667 | 0.086 | 0.759 | 0.057 | 0.683 | 0.077 | 0.837 | 0.072 |
| Group 4 (1.0 mg/kg AD05489) | 1.139 | 0.062 | 1.058 | 0.110 | 1.040 | 0.175 | 1.068 | 0.153 | | |
| Group 5 (1.0 mg/kg AD05490) | 0.986 | 0.043 | 1.064 | 0.025 | 1.021 | 0.140 | 0.779 | 0.427 | | |
| Group 6 (1.0 mg/kg AD05491) | 1.047 | 0.069 | 1.029 | 0.072 | 0.934 | 0.048 | 0.960 | 0.072 | | |
| Group 7 (1.0 mg/kg AD05492) | 0.957 | 0.048 | 0.883 | 0.059 | 0.907 | 0.059 | 1.001 | 0.040 | | |
| Group 8 (1.0 mg/kg AD05493) | 1.060 | 0.006 | 0.879 | 0.066 | 0.952 | 0.068 | 1.011 | 0.110 | | |
| Group 9 (1.0 mg/kg AD05494) | 0.823 | 0.045 | 0.829 | 0.075 | 0.980 | 0.054 | 0.793 | 0.100 | 0.947 | 0.051 |
| Group 10 (1.0 mg/kg AD05495) | 0.930 | 0.128 | 0.919 | 0.082 | 1.025 | 0.167 | 0.758 | 0.240 | | |
| Group 11 (1.0 mg/kg AD05308) | 0.868 | 0.018 | 0.793 | 0.026 | 0.770 | 0.081 | 0.819 | 0.073 | 1.073 | 0.149 |
| Group 12 (0.5 mg/kg AD05308) | 0.992 | 0.061 | 0.838 | 0.028 | 1.000 | 0.046 | 0.958 | 0.059 | 1.157 | 0.088 |
| Group 13 (1.0 mg/kg AD05418) | 0.818 | 0.071 | 0.761 | 0.087 | 0.915 | 0.105 | 0.853 | 0.039 | 1.002 | 0.076 |

TABLE 21

Average HDL Normalized to Pre-Treatment and Control from Example 4

| Group ID | Day 8 | | Day 15 | | Day 22 | | Day 29 | | Day 43 | |
|---|---|---|---|---|---|---|---|---|---|---|
| | Avg HDL | Std Dev (+/−) | Avg HDL | Std Dev (+/−) | Avg HDL | Std Dev (+/−) | Avg HDL | Std Dev (+/−) | Avg HDL | Std Dev (+/−) |
| Group 1 (D5W) | 1.000 | 0.090 | 1.000 | 0.158 | 1.000 | 0.087 | 1.000 | 0.158 | 1.000 | 0.141 |
| Group 2 (1.0 mg/kg AD05487) | 0.716 | 0.074 | 0.918 | 0.120 | 0.658 | 0.050 | 0.745 | 0.065 | 0.934 | 0.094 |
| Group 3 (1.0 mg/kg AD05488) | 0.839 | 0.094 | 0.644 | 0.061 | 0.727 | 0.035 | 0.771 | 0.104 | 0.833 | 0.079 |
| Group 4 (1.0 mg/kg AD05489) | 1.203 | 0.071 | 1.068 | 0.116 | 1.056 | 0.195 | 1.111 | 0.177 | | |
| Group 5 (1.0 mg/kg AD05490) | 1.022 | 0.020 | 1.043 | 0.027 | 0.981 | 0.109 | 1.021 | 0.153 | | |
| Group 6 (1.0 mg/kg AD05491) | 1.071 | 0.052 | 1.015 | 0.065 | 0.905 | 0.058 | 0.979 | 0.093 | | |
| Group 7 (1.0 mg/kg AD05492) | 1.003 | 0.076 | 0.920 | 0.088 | 0.920 | 0.092 | 1.047 | 0.055 | | |
| Group 8 (1.0 mg/kg AD05493) | 1.096 | 0.006 | 0.882 | 0.053 | 0.966 | 0.061 | 1.046 | 0.110 | | |
| Group 9 (1.0 mg/kg AD05494) | 0.874 | 0.059 | 0.782 | 0.065 | 0.911 | 0.045 | 0.802 | 0.083 | 0.978 | 0.073 |
| Group 10 (1.0 mg/kg AD05495) | 0.931 | 0.124 | 0.863 | 0.096 | 0.953 | 0.157 | 0.978 | 0.091 | | |
| Group 11 (1.0 mg/kg AD05308) | 0.904 | 0.026 | 0.801 | 0.039 | 0.728 | 0.078 | 0.824 | 0.082 | 1.096 | 0.196 |
| Group 12 (0.5 mg/kg AD05308) | 1.007 | 0.085 | 0.770 | 0.021 | 0.921 | 0.037 | 0.934 | 0.064 | 1.101 | 0.106 |
| Group 13 (1.0 mg/kg AD05418) | 0.828 | 0.103 | 0.730 | 0.115 | 0.846 | 0.104 | 0.845 | 0.050 | 1.018 | 0.082 |

TABLE 22

Average LDL Normalized to Pre-Treatment and Control from Example 4

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) | Day 43 Avg LDL | Day 43 Std Dev (+/−) |
|---|---|---|---|---|---|---|---|---|---|---|
| Group 1 (D5W) | 1.000 | 0.166 | 1.000 | 0.257 | 1.000 | 0.244 | 1.000 | 0.122 | 1.000 | 0.247 |
| Group 2 (1.0 mg/kg AD05487) | 0.916 | 0.207 | 1.125 | 0.079 | 0.845 | 0.020 | 0.744 | 0.095 | 0.989 | 0.031 |
| Group 3 (1.0 mg/kg AD05488) | 0.936 | 0.201 | 0.714 | 0.189 | 0.811 | 0.105 | 0.801 | 0.084 | 0.902 | 0.189 |
| Group 4 (1.0 mg/kg AD05489) | 1.197 | 0.191 | 0.874 | 0.068 | 0.985 | 0.226 | 0.943 | 0.132 | 0.000 | 0.000 |
| Group 5 (1.0 mg/kg AD05490) | 0.937 | 0.059 | 1.045 | 0.183 | 1.116 | 0.235 | 1.135 | 0.138 | 0.000 | 0.000 |
| Group 6 (1.0 mg/kg AD05491) | 0.966 | 0.199 | 0.867 | 0.147 | 0.912 | 0.202 | 0.839 | 0.197 | 0.000 | 0.000 |
| Group 7 (1.0 mg/kg AD05492) | 0.857 | 0.135 | 0.777 | 0.118 | 0.747 | 0.116 | 0.851 | 0.157 | 0.000 | 0.000 |
| Group 8 (1.0 mg/kg AD05493) | 0.946 | 0.014 | 0.776 | 0.112 | 0.782 | 0.053 | 0.927 | 0.329 | 0.000 | 0.000 |
| Group 9 (1.0 mg/kg AD05494) | 0.846 | 0.030 | 1.129 | 0.203 | 1.086 | 0.054 | 0.922 | 0.132 | 0.845 | 0.081 |
| Group 10 (1.0 mg/kg AD05495) | 1.192 | 0.150 | 1.084 | 0.087 | 1.232 | 0.263 | 0.898 | 0.114 | 0.000 | 0.000 |
| Group 11 (1.0 mg/kg AD05308) | 0.842 | 0.103 | 0.688 | 0.072 | 0.829 | 0.144 | 0.897 | 0.143 | 1.033 | 0.164 |
| Group 12 (0.5 mg/kg AD05308) | 0.965 | 0.172 | 0.830 | 0.055 | 1.209 | 0.146 | 1.251 | 0.139 | 1.375 | 0.102 |
| Group 13 (1.0 mg/kg AD05418) | 1.044 | 0.035 | 0.841 | 0.033 | 1.142 | 0.231 | 0.966 | 0.080 | 0.921 | 0.135 |

The ANGPTL3 RNAi agents AD05487 and AD05488 (Groups 2 and 3) included nucleotide sequences that were designed to inhibit expression of an ANGPTL3 gene at position 304 of the gene; ANGPTL3 RNAi agent AD05489 and AD05490 (Groups 4 and 5) included nucleotide sequences designed to inhibit expression of an ANGPTL3 gene at position 172 of the gene; ANGPTL3 RNAi agents AD05491 and AD05492 (Groups 6 and 7) included nucleotide sequences designed to inhibit expression of an ANGPTL3 gene at position 1008 of the gene; ANGPTL3 RNAi agent AD0593 (Group 8) included nucleotide sequences designed to inhibit expression of an ANGPTL3 gene at position 1009 of the gene; ANGPTL3 RNAi agents AD05494, AD05495, and AD05308 (Groups 9, 10, 11, and 12) included nucleotide sequences designed to inhibit expression of an ANGPTL3 gene at position 1302 of the gene; and ANGPTL3 RNAi agents AD05418 (Group 13) included nucleotide sequences designed to inhibit expression of an ANGPTL3 gene at position 921 of the gene. (See SEQ ID NO:1 for the ANGPTL3 gene sequence referenced).

As shown in Table 18 above, while most of the RNAi agents achieved a reduction in ANGPTL3 protein levels at nearly every time point measured, the ANGPTL3 RNAi agents in Group 2 (AD05487) and Group 3 (AD05488), which each included nucleotide sequences designed to inhibit ANGPTL3 gene expression at position 304 of the gene, outperformed the other Groups in this study. For example, at days 15 and 22, ANGPTL3 RNAi agent AD05488 (Group 3) achieved greater than 90% knockdown of ANGPTL3 protein (i.e., 0.070 on day 15 and 0.092 on day 22). Similarly, ANGPTL3 RNAi agent AD05487 (Group 2) achieved nearly 75% knockdown on days 15 and 22 (i.e., 0.170 on day 15 and 0.138 on day 22). Moreover, the same trends were seen across the additional measured parameters including TG, total cholesterol, and LDL, as both Group 2 (AD05487) and Group 3 (AD05488) generally outperformed the other RNAi agents tested (see Tables 19-22). For example, For Groups 2 and 3, on day 29, triglyceride levels were reduced by at least 28% (i.e., 0.556 or 0.721), total cholesterol was reduced by at least 31% (i.e., 0.560 or 0.683), and LDL levels were reduced by nearly 20% (0.744 or 0.801).

Example 5. In Vivo Testing of ANGPTL3 RNAi Agents in Cynomolgus Monkeys

ANGPTL3 RNAi agents were evaluated in cynomolgus monkeys. On day 1, cynomolgus macaque (*Macaca fascicularis*) primates (also referred to herein as "cynos") were administered a single subcutaneous injection of 0.3 mL/kg (approximately 2-3 mL volume, depending on animal mass) containing 3.0 mg/kg of ANGPTL3 RNAi agent AD05308 or AD05418, formulated in saline. Each of the ANGPTL3 RNAi agents contained modified nucleotides and included N-acetyl-galactosamine targeting ligands conjugated to the 5'-terminal end of the sense strand, as shown in Tables 3, 4, and 5.

Two (2) cynos in each group were tested (n=2). Blood samples were drawn and serum samples were analyzed on days −37 (pre-dose), −15 (pre-dose), and −1 (pre-dose), 8, 16, 23, 30, and 37. Cynos were fasted overnight prior to each collection. ANGPTL3 protein levels in serum were measured by ELISA assay (R&D Systems), according to the manufacturer's recommendations. The ANGPTL3 protein levels were normalized. For normalization, the level of ANGPTL3 protein for each animal at a time point, was divided by the average pre-treatment level of expression in that animal (in this case at days −37, −15, and −1) to determine the ratio of expression "normalized to pre-treatment."

Data from the study set forth in this Example are shown in the following Tables 23 and 24:

TABLE 23

Average ANGPTL3 Protein Normalized to Pre-Treatment from Example 5 By Group

| | Day 8 | | Day 16 | | Day 23 | | Day 30 | | Day 37 | |
|---|---|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (3.0 mg/kg AD05308) | 0.416 | 0.183 | 0.447 | 0.034 | 0.649 | 0.260 | 0.647 | 0.106 | 0.565 | 0.204 |
| Group 2 (3.0 mg/kg AD05418) | 0.544 | 0.058 | 0.334 | 0.035 | 0.300 | 0.057 | 0.389 | 0.110 | 0.270 | 0.082 |

TABLE 24

Average ANGPTL3 Protein Normalized to Pre-Treatment from Example 5 By Individual Animal

| | Day 8 | | Day 16 | | Day 23 | | Day 30 | | Day 37 | |
|---|---|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| AD05308 (3.0 mg/kg) (Cyno A) | 0.545 | 0.021 | 0.423 | 0.011 | 0.832 | 0.014 | 0.722 | 0.025 | 0.709 | 0.020 |
| AD05308 (3.0 mg/kg) (Cyno B) | 0.287 | 0.004 | 0.471 | 0.010 | 0.465 | 0.017 | 0.572 | 0.025 | 0.421 | 0.002 |
| AD05418 (3.0 mg/kg) (Cyno A) | 0.585 | 0.006 | 0.358 | 0.008 | 0.260 | 0.012 | 0.311 | 0.010 | 0.212 | 0.001 |
| AD05418 (3.0 mg/kg) (Cyno B) | 0.503 | 0.013 | 0.309 | 0.008 | 0.340 | 0.021 | 0.467 | 0.022 | 0.328 | 0.010 |

Each of the cynomolgus monkeys dosed with either AD05308 or AD05418 showed a reduction in ANGPTL3 protein compared to pre-treatment measurements across all measured time points. For example, for individual animals, on Day 16, the cynos dosed with AD05418 showed a reduction of either approximately 64% (0.358 normalized protein level) or 69% (0.309 normalized protein level) in ANGPTL3 protein. Further, even on day 37, the cynos of Group 2 (AD05418) showed an average reduction of approximately 73% (0.270) in ANGPTL protein levels.

Example 6. In Vivo Testing of ANGPTL3 RNAi Agents in Mice

To assess the in vivo activity of additional ANGPTL3 RNAi agents that are designed to target position 304 on the ANGPTL3 gene, six- to eight-week-old female C57bl/6 mice were used. Pre-dose serum samples were taken at day −1 after a four hour fast. At day 1, each mouse was given a single subcutaneous administration of 200 μl containing 0.5 mg/kg (mpk) of an ANGPTL3 RNAi agent in D5W (dextrose in 5% water), or control (D5W) with no RNAi agent, according to the dosing groups recited in Table 25.

TABLE 25

Dosing Groups of Example 6

| Group | RNAi Agent and Dose | Dosing Regimen |
|---|---|---|
| 1 | D5W (no RNAi agent) | Single injection on day 1 |
| 2 | 0.5 mg/kg AD05488 | Single injection on day 1 |
| 3 | 0.5 mg/kg AD05652 | Single injection on day 1 |
| 4 | 0.5 mg/kg AD05653 | Single injection on day 1 |
| 5 | 0.5 mg/kg AD05654 | Single injection on day 1 |
| 6 | 0.5 mg/kg AD05655 | Single injection on day 1 |

TABLE 25-continued

Dosing Groups of Example 6

| Group | RNAi Agent and Dose | Dosing Regimen |
|---|---|---|
| 7 | 0.5 mg/kg AD05656 | Single injection on day 1 |
| 8 | 0.5 mg/kg AD05657 | Single injection on day 1 |
| 9 | 0.5 mg/kg AD05658 | Single injection on day 1 |
| 10 | 0.5 mg/kg AD05660 | Single injection on day 1 |
| 11 | 0.5 mg/kg AD05661 | Single injection on day 1 |
| 12 | 0.5 mg/kg AD05662 | Single injection on day 1 |

Each of the RNAi agents included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Three (3) mice in each group were tested (n=3). Serum was collected on days 8, 15, 22, 30, and on day 43 for certain groups (i.e., Groups 1, 2, 5, and 10 only). Mice were fasted for four hours prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables:

TABLE 26

Average ANGPTL3 Protein Normalized to Pre-Treatment and Control from Example 6

| Group ID | Day 8 Avg ANGPTL3 | Day 8 Std Dev (+/−) | Day 15 Avg ANGPTL3 | Day 15 Std Dev (+/−) | Day 22 Avg ANGPTL3 | Day 22 Std Dev (+/−) | Day 30 Avg ANGPTL3 | Day 30 Std Dev (+/−) | Day 43 Avg ANGPTL3 | Day 43 Std Dev (+/−) |
|---|---|---|---|---|---|---|---|---|---|---|
| Group 1 (D5W) | 1.000 | 0.117 | 1.000 | 0.134 | 1.000 | 0.136 | 1.000 | 0.013 | 1.000 | 0.100 |
| Group 2 (0.5 mg/kg AD05488) | 0.221 | 0.031 | 0.272 | 0.046 | 0.254 | 0.022 | 0.381 | 0.043 | 0.475 | 0.054 |
| Group 3 (0.5 mg/kg AD05652) | 0.394 | 0.130 | 0.346 | 0.089 | 0.333 | 0.102 | 0.478 | 0.047 | | |
| Group 4 (0.5 mg/kg AD05653) | 0.388 | 0.056 | 0.416 | 0.087 | 0.378 | 0.055 | 0.548 | 0.055 | | |
| Group 5 (0.5 mg/kg AD05654) | 0.261 | 0.061 | 0.305 | 0.014 | 0.308 | 0.048 | 0.340 | 0.012 | 0.413 | 0.051 |
| Group 6 (0.5 mg/kg AD05655) | 0.301 | 0.037 | 0.338 | 0.027 | 0.304 | 0.017 | 0.403 | 0.052 | | |
| Group 7 (0.5 mg/kg AD05656) | 0.402 | 0.138 | 0.347 | 0.074 | 0.328 | 0.039 | 0.445 | 0.078 | | |
| Group 8 (0.5 mg/kg AD05657) | 0.341 | 0.137 | 0.385 | 0.052 | 0.371 | 0.011 | 0.425 | 0.121 | | |
| Group 9 (0.5 mg/kg AD05658) | 0.427 | 0.077 | 0.484 | 0.093 | 0.492 | 0.032 | 0.477 | 0.045 | | |
| Group 10 (0.5 mg/kg AD05660) | 0.342 | 0.042 | 0.372 | 0.047 | 0.368 | 0.085 | 0.404 | 0.032 | 0.485 | 0.081 |
| Group 11 (0.5 mg/kg AD05661) | 0.436 | 0.120 | 0.322 | 0.057 | 0.372 | 0.028 | 0.430 | 0.037 | | |
| Group 12 (0.5 mg/kg AD05662) | 0.602 | 0.106 | 0.609 | 0.189 | 0.688 | 0.294 | 0.736 | 0.128 | | |

TABLE 27

Average Triglycerides Normalized to Pre-Treatment and Control from Example 6

| Group ID | Day 8 Avg TG | Day 8 Std Dev (+/−) | Day 15 Avg TG | Day 15 Std Dev (+/−) | Day 22 Avg TG | Day 22 Std Dev (+/−) | Day 30 Avg TG | Day 30 Std Dev (+/−) | Day 43 Avg TG | Day 43 Std Dev (+/−) |
|---|---|---|---|---|---|---|---|---|---|---|
| Group 1 (D5W) | 1.000 | 0.181 | 1.000 | 0.078 | 1.000 | 0.171 | 1.000 | 0.203 | 1.000 | 0.065 |
| Group 2 (0.5 mg/kg AD05488) | 0.568 | 0.095 | 0.637 | 0.035 | 0.484 | 0.052 | 0.652 | 0.086 | 0.689 | 0.089 |
| Group 3 (0.5 mg/kg AD05652) | 0.653 | 0.102 | 0.636 | 0.058 | 0.582 | 0.120 | 0.858 | 0.182 | | |
| Group 4 (0.5 mg/kg AD05653) | 0.628 | 0.205 | 0.528 | 0.123 | 0.469 | 0.111 | 0.737 | 0.036 | | |
| Group 5 (0.5 mg/kg AD05654) | 0.522 | 0.054 | 0.624 | 0.110 | 0.536 | 0.047 | 0.652 | 0.060 | 1.001 | 0.175 |
| Group 6 (0.5 mg/kg AD05655) | 0.512 | 0.142 | 0.672 | 0.162 | 0.491 | 0.095 | 0.785 | 0.132 | | |
| Group 7 (0.5 mg/kg AD05656) | 0.633 | 0.109 | 0.631 | 0.044 | 0.442 | 0.021 | 0.657 | 0.031 | | |
| Group 8 (0.5 mg/kg AD05657) | 0.579 | 0.075 | 0.589 | 0.024 | 0.416 | 0.061 | 0.670 | 0.214 | | |
| Group 9 (0.5 mg/kg AD05658) | 0.529 | 0.037 | 0.555 | 0.074 | 0.490 | 0.087 | 0.720 | 0.108 | | |
| Group 10 (0.5 mg/kg AD05660) | 0.567 | 0.032 | 0.713 | 0.083 | 0.480 | 0.153 | 0.644 | 0.074 | 1.040 | 0.228 |
| Group 11 (0.5 mg/kg AD05661) | 0.574 | 0.139 | 0.697 | 0.208 | 0.480 | 0.112 | 0.596 | 0.151 | | |
| Group 12 (0.5 mg/kg AD05662) | 0.563 | 0.091 | 0.755 | 0.086 | 0.592 | 0.078 | 0.644 | 0.062 | | |

TABLE 28

Average Total Cholesterol Normalized to Pre-Treatment and Control from Example 6

| Group ID | Day 8 Avg Total Chol | Day 8 Std Dev (+/−) | Day 15 Avg Total Chol | Day 15 Std Dev (+/−) | Day 22 Avg Total Chol | Day 22 Std Dev (+/−) | Day 30 Avg Total Chol | Day 30 Std Dev (+/−) | Day 43 Avg Total Chol | Day 43 Std Dev (+/−) |
|---|---|---|---|---|---|---|---|---|---|---|
| Group 1 (D5W) | 1.000 | 0.062 | 1.000 | 0.077 | 1.000 | 0.081 | 1.000 | 0.041 | 1.000 | 0.113 |
| Group 2 (0.5 mg/kg AD05488) | 0.782 | 0.086 | 0.768 | 0.011 | 0.801 | 0.070 | 0.961 | 0.114 | 1.037 | 0.123 |

TABLE 28-continued

Average Total Cholesterol Normalized to Pre-Treatment and Control from Example 6

| Group ID | Day 8 Avg Total Chol | Day 8 Std Dev (+/−) | Day 15 Avg Total Chol | Day 15 Std Dev (+/−) | Day 22 Avg Total Chol | Day 22 Std Dev (+/−) | Day 30 Avg Total Chol | Day 30 Std Dev (+/−) | Day 43 Avg Total Chol | Day 43 Std Dev (+/−) |
|---|---|---|---|---|---|---|---|---|---|---|
| Group 3 (0.5 mg/kg AD05652) | 0.829 | 0.094 | 0.815 | 0.078 | 0.724 | 0.069 | 0.835 | 0.069 | | |
| Group 4 (0.5 mg/kg AD05653) | 0.907 | 0.129 | 0.891 | 0.120 | 0.781 | 0.067 | 1.024 | 0.106 | | |
| Group 5 (0.5 mg/kg AD05654) | 0.752 | 0.083 | 0.741 | 0.035 | 0.741 | 0.081 | 0.788 | 0.087 | 0.764 | 0.076 |
| Group 6 (0.5 mg/kg AD05655) | 0.751 | 0.043 | 0.815 | 0.089 | 0.708 | 0.048 | 0.845 | 0.126 | | |
| Group 7 (0.5 mg/kg AD05656) | 0.779 | 0.078 | 0.696 | 0.068 | 0.717 | 0.097 | 0.842 | 0.038 | | |
| Group 8 (0.5 mg/kg AD05657) | 0.772 | 0.032 | 0.736 | 0.053 | 0.690 | 0.021 | 0.797 | 0.059 | | |
| Group 9 (0.5 mg/kg AD05658) | 0.760 | 0.068 | 0.784 | 0.075 | 0.778 | 0.037 | 0.784 | 0.062 | | |
| Group 10 (0.5 mg/kg AD05660) | 0.774 | 0.060 | 0.824 | 0.106 | 0.898 | 0.108 | 0.820 | 0.019 | 0.928 | 0.121 |
| Group 11 (0.5 mg/kg AD05661) | 0.719 | 0.076 | 0.755 | 0.013 | 0.784 | 0.076 | 0.758 | 0.061 | | |
| Group 12 (0.5 mg/kg AD05662) | 0.744 | 0.024 | 0.918 | 0.063 | 0.864 | 0.039 | 0.905 | 0.046 | | |

TABLE 29

Average HDL Normalized to Pre-Treatment and Control from Example 6

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 30 Avg HDL | Day 30 Std Dev (+/−) | Day 43 Avg HDL | Day 43 Std Dev (+/−) |
|---|---|---|---|---|---|---|---|---|---|---|
| Group 1 (D5W) | 1.000 | 0.072 | 1.000 | 0.069 | 1.000 | 0.083 | 1.000 | 0.040 | 1.000 | 0.098 |
| Group 2 (0.5 mg/kg AD05488) | 0.783 | 0.069 | 0.763 | 0.020 | 0.793 | 0.076 | 0.956 | 0.122 | 1.088 | 0.131 |
| Group 3 (0.5 mg/kg AD05652) | 0.811 | 0.106 | 0.778 | 0.087 | 0.690 | 0.098 | 0.806 | 0.054 | | |
| Group 4 (0.5 mg/kg AD05653) | 0.915 | 0.154 | 0.898 | 0.155 | 0.773 | 0.087 | 1.027 | 0.113 | | |
| Group 5 (0.5 mg/kg AD05654) | 0.708 | 0.120 | 0.725 | 0.040 | 0.717 | 0.105 | 0.776 | 0.097 | 0.731 | 0.056 |
| Group 6 (0.5 mg/kg AD05655) | 0.752 | 0.045 | 0.825 | 0.098 | 0.708 | 0.063 | 0.835 | 0.119 | | |
| Group 7 (0.5 mg/kg AD05656) | 0.747 | 0.078 | 0.682 | 0.081 | 0.726 | 0.087 | 0.833 | 0.050 | | |
| Group 8 (0.5 mg/kg AD05657) | 0.757 | 0.034 | 0.716 | 0.054 | 0.695 | 0.013 | 0.801 | 0.065 | | |
| Group 9 (0.5 mg/kg AD05658) | 0.778 | 0.084 | 0.787 | 0.075 | 0.807 | 0.062 | 0.793 | 0.069 | | |
| Group 10 (0.5 mg/kg AD05660) | 0.768 | 0.056 | 0.807 | 0.108 | 0.912 | 0.101 | 0.800 | 0.008 | 0.899 | 0.129 |
| Group 11 (0.5 mg/kg AD05661) | 0.739 | 0.082 | 0.752 | 0.014 | 0.796 | 0.086 | 0.782 | 0.034 | | |
| Group 12 (0.5 mg/kg AD05662) | 0.740 | 0.020 | 0.919 | 0.096 | 0.887 | 0.086 | 0.955 | 0.045 | | |

TABLE 30

Average LDL Normalized to Pre-Treatment and Control from Example 6

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 30 Avg LDL | Day 30 Std Dev (+/−) | Day 43 Avg LDL | Day 43 Std Dev (+/−) |
|---|---|---|---|---|---|---|---|---|---|---|
| Group 1 (D5W) | 1.000 | 0.138 | 1.000 | 0.136 | 1.000 | 0.177 | 1.000 | 0.097 | 1.000 | 0.120 |
| Group 2 (0.5 mg/kg AD05488) | 0.805 | 0.162 | 0.880 | 0.075 | 0.991 | 0.139 | 1.093 | 0.171 | 0.970 | 0.114 |
| Group 3 (0.5 mg/kg AD05652) | 0.867 | 0.093 | 1.015 | 0.060 | 0.878 | 0.102 | 0.904 | 0.175 | | |
| Group 4 (0.5 mg/kg AD05653) | 1.043 | 0.198 | 1.134 | 0.219 | 1.034 | 0.229 | 1.259 | 0.233 | | |
| Group 5 (0.5 mg/kg AD05654) | 1.087 | 0.094 | 0.845 | 0.033 | 0.893 | 0.070 | 1.006 | 0.136 | 0.840 | 0.112 |
| Group 6 (0.5 mg/kg AD05655) | 0.877 | 0.048 | 0.911 | 0.081 | 0.752 | 0.111 | 0.976 | 0.194 | | |
| Group 7 (0.5 mg/kg AD05656) | 0.818 | 0.120 | 0.837 | 0.052 | 0.782 | 0.216 | 0.963 | 0.117 | | |
| Group 8 (0.5 mg/kg AD05657) | 0.888 | 0.051 | 0.853 | 0.049 | 0.791 | 0.073 | 0.903 | 0.136 | | |
| Group 9 (0.5 mg/kg AD05658) | 0.715 | 0.065 | 0.818 | 0.070 | 0.741 | 0.041 | 0.764 | 0.076 | | |
| Group 10 (0.5 mg/kg AD05660) | 0.795 | 0.078 | 0.909 | 0.094 | 1.041 | 0.040 | 0.998 | 0.187 | 0.941 | 0.078 |

TABLE 30-continued

Average LDL Normalized to Pre-Treatment and Control from Example 6

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 30 Avg LDL | Day 30 Std Dev (+/−) | Day 43 Avg LDL | Day 43 Std Dev (+/−) |
|---|---|---|---|---|---|---|---|---|---|---|
| Group 11 (0.5 mg/kg AD05661) | 0.687 | 0.048 | 0.855 | 0.051 | 0.877 | 0.079 | 0.798 | 0.102 | | |
| Group 12 (0.5 mg/kg AD05662) | 0.723 | 0.037 | 0.908 | 0.068 | 0.865 | 0.125 | 0.832 | 0.106 | | |

Each of the ANGPTL3 RNAi agents tested (i.e., AD05488, AD05652, AD05653, AD05654, AD05655, AD05656, AD05657, AD05658, AD05660, AD05661, and AD05662) each included nucleotide sequences designed to target the ANGPTL3 gene at position 304 (see, e.g., SEQ ID NO:1). As shown above, each of the RNAi agents showed a substantial reduction in ANGPTL3 protein levels through at least day 22. Reductions in TG levels and total cholesterol were also observed.

Example 7. In Vivo Testing of ANGPTL3 RNAi Agents in Mice

To further assess the in vivo activity of additional ANGPTL3 RNAi agents that are designed to target position 304 on the ANGPTL3 gene, six- to eight-week-old female C57bl/6 mice were used. Pre-dose serum samples were taken at day −1 after a four hour fast. At day 1, each mouse was given a single subcutaneous administration of 200 μl containing 0.5 mg/kg (mpk) of an ANGPTL3 RNAi agent in D5W (dextrose in 5% water), or control (D5W) with no RNAi agent, according to the dosing groups recited in Table 31.

TABLE 31

Dosing Groups of Example 7

| Group | RNAi Agent and Dose | Dosing Regimen |
|---|---|---|
| 1 | D5W (no RNAi agent) | Single injection on day 1 |
| 2 | 0.5 mg/kg AD05488 | Single injection on day 1 |
| 3 | 0.5 mg/kg AD05774 | Single injection on day 1 |
| 4 | 0.5 mg/kg AD05775 | Single injection on day 1 |
| 5 | 0.5 mg/kg AD05776 | Single injection on day 1 |
| 6 | 0.5 mg/kg AD05777 | Single injection on day 1 |
| 7 | 0.5 mg/kg AD05308 | Single injection on day 1 |
| 8 | 0.5 mg/kg AD05418 | Single injection on day 1 |

Each of the RNAi agents included a modified sequence and an N-acetyl-galactosamine-containing targeting ligand conjugated to the 5′ terminal end of the sense strand. (See Tables 3, 4, and 5 for modified sequences and targeting ligand structures). The injections were performed between the skin and muscle (i.e. subcutaneous injections) into the loose skin over the neck and shoulder area. Three (3) mice in each group were tested (n=3). Serum was collected on days 8, 15, 22, and 29. Mice were fasted for four hours prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 32-36:

TABLE 32

Average ANGPTL3 Protein Normalized to Pre-Treatment and Control from Example 7

| Group ID | Day 8 Avg ANGPTL3 | Day 8 Std Dev (+/−) | Day 15 Avg ANGPTL3 | Day 15 Std Dev (+/−) | Day 22 Avg ANGPTL3 | Day 22 Std Dev (+/−) | Day 29 Avg ANGPTL3 | Day 29 Std Dev (+/−) |
|---|---|---|---|---|---|---|---|---|
| Group 1 (D5W) | 1.000 | 0.139 | 1.000 | 0.060 | 1.000 | 0.414 | 1.000 | 0.227 |
| Group 2 (0.5 mg/kg AD05488) | 0.339 | 0.014 | 0.379 | 0.098 | 0.346 | 0.031 | 0.469 | 0.058 |
| Group 3 (0.5 mg/kg AD05774) | 0.343 | 0.075 | 0.302 | 0.062 | 0.287 | 0.018 | 0.425 | 0.060 |
| Group 4 (0.5 mg/kg AD05775) | 0.247 | 0.033 | 0.232 | 0.038 | 0.218 | 0.008 | 0.300 | 0.061 |
| Group 5 (0.5 mg/kg AD05776) | 0.327 | 0.121 | 0.297 | 0.099 | 0.300 | 0.096 | 0.378 | 0.043 |
| Group 6 (0.5 mg/kg AD05777) | 0.297 | 0.056 | 0.246 | 0.035 | 0.257 | 0.068 | 0.345 | 0.035 |
| Group 7 (0.5 mg/kg AD05308) | 0.447 | 0.101 | 0.388 | 0.139 | 0.440 | 0.092 | 0.523 | 0.171 |
| Group 8 (0.5 mg/kg AD05418) | 0.534 | 0.117 | 0.565 | 0.077 | 0.639 | 0.042 | 0.758 | 0.119 |

TABLE 33

Average Triglycerides Normalized to Pre-Treatment and Control from Example 7

| Group ID | Day 8 | | Day 15 | | Day 22 | | Day 29 | |
|---|---|---|---|---|---|---|---|---|
| | Avg TG | Std Dev (+/−) | Avg TG | Std Dev (+/−) | Avg TG | Std Dev (+/−) | Avg TG | Std Dev (+/−) |
| Group 1 (D5W) | 1.000 | 0.074 | 1.000 | 0.116 | 1.000 | 0.151 | 1.000 | 0.089 |
| Group 2 (0.5 mg/kg AD05488) | 0.856 | 0.223 | 0.947 | 0.279 | 0.922 | 0.116 | 0.877 | 0.400 |
| Group 3 (0.5 mg/kg AD05774) | 0.867 | 0.165 | 0.641 | 0.037 | 0.832 | 0.177 | 0.723 | 0.027 |
| Group 4 (0.5 mg/kg AD05775) | 0.837 | 0.109 | 0.610 | 0.107 | 0.819 | 0.063 | 0.885 | 0.140 |
| Group 5 (0.5 mg/kg AD05776) | 0.738 | 0.130 | 0717 | 0.120 | 0.601 | 0.105 | 0.718 | 0.180 |
| Group 6 (0.5 mg/kg AD05777) | 0.755 | 0.099 | 0.702 | 0.001 | 0.700 | 0.120 | 0.648 | 0.093 |
| Group 7 (0.5 mg/kg AD05308) | 0.836 | 0.343 | 0.755 | 0.152 | 0.839 | 0.199 | 0.705 | 0.219 |
| Group 8 (0.5 mg/kg AD05418) | 0.830 | 0.316 | 0.655 | 0.049 | 0.815 | 0.184 | 0.586 | 0.243 |

TABLE 34

Average Total Cholesterol Normalized to Pre-Treatment and Control from Example 7

| Group ID | Day 8 | | Day 15 | | Day 22 | | Day 29 | |
|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.058 | 1.000 | 0.162 | 1.000 | 0.094 | 1.000 | 0.032 |
| Group 2 (0.5 mg/kg AD05488) | 0.802 | 0.033 | 0.810 | 0.012 | 0.810 | 0.043 | 0.906 | 0.064 |
| Group 3 (0.5 mg/kg AD05774) | 1.001 | 0.047 | 0.923 | 0.070 | 0.932 | 0.064 | 1.231 | 0.041 |
| Group 4 (0.5 mg/kg AD05775) | 0.794 | 0.041 | 0.777 | 0.049 | 0.812 | 0.037 | 1.108 | 0.216 |
| Group 5 (0.5 mg/kg AD05776) | 0.762 | 0.073 | 0.745 | 0.087 | 0.784 | 0.075 | 1.011 | 0.120 |
| Group 6 (0.5 mg/kg AD05777) | 0.797 | 0.078 | 0.800 | 0.019 | 0.794 | 0.122 | 0.995 | 0.127 |
| Group 7 (0.5 mg/kg AD05308) | 0.756 | 0.037 | 0.814 | 0.098 | 0.896 | 0.116 | 0.927 | 0.096 |
| Group 8 (0.5 mg/kg AD05418) | 0.950 | 0.082 | 0.878 | 0.044 | 0.926 | 0.012 | 1.023 | 0.056 |

TABLE 35

Average HDL Normalized to Pre-Treatment and Control from Example 7

| Group ID | Day 8 | | Day 15 | | Day 22 | | Day 29 | |
|---|---|---|---|---|---|---|---|---|
| | Avg HDL | Std Dev (+/−) | Avg HDL | Std Dev (+/−) | Avg HDL | Std Dev (+/−) | Avg HDL | Std Dev (+/−) |
| Group 1 (D5W) | 1.000 | 0.055 | 1.000 | 0.152 | 1.000 | 0.088 | 1.000 | 0.029 |
| Group 2 (0.5 mg/kg AD05488) | 0.783 | 0.020 | 0.793 | 0.009 | 0.780 | 0.030 | 0.886 | 0.070 |
| Group 3 (0.5 mg/kg AD05774) | 0.982 | 0.038 | 0.930 | 0.013 | 0.901 | 0.085 | 1.263 | 0.021 |
| Group 4 (0.5 mg/kg AD05775) | 0.754 | 0.028 | 0.757 | 0.038 | 0.736 | 0.017 | 1.069 | 0.193 |
| Group 5 (0.5 mg/kg AD05776) | 0.760 | 0.059 | 0.743 | 0.062 | 0.773 | 0.055 | 1.022 | 0.093 |
| Group 6 (0.5 mg/kg AD05777) | 0.784 | 0.085 | 0.768 | 0.003 | 0.801 | 0.113 | 1.008 | 0.117 |
| Group 7 (0.5 mg/kg AD05308) | 0.750 | 0.033 | 0.791 | 0.079 | 0.846 | 0.115 | 0.905 | 0.107 |
| Group 8 (0.5 mg/kg AD05418) | 0.907 | 0.087 | 0.857 | 0.035 | 0.910 | 0.014 | 1.048 | 0.050 |

TABLE 36

Average LDL Normalized to Pre-Treatment and Control from Example 7

| Group ID | Day 8 | | Day 15 | | Day 22 | | Day 29 | |
|---|---|---|---|---|---|---|---|---|
| | Avg LDL | Std Dev (+/−) | Avg LDL | Std Dev (+/−) | Avg LDL | Std Dev (+/−) | Avg LDL | Std Dev (+/−) |
| Group 1 (D5W) | 1.000 | 0.119 | 1.000 | 0.088 | 1.000 | 0.110 | 1.000 | 0.151 |
| Group 2 (0.5 mg/kg AD05488) | 0.953 | 0.186 | 0.825 | 0.074 | 0.860 | 0.187 | 1.055 | 0.095 |
| Group 3 (0.5 mg/kg AD05774) | 1.188 | 0.200 | 1.101 | 0.197 | 1.055 | 0.043 | 1.474 | 0.267 |
| Group 4 (0.5 mg/kg AD05775) | 0.975 | 0.188 | 0.918 | 0.135 | 1.095 | 0.180 | 1.534 | 0.417 |
| Group 5 (0.5 mg/kg AD05776) | 0.849 | 0.143 | 0.764 | 0.223 | 0.861 | 0.158 | 1.207 | 0.269 |

TABLE 36-continued

Average LDL Normalized to Pre-Treatment and Control from Example 7

| Group ID | Day 8 | | Day 15 | | Day 22 | | Day 29 | |
|---|---|---|---|---|---|---|---|---|
| | Avg LDL | Std Dev (+/−) | Avg LDL | Std Dev (+/−) | Avg LDL | Std Dev (+/−) | Avg LDL | Std Dev (+/−) |
| Group 6 (0.5 mg/kg AD05777) | 0.886 | 0.116 | 0.869 | 0.165 | 0.966 | 0.383 | 1.224 | 0.407 |
| Group 7 (0.5 mg/kg AD05308) | 0.710 | 0.077 | 0.801 | 0.105 | 0.933 | 0.123 | 1.047 | 0.146 |
| Group 8 (0.5 mg/kg AD05418) | 1.160 | 0.143 | 0.928 | 0.128 | 0.950 | 0.085 | 1.131 | 0.150 |

Example 8. In Vivo Testing of ANGPTL3 RNAi Agents in Cynomolgus Monkeys

Additional ANGPTL3 RNAi agents were evaluated in cynomolgus monkeys. On day 1, cynomolgus macaque (*Macaca fascicularis*) primates (also referred to herein as "cynos") were administered a single subcutaneous injection of 0.3 mL/kg (approximately 1-2 mL volume, depending on animal mass) containing 3.0 mg/kg of one of ANGPTL3 RNAi agent AD05577, AD05307, AD05488, AD05654, or AD05659, each formulated in saline. Each of the ANGPTL3 RNAi agents contained modified nucleotides and included N-acetyl-galactosamine targeting ligands conjugated to the 5'-terminal end of the sense strand, as shown in Tables 3, 4, and 5.

Two (2) cynos in each group were tested (n=2). Blood samples were drawn and serum samples were analyzed on days −8 (pre-dose), 1 (pre-dose), 8, 15, 22, 29, and 36. Cynos were fasted overnight prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the average pre-treatment level of expression in that animal (in this case at days −8, and 1 (pre-dose)) to determine the ratio of expression "normalized to pre-treatment."

Data from the study set forth in this Example are shown in the following Tables 37-41:

TABLE 37

Average ANGPTL3 Protein Normalized to Pre-Treatment from Example 8

| Group ID | Day 8 | | Day 15 | | Day 22 | | Day 29 | | Day 36 | |
|---|---|---|---|---|---|---|---|---|---|---|
| | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (3.0 mg/kg AD05577) | 0.503 | 0.015 | 0.544 | 0.037 | 0.754 | 0.147 | 0.586 | 0.026 | 0.479 | 0.054 |
| Group 2 (3.0 mg/kg AD05307) | 0.486 | 0.116 | 0.402 | 0.134 | 0.726 | 0.306 | 0.518 | 0.210 | 0.392 | 0.159 |
| Group 3 (3.0 mg/kg AD05488) | 0.423 | 0.071 | 0.334 | 0.067 | 0.343 | 0.110 | 0.276 | 0.069 | 0.229 | 0.123 |
| Group 4 (3.0 mg/kg AD05654) | 0.366 | 0.048 | 0.262 | 0.055 | 0.394 | 0.082 | 0.202 | 0.062 | 0.203 | 0.024 |
| Group 5 (3.0 mg/kg AD05659) | 0.406 | 0.040 | 0.434 | 0.095 | 0.610 | 0.033 | 0.522 | 0.014 | 0.349 | 0.030 |

TABLE 38

Average Triglycerides Normalized to Pre-Treatment from Example 8

| Group ID | Day 8 | | Day 15 | | Day 22 | | Day 29 | | Day 36 | |
|---|---|---|---|---|---|---|---|---|---|---|
| | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 1 (3.0 mg/kg AD05577) | 1.159 | 0.247 | 0.977 | 0.076 | 0.855 | 0.034 | 0.886 | 0.010 | 0.748 | 0.014 |
| Group 2 (3.0 mg/kg AD05307) | 1.157 | 0.127 | 1.058 | 0.389 | 0.895 | 0.118 | 0.969 | 0.264 | 0.806 | 0.008 |
| Group 3 (3.0 mg/kg AD05488) | 0.727 | 0.158 | 0.586 | 0.175 | 0.399 | 0.075 | 0.534 | 0.157 | 0.364 | 0.079 |
| Group 4 (3.0 mg/kg AD05654) | 0.949 | 0.282 | 0.645 | 0.293 | 0.534 | 0.292 | 0.542 | 0.281 | 0.429 | 0.231 |

TABLE 38-continued

Average Triglycerides Normalized to Pre-Treatment from Example 8

| | Day 8 | | Day 15 | | Day 22 | | Day 29 | | Day 36 | |
|---|---|---|---|---|---|---|---|---|---|---|
| Group ID | Avg TG | Std Dev (+/−) | Avg TG | Std Dev (+/−) | Avg TG | Std Dev (+/−) | Avg TG | Std Dev (+/−) | Avg TG | Std Dev (+/−) |
| Group 5 (3.0 mg/kg AD05659) | 0.893 | 0.225 | 0.670 | 0.194 | 0.707 | 0.092 | 0.600 | 0.044 | 0.635 | 0.094 |

TABLE 39

Average Total Cholesterol Normalized to Pre-Treatment from Example 8

| | Day 8 | | Day 15 | | Day 22 | | Day 29 | | Day 36 | |
|---|---|---|---|---|---|---|---|---|---|---|
| Group ID | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (3.0 mg/kg AD05577) | 0.885 | 0.110 | 0.931 | 0.123 | 0.844 | 0.181 | 0.839 | 0.188 | 0.936 | 0.195 |
| Group 2 (3.0 mg/kg AD05307) | 0.994 | 0.017 | 1.006 | 0.017 | 0.905 | 0.021 | 0.954 | 0.074 | 0.909 | 0.038 |
| Group 3 (3.0 mg/kg AD05488) | 0.840 | 0.020 | 0.779 | 0.067 | 0.743 | 0.033 | 0.674 | 0.004 | 0.722 | 0.021 |
| Group 4 (3.0 mg/kg AD05654) | 0.912 | 0.007 | 0.933 | 0.004 | 0.794 | 0.071 | 0.806 | 0.011 | 0.832 | 0.042 |
| Group 5 (3.0 mg/kg AD05659) | 0.928 | 0.053 | 0.841 | 0.004 | 0.748 | 0.020 | 0.796 | 0.048 | 0.797 | 0.028 |

TABLE 40

Average HDL Normalized to Pre-Treatment from Example 8

| | Day 8 | | Day 15 | | Day 22 | | Day 29 | | Day 36 | |
|---|---|---|---|---|---|---|---|---|---|---|
| Group ID | Avg HDL | Std Dev (+/−) | Avg HDL | Std Dev (+/−) | Avg HDL | Std Dev (+/−) | Avg HDL | Std Dev (+/−) | Avg HDL | Std Dev (+/−) |
| Group 1 (3.0 mg/kg AD05577) | 0.855 | 0.101 | 0.788 | 0.096 | 0.818 | 0.192 | 0.857 | 0.124 | 0.852 | 0.119 |
| Group 2 (3.0 mg/kg AD05307) | 1.007 | 0.039 | 0.946 | 0.088 | 0.879 | 0.022 | 0.998 | 0.063 | 0.863 | 0.070 |
| Group 3 (3.0 mg/kg AD05488) | 0.832 | 0.006 | 0.695 | 0.075 | 0.688 | 0.097 | 0.657 | 0.032 | 0.622 | 0.099 |
| Group 4 (3.0 mg/kg AD05654) | 0.865 | 0.018 | 0.804 | 0.017 | 0.698 | 0.056 | 0.760 | 0.014 | 0.682 | 0.015 |
| Group 5 (3.0 mg/kg AD05659) | 0.910 | 0.008 | 0.865 | 0.084 | 0.765 | 0.073 | 0.857 | 0.129 | 0.761 | 0.104 |

TABLE 41

Average LDL Normalized to Pre-Treatment from Example 8

| | Day 8 | | Day 15 | | Day 22 | | Day 29 | | Day 36 | |
|---|---|---|---|---|---|---|---|---|---|---|
| Group ID | Avg LDL | Std Dev (+/−) | Avg LDL | Std Dev (+/−) | Avg LDL | Std Dev (+/−) | Avg LDL | Std Dev (+/−) | Avg LDL | Std Dev (+/−) |
| Group 1 (3.0 mg/kg AD05577) | 0.951 | 0.136 | 1.091 | 0.150 | 0.860 | 0.220 | 0.991 | 0.288 | 0.925 | 0.258 |
| Group 2 (3.0 mg/kg AD05307) | 1.008 | 0.093 | 1.102 | 0.012 | 0.971 | 0.113 | 1.106 | 0.103 | 0.894 | 0.021 |
| Group 3 (3.0 mg/kg AD05488) | 0.934 | 0.051 | 0.926 | 0.020 | 0.891 | 0.092 | 0.872 | 0.085 | 0.805 | 0.081 |
| Group 4 (3.0 mg/kg AD05654) | 1.015 | 0.014 | 1.134 | 0.026 | 0.957 | 0.097 | 1.022 | 0.035 | 0.962 | 0.068 |
| Group 5 (3.0 mg/kg AD05659) | 1.188 | 0.065 | 1.085 | 0.099 | 0.928 | 0.045 | 1.105 | 0.208 | 0.952 | 0.024 |

Each of the cynomolgus monkeys dosed with any of AD05577, AD05307, AD05488, AD05654, or AD05659 showed a reduction in ANGPTL3 protein compared to pre-treatment measurements across all measured time points.

Example 9. In Vivo Testing of ANGPTL3 RNAi Agents in Cynomolgus Monkeys

Additional ANGPTL3 RNAi agents were evaluated in cynomolgus monkeys. On day 1, cynomolgus macaque (*Macaca fascicularis*) primates (also referred to herein as "cynos") were administered a single subcutaneous injection of 0.3 mL/kg (approximately 2-3 mL volume, depending on animal mass) containing 2.0 mg/kg of an ANGPTL3 RNAi agent, which included either AD05488, AD05743, AD05775, or AD05841, each formulated in saline. Each of the ANGPTL3 RNAi agents contained modified nucleotides and included N-acetyl-galactosamine targeting ligands conjugated to the 5'-terminal end of the sense strand, as shown in Tables 3, 4, and 5. ANGPTL3 RNAi agents AD05488, AD05743, and AD05775 included nucleotide sequences designed to target position 304 of the ANGPTL3 gene. ANGPTL3 RNAi agent AD05841 included nucleotide sequences designed to target position 1035 of the ANGPTL3 gene.

Three (3) cynos in each group were tested (n=3). Blood samples were drawn and serum samples were analyzed on days −14 (predose), −7 (predose), 1 (pre-dose), 8, 15, 22, 29, and 35. Cynos were fasted overnight prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the average pre-treatment level of expression in that animal (in this case at days −14, −7, and 1) to determine the ratio of expression "normalized to pre-treatment."

Data from the study set forth in this Example are shown in the following Tables 42-45:

TABLE 42

Average ANGPTL3 Protein Normalized to Pre-Treatment from Example 9

| Group ID | Day 8 Avg ANGPTL3 | Std Dev (+/−) | Day 15 Avg ANGPTL3 | Std Dev (+/−) | Day 22 Avg ANGPTL3 | Std Dev (+/−) | Day 29 Avg ANGPTL3 | Std Dev (+/−) | Day 35 Avg ANGPTL3 | Std Dev (+/−) |
|---|---|---|---|---|---|---|---|---|---|---|
| Group 1 (2.0 mg/kg AD05488) | 0.232 | 0.083 | 0.240 | 0.114 | 0.239 | 0.087 | 0.258 | 0.090 | 0.332 | 0.133 |
| Group 2 (2.0 mg/kg AD05743) | 0.349 | 0.029 | 0.316 | 0.070 | 0.322 | 0.075 | 0.381 | 0.068 | 0.346 | 0.066 |
| Group 3 (2.0 mg/kg AD05775) | 0.463 | 0.089 | 0.352 | 0.053 | 0.330 | 0.053 | 0.365 | 0.106 | 0.379 | 0.111 |
| Group 4 (2.0 mg/kg AD05841) | 0.672 | 0.188 | 0.646 | 0.213 | 0.489 | 0.196 | 0.582 | 0.187 | 0.460 | 0.154 |

TABLE 43

Average Triglycerides Normalized to Pre-Treatment from Example 9

| Group ID | Day 8 Avg TG | Std Dev (+/−) | Day 15 Avg TG | Std Dev (+/−) | Day 22 Avg TG | Std Dev (+/−) | Day 29 Avg TG | Std Dev (+/−) | Day 35 Avg TG | Std Dev (+/−) |
|---|---|---|---|---|---|---|---|---|---|---|
| Group 1 (2.0 mg/kg AD05488) | 0.413 | 0.081 | 0.403 | 0.131 | 0.288 | 0.184 | 0.344 | 0.254 | 0.350 | 0.083 |
| Group 2 (2.0 mg/kg AD05743) | 0.646 | 0.134 | 0.708 | 0.373 | 0.458 | 0.163 | 0.479 | 0.063 | 0.521 | 0.101 |
| Group 3 (2.0 mg/kg AD05775) | 0.466 | 0.209 | 0.427 | 0.065 | 0.552 | 0.254 | 0.391 | 0.056 | 0.431 | 0.150 |
| Group 4 (2.0 mg/kg AD05841) | 0.600 | 0.160 | 0.506 | 0.083 | 0.579 | 0.073 | 0.687 | 0.182 | 0.600 | 0.107 |

TABLE 44

Average Total Cholesterol Normalized to Pre-Treatment from Example 8

| Group ID | Day 8 | | Day 15 | | Day 22 | | Day 29 | | Day 35 | |
|---|---|---|---|---|---|---|---|---|---|---|
| | Avg Total Chol | Std Dev (+/−) | Avg Total Chol | Std Dev (+/−) | Avg Total Chol | Std Dev (+/−) | Avg Total Chol | Std Dev (+/−) | Avg Total Chol | Std Dev (+/−) |
| Group 1 (2.0 mg/kg AD05488) | 0.823 | 0.065 | 0.744 | 0.014 | 0.709 | 0.037 | 0.687 | 0.029 | 0.659 | 0.041 |
| Group 2 (2.0 mg/kg AD05743) | 0.925 | 0.050 | 0.758 | 0.042 | 0.768 | 0.041 | 0.807 | 0.093 | 0.752 | 0.055 |
| Group 3 (2.0 mg/kg AD05775) | 0.965 | 0.067 | 0.811 | 0.058 | 0.811 | 0.075 | 0.813 | 0.015 | 0.770 | 0.022 |
| Group 4 (2.0 mg/kg AD05841) | 0.863 | 0.209 | 0.844 | 0.178 | 0.820 | 0.141 | 0.819 | 0.265 | 0.798 | 0.069 |

TABLE 45

Average HDL Normalized to Pre-Treatment from Example 9

| Group ID | Day 8 | | Day 15 | | Day 22 | | Day 29 | | Day 35 | |
|---|---|---|---|---|---|---|---|---|---|---|
| | Avg HDL | Std Dev (+/−) | Avg HDL | Std Dev (+/−) | Avg HDL | Std Dev (+/−) | Avg HDL | Std Dev (+/−) | Avg HDL | Std Dev (+/−) |
| Group 1 (2.0 mg/kg AD05488) | 0.985 | 0.354 | 0.911 | 0.261 | 0.849 | 0.353 | 0.856 | 0.333 | 0.810 | 0.296 |
| Group 2 (2.0 mg/kg AD05743) | 0.849 | 0.048 | 0.797 | 0.058 | 0.666 | 0.155 | 0.757 | 0.138 | 0.677 | 0.135 |
| Group 3 (2.0 mg/kg AD05775) | 0.904 | 0.078 | 0.871 | 0.161 | 0.737 | 0.085 | 0.781 | 0.055 | 0.723 | 0.042 |
| Group 4 (2.0 mg/kg AD05841) | 0.842 | 0.268 | 0.919 | 0.186 | 0.876 | 0.204 | 0.896 | 0.247 | 0.919 | 0.102 |

TABLE 46

Average LDL Normalized to Pre-Treatment from Example 9

| Group ID | Day 8 | | Day 15 | | Day 22 | | Day 29 | | Day 35 | |
|---|---|---|---|---|---|---|---|---|---|---|
| | Avg LDL | Std Dev (+/−) | Avg LDL | Std Dev (+/−) | Avg LDL | Std Dev (+/−) | Avg LDL | Std Dev (+/−) | Avg LDL | Std Dev (+/−) |
| Group 1 (2.0 mg/kg AD05488) | 0.971 | 0.291 | 0.913 | 0.193 | 0.949 | 0.216 | 0.853 | 0.145 | 0.845 | 0.108 |
| Group 2 (2.0 mg/kg AD05743) | 1.055 | 0.061 | 0.825 | 0.054 | 0.986 | 0.013 | 0.941 | 0.124 | 0.911 | 0.069 |
| Group 3 (2.0 mg/kg AD05775) | 1.134 | 0.156 | 0.909 | 0.111 | 1.089 | 0.180 | 1.034 | 0.184 | 1.008 | 0.143 |
| Group 4 (2.0 mg/kg AD05841) | 0.918 | 0.135 | 0.953 | 0.193 | 0.980 | 0.069 | 0.894 | 0.270 | 1.002 | 0.048 |

Each of the cynomolgus monkeys dosed with any of AD05488, AD05743, AD05775, and AD05841, each at 2.0 mg/kg dosage levels, showed a reduction in ANGPTL3 protein compared to pre-treatment measurements across each of the measured time points.

Example 10. Additional In Vivo Testing of ANGPTL3 RNAi Agents in Mice

To assess the in vivo activity of further ANGPTL3 RNAi agents that are designed to target position 304 on the ANGPTL3 gene, six- to eight-week-old female C57bl/6 mice were used. Pre-dose serum samples were taken at day −1 after a four hour fast. At day 1, each mouse was given a single subcutaneous administration of 200 μl containing 0.5 mg/kg (mpk) of an ANGPTL3 RNAi agent in D5W (dextrose in 5% water), or control (D5W) with no RNAi agent, according to the dosing groups recited in Table 47.

TABLE 47

Dosing Groups of Example 10

| Group | RNAi Agent and Dose | Dosing Regimen |
|---|---|---|
| 1 | D5W (no RNAi agent) | Single injection on day 1 |
| 2 | 0.5 mg/kg AD05488 | Single injection on day 1 |
| 3 | 0.5 mg/kg AD05790 | Single injection on day 1 |
| 4 | 0.5 mg/kg AD05791 | Single injection on day 1 |
| 5 | 0.5 mg/kg AD05792 | Single injection on day 1 |
| 6 | 0.5 mg/kg AD05793 | Single injection on day 1 |
| 7 | 0.5 mg/kg AD05794 | Single injection on day 1 |
| 8 | 0.5 mg/kg AD05795 | Single injection on day 1 |
| 9 | 0.5 mg/kg AD05796 | Single injection on day 1 |
| 10 | 0.5 mg/kg AD05797 | Single injection on day 1 |
| 11 | 0.5 mg/kg AD05798 | Single injection on day 1 |
| 12 | 0.5 mg/kg AD05799 | Single injection on day 1 |
| 13 | 0.5 mg/kg AD05800 | Single injection on day 1 |

Each of the RNAi agents included a modified sequence and an N-acetyl-galactosamine-containing targeting ligand conjugated to the 5' terminal end of the sense strand. (See Tables 3, 4, and 5 for modified sequences and targeting ligand structures). As noted above, each of the ANGPTL3 RNAi agents dosed in this study included nucleotide sequences designed to target the ANGPTL3 gene at position 304. The injections were performed between the skin and muscle (i.e. subcutaneous injections) into the loose skin over the neck and shoulder area. Three (3) mice in each group were tested (n=3). Serum was collected on days 8, 15, 22, 29, and for some groups on day 36 (i.e., Groups 1, 2, and 9-13 only). Mice were fasted for four hours prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 48-52:

TABLE 48

Average ANGPTL3 Protein Normalized to Pre-Treatment and Control from Example 10

| Group ID | Day 8 Avg ANGPTL3 | Day 8 Std Dev (+/−) | Day 15 Avg ANGPTL3 | Day 15 Std Dev (+/−) | Day 22 Avg ANGPTL3 | Day 22 Std Dev (+/−) | Day 29 Avg ANGPTL3 | Day 29 Std Dev (+/−) | Day 36 Avg ANGPTL3 | Day 36 Std Dev (+/−) |
|---|---|---|---|---|---|---|---|---|---|---|
| Group 1 (D5W) | 1.000 | 0.128 | 1.000 | 0.246 | 1.000 | 0.116 | 1.000 | 0.202 | 1.000 | 0.218 |
| Group 2 (0.5 mg/kg AD05488) | 0.179 | 0.019 | 0.197 | 0.010 | 0.196 | 0.014 | 0.258 | 0.042 | 0.297 | 0.039 |
| Group 3 (0.5 mg/kg AD05790) | 0.207 | 0.076 | 0.144 | 0.025 | 0.208 | 0.017 | 0.308 | 0.036 | | |
| Group 4 (0.5 mg/kg AD05791) | 0.145 | 0.040 | 0.170 | 0.016 | 0.214 | 0.076 | 0.246 | 0.045 | | |
| Group 5 (0.5 mg/kg AD05792) | 0.195 | 0.049 | 0.192 | 0.097 | 0.171 | 0.046 | 0.309 | 0.184 | | |
| Group 6 (0.5 mg/kg AD05793) | 0.205 | 0.038 | 0.156 | 0.048 | 0.162 | 0.011 | 0.287 | 0.016 | | |
| Group 7 (0.5 mg/kg AD05794) | 0.223 | 0.014 | 0.217 | 0.031 | 0.224 | 0.048 | 0.285 | 0.044 | | |
| Group 8 (0.5 mg/kg AD05795) | 0.246 | 0.076 | 0.343 | 0.021 | 0.288 | 0.042 | 0.453 | 0.134 | | |
| Group 9 (0.5 mg/kg AD05796) | 0.183 | 0.058 | 0.213 | 0.062 | 0.223 | 0.047 | 0.241 | 0.040 | 0.315 | 0.098 |
| Group 10 (0.5 mg/kg AD05797) | 0.250 | 0.098 | 0.201 | 0.051 | 0.238 | 0.097 | 0.269 | 0.027 | 0.371 | 0.042 |
| Group 11 (0.5 mg/kg AD05798) | 0.175 | 0.018 | 0.167 | 0.015 | 0.228 | 0.044 | 0.233 | 0.069 | 0.242 | 0.033 |
| Group 12 (0.5 mg/kg AD05799) | 0.167 | 0.047 | 0.150 | 0.026 | 0.227 | 0.032 | 0.221 | 0.024 | 0.231 | 0.015 |
| Group 13 (0.5 mg/kg AD05800) | 0.194 | 0.013 | 0.196 | 0.050 | 0.214 | 0.029 | 0.227 | 0.053 | 0.235 | 0.005 |

TABLE 49

Average Triglycerides Normalized to Pre-Treatment and Control from Example 10

| Group ID | Day 8 Avg TG | Day 8 Std Dev (+/−) | Day 15 Avg TG | Day 15 Std Dev (+/−) | Day 22 Avg TG | Day 22 Std Dev (+/−) | Day 29 Avg TG | Day 29 Std Dev (+/−) | Day 36 Avg TG | Day 36 Std Dev (+/−) |
|---|---|---|---|---|---|---|---|---|---|---|
| Group 1 (D5W) | 1.000 | 0.097 | 1.000 | 0.099 | 1.000 | 0.185 | 1.000 | 0.135 | 1.000 | 0.174 |
| Group 2 (0.5 mg/kg AD05488) | 0.646 | 0.083 | 0.669 | 0.209 | 0.723 | 0.227 | 0.739 | 0.136 | 0.843 | 0.239 |
| Group 3 (0.5 mg/kg AD05790) | 0.832 | 0.086 | 0.784 | 0.172 | 0.974 | 0.242 | 0.718 | 0.085 | | |
| Group 4 (0.5 mg/kg AD05791) | 1.125 | 0.266 | 0.930 | 0.141 | 1.631 | 0.218 | 0.854 | 0.179 | | |
| Group 5 (0.5 mg/kg AD05792) | 0.888 | 0.196 | 0.796 | 0.144 | 1.094 | 0.217 | 0.794 | 0.026 | | |
| Group 6 (0.5 mg/kg AD05793) | 1.143 | 0.137 | 0.972 | 0.116 | 0.998 | 0.280 | 1.028 | 0.408 | | |
| Group 7 (0.5 mg/kg AD05794) | 0.560 | 0.083 | 0.545 | 0.145 | 0.713 | 0.097 | 0.730 | 0.175 | | |

TABLE 49-continued

Average Triglycerides Normalized to Pre-Treatment and Control from Example 10

| Group ID | Day 8 Avg TG | Std Dev (+/−) | Day 15 Avg TG | Std Dev (+/−) | Day 22 Avg TG | Std Dev (+/−) | Day 29 Avg TG | Std Dev (+/−) | Day 36 Avg TG | Std Dev (+/−) |
|---|---|---|---|---|---|---|---|---|---|---|
| Group 8 (0.5 mg/kg AD05795) | 0.739 | 0.072 | 0.753 | 0.078 | 1.034 | 0.121 | 0.842 | 0.065 | | |
| Group 9 (0.5 mg/kg AD05796) | 0.602 | 0.075 | 0.586 | 0.142 | 0.832 | 0.132 | 0.702 | 0.085 | 0.958 | 0.076 |
| Group 10 (0.5 mg/kg AD05797) | 0.851 | 0.159 | 0.651 | 0.075 | 0.969 | 0.065 | 0.713 | 0.030 | 0.929 | 0.186 |
| Group 11 (0.5 mg/kg AD05798) | 0.869 | 0.166 | 0.586 | 0.107 | 0.653 | 0.059 | 0.573 | 0.118 | 0.690 | 0.081 |
| Group 12 (0.5 mg/kg AD05799) | 0.683 | 0.092 | 0.593 | 0.166 | 0.751 | 0.061 | 0.546 | 0.075 | 0.725 | 0.179 |
| Group 13 (0.5 mg/kg AD05800) | 0.676 | 0.046 | 0.634 | 0.048 | 0.655 | 0.019 | 0.635 | 0.088 | 1.033 | 0.068 |

TABLE 50

Average Total Cholesterol Normalized to Pre-Treatment and Control from Example 10

| Group ID | Day 8 Avg Total Chol | Std Dev (+/−) | Day 15 Avg Total Chol | Std Dev (+/−) | Day 22 Avg Total Chol | Std Dev (+/−) | Day 29 Avg Total Chol | Std Dev (+/−) | Day 36 Avg Total Chol | Std Dev (+/−) |
|---|---|---|---|---|---|---|---|---|---|---|
| Group 1 (D5W) | 1.000 | 0.060 | 1.000 | 0.018 | 1.000 | 0.104 | 1.000 | 0.038 | 1.000 | 0.056 |
| Group 2 (0.5 mg/kg AD05488) | 0.659 | 0.023 | 0.808 | 0.018 | 0.763 | 0.113 | 0.743 | 0.028 | 0.824 | 0.065 |
| Group 3 (0.5 mg/kg AD05790) | 0.698 | 0.104 | 0.730 | 0.026 | 0.711 | 0.031 | 0.757 | 0.083 | | |
| Group 4 (0.5 mg/kg AD05791) | 0.664 | 0.035 | 0.694 | 0.062 | 0.631 | 0.041 | 0.677 | 0.046 | | |
| Group 5 (0.5 mg/kg AD05792) | 0.716 | 0.055 | 0.725 | 0.081 | 0.568 | 0.074 | 0.727 | 0.133 | | |
| Group 6 (0.5 mg/kg AD05793) | 0.813 | 0.102 | 0.805 | 0.091 | 0.689 | 0.026 | 0.769 | 0.128 | | |
| Group 7 (0.5 mg/kg AD05794) | 0.715 | 0.055 | 0.861 | 0.031 | 0.673 | 0.080 | 0.768 | 0.110 | | |
| Group 8 (0.5 mg/kg AD05795) | 0.852 | 0.124 | 0.973 | 0.187 | 0.745 | 0.087 | 0.866 | 0.067 | | |
| Group 9 (0.5 mg/kg AD05796) | 0.666 | 0.113 | 0.793 | 0.047 | 0.595 | 0.054 | 0.735 | 0.082 | 0.795 | 0.125 |
| Group 10 (0.5 mg/kg AD05797) | 0.734 | 0.024 | 0.734 | 0.017 | 0.642 | 0.026 | 0.741 | 0.113 | 0.861 | 0.102 |
| Group 11 (0.5 mg/kg AD05798) | 0.719 | 0.031 | 0.784 | 0.065 | 0.711 | 0.077 | 0.721 | 0.086 | 0.649 | 0.019 |
| Group 12 (0.5 mg/kg AD05799) | 0.700 | 0.052 | 0.684 | 0.014 | 0.698 | 0.092 | 0.632 | 0.070 | 0.714 | 0.040 |
| Group 13 (0.5 mg/kg AD05800) | 0.842 | 0.079 | 0.794 | 0.048 | 0.691 | 0.071 | 0.750 | 0.100 | 0.853 | 0.186 |

TABLE 51

Average HDL Normalized to Pre-Treatment and Control from Example 10

| Group ID | Day 8 Avg HDL | Std Dev (+/−) | Day 15 Avg HDL | Std Dev (+/−) | Day 22 Avg HDL | Std Dev (+/−) | Day 29 Avg HDL | Std Dev (+/−) | Day 36 Avg HDL | Std Dev (+/−) |
|---|---|---|---|---|---|---|---|---|---|---|
| Group 1 (D5W) | 1.000 | 0.090 | 1.000 | 0.014 | 1.000 | 0.123 | 1.000 | 0.058 | 1.000 | 0.036 |
| Group 2 (0.5 mg/kg AD05488) | 0.648 | 0.029 | 0.807 | 0.041 | 0.733 | 0.096 | 0.746 | 0.012 | 0.816 | 0.038 |
| Group 3 (0.5 mg/kg AD05790) | 0.674 | 0.110 | 0.705 | 0.040 | 0.649 | 0.030 | 0.748 | 0.095 | | |
| Group 4 (0.5 mg/kg AD05791) | 0.632 | 0.029 | 0.674 | 0.063 | 0.563 | 0.036 | 0.679 | 0.041 | | |

TABLE 51-continued

Average HDL Normalized to Pre-Treatment and Control from Example 10

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) | Day 36 Avg HDL | Day 36 Std Dev (+/−) |
|---|---|---|---|---|---|---|---|---|---|---|
| Group 5 (0.5 mg/kg AD05792) | 0.676 | 0.055 | 0.683 | 0.086 | 0.509 | 0.061 | 0.712 | 0.135 | | |
| Group 6 (0.5 mg/kg AD05793) | 0.721 | 0.082 | 0.724 | 0.079 | 0.600 | 0.015 | 0.696 | 0.088 | | |
| Group 7 (0.5 mg/kg AD05794) | 0.652 | 0.041 | 0.823 | 0.047 | 0.611 | 0.059 | 0.736 | 0.090 | | |
| Group 8 (0.5 mg/kg AD05795) | 0.757 | 0.117 | 0.905 | 0.189 | 0.644 | 0.074 | 0.817 | 0.085 | | |
| Group 9 (0.5 mg/kg AD05796) | 0.610 | 0.107 | 0.760 | 0.062 | 0.535 | 0.075 | 0.696 | 0.080 | 0.734 | 0.117 |
| Group 10 (0.5 mg/kg AD05797) | 0.676 | 0.020 | 0.688 | 0.005 | 0.564 | 0.037 | 0.701 | 0.092 | 0.790 | 0.089 |
| Group 11 (0.5 mg/kg AD05798) | 0.709 | 0.030 | 0.808 | 0.068 | 0.719 | 0.094 | 0.759 | 0.117 | 0.653 | 0.024 |
| Group 12 (0.5 mg/kg AD05799) | 0.666 | 0.085 | 0.674 | 0.039 | 0.695 | 0.083 | 0.667 | 0.088 | 0.707 | 0.033 |
| Group 13 (0.5 mg/kg AD05800) | 0.806 | 0.060 | 0.796 | 0.065 | 0.706 | 0.075 | 0.772 | 0.088 | 0.801 | 0.158 |

TABLE 52

Average LDL Normalized to Pre-Treatment and Control from Example 10

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) | Day 36 Avg LDL | Day 36 Std Dev (+/−) |
|---|---|---|---|---|---|---|---|---|---|---|
| Group 1 (D5W) | 1.000 | 0.123 | 1.000 | 0.172 | 1.000 | 0.146 | 1.000 | 0.180 | 1.000 | 0.202 |
| Group 2 (0.5 mg/kg AD05488) | 0.836 | 0.057 | 0.969 | 0.033 | 0.901 | 0.129 | 0.762 | 0.165 | 0.863 | 0.153 |
| Group 3 (0.5 mg/kg AD05790) | 0.922 | 0.174 | 0.944 | 0.082 | 0.916 | 0.126 | 0.899 | 0.153 | | |
| Group 4 (0.5 mg/kg AD05791) | 0.878 | 0.119 | 0.744 | 0.097 | 0.848 | 0.158 | 0.755 | 0.145 | | |
| Group 5 (0.5 mg/kg AD05792) | 0.805 | 0.060 | 0.776 | 0.058 | 0.623 | 0.017 | 0.745 | 0.082 | | |
| Group 6 (0.5 mg/kg AD05793) | 0.968 | 0.181 | 0.828 | 0.106 | 0.768 | 0.049 | 0.751 | 0.200 | | |
| Group 7 (0.5 mg/kg AD05794) | 0.853 | 0.057 | 0.847 | 0.031 | 0.677 | 0.233 | 0.714 | 0.156 | | |
| Group 8 (0.5 mg/kg AD05795) | 1.044 | 0.073 | 0.956 | 0.219 | 0.805 | 0.159 | 0.777 | 0.040 | | |
| Group 9 (0.5 mg/kg AD05796) | 0.807 | 0.143 | 0.760 | 0.056 | 0.606 | 0.087 | 0.697 | 0.055 | 0.784 | 0.150 |
| Group 10 (0.5 mg/kg AD05797) | 0.786 | 0.102 | 0.749 | 0.013 | 0.688 | 0.024 | 0.689 | 0.155 | 0.879 | 0.225 |
| Group 11 (0.5 mg/kg AD05798) | 0.879 | 0.159 | 0.896 | 0.203 | 0.648 | 0.039 | 0.738 | 0.055 | 0.762 | 0.065 |
| Group 12 (0.5 mg/kg AD05799) | 0.853 | 0.104 | 0.837 | 0.196 | 0.678 | 0.176 | 0.652 | 0.138 | 0.873 | 0.157 |
| Group 13 (0.5 mg/kg AD05800) | 0.951 | 0.268 | 0.885 | 0.041 | 0.682 | 0.130 | 0.826 | 0.244 | 1.107 | 0.298 |

As indicated in Table 48 above, each of the ANGPTL3 RNAi agents tested showed a significant reduction in ANGPTL3 protein across all time points, and similar trends are seen with respect to reductions in TG levels, total cholesterol levels, and LDL levels.

Example 11. In Vivo Testing of ANGPTL3 RNAi Agents in Mice

To assess the dose response of ANGPTL3 RNAi agent AD05488, six- to eight-week-old female C57bl/6 mice were used. Pre-dose serum samples were taken at day −1 after a four hour fast. At day 1, each mouse was given a single subcutaneous administration of 200 μl containing the respective mg/kg dose of an ANGPTL3 RNAi agent in D5W (dextrose in 5% water), or control (D5W) with no RNAi agent, according to the dosing groups recited in Table 53:

TABLE 53

Dosing Groups of Example 11

| Group | RNAi Agent and Dose | Dosing Regimen |
|---|---|---|
| 1 | D5W (no RNAi agent) | Single injection on day 1 |
| 2 | 0.05 mg/kg AD05488 | Single injection on day 1 |
| 3 | 0.1 mg/kg AD05488 | Single injection on day 1 |
| 4 | 0.5 mg/kg AD05488 | Single injection on day 1 |
| 5 | 1.0 mg/kg AD05488 | Single injection on day 1 |
| 6 | 2.5 mg/kg AD05488 | Single injection on day 1 |
| 7 | 5.0 mg/kg AD05488 | Single injection on day 1 |

The RNAi agent tested (AD05488) included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Four (4) mice in each group were tested (n=4). Serum was collected on days 8, 15, 22, and 29. Mice were fasted for four hours prior to each collection. ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the pre-treatment level of expression in that animal (in this case at day −1) to determine the ratio of expression "normalized to pre-treatment." Expression at a specific time point was then normalized to the D5W control group by dividing the "normalized to pre-treatment" ratio for an individual animal by the mean "normalized to pretreatment" ratio of all mice in the D5W control group. This resulted in expression for each time point normalized to that in the control group.

Data from the study set forth in this Example are shown in the following Tables 54-58:

TABLE 54

Average ANGPTL3 Protein Normalized to Pre-Treatment and Control from Example 11

| Group ID | Day 8 | | Day 15 | | Day 22 | | Day 29 | |
| --- | --- | --- | --- | --- | --- | --- | --- | --- |
| | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (D5W) | 1.000 | 0.291 | 1.000 | 0.170 | 1.000 | 0.224 | 1.000 | 0.293 |
| Group 2 (0.05 mg/kg AD05488) | 0.788 | 0.110 | 0.929 | 0.203 | 1.106 | 0.117 | 0.990 | 0.175 |
| Group 3 (0.1 mg/kg AD05488) | 0.511 | 0.109 | 0.757 | 0.092 | 0.720 | 0.069 | 0.734 | 0.058 |
| Group 4 (0.5 mg/kg AD05488) | 0.207 | 0.039 | 0.261 | 0.050 | 0.310 | 0.080 | 0.349 | 0.090 |
| Group 5 (1.0 mg/kg AD05488) | 0.116 | 0.038 | 0.141 | 0.027 | 0.171 | 0.066 | 0.199 | 0.054 |
| Group 6 (2.5 mg/kg AD05488) | 0.064 | 0.010 | 0.047 | 0.012 | 0.056 | 0.009 | 0.063 | 0.002 |
| Group 7 (5.0 mg/kg AD05488) | 0.018 | 0.005 | 0.019 | 0.004 | 0.029 | 0.010 | 0.031 | 0.003 |

TABLE 55

Average Triglycerides Normalized to Pre-Treatment and Control from Example 11

| Group ID | Day 8 | | Day 15 | | Day 22 | | Day 29 | |
| --- | --- | --- | --- | --- | --- | --- | --- | --- |
| | Avg TG | Std Dev (+/−) | Avg TG | Std Dev (+/−) | Avg TG | Std Dev (+/−) | Avg TG | Std Dev (+/−) |
| Group 1 (D5W) | 1.000 | 0.181 | 1.000 | 0.120 | 1.000 | 0.135 | 1.000 | 0.221 |
| Group 2 (0.05 mg/kg AD05488) | 1.296 | 0.168 | 1.274 | 0.180 | 1.202 | 0.016 | 1.999 | 0.356 |
| Group 3 (0.1 mg/kg AD05488) | 1.116 | 0.193 | 1.141 | 0.256 | 1.234 | 0.184 | 1.798 | 0.555 |
| Group 4 (0.5 mg/kg AD05488) | 1.028 | 0.266 | 1.027 | 0.283 | 0.864 | 0.208 | 1.855 | 0.364 |
| Group 5 (1.0 mg/kg AD05488) | 0.860 | 0.186 | 0.755 | 0.228 | 0.720 | 0.140 | 1.254 | 0.195 |
| Group 6 (2.5 mg/kg AD05488) | 0.623 | 0.197 | 0.556 | 0.139 | 0.447 | 0.075 | 0.772 | 0.269 |
| Group 7 (5.0 mg/kg AD05488) | 0.923 | 0.150 | 0.892 | 0.105 | 0.781 | 0.107 | 1.128 | 0.299 |

TABLE 56

Average Total Cholesterol Normalized to Pre-Treatment and Control from Example 11

| Group ID | Day 8 | | Day 15 | | Day 22 | | Day 29 | |
| --- | --- | --- | --- | --- | --- | --- | --- | --- |
| | Avg Total Chol | Std Dev (+/−) | Avg Total Chol | Std Dev (+/−) | Avg Total Chol | Std Dev (+/−) | Avg Total Chol | Std Dev (+/−) |
| Group 1 (D5W) | 1.000 | 0.061 | 1.000 | 0.058 | 1.000 | 0.124 | 1.000 | 0.069 |
| Group 2 (0.05 mg/kg AD05488) | 0.856 | 0.030 | 1.090 | 0.092 | 0.946 | 0.081 | 0.915 | 0.059 |
| Group 3 (0.1 mg/kg AD05488) | 0.820 | 0.095 | 0.974 | 0.097 | 0.785 | 0.078 | 0.945 | 0.074 |
| Group 4 (0.5 mg/kg AD05488) | 0.740 | 0.061 | 0.918 | 0.081 | 0.897 | 0.102 | 0.883 | 0.071 |
| Group 5 (1.0 mg/kg AD05488) | 0.610 | 0.072 | 0.816 | 0.074 | 0.857 | 0.099 | 0.920 | 0.063 |
| Group 6 (2.5 mg/kg AD05488) | 0.647 | 0.076 | 0.832 | 0.119 | 0.772 | 0.174 | 0.694 | 0.117 |
| Group 7 (5.0 mg/kg AD05488) | 0.583 | 0.086 | 0.787 | 0.030 | 0.790 | 0.136 | 0.783 | 0.176 |

TABLE 57

Average HDL Normalized to Pre-Treatment and Control from Example 11

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 1 (D5W) | 1.000 | 0.054 | 1.000 | 0.049 | 1.000 | 0.101 | 1.000 | 0.070 |
| Group 2 (0.05 mg/kg AD05488) | 0.851 | 0.030 | 1.052 | 0.104 | 0.982 | 0.083 | 0.894 | 0.071 |
| Group 3 (0.1 mg/kg AD05488) | 0.807 | 0.101 | 0.950 | 0.077 | 0.806 | 0.064 | 0.910 | 0.063 |
| Group 4 (0.5 mg/kg AD05488) | 0.727 | 0.066 | 0.876 | 0.087 | 0.906 | 0.091 | 0.897 | 0.084 |
| Group 5 (1.0 mg/kg AD05488) | 0.575 | 0.079 | 0.785 | 0.077 | 0.839 | 0.113 | 0.888 | 0.043 |
| Group 6 (2.5 mg/kg AD05488) | 0.618 | 0.069 | 0.787 | 0.109 | 0.782 | 0.181 | 0.701 | 0.116 |
| Group 7 (5.0 mg/kg AD05488) | 0.534 | 0.082 | 0.717 | 0.018 | 0.760 | 0.140 | 0.759 | 0.156 |

TABLE 58

Average LDL Normalized to Pre-Treatment and Control from Example 11

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) |
|---|---|---|---|---|---|---|---|---|
| Group 1 (D5W) | 1.000 | 0.130 | 1.000 | 0.174 | 1.000 | 0.216 | 1.000 | 0.118 |
| Group 2 (0.05 mg/kg AD05488) | 0.798 | 0.036 | 1.147 | 0.107 | 0.772 | 0.097 | 0.822 | 0.076 |
| Group 3 (0.1 mg/kg AD05488) | 0.878 | 0.160 | 1.153 | 0.172 | 0.732 | 0.183 | 0.845 | 0.202 |
| Group 4 (0.5 mg/kg AD05488) | 0.816 | 0.138 | 1.137 | 0.217 | 0.866 | 0.011 | 0.896 | 0.099 |
| Group 5 (1.0 mg/kg AD05488) | 0.760 | 0.094 | 1.145 | 0.101 | 0.993 | 0.194 | 1.123 | 0.270 |
| Group 6 (2.5 mg/kg AD05488) | 0.805 | 0.101 | 1.185 | 0.191 | 0.915 | 0.209 | 0.814 | 0.049 |
| Group 7 (5.0 mg/kg AD05488) | 0.802 | 0.148 | 1.170 | 0.129 | 0.909 | 0.076 | 0.932 | 0.171 |

Additionally, ANGPTL3 mRNA levels were also assessed. All of the mice from each respective group were sacrificed on day 29 after serum collection, livers were harvested, and approximately 100 mg liver samples were collected and snap-frozen in liquid nitrogen for RNA isolation. Levels of ANGPTL3 mRNA in the mice livers were then measured by RT-qPCR, the results of which are set forth in the following Table 59:

TABLE 59

Average ANGPTL3 mRNA Level at Day 29, Normalized to Control from Example 11

| Group ID | Day 29 Avg Relative ANGPTL3 mRNA | Low Variance (Error) | High Variance (Error) |
|---|---|---|---|
| Group 1 (D5W) | 1.000 | 0.075 | 0.081 |
| Group 2 (0.05 mg/kg AD05488) | 0.798 | 0.126 | 0.149 |
| Group 3 (0.1 mg/kg AD05488) | 0.563 | 0.054 | 0.059 |
| Group 4 (0.5 mg/kg AD05488) | 0.277 | 0.074 | 0.100 |
| Group 5 (1.0 mg/kg AD05488) | 0.123 | 0.035 | 0.049 |
| Group 6 (2.5 mg/kg AD05488) | 0.036 | 0.007 | 0.009 |
| Group 7 (5.0 mg/kg AD05488) | 0.038 | 0.011 | 0.016 |

As shown in, among other things, Tables 54 and 59, the administration of ANGPTL3 RNAi agent AD05488 showed a reduction in both ANGPTL3 protein and ANGPTL3 mRNA.

Example 12. In Vivo Testing of ANGPTL3 RNAi Agents in LDL Receptor (LDLR) Knockout Mice To evaluate the effect of RNAi agent administration in a disease model, mice having a genetic mutation for the LDL receptor (referred to herein as LDLR KO mice) were commercially obtained (The Jackson Laboratory). The LDLR KO mice are homozygous for the $Ldlr^{tm1Her}$ mutation, and have elevated serum cholesterol levels, particularly when placed on a high fat diet. For three weeks prior to the onset of the study, thirty-nine (39) LDLR KO mice were placed on a high fat diet (Teklad Custom Diets TD. 88137). An additional eight (8) LDLR KO mice were placed on a normal chow diet over the same three-week period. Pre-dose serum samples were taken on day −15 and day −1 after a four hour fast. At day 1, each mouse was given a single subcutaneous administration of 200 μl/30 g animal body weight containing the respective mg/kg dose of an ANGPTL3 RNAi agent in D5W (dextrose in 5% water), control (D5W) with no RNAi agent, or a control RNAi agent that included a nucleotide sequence designed to target the Hepatitis B Virus (HBV) genome. A second injection of the same formulation was administered to the animals on day 29. The dosing regimen for the study is recited in the following Table 60:

TABLE 60

Dosing Groups of Example 12

| Group | RNAi Agent and Dose | Diet | Dosing Regimen | Number of LDL KO Mice (n=) |
|---|---|---|---|---|
| 1 | D5W (no RNAi agent) | High Fat ("Western") Diet | Injection on day 1, remaining animals received a second injection on day 29 | 13 |
| 2 | 3.0 mg/kg AD05488 | High Fat ("Western") Diet | Injection on day 1, remaining animals received a second injection on day 29 | 13 |

TABLE 60-continued

Dosing Groups of Example 12

| Group | RNAi Agent and Dose | Diet | Dosing Regimen | Number of LDL KO Mice (n=) |
|---|---|---|---|---|
| 3 | 3.0 mg/kg of a control RNAi agent directed to HBV | High Fat ("Western") Diet | Injection on day 1, remaining animals received a second injection on day 29 | 13 |
| 4 | D5W (no RNAi agent) | Normal Chow-Fed Diet | Injection on day 1 and a second single injection on day 29 | 4 |
| 5 | 3.0 mg/kg AD05488 | Normal Chow-Fed Diet | Injection on day 1, and a second injection on day 29 | 4 |

Each mouse remained on its respective diet through the duration of study. The RNAi agent tested (AD05488) included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Serum was collected on days 8, 15, 22, 29 (pre-second dose), 36, 43, 50, and 57. LDLR KO mice were fasted for four hours prior to each collection. On day 15, four (4) LDLR KO mice from Groups 1, 2, and 3 (i.e., the groups being administered the high fat "Western" diet) were sacrificed after serum collection, and on day 29, an additional four (4) LDLR KO mice from Groups 1, 2, and 3 were sacrificed after serum collection, for the purpose of performing mRNA assessments.

ANGPTL3 protein levels in serum were measured by ELISA assay (R&D Systems), according to the manufacturer's recommendations. Triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, respective levels of ANGPTL3 protein, TG, total cholesterol, HDL, or LDL for each animal at a time point was divided by the average pre-treatment level of expression in that animal (in this case the average of day −15 and day −1) to determine the ratio of expression "normalized to pre-treatment."

Expression at a specific time point was then normalized to the D5W control group that was administered the same diet (i.e., either the high fat "Western" diet or the normal chow-fed diet) by dividing the "normalized to pre-treatment" ratio for an individual animal by the mean "normalized to pretreatment" ratio of all mice in the D5W control group on the respective same diet, resulting in expression for each time point normalized to that in the control group.

Data from the study set forth in this Example are shown in the following Tables 61-65:

TABLE 61

Average ANGPTL3 Protein Normalized to Pre-Treatment and Control (Diet Matched) from Example 12

| | Day 8 | | Day 15 | | Day 22 | | Day 29 | |
|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (D5W) (High Fat Diet) | 1.000 | 0.130 | 1.000 | 0.125 | 1.000 | 0.190 | 1.000 | 0.127 |
| Group 2 (3.0 mg/kg AD05488) (High Fat Diet) | 0.013 | 0.008 | 0.009 | 0.007 | 0.011 | 0.006 | 0.011 | 0.005 |
| Group 3 (3.0 mg/kg HBV Control RNAi agent) (High Fat Diet) | 0.958 | 0.093 | 1.116 | 0.126 | 0.925 | 0.218 | 0.962 | 0.268 |
| Group 4 (D5W) (Normal Diet) | 1.000 | 0.094 | 1.000 | 0.061 | 1.000 | 0.140 | 1.000 | 0.277 |
| Group 5 (3.0 mg/kg AD05488) (Normal Diet) | 0.042 | 0.013 | 0.037 | 0.013 | 0.043 | 0.017 | 0.060 | 0.026 |
| | Day 36 | | Day 43 | | Day 50 | | Day 57 | |
| Group 1 (D5W) (High Fat Diet) | 1.000 | 0.182 | 1.000 | 0.266 | 1.000 | 0.174 | 1.000 | 0.237 |
| Group 2 (3.0 mg/kg AD05488) (High Fat Diet) | 0.005 | 0.001 | 0.005 | 0.002 | 0.005 | 0.003 | 0.007 | 0.004 |
| Group 3 (3.0 mg/kg HBV Control RNAi agent) (High Fat Diet) | 1.356 | 0.438 | 1.371 | 0.381 | 1.230 | 0.331 | 1.006 | 0.373 |
| Group 4 (D5W) (Normal Diet) | 1.000 | 0.183 | 1.000 | 0.114 | 1.000 | 0.047 | 1.000 | 0.149 |
| Group 5 (3.0 mg/kg AD05488) (Normal Diet) | 0.024 | 0.010 | 0.024 | 0.008 | 0.032 | 0.008 | 0.037 | 0.016 |

TABLE 62

Average Triglycerides Normalized to Pre-Treatment and Control (Diet Matched) from Example 12

| Group ID | Day 8 Avg TG | Day 8 Std Dev (+/−) | Day 15 Avg TG | Day 15 Std Dev (+/−) | Day 22 Avg TG | Day 22 Std Dev (+/−) | Day 29 Avg TG | Day 29 Std Dev (+/−) |
|---|---|---|---|---|---|---|---|---|
| Group 1 (D5W) (High Fat Diet) | 1.000 | 0.272 | 1.000 | 0.381 | 1.000 | 0.276 | 1.000 | 0.265 |
| Group 2 (3.0 mg/kg AD05488) (High Fat Diet) | 0.121 | 0.022 | 0.086 | 0.027 | 0.094 | 0.032 | 0.096 | 0.027 |
| Group 3 (3.0 mg/kg HBV Control RNAi agent) (High Fat Diet) | 0.923 | 0.345 | 0.864 | 0.321 | 0.735 | 0.210 | 0.775 | 0.174 |
| Group 4 (D5W) (Normal Diet) | 1.000 | 0.172 | 1.000 | 0.092 | 1.000 | 0.099 | 1.000 | 0.138 |
| Group 5 (3.0 mg/kg AD05488) (Normal Diet) | 0.472 | 0.039 | 0.503 | 0.018 | 0.473 | 0.086 | 0.480 | 0.052 |

| Group ID | Day 36 Avg TG | Day 36 Std Dev (+/−) | Day 43 Avg TG | Day 43 Std Dev (+/−) | Day 50 Avg TG | Day 50 Std Dev (+/−) | Day 57 Avg TG | Day 57 Std Dev (+/−) |
|---|---|---|---|---|---|---|---|---|
| Group 1 (D5W) (High Fat Diet) | 1.000 | 0.331 | 1.000 | 0.363 | 1.000 | 0.377 | 1.000 | 0.476 |
| Group 2 (3.0 mg/kg AD05488) (High Fat Diet) | 0.104 | 0.031 | 0.084 | 0.025 | 0.091 | 0.027 | 0.079 | 0.025 |
| Group 3 (3.0 mg/kg HBV Control RNAi agent) (High Fat Diet) | 0.746 | 0.171 | 0.520 | 0.097 | 0.683 | 0.104 | 0.713 | 0.154 |
| Group 4 (D5W) (Normal Diet) | 1.000 | 0.096 | 1.000 | 0.241 | 1.000 | 0.043 | 1.000 | 0.289 |
| Group 5 (3.0 mg/kg AD05488) (Normal Diet) | 0.548 | 0.051 | 0.348 | 0.053 | 0.625 | 0.061 | 0.438 | 0.087 |

TABLE 63

Average Total Cholesterol Normalized to Pre-Treatment and Control (Diet Matched) from Example 12

| Group ID | Day 8 Avg Total Chol | Day 8 Std Dev (+/−) | Day 15 Avg Total Chol | Day 15 Std Dev (+/−) | Day 22 Avg Total Chol | Day 22 Std Dev (+/−) | Day 29 Avg Total Chol | Day 29 Std Dev (+/−) |
|---|---|---|---|---|---|---|---|---|
| Group 1 (D5W) (High Fat Diet) | 1.000 | 0.101 | 1.000 | 0.142 | 1.000 | 0.187 | 1.000 | 0.161 |
| Group 2 (3.0 mg/kg AD05488) (High Fat Diet) | 0.524 | 0.045 | 0.438 | 0.034 | 0.410 | 0.037 | 0.410 | 0.058 |
| Group 3 (3.0 mg/kg HBV Control RNAi agent) (High Fat Diet) | 0.942 | 0.125 | 0.969 | 0.188 | 0.980 | 0.177 | 1.017 | 0.198 |
| Group 4 (D5W) (Normal Diet) | 1.000 | 0.072 | 1.000 | 0.052 | 1.000 | 0.102 | 1.000 | 0.088 |
| Group 5 (3.0 mg/kg AD05488) (Normal Diet) | 0.645 | 0.100 | 0.683 | 0.100 | 0.691 | 0.122 | 0.636 | 0.083 |

| Group ID | Day 36 Avg Total Chol | Day 36 Std Dev (+/−) | Day 43 Avg Total Chol | Day 43 Std Dev (+/−) | Day 50 Avg Total Chol | Day 50 Std Dev (+/−) | Day 57 Avg Total Chol | Day 57 Std Dev (+/−) |
|---|---|---|---|---|---|---|---|---|
| Group 1 (D5W) (High Fat Diet) | 1.000 | 0.100 | 1.000 | 0.158 | 1.000 | 0.176 | 1.000 | 0.213 |
| Group 2 (3.0 mg/kg AD05488) (High Fat Diet) | 0.438 | 0.042 | 0.363 | 0.043 | 0.374 | 0.055 | 0.341 | 0.058 |
| Group 3 (3.0 mg/kg HBV Control RNAi agent) (High Fat Diet) | 1.029 | 0.143 | 0.847 | 0.105 | 0.932 | 0.129 | 0.860 | 0.124 |
| Group 4 (D5W) (Normal Diet) | 1.000 | 0.150 | 1.000 | 0.180 | 1.000 | 0.115 | 1.000 | 0.088 |
| Group 5 (3.0 mg/kg AD05488) (Normal Diet) | 0.758 | 0.114 | 0.657 | 0.161 | 0.824 | 0.135 | 0.684 | 0.096 |

TABLE 64

Average HDL Normalized to Pre-Treatment and Control (Diet Matched) from Example 12

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 1 (D5W) (High Fat Diet) | 1.000 | 0.061 | 1.000 | 0.083 | 1.000 | 0.083 | 1.000 | 0.072 |

TABLE 64-continued

Average HDL Normalized to Pre-Treatment and Control (Diet Matched) from Example 12

| Group ID | Day 8 Avg HDL | Day 8 Std Dev (+/−) | Day 15 Avg HDL | Day 15 Std Dev (+/−) | Day 22 Avg HDL | Day 22 Std Dev (+/−) | Day 29 Avg HDL | Day 29 Std Dev (+/−) |
|---|---|---|---|---|---|---|---|---|
| Group 2 (3.0 mg/kg AD05488) (High Fat Diet) | 0.693 | 0.042 | 0.735 | 0.066 | 0.716 | 0.062 | 0.711 | 0.078 |
| Group 3 (3.0 mg/kg HBV Control RNAi agent) (High Fat Diet) | 0.869 | 0.177 | 0.870 | 0.136 | 0.908 | 0.122 | 0.919 | 0.155 |
| Group 4 (D5W) (Normal Diet) | 1.000 | 0.016 | 1.000 | 0.024 | 1.00 | 0.053 | 1.000 | 0.068 |
| Group 5 (3.0 mg/kg AD05488) (Normal Diet) | 0.645 | 0.069 | 0.745 | 0.088 | 0.766 | 0.087 | 0.737 | 0.088 |

TABLE 65

Average LDL Normalized to Pre-Treatment and Control (Diet Matched) from Example 12

| Group ID | Day 8 Avg LDL | Day 8 Std Dev (+/−) | Day 15 Avg LDL | Day 15 Std Dev (+/−) | Day 22 Avg LDL | Day 22 Std Dev (+/−) | Day 29 Avg LDL | Day 29 Std Dev (+/−) |
|---|---|---|---|---|---|---|---|---|
| Group 1 (D5W) (High Fat Diet) | 1.000 | 0.105 | 1.000 | 0.133 | 1.000 | 0.195 | 1.000 | 0.192 |
| Group 2 (3.0 mg/kg AD05488) (High Fat Diet) | 0.547 | 0.060 | 0.476 | 0.041 | 0.429 | 0.054 | 0.419 | 0.075 |
| Group 3 (3.0 mg/kg HBV Control RNAi agent) (High Fat Diet) | 0.959 | 0.150 | 1.000 | 0.207 | 1.004 | 0.197 | 1.063 | 0.230 |
| Group 4 (D5W) (Normal Diet) | 1.000 | 0.134 | 1.000 | 0.088 | 1.000 | 0.160 | 1.000 | 0.160 |
| Group 5 (3.0 mg/kg AD05488) (Normal Diet) | 0.558 | 0.116 | 0.606 | 0.107 | 0.662 | 0.147 | 0.563 | 0.091 |

As shown in Tables 61-65, the groups dosed with 3.0 mg/kg of ANGPTL3 RNAi agent AD05488 (i.e., Groups 2 and 5) showed significant reductions in ANGPTL3 protein levels, TG levels, and total cholesterol in this model. The LDLR KO mice on a high fat "Western" diet showed particularly reduced levels, with an approximately 99% reduction in ANGPTL3 protein levels at day 57 (0.007) compared to control from the administration of two 3 mg/kg dose of ANGPTL3 RNAi agent AD05488. It is also noted that Group 3, which included an RNAi agent control that included nucleotide sequences designed to target an HBV mRNA, performed as expected and showed essentially no inhibition of ANGPTL3.

Additionally, ANGPTL3 mRNA levels were also assessed. On day 15, four (4) mice were sacrificed from each of Groups 1, 2, and 3. On day 29, an additional four (4) mice were sacrificed from each of Groups 1, 2, and 3. On day 57, all remaining animals from all Groups were sacrificed. At sacrifice, livers were harvested, and approximately 100 mg liver samples from the median lobes were collected and snap-frozen in liquid nitrogen for RNA isolation. Levels of ANGPTL3 mRNA in the mice livers were then measured by RT-qPCR, and normalized to the mRNA levels of the mice in Group 1 (high fat "Western" diet; D5W administration; day 15 sacrifice), the results of which are set forth in the following Table 66:

TABLE 66

Average ANGPTL3 mRNA Level at Day 29, Normalized to Control from Example 12

| Group ID | Day of Sacrifice | Number of Animals (n=) | Avg Relative ANGPTL3 mRNA | Low Variance (Error) | High Variance (Error) |
|---|---|---|---|---|---|
| Group 1 (D5W, high fat diet) (day 15 sacrifice) | 15 | 4 | 1.000 | 0.213 | 0.271 |
| Group 1 (D5W, high fat diet) (day 29 sacrifice) | 29 | 4 | 1.133 | 0.074 | 0.079 |
| Group 1 (D5W, high fat diet) (day 57 sacrifice) | 57 | 5 | 0.949 | 0.106 | 0.119 |
| Group 2 (3.0 mg/kg AD05488, high fat diet) (day 15 sacrifice) | 15 | 4 | 0.019 | 0.006 | 0.009 |

TABLE 66-continued

Average ANGPTL3 mRNA Level at Day 29,
Normalized to Control from Example 12

| Group ID | Day of Sacrifice | Number of Animals (n=) | Avg Relative ANGPTL3 mRNA | Low Variance (Error) | High Variance (Error) |
|---|---|---|---|---|---|
| Group 2 (3.0 mg/kg AD05488, high fat diet) (day 29 sacrifice) | 29 | 4 | 0.032 | 0.007 | 0.009 |
| Group 2B (3.0 mg/kg AD05488, high fat diet) (day 57 sacrifice) | 57 | 5 | 0.024 | 0.005 | 0.006 |
| Group 3 (3.0 mg/kg HBV control RNAi agent, high fat diet) (day 15 sacrifice) | 15 | 4 | 1.044 | 0.138 | 0.159 |
| Group 3 (3.0 mg/kg HBV control RNAi agent, high fat diet) (day 29 sacrifice) | 29 | 4 | 1.095 | 0.206 | 0.254 |
| Group 3 (3.0 mg/kg HBV control RNAi agent, high fat diet) (day 57 sacrifice) | 57 | 5 | 0.994 | 0.134 | 0.155 |
| Group 4 (D5W, normal chow) | 57 | 4 | 1.397 | 0.055 | 0.057 |
| Group 5 (3.0 mg/kg AD05488, normal chow) | 57 | 4 | 0.060 | 0.009 | 0.010 |

The administration of ANGPTL3 RNAi agent AD05488 showed a significant reduction in ANGPTL3 mRNA levels in both the animals on the high fat "Western" diet and the animals on the normal chow-fed diet.

Example 13. In Vivo Testing of ANGPTL3 RNAi Agents in High Fructose Corn Syrup (HFCS) Diet-Fed Rhesus Monkeys ANGPTL3 RNAi agent AD05488 was further evaluated in high-fructose corn syrup (HFCS) diet-fed Rhesus monkeys. Rhesus monkeys were placed on an HFCS diet 37 days prior to dosing. These animals were known to develop increased plasma triglycerides greater than 180 mg/dL on the HFCS diet. On day 1 and again on day 29, four (4) Rhesus monkeys were administered a subcutaneous injection containing 4.0 mg/kg of ANGPTL3 RNAi agent AD05488 formulated in saline (n=4). Two additional Rhesus monkeys were administered normal saline control. ANGPTL3 RNAi agent AD05488 contained modified nucleotides and included N-acetyl-galactosamine targeting ligands conjugated to the 5'-terminal end of the sense strand, as shown in Tables 3, 4, and 5.

Fasted blood samples were drawn for analysis, and serum samples were analyzed on days −8 (predose), 8, 15, 21, 29, and 36. ANGPTL3 expression levels, triglycerides, total cholesterol, high-density lipoprotein (HDL), and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, the level of ANGPTL3 protein, triglyceride, HDL, and total cholesterol, respectively, for each animal at a time point, was divided by the pre-treatment level of expression in that animal (in this case at day −8) to determine the ratio of expression "normalized to pre-treatment."

Data from the study set forth in this Example are shown in the following Tables 67-71:

TABLE 67

Average ANGPTL3 Protein Normalized to Pre-Treatment from Example 13 (Fasted)

| | Day 8 | | Day 15 | | Day 21 | | Day 29 | | Day 36 | |
|---|---|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (saline control) | 1.087 | 0.419 | 1.282 | 0.436 | 1.214 | 0.334 | 1.363 | 0.230 | 1.134 | 0.248 |
| Group 2 (4.0 mg/kg AD05488) | 0.229 | 0.082 | 0.154 | 0.090 | 0.116 | 0.080 | 0.114 | 0.047 | 0.064 | 0.044 |

TABLE 68

Average Triglycerides Normalized to Pre-Treatment from Example 13 (Fasted)

| Group ID | Day 8 Avg TG | Day 8 Std Dev (+/−) | Day 15 Avg TG | Day 15 Std Dev (+/−) | Day 21 Avg TG | Day 21 Std Dev (+/−) | Day 29 Avg TG | Day 29 Std Dev (+/−) | Day 36 Avg TG | Day 36 Std Dev (+/−) |
|---|---|---|---|---|---|---|---|---|---|---|
| Group 1 (saline control) | 0.743 | 0.055 | 0.717 | 0.054 | 1.017 | 0.155 | 0.758 | 0.263 | 0.659 | 0.111 |
| Group 2 (4.0 mg/kg AD05488) | 0.351 | 0.241 | 0.244 | 0.094 | 0.233 | 0.089 | 0.302 | 0.192 | 0.177 | 0.076 |

TABLE 69

Average Cholesterol Normalized to Pre-Treatment from Example 13 (Fasted)

| Group ID | Day 8 Avg Chol | Day 8 Std Dev (+/−) | Day 15 Avg Chol | Day 15 Std Dev (+/−) | Day 21 Avg Chol | Day 21 Std Dev (+/−) | Day 29 Avg Chol | Day 29 Std Dev (+/−) | Day 36 Avg Chol | Day 36 Std Dev (+/−) |
|---|---|---|---|---|---|---|---|---|---|---|
| Group 1 (saline control) | 0.972 | 0.050 | 0.944 | 0.079 | 0.957 | 0.0.18 | 0.882 | 0.021 | 0.894 | 0.038 |
| Group 2 (4.0 mg/kg AD05488) | 0.734 | 0.200 | 0.641 | 0.174 | 0.579 | 0.107 | 0.549 | 0.090 | 0.459 | 0.086 |

TABLE 70

Average HDL Normalized to Pre-Treatment from Example 13 (Fasted)

| Group ID | Day 8 Avg Chol | Day 8 Std Dev (+/−) | Day 15 Avg Chol | Day 15 Std Dev (+/−) | Day 21 Avg Chol | Day 21 Std Dev (+/−) | Day 29 Avg Chol | Day 29 Std Dev (+/−) | Day 36 Avg Chol | Day 36 Std Dev (+/−) |
|---|---|---|---|---|---|---|---|---|---|---|
| Group 1 (saline control) | 1.082 | 0.098 | 1.071 | 0.111 | 1.003 | 0.158 | 1.025 | 0.131 | 1.027 | 0.071 |
| Group 2 (4.0 mg/kg AD05488) | 1.202 | 0.276 | 1.091 | 0.322 | 0.921 | 0.296 | 0.730 | 0.232 | 0.798 | 0.349 |

TABLE 71

Average LDL Normalized to Pre-Treatment from Example 13 (Fasted)

| Group ID | Day 8 Avg Chol | Day 8 Std Dev (+/−) | Day 15 Avg Chol | Day 15 Std Dev (+/−) | Day 21 Avg Chol | Day 21 Std Dev (+/−) | Day 29 Avg Chol | Day 29 Std Dev (+/−) | Day 36 Avg Chol | Day 36 Std Dev (+/−) |
|---|---|---|---|---|---|---|---|---|---|---|
| Group 1 (saline control) | 0.892 | 0.060 | 0.928 | 0.046 | 0.823 | 0.034 | 0.804 | 0.076 | 0.804 | 0.172 |
| Group 2 (4.0 mg/kg AD05488) | 0.973 | 0.475 | 0.909 | 0.390 | 0.908 | 0.437 | 0.955 | 0.520 | 0.710 | 0.499 |

The Rhesus monkeys dosed with AD05488 at 4.0 mg/kg dosage levels showed a significant reduction in ANGPTL3 protein compared to pre-treatment measurements across each of the measured time points. Further, reductions in triglyceride and total cholesterol levels were evident.

Example 14. In Vivo Testing of ANGPTL3 RNAi Agents and Statins in LDL Receptor (LDLR) Knockout Mice To evaluate the effect of co-administration of RNAi agents and statins in a disease model, LDLR KO mice were commercially obtained (The Jackson Laboratory). For three weeks prior to the onset of the study, forty-one (41) male 7 to 8 week old LDLR KO mice were placed on a high fat ("western") diet (Teklad Custom Diets TD. 88137), and remained on that diet throughout the duration of the study. Pre-dose serum samples were taken on study Day 1 after a four hour fast. The dosing regimen for the study is recited in the following Table 72:

TABLE 72

Dosing Groups of Example 14

| Group | Atorvastatin Dose and Dosing Regimen | RNAi Agent and Dose Dosing Regimen | LDL KO Mice (n=) |
|---|---|---|---|
| 1 | Vehicle oral gavage administered daily starting on Day 1 | D5W (no RNAi agent) Injection on Day 23 | 7 |
| 2 | N/A | Single 2.5 mg/kg AD05488 Injection on Day 23 | 7 |
| 3 | 10 mg/kg atorvastatin oral gavage administered daily starting on Day 1 | Single 2.5 mg/kg AD05488 Injection on Day 23 | 8 |
| 4 | 20 mg/kg* atorvastatin oral gavage administered daily starting on Day 1 | Single 2.5 mg/kg AD05488 Injection on Day 23 | 6 |
| 5 | 10 mg/kg atorvastatin oral gavage administered daily starting on Day 1 | N/A | 7 |
| 6 | 20 mg/kg* atorvastatin oral gavage administered daily starting on Day 1 | N/A | 6 |

*Mice were treated at 40 mg/kg for the first 11 days, then switched to 20 mg/kg thereafter.

The vehicle used for the oral gavage in the study was a 1:1 mixture of Ora-Plus®:Ora-Sweet® solution, which were acquired commercially. For the preparation of the atorvastatin oral gavage administrations, the respective desired dose of atorvastatin was first dissolved in sterile water (0.3 mL water per 1 mL of desired formulation) and vortexed until smooth, followed by the addition of a mixture of 1:1 Ora-Plus®:Ora-Sweet® solution (0.7 mL vehicle per 1 mL of desired formulation) and vortexed. On day 1 and for each day thereafter an oral gavage dose was administered for each of the Groups except for Group 2. On Day 23, Groups 1, 2, 3, and 4 received a single subcutaneous administration of 2.5 mg/kg dose (31.25 µg/mL solution) of an ANGPTL3 RNAi agent in D5W (dextrose in 5% water), or vehicle control (D5W) with no RNAi agent.

The RNAi agent tested (AD05488) included a modified sequence and an N-acetyl-galactosamine-containing targeting ligand conjugated to the 5' terminal end of the sense strand. (See Tables 3, 4, and 5 for modified sequences and targeting ligand structures). The injections were performed between the skin and muscle (i.e. subcutaneous injections) into the loose skin over the neck and shoulder area. Serum was collected on days 8, 15, 22 (pre-RNAi agent injection), 29, 36, 43, and 50. LDLR KO mice were fasted for four hours prior to each collection.

ANGPTL3 protein levels in serum were measured by ELISA assay (R&D Systems), according to the manufacturer's recommendations. Among other biomarkers, triglycerides, total cholesterol, and low-density lipoprotein (LDL) in serum were measured on a Cobas® Integra 400 (Roche Diagnostics), according to the manufacturer's recommendations.

The ANGPTL3 protein levels, triglyceride levels, total cholesterol levels, HDL levels, and LDL levels for each animal were normalized. For normalization, respective levels of ANGPTL3 protein, TG, total cholesterol, or LDL for each animal at a time point was divided by the pre-treatment level of expression in that animal (in this case pre-dose levels on Day 1) to determine the ratio of expression "normalized to pre-treatment." Data from the study set forth in this Example are shown in the following Tables 73-76:

TABLE 73

Average ANGPTL3 Protein Normalized to Pre-Treatment from Example 14

| | Day 8 | | Day 15 | | Day 22 | | Day 29 | |
|---|---|---|---|---|---|---|---|---|
| Group ID | Avg ANGPTL3 | Std Dev (+/−) | Avg ANGPTL3 | Std Dev (+/−) | Avg ANGPTL3 | Std Dev (+/−) | Avg ANGPTL3 | Std Dev (+/−) |
| Group 1 (Daily Vehicle Gavage; D5W injection) | 1.511 | 0.236 | 1.787 | 0.263 | 1.680 | 0.273 | 1.650 | 0.237 |
| Group 2 (No gavage; 2.5 mg/kg AD05488) | 1.419 | 0.224 | 1.584 | 0.214 | 1.658 | 0.295 | 0.023 | 0.008 |
| Group 3 (10 mg/kg daily oral gavage atorvastatin; 2.5 mg/kg AD05488 on day 23) | 1.597 | 0.344 | 1.765 | 0.363 | 1.681 | 0.419 | 0.015 | 0.005 |
| Group 4 (20 mg/kg* daily oral gavage atorvastatin; 2.5 mg/kg AD05488 on day 23) | 1.683 | 0.216 | 1.999 | 0.282 | 1.675 | 0.376 | 0.022 | 0.042 |
| Group 5 (10 mg/kg daily oral gavage atorvastatin; no injection) | 1.577 | 0.295 | 1.839 | 0.319 | 1.693 | 0.270 | 1.764 | 0.283 |
| Group 6 (20 mg/kg* daily oral gavage atorvastatin; no injection) | 1.553 | 0.673 | 1.924 | 0.836 | 1.871 | 0.604 | 1.767 | 0.770 |

TABLE 73-continued

|  | Day 36 | | Day 43 | | Day 50 | |
| --- | --- | --- | --- | --- | --- | --- |
| Group 1 (Daily Vehicle Gavage; D5W injection) | 1.604 | 0.307 | 1.784 | 0.460 | 1.622 | 0.387 |
| Group 2 (No gavage; 2.5 mg/kg AD05488) | 0.012 | 0.004 | 0.020 | 0.014 | 0.026 | 0.005 |
| Group 3 (10 mg/kg daily oral gavage atorvastatin; 2.5 mg/kg AD05488 on day 23) | 0.005 | 0.001 | 0.007 | 0.003 | 0.010 | 0.002 |
| Group 4 (20 mg/kg* daily oral gavage atorvastatin; 2.5 mg/kg AD05488 on day 23) | 0.004 | 0.002 | 0.005 | 0.001 | 0.010 | 0.004 |
| Group 5 (10 mg/kg daily oral gavage atorvastatin; no injection) | 1.851 | 0.384 | 1.758 | 0.441 | 1.878 | 0.342 |
| Group 6 (20 mg/kg* daily oral gavage atorvastatin; no injection) | 1.981 | 0.775 | 1.935 | 0.619 | 1.847 | 0.610 |

TABLE 74

Average Triglycerides Normalized to Pre-Treatment from Example 14

| Group ID | Day 8 | | Day 15 | | Day 22 | | Day 29 | |
| --- | --- | --- | --- | --- | --- | --- | --- | --- |
|  | Avg TG | Std Dev (+/−) | Avg TG | Std Dev (+/−) | Avg TG | Std Dev (+/−) | Avg TG | Std Dev (+/−) |
| Group 1 (Daily Vehicle Gavage; D5W injection) | 0.711 | 0.151 | 0.826 | 0.193 | 1.009 | 0.304 | 0.753 | 0.219 |
| Group 2 (No gavage; 2.5 mg/kg AD05488 on day 23) | 0.988 | 0.253 | 1.247 | 0.330 | 1.524 | 0.189 | 0.166 | 0.023 |
| Group 3 (10 mg/kg daily oral gavage atorvastatin; 2.5 mg/kg AD05488 on day 23) | 0.613 | 0.338 | 0.436 | 0.213 | 0.614 | 0.162 | 0.072 | 0.020 |
| Group 4 (20 mg/kg* daily oral gavage atorvastatin; 2.5 mg/kg AD05488 on day 23) | 0.567 | 0.233 | 0.526 | 0.280 | 0.748 | 0.208 | 0.071 | 0.021 |
| Group 5 (10 mg/kg daily oral gavage atorvastatin; no injection) | 0.667 | 0.353 | 0.601 | 0.319 | 1.086 | 0.546 | 0.803 | 0.297 |
| Group 6 (20 mg/kg* daily oral gavage atorvastatin; no injection) | 0.477 | 0.328 | 0.362 | 0.200 | 0.505 | 0.248 | 0.552 | 0.250 |

|  | Day 36 | | Day 43 | | Day 50 | |
| --- | --- | --- | --- | --- | --- | --- |
| Group 1 (Daily Vehicle Gavage; D5W injection) | 1.060 | 0.388 | 0.986 | 0.251 | 0.948 | 0.239 |
| Group 2 (No gavage; 2.5 mg/kg AD05488) | 0.125 | 0.037 | 0.139 | 0.034 | 0.153 | 0.012 |
| Group 3 (10 mg/kg daily oral gavage atorvastatin; 2.5 mg/kg AD05488 on day 23) | 0.058 | 0.013 | 0.076 | 0.019 | 0.065 | 0.016 |
| Group 4 (20 mg/kg* daily oral gavage atorvastatin; 2.5 mg/kg AD05488 on day 23) | 0.058 | 0.011 | 0.089 | 0.024 | 0.082 | 0.016 |
| Group 5 (10 mg/kg daily oral gavage atorvastatin; no injection) | 0.958 | 0.558 | 0.862 | 0.338 | 0.977 | 0.634 |
| Group 6 (20 mg/kg* daily oral gavage atorvastatin; no injection) | 0.598 | 0.260 | 0.603 | 0.194 | 0.677 | 0.219 |

TABLE 75

Average Total Cholesterol Normalized to Pre-Treatment from Example 14

| Group ID | Day 8 | | Day 15 | | Day 22 | | Day 29 | |
| --- | --- | --- | --- | --- | --- | --- | --- | --- |
|  | Avg Total Chol | Std Dev (+/−) | Avg Total Chol | Std Dev (+/−) | Avg Total Chol | Std Dev (+/−) | Avg Total Chol | Std Dev (+/−) |
| Group 1 (Daily Vehicle Gavage; D5W injection) | 0.996 | 0.107 | 1.009 | 0.192 | 1.142 | 0.183 | 1.087 | 0.187 |
| Group 2 (No gavage; 2.5 mg/kg AD05488) | 0.962 | 0.109 | 1.122 | 0.133 | 1.261 | 0.160 | 0.645 | 0.092 |

TABLE 75-continued

| | | | | | | | | |
|---|---|---|---|---|---|---|---|---|
| Group 3 (10 mg/kg daily oral gavage atorvastatin; 2.5 mg/kg AD05488 on day 23) | 0.763 | 0.204 | 0.620 | 0.166 | 0.758 | 0.108 | 0.444 | 0.074 |
| Group 4 (20 mg/kg* daily oral gavage atorvastatin; 2.5 mg/kg AD05488 on day 23) | 0.682 | 0.171 | 0.622 | 0.200 | 0.857 | 0.326 | 0.448 | 0.141 |
| Group 5 (10 mg/kg daily oral gavage atorvastatin; no injection) | 0.821 | 0.244 | 0.774 | 0.257 | 0.980 | 0.359 | 0.943 | 0.318 |
| Group 6 (20 mg/kg* daily oral gavage atorvastatin; no injection) | 0.586 | 0.248 | 0.620 | 0.190 | 0.767 | 0.220 | 0.761 | 0.157 |

| | Day 36 | | Day 43 | | Day 50 | |
|---|---|---|---|---|---|---|
| Group 1 (Daily Vehicle Gavage; D5W injection) | 1.201 | 0.223 | 1.237 | 0.230 | 1.125 | 0.309 |
| Group 2 (No gavage; 2.5 mg/kg AD05488) | 0.518 | 0.085 | 0.512 | 0.082 | 0.515 | 0.073 |
| Group 3 (10 mg/kg daily oral gavage atorvastatin; 2.5 mg/kg AD05488 on day 23) | 0.362 | 0.070 | 0.331 | 0.054 | 0.322 | 0.048 |
| Group 4 (20 mg/kg* daily oral gavage atorvastatin; 2.5 mg/kg AD05488 on day 23) | 0.295 | 0.045 | 0.293 | 0.036 | 0.310 | 0.043 |
| Group 5 (10 mg/kg daily oral gavage atorvastatin; no injection) | 1.105 | 0.365 | 0.998 | 0.276 | 0.987 | 0.376 |
| Group 6 (20 mg/kg* daily oral gavage atorvastatin; no injection) | 0.825 | 0.082 | 0.767 | 0.148 | 0.807 | 0.114 |

TABLE 76

Average LDL Normalized to Pre-Treatment from Example 14

| | Day 8 | | Day 15 | | Day 22 | | Day 29 | |
|---|---|---|---|---|---|---|---|---|
| Group ID | Avg LDL | Std Dev (+/−) | Avg LDL | Std Dev (+/−) | Avg LDL | Std Dev (+/−) | Avg LDL | Std Dev (+/−) |
| Group 1 (Daily Vehicle Gavage; D5W injection) | 0.951 | 0.138 | 0.969 | 0.238 | 1.044 | 0.222 | 1.093 | 0.243 |
| Group 2 (No gavage; 2.5 mg/kg AD05488) | 0.893 | 0.107 | 1.051 | 0.126 | 1.113 | 0.178 | 0.653 | 0.119 |
| Group 3 (10 mg/kg daily oral gavage atorvastatin; 2.5 mg/kg AD05488 on day 23) | 0.692 | 0.170 | 0.537 | 0.154 | 0.659 | 0.112 | 0.422 | 0.097 |
| Group 4 (20 mg/kg* daily oral gavage atorvastatin; 2.5 mg/kg AD05488 on day 23) | 0.572 | 0.193 | 0.515 | 0.222 | 0.755 | 0.388 | 0.434 | 0.166 |
| Group 5 (10 mg/kg daily oral gavage atorvastatin; no injection) | 0.778 | 0.255 | 0.695 | 0.266 | 0.861 | 0.365 | 0.881 | 0.362 |
| Group 6 (20 mg/kg* daily oral gavage atorvastatin; no injection) | 0.490 | 0.254 | 0.556 | 0.195 | 0.687 | 0.209 | 0.700 | 0.171 |

| | Day 36 | | Day 43 | | Day 50 | |
|---|---|---|---|---|---|---|
| Group 1 (Daily Vehicle Gavage; D5W injection) | 1.130 | 0.237 | 1.242 | 0.286 | 1.050 | 0.348 |
| Group 2 (No gavage; 2.5 mg/kg AD05488) | 0.492 | 0.103 | 0.443 | 0.166 | 0.480 | 0.086 |
| Group 3 (10 mg/kg daily oral gavage atorvastatin; 2.5 mg/kg AD05488 on day 23) | 0.312 | 0.083 | 0.264 | 0.055 | 0.256 | 0.050 |
| Group 4 (20 mg/kg* daily oral gavage atorvastatin; 2.5 mg/kg AD05488 on day 23) | 0.240 | 0.060 | 0.217 | 0.038 | 0.242 | 0.029 |
| Group 5 (10 mg/kg daily oral gavage atorvastatin; no injection) | 0.996 | 0.357 | 0.929 | 0.303 | 0.872 | 0.356 |
| Group 6 (20 mg/kg* daily oral gavage atorvastatin; no injection) | 0.716 | 0.071 | 0.689 | 0.153 | 0.687 | 0.100 |

Mice administered with daily atorvastatin showed approximately 40-60% reduction in triglycerides, approximately 23-40% reduction in total cholesterol, and approximately 30-45% reduction in LDL, respectively. Mice treated with higher doses of atorvastatin typically gave deeper reductions.

Administration with ANGPTL3 RNAi agent AD05488 with the co-administration of atorvastatin (i.e., Groups 3 and 4) showed additive effects on lipid parameters. For example, for Groups that involved co-administration of atorvastatin and RNAi agent, total reductions in triglycerides, total cholesterol, and LDL, were ~95%, ~70%, and ~80%, respectively. Overall lipid parameters profile with the co-administration of atorvastatin was slightly better than administration of ANGPTL3 RNAi agent AD05488 alone.

Further, Groups with ANGPTL3 RNAi agent AD05488 showed a clear reduction in ANGPTL3 protein levels, while no reduction in ANGPTL3 protein was seen in groups that did not involve the administration of an ANGPTL3 RNAi agent.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

The invention claimed is:

1. An RNAi agent for inhibiting expression of an ANGPTL3 gene, comprising:
   an antisense strand that consists of the modified nucleotide sequence of (5'→3') usAfscsUfgAfuCfaAfa-UfaUfgUfuGfaGfsc (SEQ ID NO:2), and
   a sense strand that consists of the sequence of (5'→3') (NAG37)s(invAb)sgcucaacaUfAfUfuugaucaguas(invAb) (SEQ ID NO:300);
wherein a is 2'-O-methyl adenosine; c is 2'-O-methyl cytidine; g is 2'-O-methyl guanosine; u is 2'-O-methyl uridine; Af is 2'-fluoro adenosine, Cf is 2'-fluoro cytidine; Gf is 2'-fluoro guanosine; Uf is 2'-fluoro adenosine; s is a phosphorothioate linkage; (invAb) is an inverted abasic deoxyribose residue; and (NAG37)s has the following chemical structure:

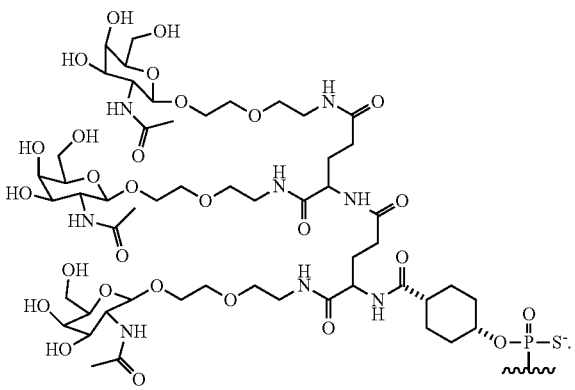

2. A pharmaceutically acceptable salt of the RNAi agent of claim 1.

3. The pharmaceutically acceptable salt of claim 2, wherein the pharmaceutically acceptable salt is a sodium salt.

4. A pharmaceutical composition comprising the RNAi agent of claim 1 and a pharmaceutically acceptable excipient.

5. The pharmaceutical composition of claim 4, wherein the pharmaceutically acceptable excipient comprises saline.

6. The pharmaceutical composition of claim 4, wherein the pharmaceutically acceptable excipient comprises water for injection.

7. The pharmaceutical composition of claim 6 further comprising a pharmaceutically acceptable buffering agent.

8. The pharmaceutical composition of claim 4, wherein the pharmaceutically acceptable excipient comprises buffered saline.

9. The pharmaceutical composition of claim 4, wherein the pharmaceutical composition is packaged in a pre-filled syringe.

10. The pharmaceutical composition of claim 4, wherein the pharmaceutical composition is packaged in a vial.

11. A method of treating an ANGPTL3-related disease or disorder, the method comprising administering to a human subject in need thereof a therapeutically effective amount of the RNAi agent of claim 1.

12. The method of claim 11, wherein the disease is a cardiometabolic disease.

13. The method of claim 11, wherein disease is hypertriglyceridemia, obesity, hyperlipidemia, abnormal lipid and/or cholesterol metabolism, atherosclerosis, type II diabetes mellitus, cardiovascular disease, coronary artery disease, non-alcoholic steatohepatitis, non-alcoholic fatty liver disease, homozygous and/or heterozygous familial hypercholesterolemia, or statin resistant hypercholesterolemia.

14. The method of claim 11, wherein the RNAi agent is administered at a dose of about 0.05 mg/kg to about 5.0 mg/kg of body weight of the human subject.

15. A method of lowering triglyceride levels in a subject, the method comprising administering to the subject an effective amount of the RNAi agent of claim 1.

16. A method of lowering total cholesterol levels in a subject, the method comprising administering to the subject an effective amount of the RNAi agent of claim 1.

17. A method of lowering low density lipoprotein (LDL) cholesterol levels in a subject, the method comprising administering to the subject an effective amount of a pharmaceutical composition of claim 4.

18. The method of claim 11, wherein the method further comprises administration of a statin.

19. The method of claim 18, wherein the statin is selected from the group consisting of: atorvastatin, fluvastatin, pravastatin, pitavastatin, rosuvastatin, and simvastatin.

* * * * *

SEQUENCE LISTING

```
<160> NUMBER OF SEQ ID NOS: 450

<210> SEQ ID NO 1
<211> LENGTH: 2951
<212> TYPE: DNA
<213> ORGANISM: Artificial sequence
<220> FEATURE:
<223> OTHER INFORMATION: Homo Sapiens angiopoietin-like 3 (ANGPTL3)
      transcript, GenBank NM_014495.3

<400> SEQUENCE: 1
atatatagag ttaagaagtc taggtctgct tccagaagaa aacagttcca cgttgcttga      60
aattgaaaat caagataaaa atgttcacaa ttaagctcct tcttttttatt gttcctctag    120 ttatttcctc cagaattgat caagacaatt catcatttga ttctctatct ccagagccaa    180
aatcaagatt tgctatgtta gacgatgtaa aaattttagc caatggcctc cttcagttgg    240
gacatggtct taaagacttt gtccataaga cgaagggcca aattaatgac atatttcaaa    300
aactcaacat atttgatcag tcttttttatg atctatcgct gcaaaccagt gaaatcaaag    360
aagaagaaaa ggaactgaga agaactacat ataaactaca agtcaaaaat gaagaggtaa    420
agaatatgtc acttgaactc aactcaaaac ttgaaagcct cctagaagaa aaaattctac    480
ttcaacaaaa agtgaaatat ttagaagagc aactaactaa cttaattcaa aatcaacctg    540
aaactccaga acacccagaa gtaacttcac ttaaaacttt tgtagaaaaa caagataata    600
gcatcaaaga ccttctccag accgtggaag accaatataa acaattaaac caacagcata    660
gtcaaataaa agaaatagaa aatcagctca gaaggactag tattcaagaa cccacagaaa    720
tttctctatc ttccaagcca agagcaccaa gaactactcc ctttcttcag ttgaatgaaa    780
taagaaatgt aaaacatgat ggcattcctg ctgaatgtac caccatttat aacagaggtg    840
aacatacaag tggcatgtat gccatcagac ccagcaactc tcaagttttt catgtctact    900
gtgatgttat atcaggtagt ccatggacat taattcaaca tcgaatagat ggatcacaaa    960
acttcaatga aacgtgggag aactacaaat atggttttgg gaggcttgat ggagaatttt    1020
ggttgggcct agagaagata tactccatag tgaagcaatc taattatgtt ttacgaattg    1080
agttggaaga ctggaaagac aacaaacatt atattgaata ttcttttttac ttgggaaatc    1140 acgaaaccaa ctatacgcta catctagttg cgattactgg caatgtcccc aatgcaatcc    1200
cggaaaacaa agatttggtg ttttctactt gggatcacaa agcaaaagga cacttcaact    1260
gtccagaggg ttattcagga ggctggtggt ggcatgatga gtgtggagaa aacaacctaa    1320
atggtaaata taacaaacca agagcaaaat ctaagccaga gaggagaaga ggattatctt    1380
```

-continued

```
ggaagtctca aaatggaagg ttatactcta taaaatcaac caaaatgttg atccatccaa   1440
cagattcaga aagctttgaa tgaactgagg caaatttaaa aggcaataat ttaaacatta   1500
acctcattcc aagttaatgt ggtctaataa tctggtatta aatccttaag agaaagcttg   1560
agaaatagat ttttttatc ttaaagtcac tgtctattta agattaaaca tacaatcaca   1620
taaccttaaa gaataccgtt tacatttctc aatcaaaatt cttataatac tatttgtttt   1680 aaatttgtg atgtgggaat caattttaga tggtcacaat ctagattata atcaataggt   1740
gaacttatta ataaacttt ctaaataaaa aatttagaga cttttatttt aaaaggcatc   1800
atatgagcta atatcacaac tttcccagtt taaaaaacta gtactcttgt taaaactcta   1860
aacttgacta aatacagagg actggtaatt gtacagttct taaatgttgt agtattaatt   1920
tcaaaactaa aaatcgtcag cacagagtat gtgtaaaaat ctgtaataca aattttaaa    1980 ctgatgcttc attttgctac aaaataattt ggagtaaatg tttgatatga tttatttatg   2040
aaacctaatg aagcagaatt aaatactgta ttaaataag ttcgctgtct ttaaacaaat    2100
ggagatgact actaagtcac attgactttta acatgaggta tcactatacc ttatttgtta   2160
aaatatatac tgtatacatt ttatatattt taacacttaa tactatgaaa acaaataatt    2220 gtaaggaat cttgtcagat tacagtaaga atgaacatat ttgtggcatc gagttaaagt    2280
ttatatttcc cctaaatatg ctgtgattct aatacattcg tgtaggtttt caagtagaaa   2340
taaacctcgt aacaagttac tgaacgttta aacagcctga caagcatgta tatatgttta   2400
aaattcaata aacaaagacc cagtccctaa attatagaaa tttaaattat tcttgcatgt   2460
ttatcgacat cacaacagat ccctaaatcc ctaaatccct aaagattaga tacaaatttt   2520
ttaccacagt atcacttgtc agaatttatt tttaaatatg attttttaaa actgccagta   2580
agaaatttta aattaaaccc atttgttaaa ggatatagtg cccaagttat atggtgacct   2640
acctttgtca atacttagca ttatgtattt caaattatcc aatatacatg tcatatatat   2700
ttttatatgt cacatatata aaagatatgt atgatctatg tgaatcctaa gtaaatattt   2760
tgttccagaa aagtacaaaa taataaaggt aaaaataatc tataattttc aggaccacag   2820
actaagctgt cgaaattaac gctgattttt ttagggccag aataccaaaa tggctcctct   2880
cttcccccaa aattggacaa tttcaaatgc aaaataattc attatttaat atatgagttg   2940
cttcctctat t                                                       2951
```

<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2
uacugaucaa auauguugag c          21

<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 3
uacugaucaa auauguugag c          21

-continued

```
<210> SEQ ID NO 4
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 4
uacugaucaa auauguugag c                                              21

<210> SEQ ID NO 5
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 5
uacugaucaa auauguugag u                                              21

<210> SEQ ID NO 6
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 6
uacugaucaa auauguugag u                                              21

<210> SEQ ID NO 7
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 7
uuugaauuaa uguccauggg c                                              21

<210> SEQ ID NO 8
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 8
uuugaauuaa uguccauggg c                                              21

<210> SEQ ID NO 9
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 9
uuugaauuaa uguccauggg u                                              21

<210> SEQ ID NO 10
<211> LENGTH: 21
<212> TYPE: RNA
<213> ORGANISM: Artificial sequence
```

```
<220> FEATURE:
<223> OTHER INFORMATION: RNAi agent antisense strand underlying base
      sequence

<400> SEQUENCE: 10
uuugaauuaa uguccauggg u                                              21

<210> SEQ ID NO 11
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 11
uguugaauua auguccaugg a                                              21

<210> SEQ ID NO 12
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 12
uguugaauua auguccaugg a                                              21

<210> SEQ ID NO 13
<211> LENGTH: 21
<212> TYPE: DNA
<213> ORGANISM: Artificial sequence
<220> FEATURE:
<223> OTHER INFORMATION: RNAi agent antisense strand modified sequence

<400> SEQUENCE: 13
uguugaauua auguccaugg a                                              21

<210> SEQ ID NO 14
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 14
acaucgucua acauagcaac c                                              21

<210> SEQ ID NO 15
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 15
acaucgucua acauagcaac c                                              21

<210> SEQ ID NO 16
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 16
```
gcucaacaua uuugaucagu a                     21

<210> SEQ ID NO 17
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 17
gcucaacaua uuugaucagu a                     21

<210> SEQ ID NO 18
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate

<400> SEQUENCE: 18
gcucaacaun uuugaucagu a                     21

<210> SEQ ID NO 19
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = 2-aminoadenine

<400> SEQUENCE: 19
gcucaacaun uuugaucagu a                     21

<210> SEQ ID NO 20
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 8, 10
<223> OTHER INFORMATION: n = 2'-O-methyl-2-aminoadenosine-3'-phosphate

<400> SEQUENCE: 20
gcucaacnun uuugaucagu a                     21

<210> SEQ ID NO 21
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 8, 10
<223> OTHER INFORMATION: n = 2-aminoadenine

<400> SEQUENCE: 21
gcucaacnun uuugaucagu a                      21

<210> SEQ ID NO 22
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 22
gcucaacaua uuugaucagu a                      21

<210> SEQ ID NO 23
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 23
acucaacaua uuugaucagu a                      21

<210> SEQ ID NO 24
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 24
acucaacaua uuugaucagu a                      21

<210> SEQ ID NO 25
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 25
gcccauggac auuaauucaa a                      21

<210> SEQ ID NO 26
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 26
gcccauggac auuaauucaa a                      21

<210> SEQ ID NO 27
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 27
acccauggac auuaauucaa a                      21

<210> SEQ ID NO 28

```
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 28
acccauggac auuaauucaa a                                              21

<210> SEQ ID NO 29
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 29
uccauggaca uuaauucaac a                                              21

<210> SEQ ID NO 30
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 30
uccauggaca uuaauucaac a                                              21

<210> SEQ ID NO 31
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 31
gguugcuaug uuagacgaug u                                              21

<210> SEQ ID NO 32
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 32
gguugcuaug uuagacgaug u                                              21

<210> SEQ ID NO 33
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 33
ucaacauauu ugaucaguc                                                 19

<210> SEQ ID NO 34
<211> LENGTH: 19
<212> TYPE: RNA
<213> ORGANISM: Artificial sequence
<220> FEATURE:
```

```
<223> OTHER INFORMATION: ANGPTL3 gene transcript (mRNA) target sequence

<400> SEQUENCE: 34
cauggacauu aauucaaca                                                19

<210> SEQ ID NO 35
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 35
ccauggacau uaauucaac                                                19

<210> SEQ ID NO 36
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 36
uugcuauguu agacgaugu                                                19

<210> SEQ ID NO 37
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 37
aagauauacu ccauaguga                                                19

<210> SEQ ID NO 38
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 38
cagagccaaa aucaagauu                                                19

<210> SEQ ID NO 39
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 39
gacauggucu uaaagacuu                                                19

<210> SEQ ID NO 40
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 40
agcaccaaga acuacuccc                                                19
```

```
<210> SEQ ID NO 41
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 41
gcaccaagaa cuacuccccu                                                19

<210> SEQ ID NO 42
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 42
gauggagaau uuugguugg                                                 19

<210> SEQ ID NO 43
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 43
auggagaauu uugguuggg                                                 19

<210> SEQ ID NO 44
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 44
acuccauagu gaagcaauc                                                 19

<210> SEQ ID NO 45
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 45
cacgaaacca acuauacgc                                                 19

<210> SEQ ID NO 46
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 46
cuacuuggga ucacaaagc                                                 19

<210> SEQ ID NO 47
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence
```

```
<400> SEQUENCE: 47
cuugggauca caaagcaaa                                                19

<210> SEQ ID NO 48
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 48
uguggagaaa acaaccuaa                                                19

<210> SEQ ID NO 49
<211> LENGTH: 19
<212> TYPE: RNA
<213> ORGANISM: Artificial sequence
<220> FEATURE:
<223> OTHER INFORMATION: ANGPTL3 gene transcript (mRNA) target sequence

<400> SEQUENCE: 49
uggagaaaac aaccuaaau                                                19

<210> SEQ ID NO 50
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 50
uacugaucaa auauguuga                                                19

<210> SEQ ID NO 51
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 51
aacugaucaa auauguuga                                                19

<210> SEQ ID NO 52
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 52
gacugaucaa auauguuga                                                19

<210> SEQ ID NO 53
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase
```

```
<400> SEQUENCE: 53
nacugaucaa auauguuga                                              19

<210> SEQ ID NO 54
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 54
nacugaucaa auauguugn                                              19

<210> SEQ ID NO 55
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 55
uguugaauua auguccaug                                              19

<210> SEQ ID NO 56
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 56
aguugaauua auguccaug                                              19

<210> SEQ ID NO 57
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 57
nguugaauua auguccaug                                              19

<210> SEQ ID NO 58
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 58
```

-continued nguugaauua auguccaun                                     19

<210> SEQ ID NO 59
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 59
guugaauuaa uguccaugg                                     19

<210> SEQ ID NO 60
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 60
uuugaauuaa uguccaugg                                     19

<210> SEQ ID NO 61
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 61
auugaauuaa uguccaugg                                     19

<210> SEQ ID NO 62
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 62
nuugaauuaa uguccaugg                                     19

<210> SEQ ID NO 63
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 63
nuugaauuaa uguccaugn                                     19

<210> SEQ ID NO 64
<211> LENGTH: 19

-continued

```
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 64
acaucgucua acauagcaa                                                19

<210> SEQ ID NO 65
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 65
ucaucgucua acauagcaa                                                19

<210> SEQ ID NO 66
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 66
ncaucgucua acauagcaa                                                19

<210> SEQ ID NO 67
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 67
ncaucgucua acauagcan                                                19

<210> SEQ ID NO 68
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 68
ucacuaugga guauaucuu                                                19

<210> SEQ ID NO 69
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
```

```
<400> SEQUENCE: 69
acacuaugga guauaucuu                                              19

<210> SEQ ID NO 70
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 70
ncacuaugga guauaucuu                                              19

<210> SEQ ID NO 71
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 71
ncacuaugga guauaucun                                              19

<210> SEQ ID NO 72
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 72
aaucuugauu uuggcucug                                              19

<210> SEQ ID NO 73
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 73
uaucuugauu uuggcucug                                              19

<210> SEQ ID NO 74
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 74
```
naucuugauu uuggcucug          19

<210> SEQ ID NO 75
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 75
naucuugauu uuggcucun          19

<210> SEQ ID NO 76
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 76
aagucuuuaa gaccauguc          19

<210> SEQ ID NO 77
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 77
uagucuuuaa gaccauguc          19

<210> SEQ ID NO 78
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 78
nagucuuuaa gaccauguc          19

<210> SEQ ID NO 79
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 79
nagucuuuaa gaccaugun          19

```
<210> SEQ ID NO 80
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 80
gggaguaguu cuuggugcu                                                  19

<210> SEQ ID NO 81
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 81
uggaguaguu cuuggugcu                                                  19

<210> SEQ ID NO 82
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 82
aggaguaguu cuuggugcu                                                  19

<210> SEQ ID NO 83
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 83
nggaguaguu cuuggugcu                                                  19

<210> SEQ ID NO 84
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 84
nggaguaguu cuuggugcn                                                  19

<210> SEQ ID NO 85
<211> LENGTH: 19
<212> TYPE: RNA
<213> ORGANISM: Artificial sequence
<220> FEATURE:
```

```
<223> OTHER INFORMATION: RNAi agent antisense strand core 19-mer base
      sequence

<400> SEQUENCE: 85
agggaguagu ucuuggugc                                               19

<210> SEQ ID NO 86
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 86
ugggaguagu ucuuggugc                                               19

<210> SEQ ID NO 87
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 87
ngggaguagu ucuuggugc                                               19

<210> SEQ ID NO 88
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 88
ngggaguagu ucuuggugn                                               19

<210> SEQ ID NO 89
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 89
agagaguagu ucuuggugc                                               19

<210> SEQ ID NO 90
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 90
ugagaguagu ucuuggugc                                               19
```

<210> SEQ ID NO 91
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 91
ngagaguagu ucuuggugc                                                 19

<210> SEQ ID NO 92
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 92
ngagaguagu ucuuggugn                                                 19

<210> SEQ ID NO 93
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 93
ccaaccaaaa uucuccauc                                                 19

<210> SEQ ID NO 94
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 94
ucaaccaaaa uucuccauc                                                 19

<210> SEQ ID NO 95
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 95
acaaccaaaa uucuccauc                                                 19

<210> SEQ ID NO 96
<211> LENGTH: 19
<212> TYPE: RNA
<213> ORGANISM: Artificial sequence

```
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 96
ncaaccaaaa uucuccauc                                                  19

<210> SEQ ID NO 97
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 97
ncaaccaaaa uucuccaun                                                  19

<210> SEQ ID NO 98
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 98
cccaaccaaa auucuccau                                                  19

<210> SEQ ID NO 99
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 99
uccaaccaaa auucuccau                                                  19

<210> SEQ ID NO 100
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 100
accaaccaaa auucuccau                                                  19

<210> SEQ ID NO 101
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
```

```
<223> OTHER INFORMATION: n = any nucleobase

<400> SEQUENCE: 101
nccaaccaaa auucuccau                                                    19

<210> SEQ ID NO 102
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 102
nccaaccaaa auucuccan                                                    19

<210> SEQ ID NO 103
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 103
uauugcuuca cuauggagu                                                    19

<210> SEQ ID NO 104
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 104
aauugcuuca cuauggagu                                                    19

<210> SEQ ID NO 105
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 105
gauugcuuca cuauggagu                                                    19

<210> SEQ ID NO 106
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 106
nauugcuuca cuauggagu                                                    19
```

```
<210> SEQ ID NO 107
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 107
nauugcuuca cuauggagn                                                    19

<210> SEQ ID NO 108
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 108
ucguauaguu gguuucgug                                                    19

<210> SEQ ID NO 109
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 109
acguauaguu gguuucgug                                                    19

<210> SEQ ID NO 110
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 110
gcguauaguu gguuucgug                                                    19

<210> SEQ ID NO 111
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 111
ncguauaguu gguuucgug                                                    19

<210> SEQ ID NO 112
<211> LENGTH: 19
<212> TYPE: RNA
<213> ORGANISM: Artificial sequence
<220> FEATURE:
```

<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 112
ncguauaguu gguuucgun                                                19

<210> SEQ ID NO 113
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 113
ucuuugugau cccaaguag                                                19

<210> SEQ ID NO 114
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 114
acuuugugau cccaaguag                                                19

<210> SEQ ID NO 115
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 115
gcuuugugau cccaaguag                                                19

<210> SEQ ID NO 116
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 116
ncuuugugau cccaaguag                                                19

<210> SEQ ID NO 117
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

```
<400> SEQUENCE: 117
ncuuugugau cccaaguan                                              19

<210> SEQ ID NO 118
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 118
uuugcuuugu gaucccaag                                              19

<210> SEQ ID NO 119
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 119
auugcuuugu gaucccaag                                              19

<210> SEQ ID NO 120
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 120
nuugcuuugu gaucccaag                                              19

<210> SEQ ID NO 121
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 121
nuugcuuugu gaucccaan                                              19

<210> SEQ ID NO 122
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 122
uuagguuguu uucuccaca                                              19
```

```
<210> SEQ ID NO 123
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 123
auagguuguu uucuccaca                                                   19

<210> SEQ ID NO 124
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 124
nuagguuguu uucuccaca                                                   19

<210> SEQ ID NO 125
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 125
nuagguuguu uucuccacn                                                   19

<210> SEQ ID NO 126
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 126
auuuagguug uuucucca                                                    19

<210> SEQ ID NO 127
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 127
uuuuagguug uuucucca                                                    19

<210> SEQ ID NO 128
<211> LENGTH: 19
<212> TYPE: RNA
<213> ORGANISM: Artificial sequence
<220> FEATURE:
<223> OTHER INFORMATION: RNAi agent antisense strand core 19-mer base
```

-continued

```
      sequence
<220> FEATURE:
<221> NAME/KEY: modified_base
<222> LOCATION: 1
<223> OTHER INFORMATION: n = any nucleobase

<400> SEQUENCE: 128
nuuuagguug uuucucca                                                   19

<210> SEQ ID NO 129
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 129
nuuuagguug uuucuccn                                                   19

<210> SEQ ID NO 130
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 130
ucaacauauu ugaucagua                                                  19

<210> SEQ ID NO 131
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 8
<223> OTHER INFORMATION: n = 2-aminoadenine

<400> SEQUENCE: 131
ucaacaunuu ugaucagua                                                  19

<210> SEQ ID NO 132
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 6, 8
<223> OTHER INFORMATION: n = 2-aminoadenine

<400> SEQUENCE: 132
ucaacnunuu ugaucagua                                                  19

<210> SEQ ID NO 133
<211> LENGTH: 19
<212> TYPE: RNA
<213> ORGANISM: Artificial sequence
```

```
<220> FEATURE:
<223> OTHER INFORMATION: RNAi agent sense strand core 19-mer base
      sequence

<400> SEQUENCE: 133
ucaacauauu ugaucaguu                                                    19

<210> SEQ ID NO 134
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 8
<223> OTHER INFORMATION: n = 2-aminoadenine

<400> SEQUENCE: 134
ucaacaunuu ugaucaguu                                                    19

<210> SEQ ID NO 135
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 6, 8
<223> OTHER INFORMATION: n = 2-aminoadenine

<400> SEQUENCE: 135
ucaacnunuu ugaucaguu                                                    19

<210> SEQ ID NO 136
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 136
ucaacauauu ugaucaguc                                                    19

<210> SEQ ID NO 137
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 8
<223> OTHER INFORMATION: n = 2-aminoadenine

<400> SEQUENCE: 137
ucaacaunuu ugaucaguc                                                    19

<210> SEQ ID NO 138
<211> LENGTH: 19
<212> TYPE: RNA
<213> ORGANISM: Artificial sequence
<220> FEATURE:
<223> OTHER INFORMATION: RNAi agent sense strand core 19-mer base
```

```
                         sequence
<220> FEATURE:
<221> NAME/KEY: modified_base
<222> LOCATION: 6, 8
<223> OTHER INFORMATION: n = 2-aminoadenine

<400> SEQUENCE: 138
ucaacnunuu ugaucaguc                                                     19

<210> SEQ ID NO 139
<211> LENGTH: 19
<212> TYPE: RNA
<213> ORGANISM: Artificial sequence
<220> FEATURE:
<223> OTHER INFORMATION: RNAi agent sense strand core 19-mer base
                         sequence
<220> FEATURE:
<221> NAME/KEY: modified_base
<222> LOCATION: 19
<223> OTHER INFORMATION: n = any nucleobase

<400> SEQUENCE: 139
ucaacauauu ugaucagun                                                     19

<210> SEQ ID NO 140
<211> LENGTH: 19
<212> TYPE: RNA
<213> ORGANISM: Artificial sequence
<220> FEATURE:
<223> OTHER INFORMATION: RNAi agent sense strand core 19-mer base
                         sequence
<220> FEATURE:
<221> NAME/KEY: modified_base
<222> LOCATION: 8
<223> OTHER INFORMATION: n = 2-aminoadenine
<220> FEATURE:
<221> NAME/KEY: modified_base
<222> LOCATION: 19
<223> OTHER INFORMATION: n = any nucleobase

<400> SEQUENCE: 140
ucaacaunuu ugaucagun                                                     19

<210> SEQ ID NO 141
<211> LENGTH: 19
<212> TYPE: RNA
<213> ORGANISM: Artificial sequence
<220> FEATURE:
<223> OTHER INFORMATION: RNAi agent sense strand core 19-mer base
                         sequence
<220> FEATURE:
<221> NAME/KEY: modified_base
<222> LOCATION: 6, 8
<223> OTHER INFORMATION: n = 2-aminoadenine
<220> FEATURE:
<221> NAME/KEY: modified_base
<222> LOCATION: 19
<223> OTHER INFORMATION: n = any nucleobase

<400> SEQUENCE: 141
ucaacnunuu ugaucagun                                                     19

<210> SEQ ID NO 142
<211> LENGTH: 19
<212> TYPE: RNA
<213> ORGANISM: Artificial sequence
<220> FEATURE:
<223> OTHER INFORMATION: RNAi agent sense strand core 19-mer base
                         sequence
<220> FEATURE:
<221> NAME/KEY: modified_base
```

```
<222> LOCATION: 1, 19
<223> OTHER INFORMATION: n = any nucleobase

<400> SEQUENCE: 142
ncaacauauu ugaucagun                                              19

<210> SEQ ID NO 143
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 8
<223> OTHER INFORMATION: n = 2-aminoadenine

<400> SEQUENCE: 143
ncaacaunuu ugaucagun                                              19

<210> SEQ ID NO 144
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 6, 8
<223> OTHER INFORMATION: n = 2-aminoadenine

<400> SEQUENCE: 144
ncaacnunuu ugaucagun                                              19

<210> SEQ ID NO 145
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 145
cauggacauu aaucaaca                                               19

<210> SEQ ID NO 146
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 146
cauggacauu aaucaacu                                               19

<210> SEQ ID NO 147
<211> LENGTH: 19
<212> TYPE: RNA
```

```
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 147
cauggacauu aauucaacn                                                   19

<210> SEQ ID NO 148
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 148
nauggacauu aauucaacn                                                   19

<210> SEQ ID NO 149
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 149
ccauggacau uaauucaac                                                   19

<210> SEQ ID NO 150
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 150
ccauggacau uaauucaaa                                                   19

<210> SEQ ID NO 151
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 151
ccauggacau uaauucaau                                                   19

<210> SEQ ID NO 152
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
```

```
<222> LOCATION: 19
<223> OTHER INFORMATION: n = any nucleobase

<400> SEQUENCE: 152
ccauggacau uaauucaan                                                19

<210> SEQ ID NO 153
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 153
ncauggacau uaauucaan                                                19

<210> SEQ ID NO 154
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 154
uugcuauguu agacgaugu                                                19

<210> SEQ ID NO 155
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 155
uugcuauguu agacgauga                                                19

<210> SEQ ID NO 156
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 156
uugcuauguu agacgaugn                                                19

<210> SEQ ID NO 157
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
```

<400> SEQUENCE: 157
nugcuauguu agacgaugn					19

<210> SEQ ID NO 158
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 158
aagauauacu ccauaguga					19

<210> SEQ ID NO 159
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 159
aagauauacu ccauagugu					19

<210> SEQ ID NO 160
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 160
aagauauacu ccauagugn					19

<210> SEQ ID NO 161
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 161
nagauauacu ccauagugn					19

<210> SEQ ID NO 162
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 162
cagagccaaa aucaagauu					19

```
<210> SEQ ID NO 163
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 163
cagagccaaa aucaagaua                                               19

<210> SEQ ID NO 164
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 164
cagagccaaa aucaagaun                                               19

<210> SEQ ID NO 165
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 165
nagagccaaa aucaagaun                                               19

<210> SEQ ID NO 166
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 166
gacauggucu uaaagacuu                                               19

<210> SEQ ID NO 167
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 167
gacauggucu uaaagacua                                               19

<210> SEQ ID NO 168
<211> LENGTH: 19
<212> TYPE: RNA
<213> ORGANISM: Artificial sequence
<220> FEATURE:
<223> OTHER INFORMATION: RNAi agent sense strand core 19-mer base
```

```
        sequence
<220> FEATURE:
<221> NAME/KEY: modified_base
<222> LOCATION: 19
<223> OTHER INFORMATION: n = any nucleobase

<400> SEQUENCE: 168
gacauggucu uaaagacun                                                        19

<210> SEQ ID NO 169
<211> LENGTH: 19
<212> TYPE: RNA
<213> ORGANISM: Artificial sequence
<220> FEATURE:
<223> OTHER INFORMATION: RNAi agent sense strand core 19-mer base
        sequence
<220> FEATURE:
<221> NAME/KEY: modified_base
<222> LOCATION: 1, 19
<223> OTHER INFORMATION: n = any nucleobase

<400> SEQUENCE: 169
nacauggucu uaaagacun                                                        19

<210> SEQ ID NO 170
<211> LENGTH: 19
<212> TYPE: RNA
<213> ORGANISM: Artificial sequence
<220> FEATURE:
<223> OTHER INFORMATION: RNAi agent sense strand core 19-mer base
        sequence

<400> SEQUENCE: 170
agcaccaaga acuacuccc                                                        19

<210> SEQ ID NO 171
<211> LENGTH: 19
<212> TYPE: RNA
<213> ORGANISM: Artificial sequence
<220> FEATURE:
<223> OTHER INFORMATION: RNAi agent sense strand core 19-mer base
        sequence

<400> SEQUENCE: 171
agcaccaaga acuacucca                                                        19

<210> SEQ ID NO 172
<211> LENGTH: 19
<212> TYPE: RNA
<213> ORGANISM: Artificial sequence
<220> FEATURE:
<223> OTHER INFORMATION: RNAi agent sense strand core 19-mer base
        sequence

<400> SEQUENCE: 172
agcaccaaga acuacuccu                                                        19

<210> SEQ ID NO 173
<211> LENGTH: 19
<212> TYPE: RNA
<213> ORGANISM: Artificial sequence
<220> FEATURE:
<223> OTHER INFORMATION: RNAi agent sense strand core 19-mer base
        sequence
<220> FEATURE:
<221> NAME/KEY: modified_base
<222> LOCATION: 19
<223> OTHER INFORMATION: n = any nucleobase
```

```
<400> SEQUENCE: 173
agcaccaaga acuacuccn                                              19

<210> SEQ ID NO 174
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 174
ngcaccaaga acuacuccn                                              19

<210> SEQ ID NO 175
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 175
gcaccaagaa cuacuccu                                               19

<210> SEQ ID NO 176
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 176
gcaccaagaa cuacucca                                               19

<210> SEQ ID NO 177
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 177
gcaccaagaa cuacuccn                                               19

<210> SEQ ID NO 178
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 178
```

```
ncaccaagaa cuacucccn                                                      19
```

<210> SEQ ID NO 179
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 179

```
gcaccaagaa cuacucucu                                                      19
```

<210> SEQ ID NO 180
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 180

```
gcaccaagaa cuacucuca                                                      19
```

<210> SEQ ID NO 181
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 181

```
gcaccaagaa cuacucucn                                                      19
```

<210> SEQ ID NO 182
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 182

```
ncaccaagaa cuacucucn                                                      19
```

<210> SEQ ID NO 183
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 183

```
gauggagaau uuugguugg                                                      19
```

<210> SEQ ID NO 184
<211> LENGTH: 19
<212> TYPE: RNA

```
<213> ORGANISM: Artificial sequence
<220> FEATURE:
<223> OTHER INFORMATION: RNAi agent sense strand core 19-mer base
      sequence

<400> SEQUENCE: 184
gauggagaau uuugguuga                                                19

<210> SEQ ID NO 185
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 185
gauggagaau uuugguugu                                                19

<210> SEQ ID NO 186
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 186
gauggagaau uuugguugn                                                19

<210> SEQ ID NO 187
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 187
nauggagaau uuugguugn                                                19

<210> SEQ ID NO 188
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 188
auggagaauu uugguuggg                                                19

<210> SEQ ID NO 189
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 189
```

```
auggagaauu uugguugga                                                19

<210> SEQ ID NO 190
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 190
auggagaauu uugguuggu                                                19

<210> SEQ ID NO 191
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 191
auggagaauu uugguuggn                                                19

<210> SEQ ID NO 192
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 192
nuggagaauu uugguuggn                                                19

<210> SEQ ID NO 193
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 193
acuccauagu gaagcaaua                                                19

<210> SEQ ID NO 194
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 194
acuccauagu gaagcaauu                                                19

<210> SEQ ID NO 195
<211> LENGTH: 19
```

```
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 195
acuccauagu gaagcaauc                                              19

<210> SEQ ID NO 196
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 196
acuccauagu gaagcaaun                                              19

<210> SEQ ID NO 197
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 197
acuccauagu gaagcaaun                                              19

<210> SEQ ID NO 198
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 198
cacgaaacca acuauacga                                              19

<210> SEQ ID NO 199
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 199
cacgaaacca acuauacgu                                              19

<210> SEQ ID NO 200
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<400> SEQUENCE: 200
cacgaaacca acuauacgc                                                19

<210> SEQ ID NO 201
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 201
cacgaaacca acuauacgn                                                19

<210> SEQ ID NO 202
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 202
nacgaaacca acuauacgn                                                19

<210> SEQ ID NO 203
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 203
cuacuuggga ucacaaaga                                                19

<210> SEQ ID NO 204
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 204
cuacuuggga ucacaaagu                                                19

<210> SEQ ID NO 205
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 205
cuacuuggga ucacaaagc                                                19

<210> SEQ ID NO 206
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 206
cuacuuggga ucacaaagn                                                    19

<210> SEQ ID NO 207
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 207
nuacuuggga ucacaaagn                                                    19

<210> SEQ ID NO 208
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 208
cuugggauca caaagcaaa                                                    19

<210> SEQ ID NO 209
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 209
cuugggauca caaagcaau                                                    19

<210> SEQ ID NO 210
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 210
cuugggauca caaagcaan                                                    19

<210> SEQ ID NO 211
<211> LENGTH: 19
<212> TYPE: RNA
```

```
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 211
nuugggauca caaagcaan                                                       19

<210> SEQ ID NO 212
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 212
uguggagaaa acaaccuaa                                                       19

<210> SEQ ID NO 213
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 213
uguggagaaa acaaccuau                                                       19

<210> SEQ ID NO 214
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 214
uguggagaaa acaaccuan                                                       19

<210> SEQ ID NO 215
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 215
nguggagaaa acaaccuan                                                       19

<210> SEQ ID NO 216
<211> LENGTH: 19
<212> TYPE: RNA
<213> ORGANISM: Artificial sequence
<220> FEATURE:
```

```
<223> OTHER INFORMATION: RNAi agent sense strand core 19-mer base
      sequence

<400> SEQUENCE: 216
uggagaaaac aaccuaaau                                                    19

<210> SEQ ID NO 217
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 217
uggagaaaac aaccuaaaa                                                    19

<210> SEQ ID NO 218
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 218
uggagaaaac aaccuaaan                                                    19

<210> SEQ ID NO 219
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 219
nggagaaaac aaccuaaan                                                    19

<210> SEQ ID NO 220
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 220
uuugaauuaa uguccaugga c                                                 21

<210> SEQ ID NO 221
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 221
uguugaauua auguccaugg c                                                 21
```

```
<210> SEQ ID NO 222
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 222
uuagguuguu uucuccacac u                                              21

<210> SEQ ID NO 223
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 223
uuagguuguu uucuccacac c                                              21

<210> SEQ ID NO 224
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 224
uuuuagguug uuucuccac c                                               21

<210> SEQ ID NO 225
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 225
uggaguaguu cuuggugcuc u                                              21

<210> SEQ ID NO 226
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 226
uggaguaguu cuuggugcuc c                                              21

<210> SEQ ID NO 227
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 227
agggaguagu ucuuggugcu c                                              21

<210> SEQ ID NO 228
<211> LENGTH: 21
<212> TYPE: RNA
<213> ORGANISM: Artificial sequence
<220> FEATURE:
<223> OTHER INFORMATION: RNAi agent antisense strand modified sequence
```

```
<400> SEQUENCE: 228
uuugaauuaa uguccaugga g                                              21

<210> SEQ ID NO 229
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 229
uuugaauuaa uguccaugga g                                              21

<210> SEQ ID NO 230
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 230
uuugaauuaa uguccauggc g                                              21

<210> SEQ ID NO 231
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 231
uuugaauuaa uguccauggg g                                              21

<210> SEQ ID NO 232
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 232
uguugaauua auguccaugg g                                              21

<210> SEQ ID NO 233
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 233
uguugaauua auguccaugg u                                              21

<210> SEQ ID NO 234
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 234
uguugaauua auguccaugg u                                              21

<210> SEQ ID NO 235
<211> LENGTH: 21
```

```
<212> TYPE: RNA
<213> ORGANISM: Artificial sequence
<220> FEATURE:
<223> OTHER INFORMATION: RNAi agent antisense strand modified sequence

<400> SEQUENCE: 235
aaucuugauu uuggcucugg a                                              21

<210> SEQ ID NO 236
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 236
aaucuugauu uuggcucugg u                                              21

<210> SEQ ID NO 237
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 237
ucaaccaaaa uucuccauca c                                              21

<210> SEQ ID NO 238
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 238
ucaaccaaaa uucuccaucg c                                              21

<210> SEQ ID NO 239
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 239
uccaaccaaa auucuccauc a                                              21

<210> SEQ ID NO 240
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 240
uguugaauua auguccaugg a                                              21

<210> SEQ ID NO 241
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 241
```
uguugaauua auguccaugg a                                    21

<210> SEQ ID NO 242
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 242
uguugaauua auguccaugg a                                    21

<210> SEQ ID NO 243
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 243
uguugaauua auguccaugg a                                    21

<210> SEQ ID NO 244
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 244
uguugaauua auguccaugg a                                    21

<210> SEQ ID NO 245
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 245
uguugaauua auguccaugg a                                    21

<210> SEQ ID NO 246
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 246
uguugaauua auguccaugg g                                    21

<210> SEQ ID NO 247
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 247
aacugaucaa auauguugag c                                    21

<210> SEQ ID NO 248
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 248
uacugaucaa auauguugag c 21

<210> SEQ ID NO 249
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 249
uacugaucaa auauguugag c 21

<210> SEQ ID NO 250
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 250
uacugaucaa auauguugag c 21

<210> SEQ ID NO 251
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 251
uacugaucaa auauguugag g 21

<210> SEQ ID NO 252
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 252
uacugaucaa auauguuggg c 21

<210> SEQ ID NO 253
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 253
uacugaucaa auauguugcg c 21

<210> SEQ ID NO 254
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 254
uacugaucaa auauguuggg u 21

<210> SEQ ID NO 255
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 255
uacugaucaa auauguugcg u                                              21

<210> SEQ ID NO 256
<211> LENGTH: 21
<212> TYPE: DNA
<213> ORGANISM: Artificial sequence
<220> FEATURE:
<223> OTHER INFORMATION: RNAi agent antisense strand modified sequence

<400> SEQUENCE: 256
uutgaauuaa uguccauggg u                                              21

<210> SEQ ID NO 257
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 257
uuugaauuaa uguccauggg u                                              21

<210> SEQ ID NO 258
<211> LENGTH: 21
<212> TYPE: DNA
<213> ORGANISM: Artificial sequence
<220> FEATURE:
<223> OTHER INFORMATION: RNAi agent antisense strand modified sequence

<400> SEQUENCE: 258
uuugaatuaa uguccauggg u                                              21

<210> SEQ ID NO 259
<211> LENGTH: 21
<212> TYPE: DNA
<213> ORGANISM: Artificial sequence
<220> FEATURE:
<223> OTHER INFORMATION: RNAi agent antisense strand modified sequence

<400> SEQUENCE: 259
uutgaauuaa uguccauggg u                                              21

<210> SEQ ID NO 260
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 260
uacugaucaa auauguugag c                                              21

<210> SEQ ID NO 261
<211> LENGTH: 21
<212> TYPE: RNA
<213> ORGANISM: Artificial sequence
<220> FEATURE:
<223> OTHER INFORMATION: RNAi agent antisense strand modified sequence -continued

<400> SEQUENCE: 261
uacugaucaa auauguugag c                                          21

<210> SEQ ID NO 262
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 262
uacugaucaa auauguugag c                                          21

<210> SEQ ID NO 263
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 11
<223> OTHER INFORMATION: n = 2'-O-methylinosine-3'-phosphate

<400> SEQUENCE: 263
uacugaucaa nuauguugag c                                          21

<210> SEQ ID NO 264
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 264
uacugaucaa auauguugag c                                          21

<210> SEQ ID NO 265
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 265
uacugaucaa auauguugag c                                          21

<210> SEQ ID NO 266
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 266
uuugaauuaa uguccauggg u                                          21

<210> SEQ ID NO 267
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 267
aagucuuuaa gaccaugucc c                                              21

<210> SEQ ID NO 268
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 268
uauugcuuca cuauggagua g                                              21

<210> SEQ ID NO 269
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 269
uuugcuuugu gaucccaagu c                                              21

<210> SEQ ID NO 270
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 270
ucacuaugga guauaucuuc c                                              21

<210> SEQ ID NO 271
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 271
ucguauaguu gguuucguga c                                              21

<210> SEQ ID NO 272
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 272
ucuuugugau cccaaguaga c                                              21

<210> SEQ ID NO 273
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 273
ucacuaugga guauaucuuc c                                              21

<210> SEQ ID NO 274
<211> LENGTH: 21
<212> TYPE: RNA
<213> ORGANISM: Artificial sequence

```
<220> FEATURE:
<223> OTHER INFORMATION: RNAi agent sense strand modified sequence

<400> SEQUENCE: 274
agagcaccaa gaacuacucc a                                              21

<210> SEQ ID NO 275
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 275
ggagcaccaa gaacuacuuc a                                              21

<210> SEQ ID NO 276
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 276
gagcaccaag aacuacucuc u                                              21

<210> SEQ ID NO 277
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 277
guccauggac auuaauucaa a                                              21

<210> SEQ ID NO 278
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 278
gcccauggac auuaauucaa a                                              21

<210> SEQ ID NO 279
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 279
uccauggaca uuaauucaac a                                              21

<210> SEQ ID NO 280
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 280
gccauggaca uuaauucaac a                                              21
```

<210> SEQ ID NO 281
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 281
aguguggaga aaacaaccua a                                               21

<210> SEQ ID NO 282
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 282
gguguggaga aaacaaccua a                                               21

<210> SEQ ID NO 283
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 283 ggugagaaa acaaccuaaa a                                                21

<210> SEQ ID NO 284
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 284
cuccauggac auuaauucaa a                                               21

<210> SEQ ID NO 285
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 285
cuccauggac auuaauucaa a                                               21

<210> SEQ ID NO 286
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 286
cuccauggac auuaauucaa a                                               21

<210> SEQ ID NO 287
<211> LENGTH: 21
<212> TYPE: RNA
<213> ORGANISM: Artificial sequence
<220> FEATURE:
<223> OTHER INFORMATION: RNAi agent sense strand modified sequence

```
<220> FEATURE:
<221> NAME/KEY: modified_base
<222> LOCATION: 20
<223> OTHER INFORMATION: n = 2'-O-methyl-2-aminoadenosine-3'-phosphate

<400> SEQUENCE: 287
cuccauggac auuaauucan a                                               21

<210> SEQ ID NO 288
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 288
cuccauggac auuaauucna a                                               21

<210> SEQ ID NO 289
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 289
cuccauggac auunauucaa a                                               21

<210> SEQ ID NO 290
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 290
cgccauggac auuaauucaa a                                               21

<210> SEQ ID NO 291
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 291
ccccauggac auuaauucaa a                                               21

<210> SEQ ID NO 292
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 292
acccauggac auuaauucaa a                                               21

<210> SEQ ID NO 293
```

```
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 293
cccauggaca uuaauucaac a                                              21

<210> SEQ ID NO 294
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 294
accauggaca uuaauucaac a                                              21

<210> SEQ ID NO 295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 295
accauggaca uuaauucaac a                                              21

<210> SEQ ID NO 296
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 296
accauggaca uuanuucaac a                                              21

<210> SEQ ID NO 297
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 4
<223> OTHER INFORMATION: n = 2'-O-methyl-2-aminoadenosine-3'-phosphate

<400> SEQUENCE: 297
accnuggaca uuaauucaac a                                              21

<210> SEQ ID NO 298
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1
<223> OTHER INFORMATION: n = 2'-O-methyl-2-aminoadenosine-3'-phosphate

<400> SEQUENCE: 298
```

```
nccauggaca uuaauucaac a                                              21

<210> SEQ ID NO 299
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 299
acucaacaua uuugaucagu a                                              21

<210> SEQ ID NO 300
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 300
gcucaacaua uuugaucagu a                                              21

<210> SEQ ID NO 301
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 301
uccagagcca aaaucaagau u                                              21

<210> SEQ ID NO 302
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 302
accagagcca aaaucaagau u                                              21

<210> SEQ ID NO 303
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 303
gugauggaga auuuugguug a                                              21

<210> SEQ ID NO 304
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 304
gcgauggaga auuuugguug a                                              21

<210> SEQ ID NO 305
<211> LENGTH: 21
<212> TYPE: RNA
```

```
<213> ORGANISM: Artificial sequence
<220> FEATURE:
<223> OTHER INFORMATION: RNAi agent sense strand modified sequence

<400> SEQUENCE: 305
ugauggagaa uuuugguugg a                                              21

<210> SEQ ID NO 306
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 306
uccauggaca uuaauucaac a                                              21

<210> SEQ ID NO 307
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 307
accauggaca uuaauucaac a                                              21

<210> SEQ ID NO 308
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 308
uccauggaca uuaauucanc a                                              21

<210> SEQ ID NO 309
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 309
uccauggaca uuaauucnac a                                              21

<210> SEQ ID NO 310
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 310
uccauggaca uuaauucaac a                                              21

<210> SEQ ID NO 311
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 311
uccauggaca uuaauucaac a                                              21

<210> SEQ ID NO 312
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 312
uccauggaca uuaauucaac a                                              21

<210> SEQ ID NO 313
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 313
cccauggaca uuaauucaac a                                              21

<210> SEQ ID NO 314
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 314
acccauggac auuaauucaa a                                              21

<210> SEQ ID NO 315
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 315
gcucaacaua uuugaucagu u                                              21

<210> SEQ ID NO 316
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 316
gcucaacaua uuugaucanu a                                              21

<210> SEQ ID NO 317
<211> LENGTH: 21
<212> TYPE: RNA
<213> ORGANISM: Artificial sequence
<220> FEATURE:
```

<223> OTHER INFORMATION: RNAi agent sense strand modified sequence

<400> SEQUENCE: 317
gcucaacaua uuugaucagu a         21

<210> SEQ ID NO 318
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 318
ccucaacaua uuugaucagu a         21

<210> SEQ ID NO 319
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 319
gcccaacaua uuugaucagu a         21

<210> SEQ ID NO 320
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 320
gcgcaacaua uuugaucagu a         21

<210> SEQ ID NO 321
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 321
acccaacaua uuugaucagu a         21

<210> SEQ ID NO 322
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 322
acgcaacaua uuugaucagu a         21

<210> SEQ ID NO 323
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 323
acccauggac auuaauucaa a         21

```
<210> SEQ ID NO 324
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 324
acccauggac auuaauucaa a                                              21

<210> SEQ ID NO 325
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 325
acccauggac auuaatucaa a                                              21

<210> SEQ ID NO 326
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 326
gcucaacaua uuugaucagu a                                              21

<210> SEQ ID NO 327
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 327
gcucaacaua uuugaucagu a                                              21

<210> SEQ ID NO 328
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 328
gcucaacaua uuugaucagu a                                              21

<210> SEQ ID NO 329
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 329
gcucaacaua uuugaucagu a                                              21

<210> SEQ ID NO 330
<211> LENGTH: 21
<212> TYPE: RNA
<213> ORGANISM: Artificial sequence
<220> FEATURE:
<223> OTHER INFORMATION: RNAi agent sense strand modified sequence
```

<400> SEQUENCE: 330
gcucaacaua uuugaucagu a                                                    21

<210> SEQ ID NO 331
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 331
gcucaacaua uuugaucagu a                                                    21

<210> SEQ ID NO 332
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 332
gcucaacaua uuugaucagu a                                                    21

<210> SEQ ID NO 333
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 15
<223> OTHER INFORMATION: n = 2'-O-methyl-2-aminoadenosine-3'-phosphate

<400> SEQUENCE: 333
gcucaacaua uuugnucagu a                                                    21

<210> SEQ ID NO 334
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate

<400> SEQUENCE: 334
gcucaacaun uuugaucagu a                                                    21

<210> SEQ ID NO 335
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 8
<223> OTHER INFORMATION: n = 2'-O-methyl-2-aminoadenosine-3'-phosphate

<400> SEQUENCE: 335
gcucaacnua uuugaucagu a                                                    21

<210> SEQ ID NO 336
<211> LENGTH: 21

```
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 8, 10
<223> OTHER INFORMATION: n = 2'-O-methyl-2-aminoadenosine-3'-phosphate

<400> SEQUENCE: 336
gcucaacnun uuugaucagu a                                          21

<210> SEQ ID NO 337
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 337
gcucaacaua uuugaucagu a                                          21

<210> SEQ ID NO 338
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 338
gcucaacaua uuugaucagu a                                          21

<210> SEQ ID NO 339
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 339
gcucaacaua uuugaucagu a                                          21

<210> SEQ ID NO 340
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 340
gcucaacaua uuugaucagu a                                          21

<210> SEQ ID NO 341
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 341
gcucaacaua uuugaucagu a                                          21

<210> SEQ ID NO 342
<211> LENGTH: 21
<212> TYPE: RNA
<213> ORGANISM: Artificial sequence
<220> FEATURE:
```

<223> OTHER INFORMATION: RNAi agent sense strand modified sequence

<400> SEQUENCE: 342
gcucaacaua uuugaucagu a    21

<210> SEQ ID NO 343
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 343
gcucaacaua uuugaucagu a    21

<210> SEQ ID NO 344
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 344
gcucaacaua uuugaucagu a    21

<210> SEQ ID NO 345
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 345
gcucaacaua uuugaucagu a    21

<210> SEQ ID NO 346
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 346
acccauggac auuaauucaa a    21

<210> SEQ ID NO 347
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 347
acccauggac auuaauucaa a    21

<210> SEQ ID NO 348
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 348
acccauggac auuaauucaa a    21

```
<210> SEQ ID NO 349
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 349
acccauggac auuaauucaa a                                              21

<210> SEQ ID NO 350
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 350
acccauggac auuaatucaa a                                              21

<210> SEQ ID NO 351
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 351
acccauggac auuaauucaa a                                              21

<210> SEQ ID NO 352
<211> LENGTH: 21
<212> TYPE: DNA
<213> ORGANISM: Artificial sequence
<220> FEATURE:
<223> OTHER INFORMATION: RNAi agent sense strand modified sequence

<400> SEQUENCE: 352
acccauggac auuaatucaa a                                              21

<210> SEQ ID NO 353
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 353
acccauggac auuaauucaa a                                              21

<210> SEQ ID NO 354
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 354
gggacauggu cuuaaagacu u                                              21

<210> SEQ ID NO 355
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 355
cuacuccaua gugaagcaau a                                           21

<210> SEQ ID NO 356
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 356
gacuugggau cacaaagcaa a                                           21

<210> SEQ ID NO 357
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 357
gguugcuaug uuagacgaug u                                           21

<210> SEQ ID NO 358
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 358
ggaagauaua cuccauagug a                                           21

<210> SEQ ID NO 359
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 359
gucacgaaac caacuauacg a                                           21

<210> SEQ ID NO 360
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 360
gucuacuugg gaucacaaag a                                           21

<210> SEQ ID NO 361
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 361
ggaagauaua cuccauagug a                                           21

<210> SEQ ID NO 362
<211> LENGTH: 21
```

```
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 362
ggaagauaua cuccauanug a                                              21

<210> SEQ ID NO 363
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 363
uuugaauuaa uguccaugga c                                              21

<210> SEQ ID NO 364
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 364
uguugaauua auguccaugg c                                              21

<210> SEQ ID NO 365
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 365 uuaggutuguu uucuccacac u                                             21

<210> SEQ ID NO 366
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 366
uuagguuguu uucuccacac c                                              21

<210> SEQ ID NO 367
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 367
uuuuagguug uuuucuccac c                                              21
```

```
<210> SEQ ID NO 368
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 368
uggaguaguu cuuggugcuc u                                              21

<210> SEQ ID NO 369
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 369
uggaguaguu cuuggugcuc c                                              21

<210> SEQ ID NO 370
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 370
agggaguagu ucuuggugcu c                                              21

<210> SEQ ID NO 371
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 371
uuugaauuaa uguccaugga g                                              21

<210> SEQ ID NO 372
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 372
uuugaauuaa uguccauggc g                                              21

<210> SEQ ID NO 373
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 373
uuugaauuaa uguccauggg g                                              21

<210> SEQ ID NO 374
```

-continued

```
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 374
uguugaauua auguccaugg g                                                 21

<210> SEQ ID NO 375
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 375
uguugaauua auguccaugg u                                                 21

<210> SEQ ID NO 376
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 376
aaucuugauu uuggcucugg a                                                 21

<210> SEQ ID NO 377
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 377
aaucuugauu uuggcucugg u                                                 21

<210> SEQ ID NO 378
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 378
ucaaccaaaa uucuccauca c                                                 21

<210> SEQ ID NO 379
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 379
ucaaccaaaa uucuccaucg c                                                 21

<210> SEQ ID NO 380
<211> LENGTH: 21
```

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 380
uccaaccaaa auucuccauc a                                              21

<210> SEQ ID NO 381
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 381
uguugaauua auguccaugg a                                              21

<210> SEQ ID NO 382
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 382
aacugaucaa auauguugag c                                              21

<210> SEQ ID NO 383
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 383
uacugaucaa auauguugag c                                              21

<210> SEQ ID NO 384
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 384
uacugaucaa auauguugag c                                              21

<210> SEQ ID NO 385
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 385
uacugaucaa auauguugag g                                              21

<210> SEQ ID NO 386
<211> LENGTH: 21
<212> TYPE: RNA
```

```
<213> ORGANISM: Artificial sequence
<220> FEATURE:
<223> OTHER INFORMATION: RNAi agent antisense strand underlying base
      sequence

<400> SEQUENCE: 386
uacugaucaa auauguuggg c                                             21

<210> SEQ ID NO 387
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 387
uacugaucaa auauguugcg c                                             21

<210> SEQ ID NO 388
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 388
uacugaucaa auauguuggg u                                             21

<210> SEQ ID NO 389
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 389
uacugaucaa auauguugcg u                                             21

<210> SEQ ID NO 390
<211> LENGTH: 21
<212> TYPE: DNA
<213> ORGANISM: Artificial sequence
<220> FEATURE:
<223> OTHER INFORMATION: RNAi agent antisense strand underlying base
      sequence

<400> SEQUENCE: 390
uutgaauuaa uguccauggg u                                             21

<210> SEQ ID NO 391
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 391
uuugaauuaa uguccauggg u                                             21

<210> SEQ ID NO 392
<211> LENGTH: 21
<212> TYPE: DNA
<213> ORGANISM: Artificial sequence
```

```
<220> FEATURE:
<223> OTHER INFORMATION: RNAi agent antisense strand underlying base
      sequence

<400> SEQUENCE: 392
uuugaauuaa uguccauggg u                                              21

<210> SEQ ID NO 393
<211> LENGTH: 21
<212> TYPE: RNA
<213> ORGANISM: Artificial sequence
<220> FEATURE:
<223> OTHER INFORMATION: RNAi agent antisense strand underlying base
      sequence
<220> FEATURE:
<221> NAME/KEY: modified_base
<222> LOCATION: 11
<223> OTHER INFORMATION: n = inosine (hypoxanthine)

<400> SEQUENCE: 393
uacugaucaa nuauguugag c                                              21

<210> SEQ ID NO 394
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 394
aagucuuuaa gaccaugucc c                                              21

<210> SEQ ID NO 395
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 395
uauugcuuca cuauggagua g                                              21

<210> SEQ ID NO 396
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 396
uuugcuuugu gaucccaagu c                                              21

<210> SEQ ID NO 397
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 397
ucacuaugga guauaucuuc c                                              21

<210> SEQ ID NO 398
```

```
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 398
ucguauaguu gguuucguga c                                              21

<210> SEQ ID NO 399
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 399
ucuuugugau cccaaguaga c                                              21

<210> SEQ ID NO 400
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 400
agagcaccaa gaacuacucc a                                              21

<210> SEQ ID NO 401
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 401
ggagcaccaa gaacuacuuc a                                              21

<210> SEQ ID NO 402
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 402
gagcaccaag aacuacucuc u                                              21

<210> SEQ ID NO 403
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 403
guccauggac auuaauucaa a                                              21

<210> SEQ ID NO 404
<211> LENGTH: 21
```

<212> TYPE: RNA
<213> ORGANISM: Artificial sequence
<220> FEATURE:
<223> OTHER INFORMATION: RNAi agent sense strand underlying base
      sequence

<400> SEQUENCE: 404
gcccauggac auuaauucaa a                                              21

<210> SEQ ID NO 405
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 405
uccauggaca uuaauucaac a                                              21

<210> SEQ ID NO 406
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 406
gccauggaca uuaauucaac a                                              21

<210> SEQ ID NO 407
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 407
aguguggaga aaacaaccua a                                              21

<210> SEQ ID NO 408
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 408
gguguggaga aaacaaccua a                                              21

<210> SEQ ID NO 409
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 409
gguggagaaa acaaccuaaa a                                              21

<210> SEQ ID NO 410
<211> LENGTH: 21
<212> TYPE: RNA

-continued

```
<213> ORGANISM: Artificial sequence
<220> FEATURE:
<223> OTHER INFORMATION: RNAi agent sense strand underlying base
      sequence

<400> SEQUENCE: 410
cuccauggac auuaauucaa a                                           21

<210> SEQ ID NO 411
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = 2-aminoadenine

<400> SEQUENCE: 411
cuccauggac auuaauucan a                                           21

<210> SEQ ID NO 412
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = 2-aminoadenine

<400> SEQUENCE: 412
cuccauggac auuaauucna a                                           21

<210> SEQ ID NO 413
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14
<223> OTHER INFORMATION: n = 2-aminoadenine

<400> SEQUENCE: 413
cuccauggac auunauucaa a                                           21

<210> SEQ ID NO 414
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 414
cgccauggac auuaauucaa a                                           21

<210> SEQ ID NO 415
<211> LENGTH: 21
<212> TYPE: RNA
<213> ORGANISM: Artificial sequence
<220> FEATURE:
```

<223> OTHER INFORMATION: RNAi agent sense strand underlying base
      sequence

<400> SEQUENCE: 415
ccccauggac auuaauucaa a                                            21

<210> SEQ ID NO 416
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 416
acccauggac auuaauucaa a                                            21

<210> SEQ ID NO 417
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 417
cccauggaca uuaauucaac a                                            21

<210> SEQ ID NO 418
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 418
accauggaca uuaauucaac a                                            21

<210> SEQ ID NO 419
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 14
<223> OTHER INFORMATION: n = 2-aminoadenine

<400> SEQUENCE: 419
accauggaca uuanuucaac a                                            21

<210> SEQ ID NO 420
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 4
<223> OTHER INFORMATION: n = 2-aminoadenine

<400> SEQUENCE: 420
accnuggaca uuaauucaac a                                            21

<210> SEQ ID NO 421
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 1
<223> OTHER INFORMATION: n = 2-aminoadenine

<400> SEQUENCE: 421
nccauggaca uuaauucaac a                                              21

<210> SEQ ID NO 422
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 422
acucaacaua uuugaucagu a                                              21

<210> SEQ ID NO 423
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 423
gcucaacaua uuugaucagu a                                              21

<210> SEQ ID NO 424
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 424
uccagagcca aaaucaagau u                                              21

<210> SEQ ID NO 425
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 425
accagagcca aaaucaagau u                                              21

<210> SEQ ID NO 426
<211> LENGTH: 21
<212> TYPE: RNA
<213> ORGANISM: Artificial sequence
<220> FEATURE:
<223> OTHER INFORMATION: RNAi agent sense strand underlying base
      sequence -continued

```
<400> SEQUENCE: 426
gugauggaga auuuugguug a                                              21

<210> SEQ ID NO 427
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 427
gcgauggaga auuuugguug a                                              21

<210> SEQ ID NO 428
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 428
ugauggagaa uuuugguugg a                                              21

<210> SEQ ID NO 429
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = 2-aminoadenine

<400> SEQUENCE: 429
uccauggaca uuaauucanc a                                              21

<210> SEQ ID NO 430
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = 2-aminoadenine

<400> SEQUENCE: 430
uccauggaca uuaauucnac a                                              21

<210> SEQ ID NO 431
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 431
gcucaacaua uuugaucagu u                                              21

<210> SEQ ID NO 432
```

```
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 432
gcucaacaua uuugaucanu a                                              21

<210> SEQ ID NO 433
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 433
ccucaacaua uuugaucagu a                                              21

<210> SEQ ID NO 434
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 434
gcccaacaua uuugaucagu a                                              21

<210> SEQ ID NO 435
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 435
gcgcaacaua uuugaucagu a                                              21

<210> SEQ ID NO 436
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 436
acccaacaua uuugaucagu a                                              21

<210> SEQ ID NO 437
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 437
acgcaacaua uuugaucagu a                                              21
```

<210> SEQ ID NO 438
<211> LENGTH: 21
<212> TYPE: DNA
<213> ORGANISM: Artificial sequence
<220> FEATURE:
<223> OTHER INFORMATION: RNAi agent sense strand underlying base
      sequence

<400> SEQUENCE: 438
acccauggac auuaatucaa a                                              21

<210> SEQ ID NO 439
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 15
<223> OTHER INFORMATION: n = 2-aminoadenine

<400> SEQUENCE: 439
gcucaacaua uuugnucagu a                                              21

<210> SEQ ID NO 440
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 10
<223> OTHER INFORMATION: n = 2-aminoadenine

<400> SEQUENCE: 440
gcucaacaun uuugaucagu a                                              21

<210> SEQ ID NO 441
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 8
<223> OTHER INFORMATION: n = 2-aminoadenine

<400> SEQUENCE: 441
gcucaacnua uuugaucagu a                                              21

<210> SEQ ID NO 442
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 8, 10
<223> OTHER INFORMATION: n = 2-aminoadenine

<400> SEQUENCE: 442
gcucaacnun uuugaucagu a                                          21

<210> SEQ ID NO 443
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 443
gggacauggu cuuaaagacu u                                          21

<210> SEQ ID NO 444
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 444
cuacuccaua gugaagcaau a                                          21

<210> SEQ ID NO 445
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 445
gacuugggau cacaaagcaa a                                          21

<210> SEQ ID NO 446
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 446
gguugcuaug uuagacgaug u                                          21

<210> SEQ ID NO 447
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 447
ggaagauaua cuccauagug a                                          21

<210> SEQ ID NO 448
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 448

```
gucacgaaac caacuauacg a                                              21

<210> SEQ ID NO 449
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 449
gucuacuugg gaucacaaag a                                              21

<210> SEQ ID NO 450
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 450
ggaagauaua cuccauanug a                                              21
```

UNITED STATES PATENT AND TRADEMARK OFFICE
CERTIFICATE OF CORRECTION

| | |
|---|---|
| PATENT NO. | : 10,995,335 B2 |
| APPLICATION NO. | : 16/130377 |
| DATED | : May 4, 2021 |
| INVENTOR(S) | : Zhen Li, Rui Zhu and So Wong |

It is certified that error appears in the above-identified patent and that said Letters Patent is hereby corrected as shown below:

In the Claims

Claim 1, at Column 329, Line 42 reads "Uf is 2′ fluoro adenosine" but should read "Uf is 2′ fluoro uridine".

Signed and Sealed this
Fifteenth Day of October, 2024

Katherine Kelly Vidal
*Director of the United States Patent and Trademark Office*